US009402803B2

(12) United States Patent
Archambeau et al.

(10) Patent No.: US 9,402,803 B2
(45) Date of Patent: *Aug. 2, 2016

(54) METHODS OF WOUND CARE AND TREATMENT

(71) Applicant: Revalesio Corporation, Tacoma, WA (US)

(72) Inventors: Gregory J. Archambeau, Puyallup, WA (US); Richard L. Watson, Ruston, WA (US); Anthony B. Wood, Tacoma, WA (US)

(73) Assignee: Revalesio Corporation, Tacoma, WA (US)

( * ) Notice: Subject to any disclaimer, the term of this patent is extended or adjusted under 35 U.S.C. 154(b) by 46 days.

This patent is subject to a terminal disclaimer.

(21) Appl. No.: 14/144,227

(22) Filed: Dec. 30, 2013

(65) Prior Publication Data

US 2014/0255454 A1 Sep. 11, 2014

Related U.S. Application Data

(63) Continuation of application No. 12/431,704, filed on Apr. 28, 2009, now Pat. No. 8,617,616, which is a continuation-in-part of application No. 11/978,137, filed on Oct. 25, 2007, now Pat. No. 8,597,689.

(60) Provisional application No. 61/048,433, filed on Apr. 28, 2008, provisional application No. 60/862,904, filed on Oct. 25, 2006, provisional application No. 60/862,953, filed on Oct. 25, 2006, provisional application No. 60/862,955, filed on Oct. 25, 2006, provisional application No. 60/862,959, filed on Oct. 25, 2006, provisional application No. 60/982,387, filed on Oct. 24, 2007.

(51) Int. Cl.
| | | |
|---|---|---|
| *A61K 33/40* | (2006.01) | |
| *A61K 9/00* | (2006.01) | |
| *A61K 33/00* | (2006.01) | |
| *A61K 33/14* | (2006.01) | |
| *A61K 45/06* | (2006.01) | |
| *B01F 3/04* | (2006.01) | |
| *B01F 3/08* | (2006.01) | |
| *B01F 7/00* | (2006.01) | |
| *B29D 11/00* | (2006.01) | |

(52) U.S. Cl.
CPC ............ *A61K 9/0014* (2013.01); *A61K 9/0048* (2013.01); *A61K 33/00* (2013.01); *A61K 33/14* (2013.01); *A61K 45/06* (2013.01); *B01F 3/04531* (2013.01); *B01F 3/0807* (2013.01); *B01F 3/0853* (2013.01); *B01F 7/00816* (2013.01); *B29D 11/00038* (2013.01); *B29D 11/00096* (2013.01)

(58) Field of Classification Search
USPC ......................................... 424/613; 977/915
See application file for complete search history.

(56) References Cited

U.S. PATENT DOCUMENTS

| | | | |
|---|---|---|---|
| 1,627,161 | A | 5/1927 | Edwards |
| 1,650,561 | A | 11/1927 | Williams |
| 1,650,612 | A | 11/1927 | Deniston |
| 1,711,154 | A | 4/1929 | Michal |
| 2,115,123 | A | 4/1938 | Russell |
| 2,159,670 | A | 5/1939 | Neitzke |
| 2,278,051 | A | 3/1942 | Ambrose |
| 2,591,966 | A | 4/1952 | Rider |
| 2,606,502 | A | 8/1952 | Carlson |
| 2,639,901 | A | 5/1953 | Teale |
| 2,688,470 | A | 9/1954 | Marco |

(Continued)

FOREIGN PATENT DOCUMENTS

| | | |
|---|---|---|
| CN | 1399559 | 2/2003 |
| CN | 1499977 | 5/2004 |

(Continued)

OTHER PUBLICATIONS

Aqueous Fluid (definition), Retrieved from http://www.thefreedictionary.com/aqueous and http://www.habazar.com/opticaldirectory/a2z.htm.

(Continued)

*Primary Examiner* — Adam C Milligan
(74) *Attorney, Agent, or Firm* — Barry L. Davison; Davis Wright Tremaine LLP

(57) ABSTRACT

Provided are electrokinetically-altered fluids (e.g., gas-enriched electrokinetic fluids) comprising an ionic aqueous solution of charge-stabilized oxygen-containing nanostructures in an amount sufficient to provide modulation of at least one of cellular membrane potential and cellular membrane conductivity, and therapeutic compositions and methods for use in treating a wound to a surface tissue or a symptom thereof. The electrokinetically-altered fluids or therapeutic compositions and methods include electrokinetically-altered ioinic aqueous fluids optionally in combination with other therapeutic agents. Particular aspects provide for regulating or modulating intracellular signal transduction associated with said inflammatory responses by modulation of at least one of cellular membranes, membrane potential, membrane proteins such as membrane receptors, including but not limited to G-Protein Coupled Receptors (GPCR), and intercellular junctions (e.g., tight junctions, gap junctions, zona adherins and desmasomes). Other embodiments include particular routes of administration or formulations for the electrokinetically-altered fluids (e.g., electrokinetically-altered gas-enriched fluids and solutions) and therapeutic compositions.

54 Claims, 91 Drawing Sheets

(56) References Cited

U.S. PATENT DOCUMENTS

| | | |
|---|---|---|
| 2,734,728 A | 2/1956 | Myers |
| 2,798,698 A | 7/1957 | Dooley |
| 2,960,318 A | 11/1960 | Caillaud |
| 2,969,960 A | 1/1961 | Gurley |
| 2,970,817 A | 2/1961 | Gurley, Jr. |
| 2,995,346 A | 8/1961 | Samples |
| 3,174,185 A | 3/1965 | Gerber |
| 3,182,975 A | 5/1965 | Stewart |
| 3,194,540 A | 7/1965 | Hager |
| 3,332,631 A | 7/1967 | Wood |
| 3,333,771 A | 8/1967 | Graham |
| 3,333,828 A | 8/1967 | Boehme |
| 3,471,131 A | 10/1969 | Fritzweiler |
| 3,514,079 A | 5/1970 | Little, Jr. |
| 3,630,498 A | 12/1971 | Bielinski |
| 3,653,637 A | 4/1972 | Eckhardt |
| 3,660,933 A | 5/1972 | Wong, Jr. |
| 3,744,763 A | 7/1973 | Schnoring |
| 3,791,349 A | 2/1974 | Schaefer |
| 3,925,243 A | 12/1975 | Brogli |
| 3,937,445 A | 2/1976 | Agosta |
| 3,938,783 A | 2/1976 | Porter |
| 3,939,073 A | 2/1976 | Bats |
| 3,980,280 A | 9/1976 | Benson |
| 3,986,709 A | 10/1976 | Vermeulen |
| 3,996,012 A | 12/1976 | Zucker |
| 3,998,433 A | 12/1976 | Iwako |
| 4,004,553 A | 1/1977 | Stenstrom |
| 4,011,027 A | 3/1977 | Selder |
| 4,014,526 A | 3/1977 | Cramer |
| 4,049,240 A | 9/1977 | Walters |
| 4,051,204 A | 9/1977 | Muller |
| 4,057,223 A | 11/1977 | Rosenberger |
| 4,057,933 A | 11/1977 | Enyeart |
| 4,069,147 A | 1/1978 | Abrams |
| 4,071,225 A | 1/1978 | Holl |
| 4,089,507 A | 5/1978 | Arai |
| 4,097,026 A | 6/1978 | Haindl |
| 4,116,164 A | 9/1978 | Shabi |
| 4,117,550 A | 9/1978 | Folland |
| 4,127,332 A | 11/1978 | Thiruvengadam |
| 4,128,342 A | 12/1978 | Renk |
| 4,136,971 A | 1/1979 | Varlamov |
| 4,143,639 A | 3/1979 | Frenette |
| 4,144,167 A | 3/1979 | Burkett |
| 4,159,944 A | 7/1979 | Erickson |
| 4,162,153 A | 7/1979 | Spector |
| 4,163,712 A | 8/1979 | Smith |
| 4,172,668 A | 10/1979 | Thompson |
| 4,175,873 A | 11/1979 | Iwako |
| 4,183,681 A | 1/1980 | Li |
| 4,201,487 A | 5/1980 | Backhaus |
| 4,213,712 A | 7/1980 | Aanonsen |
| 4,261,521 A | 4/1981 | Ashbrook |
| 4,263,003 A | 4/1981 | Vork |
| 4,284,623 A | 8/1981 | Beck |
| 4,289,733 A | 9/1981 | Saito |
| 4,294,549 A | 10/1981 | Thompson |
| 4,316,673 A | 2/1982 | Speer |
| 4,318,429 A | 3/1982 | Gouttebessis |
| 4,332,486 A | 6/1982 | Mutalibov |
| 4,361,414 A | 11/1982 | Nemes |
| 4,368,986 A | 1/1983 | Fischer |
| 4,383,767 A | 5/1983 | Jido |
| 4,388,915 A | 6/1983 | Shafran |
| 4,393,017 A | 7/1983 | Kim |
| 4,394,966 A | 7/1983 | Snyder |
| 4,408,890 A | 10/1983 | Beckmann |
| 4,416,548 A | 11/1983 | Carre |
| 4,424,797 A | 1/1984 | Perkins |
| 4,436,430 A | 3/1984 | Mayer |
| 4,441,823 A | 4/1984 | Power |
| 4,444,510 A | 4/1984 | Janssen |
| 4,469,595 A | 9/1984 | Napadow |
| 4,474,479 A | 10/1984 | Redelman |
| 4,477,338 A | 10/1984 | Hellmann |
| 4,507,285 A | 3/1985 | Kuhne |
| 4,509,861 A | 4/1985 | Sjonell |
| 4,533,254 A | 8/1985 | Cook |
| 4,539,139 A | 9/1985 | Ichikawa |
| 4,550,022 A | 10/1985 | Garabedian et al. |
| 4,594,228 A | 6/1986 | Lambert |
| 4,619,072 A | 10/1986 | Privett |
| 4,633,909 A | 1/1987 | Louboutin |
| 4,634,675 A | 1/1987 | Freedman |
| 4,645,606 A | 2/1987 | Ashbrook |
| 4,661,243 A | 4/1987 | Hotz |
| 4,663,055 A | 5/1987 | Ling |
| 4,664,680 A | 5/1987 | Weber |
| 4,684,614 A | 8/1987 | Krovak |
| 4,687,579 A | 8/1987 | Bergman |
| 4,696,283 A | 9/1987 | Kohlmetz |
| 4,715,274 A | 12/1987 | Paoletti |
| 4,733,972 A | 3/1988 | Weis |
| 4,735,133 A | 4/1988 | Paoletti |
| 4,749,493 A | 6/1988 | Hicks |
| 4,753,535 A | 6/1988 | King |
| 4,764,283 A | 8/1988 | Ashbrook |
| 4,765,807 A | 8/1988 | Henriksen |
| 4,778,336 A | 10/1988 | Husain |
| 4,793,247 A | 12/1988 | Verweij |
| 4,798,176 A | 1/1989 | Perkins |
| 4,808,007 A | 2/1989 | King |
| 4,820,381 A | 4/1989 | Brown |
| 4,834,545 A | 5/1989 | Inoue |
| 4,838,699 A | 6/1989 | Jour |
| 4,880,445 A | 11/1989 | Watten |
| 4,884,892 A | 12/1989 | Gust |
| 4,886,368 A | 12/1989 | King |
| 4,906,574 A | 3/1990 | Erdei |
| 4,908,101 A | 3/1990 | Frisk |
| 4,937,004 A | 6/1990 | Mandrin |
| 4,957,626 A | 9/1990 | Ashbrook |
| 4,972,801 A | 11/1990 | Hunt |
| 4,973,168 A | 11/1990 | Chan |
| 4,976,547 A | 12/1990 | Hisanaga |
| 4,999,015 A | 3/1991 | Demaris |
| 5,005,982 A | 4/1991 | Kistner |
| 5,006,352 A | 4/1991 | Zelenak nee Zoltai et al. |
| 5,011,372 A | 4/1991 | Nigrelli et al. |
| 5,024,647 A | 6/1991 | Jubin |
| 5,052,813 A | 10/1991 | Latto |
| 5,075,234 A | 12/1991 | Tunac |
| 5,141,328 A | 8/1992 | Dilley |
| 5,152,212 A | 10/1992 | Chauveau |
| 5,176,447 A | 1/1993 | Bata |
| 5,185,081 A | 2/1993 | Nyman |
| 5,188,090 A | 2/1993 | Griggs |
| 5,205,647 A | 4/1993 | Ricciardi |
| 5,263,774 A | 11/1993 | Delcourt |
| 5,275,486 A | 1/1994 | Fissenko |
| 5,279,262 A | 1/1994 | Muehleck |
| 5,279,463 A | 1/1994 | Holl |
| 5,281,341 A | 1/1994 | Reimers |
| 5,304,001 A | 4/1994 | Kuo |
| 5,318,702 A | 6/1994 | Ashbrook |
| 5,326,484 A | 7/1994 | Nakashima |
| 5,341,692 A | 8/1994 | Sher et al. |
| 5,341,768 A | 8/1994 | Pope |
| 5,366,288 A | 11/1994 | Dahllof |
| 5,370,824 A | 12/1994 | Nagano |
| 5,372,424 A | 12/1994 | Lecouturier |
| 5,372,824 A | 12/1994 | Record et al. |
| 5,378,321 A | 1/1995 | Delcourt |
| 5,380,089 A | 1/1995 | Karasawa |
| 5,380,471 A | 1/1995 | Ban |
| 5,403,089 A | 4/1995 | Kuo |
| 5,407,637 A | 4/1995 | Gibboney |
| 5,419,306 A | 5/1995 | Huffman |
| 5,435,913 A | 7/1995 | Ashbrook |
| 5,450,368 A | 9/1995 | Kubota |
| 5,470,153 A | 11/1995 | De Naeghel |
| 5,474,380 A | 12/1995 | Sukup |
| 5,482,369 A | 1/1996 | Verstallen |

(56) References Cited

U.S. PATENT DOCUMENTS

| | | |
|---|---|---|
| 5,496,108 A | 3/1996 | Sukup |
| 5,511,877 A | 4/1996 | King |
| 5,538,191 A | 7/1996 | Holl |
| 5,538,343 A | 7/1996 | Tynan |
| 5,551,859 A | 9/1996 | Cantrill |
| 5,552,133 A | 9/1996 | Lambert |
| 5,556,765 A | 9/1996 | Dedolph |
| 5,560,710 A | 10/1996 | Klocke |
| 5,561,944 A | 10/1996 | Ismail |
| 5,563,189 A | 10/1996 | Hosokawa |
| 5,569,416 A | 10/1996 | Cross |
| 5,575,559 A | 11/1996 | Roll |
| 5,590,961 A | 1/1997 | Rasmussen |
| 5,616,304 A | 4/1997 | Stormo |
| 5,630,909 A | 5/1997 | LaRiviere |
| 5,658,380 A | 8/1997 | Dillenbeck |
| 5,665,228 A | 9/1997 | Leaverton et al. |
| 5,671,664 A | 9/1997 | Jacobson |
| 5,674,312 A | 10/1997 | Mazzei |
| 5,697,187 A | 12/1997 | Persinger |
| 5,711,887 A | 1/1998 | Gastman et al. |
| 5,711,950 A | 1/1998 | Lorenzen |
| 5,720,551 A | 2/1998 | Shechter |
| 5,744,105 A | 4/1998 | Stormo |
| 5,766,490 A | 6/1998 | Taylor |
| 5,770,062 A | 6/1998 | Isbell |
| 5,779,996 A | 7/1998 | Stormo |
| 5,782,556 A | 7/1998 | Chu |
| 5,791,778 A | 8/1998 | Manninen |
| 5,810,052 A | 9/1998 | Kozyuk |
| 5,810,474 A | 9/1998 | Hidalgo |
| 5,813,758 A | 9/1998 | Delcourt |
| 5,814,222 A | 9/1998 | Zelenak |
| 5,823,671 A | 10/1998 | Mitchell |
| 5,845,993 A | 12/1998 | Shirtum |
| 5,851,068 A | 12/1998 | Rumph |
| 5,863,120 A | 1/1999 | Gallagher et al. |
| 5,865,537 A | 2/1999 | Streiff |
| 5,868,495 A | 2/1999 | Hidalgo |
| 5,868,944 A | 2/1999 | Wright |
| 5,885,467 A | 3/1999 | Zelenak |
| 5,887,383 A | 3/1999 | Soeda |
| 5,893,337 A | 4/1999 | Sevic |
| 5,902,042 A | 5/1999 | Imaizumi |
| 5,904,851 A | 5/1999 | Taylor |
| 5,918,976 A | 7/1999 | Hashimoto |
| 5,921,678 A | 7/1999 | Desai |
| 5,921,679 A | 7/1999 | Muzzio |
| 5,925,292 A | 7/1999 | Ziesenis |
| 5,931,771 A | 8/1999 | Kozyuk |
| 5,938,581 A | 8/1999 | Bibette |
| 5,948,326 A | 9/1999 | Pate |
| 5,951,922 A | 9/1999 | Mazzei |
| 5,957,122 A | 9/1999 | Griggs |
| 5,971,601 A | 10/1999 | Kozyuk |
| 5,993,752 A | 11/1999 | Kobayashi |
| 5,997,717 A | 12/1999 | Miyashita et al. |
| 6,000,840 A | 12/1999 | Paterson |
| 6,017,447 A | 1/2000 | Wright |
| 6,019,499 A | 2/2000 | Selivanov |
| 6,042,792 A | 3/2000 | Shefer |
| 6,086,243 A | 7/2000 | Paul |
| 6,092,921 A | 7/2000 | Wentinck |
| 6,096,221 A | 8/2000 | Kerchouche |
| 6,110,353 A | 8/2000 | Hough |
| 6,120,008 A | 9/2000 | Littman |
| 6,120,668 A | 9/2000 | Kim |
| 6,135,628 A | 10/2000 | DeStefano |
| 6,153,607 A | 11/2000 | Pflugfelder et al. |
| 6,173,526 B1 | 1/2001 | Mazzei |
| 6,180,059 B1 | 1/2001 | Divino |
| 6,190,549 B1 | 2/2001 | Schwartz |
| 6,193,786 B1 | 2/2001 | Henderson |
| 6,210,030 B1 | 4/2001 | Ibar |
| 6,228,259 B1 | 5/2001 | Schwartz |
| 6,234,206 B1 | 5/2001 | Malmberg |
| 6,238,645 B1 | 5/2001 | Spears |
| 6,238,706 B1 | 5/2001 | Sonnenschein |
| 6,241,802 B1 | 6/2001 | Spears |
| 6,250,609 B1 | 6/2001 | Cheng |
| 6,257,754 B1 | 7/2001 | Sondergaard |
| 6,276,825 B2 | 8/2001 | Running |
| 6,279,611 B2 | 8/2001 | Uematsu |
| 6,279,882 B1 | 8/2001 | Littman |
| 6,284,293 B1 | 9/2001 | Crandall |
| 6,290,857 B1 | 9/2001 | Brahmbhatt |
| 6,294,212 B1 | 9/2001 | Huber |
| 6,299,343 B1 | 10/2001 | Pekerman |
| 6,312,647 B1 | 11/2001 | Spears |
| 6,315,942 B1 | 11/2001 | Spears |
| 6,332,706 B1 | 12/2001 | Hall |
| 6,338,569 B1 | 1/2002 | McGill |
| 6,344,489 B1 | 2/2002 | Spears |
| 6,366,751 B1 | 4/2002 | Shakuto et al. |
| 6,367,783 B1 | 4/2002 | Raftis |
| 6,380,264 B1 | 4/2002 | Jameson |
| 6,382,601 B1 | 5/2002 | Ohnari |
| 6,386,751 B1 | 5/2002 | Wootan et al. |
| 6,398,402 B1 | 6/2002 | Thomas |
| 6,402,361 B1 | 6/2002 | Reinemuth |
| 6,412,714 B1 | 7/2002 | Witsken |
| 6,413,418 B2 | 7/2002 | Brahmbhatt |
| 6,431,742 B2 | 8/2002 | Mori |
| 6,443,610 B1 | 9/2002 | Shechter |
| 6,451,328 B1 | 9/2002 | Ionita-Manzatu et al. |
| 6,454,997 B1 | 9/2002 | Divino |
| 6,458,071 B1 | 10/2002 | Jacobson |
| 6,474,264 B1 | 11/2002 | Grimberg |
| 6,474,862 B2 | 11/2002 | Farrell |
| 6,481,649 B1 | 11/2002 | Schmidt |
| 6,485,003 B2 | 11/2002 | Speece |
| 6,488,401 B1 | 12/2002 | Seaman |
| 6,488,765 B1 | 12/2002 | Tseng |
| 6,494,055 B1 | 12/2002 | Meserole |
| 6,499,671 B1 | 12/2002 | Sands et al. |
| 6,521,248 B1 | 2/2003 | Holloway |
| 6,524,475 B1 | 2/2003 | Herrington |
| 6,530,895 B1 | 3/2003 | Keirn |
| 6,538,041 B1 | 3/2003 | Marelli |
| 6,540,436 B2 | 4/2003 | Ogi |
| 6,551,492 B2 | 4/2003 | Hanaoka |
| 6,557,492 B1 | 5/2003 | Robohm |
| 6,576,130 B2 | 6/2003 | Wallace |
| 6,582,387 B2 | 6/2003 | Derek |
| 6,586,441 B2 | 7/2003 | Borroni et al. |
| 6,596,235 B2 | 7/2003 | Divino |
| 6,602,468 B2 | 8/2003 | Patterson |
| 6,613,280 B2 | 9/2003 | Myrick |
| 6,619,399 B1 | 9/2003 | Chatterji |
| 6,627,784 B2 | 9/2003 | Hudson et al. |
| 6,632,014 B2 | 10/2003 | Steinberg |
| 6,649,145 B2 | 11/2003 | McGrath |
| 6,655,830 B1 | 12/2003 | Seaman |
| 6,669,966 B1 | 12/2003 | Antelman |
| 6,676,900 B1 | 1/2004 | Divino |
| 6,682,215 B2 | 1/2004 | Kinsley |
| 6,682,732 B1 | 1/2004 | Blake et al. |
| 6,688,883 B2 | 2/2004 | Tseng |
| 6,689,262 B2 | 2/2004 | Senkiw |
| 6,702,949 B2 | 3/2004 | Wood |
| 6,705,755 B1 | 3/2004 | Innings |
| 6,730,211 B2 | 5/2004 | Hanaoka |
| 6,733,172 B2 | 5/2004 | Lee |
| 6,749,329 B2 | 6/2004 | Shechter |
| 6,752,529 B2 | 6/2004 | Holl |
| 6,764,213 B2 | 7/2004 | Shechter |
| 6,782,924 B2 | 8/2004 | Daoud |
| 6,796,702 B2 | 9/2004 | Wire |
| 6,821,438 B2 | 11/2004 | Hadley |
| 6,837,986 B2 | 1/2005 | Hanaoka |
| 6,857,774 B2 | 2/2005 | Kozyuk |
| 6,869,212 B2 | 3/2005 | Uesugi |
| 6,905,523 B2 | 6/2005 | Vainshelboim |
| 6,910,448 B2 | 6/2005 | Thoma |

(56) References Cited

U.S. PATENT DOCUMENTS

| | | |
|---|---|---|
| 6,935,768 B2 | 8/2005 | Lowe |
| 6,935,770 B2 | 8/2005 | Schueler |
| 6,936,179 B2 | 8/2005 | DeWald |
| 6,936,221 B1 | 8/2005 | Divino |
| 6,955,713 B2 | 10/2005 | Rittner |
| 6,958,163 B2 | 10/2005 | Ionita-Manzatu et al. |
| 6,959,669 B2 | 11/2005 | Thoma |
| 6,974,546 B2 | 12/2005 | Wood |
| 7,008,535 B1 | 3/2006 | Spears |
| 7,037,842 B2 | 5/2006 | Verhaverbeke |
| 7,069,073 B2 | 6/2006 | Henley et al. |
| 7,089,886 B2 | 8/2006 | Thoma |
| 7,090,753 B2 | 8/2006 | Sumita |
| 7,121,714 B2 | 10/2006 | Metcalfe, III et al. |
| 7,128,278 B2 | 10/2006 | Archambeau et al. |
| 7,137,620 B2 | 11/2006 | Thomas |
| 7,137,621 B1 | 11/2006 | Bagley |
| 7,179,375 B2 | 2/2007 | Wood |
| 7,198,254 B2 | 4/2007 | Holloway et al. |
| 7,201,225 B2 | 4/2007 | Smith |
| 7,223,246 B2 | 5/2007 | Don |
| 7,237,943 B2 | 7/2007 | Brown |
| 7,241,723 B2 | 7/2007 | Zhang |
| 7,243,910 B2 | 7/2007 | Bagley |
| 7,255,881 B2 | 8/2007 | Gillis et al. |
| 7,316,501 B2 | 1/2008 | Thoma |
| 7,334,781 B2 | 2/2008 | Donnelly |
| 7,347,944 B2 | 3/2008 | Bagley |
| 7,360,755 B2 | 4/2008 | Hudson |
| 7,387,262 B2 | 6/2008 | Thoma |
| 7,396,441 B2 | 7/2008 | Senkiw |
| 7,544,365 B2 | 6/2009 | Dosch et al. |
| 7,654,728 B2 | 2/2010 | Wood et al. |
| 7,690,833 B2 | 4/2010 | Metcalfe |
| 7,731,953 B2 | 6/2010 | Leonard |
| 7,749,692 B2 | 7/2010 | Mano |
| 7,770,814 B2 | 8/2010 | Archambeau |
| 7,806,584 B2 | 10/2010 | Wood et al. |
| 7,832,920 B2 | 11/2010 | Wood et al. |
| 7,887,698 B2 | 2/2011 | Wood |
| 7,919,534 B2 | 4/2011 | Wood et al. |
| 8,349,191 B2 | 1/2013 | Wood |
| 8,410,182 B2 | 4/2013 | Wood et al. |
| 8,445,546 B2 | 5/2013 | Wood et al. |
| 8,449,172 B2 | 5/2013 | Wood et al. |
| 8,470,893 B2 | 6/2013 | Wood et al. |
| 2001/0003291 A1 | 6/2001 | Uematsu et al. |
| 2001/0022755 A1 | 9/2001 | Holtzapple |
| 2001/0031740 A1 | 10/2001 | Unger et al. |
| 2001/0040134 A1 | 11/2001 | Brahmbhatt et al. |
| 2002/0045742 A1 | 4/2002 | Jones et al. |
| 2002/0136662 A1 | 9/2002 | Myrick et al. |
| 2002/0138034 A1 | 9/2002 | Derek et al. |
| 2002/0164379 A1 | 11/2002 | Nishihara |
| 2002/0184820 A1 | 12/2002 | Mauney |
| 2002/0187203 A1 | 12/2002 | Cioca et al. |
| 2002/0196702 A1 | 12/2002 | Shechter |
| 2003/0017001 A1 | 1/2003 | Ogi |
| 2003/0022288 A1 | 1/2003 | Zuker et al. |
| 2003/0042174 A1 | 3/2003 | Austin |
| 2003/0056805 A1 | 3/2003 | Sumita |
| 2003/0057163 A1 | 3/2003 | Wood |
| 2003/0072212 A1 | 4/2003 | Wood et al. |
| 2003/0083610 A1 | 5/2003 | McGrath et al. |
| 2003/0147303 A1 | 8/2003 | Schueler |
| 2003/0188740 A1 | 10/2003 | Tribelsky |
| 2003/0199089 A1 | 10/2003 | Surber et al. |
| 2003/0232114 A1 | 12/2003 | Dekleva |
| 2004/0004042 A1 | 1/2004 | Hadley et al. |
| 2004/0019319 A1 | 1/2004 | Derek et al. |
| 2004/0022122 A1 | 2/2004 | Kozyuk |
| 2004/0027915 A1 | 2/2004 | Lowe |
| 2004/0058010 A1 | 3/2004 | Holloway, Jr. et al. |
| 2004/0060446 A1 | 4/2004 | Rittner |
| 2004/0089746 A1 | 5/2004 | Archambeau |
| 2004/0090862 A1 | 5/2004 | Uesugi |
| 2004/0118701 A1 | 6/2004 | Senkiw |
| 2004/0126468 A1 | 7/2004 | Holloway, Jr. et al. |
| 2004/0129112 A1 | 7/2004 | Gillis et al. |
| 2004/0142377 A1 | 7/2004 | Unett et al. |
| 2004/0166171 A1 | 8/2004 | McGrath et al. |
| 2004/0222106 A1 | 11/2004 | Hough |
| 2004/0235732 A1 | 11/2004 | Zhou et al. |
| 2004/0241154 A1 | 12/2004 | Davis et al. |
| 2004/0245186 A1 | 12/2004 | Wood |
| 2004/0248909 A1 | 12/2004 | Sun et al. |
| 2004/0258687 A1 | 12/2004 | Waldman et al. |
| 2004/0266693 A1 | 12/2004 | Ruben et al. |
| 2005/0047270 A1 | 3/2005 | Wood et al. |
| 2005/0048034 A1 | 3/2005 | Fraser et al. |
| 2005/0096458 A1 | 5/2005 | Edwards et al. |
| 2005/0139808 A1 | 6/2005 | Alimi |
| 2005/0142157 A1 | 6/2005 | Alimi |
| 2005/0196370 A1 | 9/2005 | Yu et al. |
| 2005/0196462 A1 | 9/2005 | Alimi |
| 2005/0249712 A1 | 11/2005 | Leonard et al. |
| 2005/0259510 A1 | 11/2005 | Thoma |
| 2005/0263607 A1 | 12/2005 | Thoma |
| 2005/0273018 A1 | 12/2005 | Don |
| 2006/0030900 A1 | 2/2006 | Eckert |
| 2006/0039902 A1 | 2/2006 | Young et al. |
| 2006/0039910 A1 | 2/2006 | Comeau et al. |
| 2006/0045796 A1 | 3/2006 | Anderle et al. |
| 2006/0054205 A1 | 3/2006 | Yabe et al. |
| 2006/0098528 A1 | 5/2006 | Wood |
| 2006/0116419 A1 | 6/2006 | Callahan et al. |
| 2006/0135585 A1 | 6/2006 | Day et al. |
| 2006/0146644 A1 | 7/2006 | Holloway et al. |
| 2006/0150491 A1 | 7/2006 | Senkiw |
| 2006/0198822 A1 | 9/2006 | Booth et al. |
| 2006/0198901 A9 | 9/2006 | Holloway, Jr. |
| 2006/0204458 A1 | 9/2006 | Holloway, Jr. et al. |
| 2006/0210613 A1 | 9/2006 | Carliss |
| 2006/0216360 A1 | 9/2006 | Upadhyay et al. |
| 2006/0235350 A1 | 10/2006 | Alimi |
| 2006/0241546 A1 | 10/2006 | Alimi |
| 2006/0253060 A1 | 11/2006 | Alimi |
| 2006/0272947 A1 | 12/2006 | Bagley |
| 2006/0272954 A1 | 12/2006 | Sumita |
| 2006/0273018 A1 | 12/2006 | Bagley |
| 2006/0273021 A1 | 12/2006 | Bagley |
| 2006/0273029 A1 | 12/2006 | Bagley |
| 2006/0273281 A1 | 12/2006 | Bagley |
| 2006/0273282 A1 | 12/2006 | Bagley |
| 2006/0273475 A1 | 12/2006 | Bagley |
| 2006/0275423 A1 | 12/2006 | Bagley |
| 2006/0292240 A1 | 12/2006 | Bagley |
| 2006/0292241 A1 | 12/2006 | Bagley |
| 2007/0003497 A1 | 1/2007 | Holloway, Jr. et al. |
| 2007/0021331 A1 | 1/2007 | Fraser et al. |
| 2007/0077553 A1 | 4/2007 | Bentwich |
| 2007/0141163 A1 | 6/2007 | Vitaliano et al. |
| 2007/0173460 A1 | 7/2007 | Alimi |
| 2007/0173755 A1 | 7/2007 | Alimi |
| 2007/0189972 A1 | 8/2007 | Chiba et al. |
| 2007/0196357 A1 | 8/2007 | Alimi |
| 2007/0196434 A1 | 8/2007 | Alimi |
| 2007/0205161 A1 | 9/2007 | Chiba et al. |
| 2007/0210180 A1 | 9/2007 | Archambeau et al. |
| 2007/0237787 A1 | 10/2007 | Leonard et al. |
| 2007/0259032 A1 | 11/2007 | Bright et al. |
| 2007/0286795 A1 | 12/2007 | Chiba et al. |
| 2007/0287917 A1 | 12/2007 | Takahashi et al. |
| 2008/0050452 A1 | 2/2008 | Chen et al. |
| 2008/0057486 A1 | 3/2008 | Mano et al. |
| 2008/0063720 A1 | 3/2008 | Gounko et al. |
| 2008/0139674 A1 | 6/2008 | Archambeau et al. |
| 2008/0146679 A1 | 6/2008 | Archambeau et al. |
| 2008/0153795 A1 | 6/2008 | Occleston |
| 2008/0161541 A1 | 7/2008 | Lazar et al. |
| 2008/0206356 A1 | 8/2008 | Guinovart Cirera et al. |
| 2008/0219088 A1 | 9/2008 | Wood et al. |
| 2008/0220089 A1 | 9/2008 | Hojo et al. |
| 2008/0241098 A1 | 10/2008 | Young et al. |

(56) References Cited

U.S. PATENT DOCUMENTS

| | | |
|---|---|---|
| 2008/0281001 A1 | 11/2008 | Wood et al. |
| 2009/0082264 A1 | 3/2009 | Fischer et al. |
| 2009/0208473 A1 | 8/2009 | Weisleder et al. |
| 2009/0227018 A1 | 9/2009 | Watson et al. |
| 2009/0247458 A1 | 10/2009 | Watson et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0015235 A1 | 1/2010 | Watson et al. |
| 2010/0021464 A1 | 1/2010 | Archambeau et al. |
| 2010/0028441 A1 | 2/2010 | Watson et al. |
| 2010/0028442 A1 | 2/2010 | Archambeau et al. |
| 2010/0028443 A1 | 2/2010 | Watson et al. |
| 2010/0029764 A1 | 2/2010 | Watson et al. |
| 2010/0038244 A1 | 2/2010 | Wood et al. |
| 2010/0098659 A1 | 4/2010 | Watson |
| 2010/0098687 A1 | 4/2010 | Watson |
| 2010/0166784 A1 | 7/2010 | Murphy et al. |
| 2010/0186680 A1 | 7/2010 | Matsumura et al. |
| 2010/0252492 A1 | 10/2010 | Wood |
| 2010/0297193 A1 | 11/2010 | Archambeau et al. |
| 2010/0303871 A1 | 12/2010 | Watson et al. |
| 2010/0303917 A1 | 12/2010 | Watson et al. |
| 2010/0303918 A1 | 12/2010 | Watson et al. |
| 2010/0310609 A1 | 12/2010 | Watson et al. |
| 2010/0310664 A1 | 12/2010 | Watson |
| 2010/0310665 A1 | 12/2010 | Watson |
| 2010/0311167 A1 | 12/2010 | Wood et al. |
| 2010/0316723 A1 | 12/2010 | Watson et al. |
| 2010/0323383 A1 | 12/2010 | Manel et al. |
| 2011/0008462 A1 | 1/2011 | Wood et al. |
| 2011/0075507 A1 | 3/2011 | Wootan et al. |
| 2011/0081384 A1 | 4/2011 | Archambeau et al. |
| 2011/0104804 A1 | 5/2011 | Wood et al. |
| 2011/0165172 A1 | 7/2011 | Yarranton |
| 2011/0245107 A1 | 10/2011 | Kuchroo et al. |
| 2012/0015083 A1 | 1/2012 | Wood |
| 2012/0034696 A1 | 2/2012 | Wood |
| 2012/0039884 A1 | 2/2012 | Watson |
| 2012/0039951 A1 | 2/2012 | Watson |
| 2012/0039958 A1 | 2/2012 | Watson |
| 2012/0114702 A1 | 5/2012 | Watson |
| 2012/0121656 A1 | 5/2012 | Watson |
| 2012/0263764 A1 | 10/2012 | Watson |
| 2013/0092368 A1 | 4/2013 | Wood |
| 2013/0252323 A1 | 9/2013 | Wood et al. |
| 2013/0260462 A1 | 10/2013 | Wood et al. |
| 2013/0270478 A1 | 10/2013 | Wood et al. |
| 2013/0295144 A1 | 11/2013 | Wood et al. |

FOREIGN PATENT DOCUMENTS

| | | |
|---|---|---|
| CN | 101237875 | 8/2008 |
| DE | 1557171 | 7/1970 |
| DE | 3123743 | 3/1982 |
| DE | 3436049 | 4/1986 |
| DE | 4008676 | 9/1991 |
| DE | 4317078 | 11/1994 |
| DE | 10105118 | 8/2002 |
| DE | 10227818 | 8/2004 |
| EP | 0363009 | 4/1990 |
| EP | 0555498 | 8/1993 |
| EP | 0682000 | 11/1995 |
| EP | 0880993 | 12/1998 |
| EP | 1201296 | 10/2001 |
| EP | 1797869 | 6/2007 |
| GB | 1279736 | 6/1972 |
| JP | 53146264 | 12/1978 |
| JP | 56161893 | 12/1981 |
| JP | 2001171627 | 7/1989 |
| JP | 2003169332 | 7/1991 |
| JP | 2004290531 | 10/1992 |
| JP | 5096470 | 4/1993 |
| JP | 6114254 | 4/1994 |
| JP | 06262050 | 9/1994 |
| JP | 07327547 | 12/1995 |
| JP | 8198969 | 8/1996 |
| JP | 9122465 | 5/1997 |
| JP | 11507874 | 7/1999 |
| JP | 2000271590 | 10/2000 |
| JP | 2003144887 | 5/2003 |
| JP | 2003520820 | 7/2003 |
| JP | 2003340938 | 9/2003 |
| JP | 2003334548 | 11/2003 |
| JP | 2004074131 | 3/2004 |
| JP | 2004121962 | 4/2004 |
| JP | 2004529090 | 9/2004 |
| JP | 2005110552 | 4/2005 |
| JP | 2005523147 | 8/2005 |
| JP | 2005245817 | 9/2005 |
| JP | 2005246293 | 9/2005 |
| JP | 2005246294 | 9/2005 |
| JP | 2006223239 | 8/2006 |
| JP | 2006273730 | 10/2006 |
| JP | 2007275089 | 10/2007 |
| JP | 2008063258 | 3/2008 |
| JP | 2008093611 | 4/2008 |
| JP | 2008093612 | 4/2008 |
| JP | 2008156320 | 7/2008 |
| JP | 2008237950 | 10/2008 |
| JP | 2008259456 | 10/2008 |
| JP | 2009039600 | 2/2009 |
| JP | 2010508088 | 3/2010 |
| NO | 152733 | 8/1985 |
| RU | 2131761 | 6/1999 |
| RU | 2165787 | 4/2001 |
| RU | 2166987 | 5/2001 |
| RU | 2284853 | 4/2005 |
| SU | 127999 | 1/1960 |
| SU | 495099 | 12/1975 |
| SU | 1337098 | 9/1987 |
| WO | WO 92/05792 | 4/1992 |
| WO | WO95/35501 | 12/1995 |
| WO | WO96/23977 | 8/1996 |
| WO | WO97/27146 | 7/1997 |
| WO | WO98/30319 | 7/1998 |
| WO | WO99/16539 | 4/1999 |
| WO | WO00/02651 | 1/2000 |
| WO | WO00/20109 | 4/2000 |
| WO | WO01/54704 | 8/2001 |
| WO | WO01/87471 | 11/2001 |
| WO | WO02/24222 | 3/2002 |
| WO | WO02/35234 | 5/2002 |
| WO | WO02/38510 | 5/2002 |
| WO | WO02/060458 | 8/2002 |
| WO | WO02/062455 | 8/2002 |
| WO | WO03/044430 | 5/2003 |
| WO | WO03/089123 | 11/2003 |
| WO | WO2004/013049 | 2/2004 |
| WO | WO2004/016344 | 2/2004 |
| WO | WO2004/022098 | 3/2004 |
| WO | WO2004/112649 | 12/2004 |
| WO | WO2005/007142 | 1/2005 |
| WO | WO2005/030649 | 4/2005 |
| WO | WO2005/032243 | 4/2005 |
| WO | WO2005/084718 | 9/2005 |
| WO | WO2005/084786 | 9/2005 |
| WO | WO2005/085141 | 9/2005 |
| WO | WO2005/113026 | 12/2005 |
| WO | WO2006/029385 | 3/2006 |
| WO | WO2006/088210 | 8/2006 |
| WO | WO2006/133113 | 12/2006 |
| WO | WO2007/096149 | 8/2007 |
| WO | WO2008/018932 | 2/2008 |
| WO | WO2008/052143 | 5/2008 |
| WO | WO2008/052145 | 5/2008 |
| WO | WO2008/115290 | 9/2008 |
| WO | WO2009/055614 | 4/2009 |
| WO | WO2009/055620 | 4/2009 |

(56) References Cited

FOREIGN PATENT DOCUMENTS

| WO | WO2009/055729 | 4/2009 |
|---|---|---|
| WO | WO2009/055824 | 4/2009 |
| WO | WO2009/134728 | 11/2009 |
| WO | WO2010/048425 | 4/2010 |
| WO | WO2010/048455 | 4/2010 |

OTHER PUBLICATIONS

Auclair et al., "Revisiting the Mechanism of P450 Enzymes with the Radical Clocks Norcarane and Spiro[2,5]octane," Journal of the American Chemical Society 124(21):6020-6027, 2002.
Austin et al., "The Non-Heme Diiron Alkane Monooxygenase of Pseudomonas oleovorans (AlkB) Hydroxylates via a Substrate Radical Intermediate," Journal of the American Chemical Society 122:11747-11748, 2000.
Austin et al., "Xylene monooxygenase, a membrane-spanning non-heme diiron enzyme that hydroxylates hydrocarbons via a substrate radical intermediate," Journal of Inorganic Chemistry, 8:733-740, 2003.
Barnes et al., "How do Corticosteroids Work in Asthma?" Ann. Intern. Med. 139:359-370, 2003.
Billington et al., "Signaling and regulation of G Protein-coupled receptors in airway smooth muscle," Respiratory Research 4(2):1-23, 2003.
Bonanno, "Corneal Metabolic Activity in Humans: Corneal Oxygen Consumption," Indiana University School of Optometry Faculty Research, http://www.opt.indiana.edu/people/faculty/bonanno/oxygen.htm, 4 pages, Apr. 9, 2003.
Boyle, "Adult Cystic Fibrosis," Journal of the American Medical Association (JAMA) 296(13):1787-1793, Oct. 17, 2001.
Bragg et al., "Hydrated Electron Dynamics: From Clusters to Bulk," Science Magazine 360(5696):669-671, Sep. 16, 2004.
Brazeau et al., "Intermediate Q from Soluble Methane Monooxygenase Hydroxylates the Mechanistic Substrate Probe Norcarane: Evidence for a Stepwise Reaction," Journal of the American Chemical Society, 123(48):11831-11837, Dec. 5, 2001.
Bucy et al., "Initial increase in blood CD4+ lymphocytes after HIV antiretroviral therapy reflects redistribution from lymphoid tissues," The Journal of Clinical Investigation 103(10):1391-1398, 1999.
Bunkin et al., "Existence of charged submicrobubble clusters in polar liquids as revealed by correlation between optical cavitation and electrical conductivity," Colloids and Surfaces A: Physiochemical and Engineering Aspects 110:207-212, 1996.
Campbell et al., "Redox Modulation of L-type Calcium Channels in Ferret Ventricular Myocytes," J. Gen. Physiol, 108:277-293, Abstract, Oct. 1996.
Cavitation Generator, English Translation of SU495099, published Dec. 15, 1975, 5 pages.
Celli et al., "Standards for the diagnosis and treatment of patients with COPD: a summary of the ATS/ERS position paper," Eur. Respir. J. 23:932-946, 2004.
Chaplin, "Declustered Water, Anomalous Water and Crystals," London South Bank University, http://Isbu.ac.uk/water/anmlous.html, 4 pages, retrieved Jul. 10, 2006.
De Angelis et al., "Electronic Structure and Reactivity of Isomeric Oxo-Mn(V) Porphyrins: Effects of Spin-State Crossing and pKa Modulation," Inorganic Chemistry 45(10):4268-4276, Feb. 22, 2006.
Ex Parte Kubin, No. 2007-0819 (B.P.A.I. May 31, 2007) ("Board Decision"), pp. 1 through 18 (in particular, pp. 10, 14 and 15).
Faul, "Sonochemistry—General Overview," Pollution Research Group, http://www.und.ac.za/prg/sonochem/ultragen.html, 2 pages, Nov. 21, 2002.
Finkel, "Redox-dependent signal transduction," FEBS Letters 476:52-54, 2000.
Florusse et al., "Stable Low-Pressure Hydrogen Clusters Stored in a Binary Clathrate Hydrate," Science Magazine 306:469-471, Oct. 15, 2004.
Forney et al., "Fast Competitive Reactions in Tyalor-Couette Flow," Ind. Eng. Chem. Res. 44(19):7306-7312, 2005.

Frauenfelder et al., "The role of structure, energy landscape, dynamics, and allostery in the enzymatic function of myoglobin," Proceedings of the National Academy of Sciences 98(5):2370-2374, Feb. 27, 2001.
Gill S. et. al., "Nanoparticles: Characteristics, mechanisms of action, and toxicity in pulmonary drug delivery—a review," Journal of Biomedical Nanotechnology 3(2):107-119, 2007.
Gomes et al., "Calcium Channel Blocker Prevents T Helper Type 2 Cell-mediated Airway Inflammation," American Journal Respir Crit Care Med. 75(11):1117-1124, 2007.
Goses et al., "Muscarinic receptor signaling in the pathophysiology of asthma and COPD," Respiratory Research 7(73):1-15, May 9, 2006.
Groves, "High-valent iron in chemical and biological oxidations," Journal of Inorganic Biochemistry 100:434-447, Jan. 14, 2006.
Groves, "Reactivity and mechanisms of metalloporphyrin-catalyzed oxidations," Journal of Porphyrins and Phthalocyanines 4:350-352, 2002.
Guerra et al., "The Effect of Oxygen Free Radicals on Calcium Current and Dihydropyridine Binding Sites in Guinea-pig Ventricular Myocytes," British Journal of Pharmacology 118:1278-1284, 1996.
Hammer et al., "How Do Small Water Clusters Bind an Excess Electron," Science Magazine 306(5696):675-679, Sep. 16, 2004.
Harvitt et al., "Corneal Oxygen Availability and Metabolism with Contact Lens Wear and Re-evaluation of the Oxygen Diffision Model for Predicting Minimum Contact Lens Dk/t Values Needed to Avoid Corneal Anoxia," http://vision.berkeley.edu/sarver/mdsl_harvitt_research.html (abstracts only), 2 pages, retrieved Apr. 9, 2003.
Headrick et al., "Spectral Signatures of Hydrated Proton Vibrations in Water Clusters," Science Magazine 308:1765-1770, Jun. 17, 2005.
Hogaboam et al., "Collagen Deposition in a Non-Fibrotic Lung," Am J. Pathol 153(6):1861-1872; abstract, Dec. 1998.
In re Robertson, 169 F.3d 743, Feb. 25, 1999.
Jia et al., "Atomic-Resolution of Oxygen Concentration in Oxide Materials," Science Magazine 303:2001-2004, Mar. 26, 2004.
Jin et al., "Unusual Kinetic Stability of a Ground-State Singlet Oxomanganese(V) Porphyrin. Evidence for a Spin State Crossing Effect," Journal of the American Chemical Society, 121:2923-2924, 1999.
Life 02 International (Asia) Co., Ltd—Medical Industry, www.lifeo2asia.com/medical.htm, 1 page, retrieved Jun. 3, 2003.
Liu, Yong-Jun, "Thymic stromal lymphopoietin: master switch for allergic inflammation," J. Experimental Medicine 203(2):269-273, 2006.
Ljunggren et al., "The Lifetime of a Colloid-Sized Gas Bubble in Water and the Cause of the Hydrophobic Attraction," Colloids and Surfaces A: Physicochemical and Engineering Aspects 129-130:151-155, 1997.
Lowenstein et al., "Nitric Oxide: A Physiologic Messenger," Annals of Internal Medicine 120(3):227-237, Abstract, Feb. 1, 1994.
Lower, "The BunkHouse: Water pseudoscience gallery, Gallery of water-related pseudoscience, Junk science in the marketplace," http://chem1.com/CO/gallery.html, 18 pages, retrieved Jul. 25, 2006.
Luo et al., "Mycobactin-mediated iron acquisition within macrophages," Nature Chemical Biology 1(3):149-153, Aug. 2005.
Miyazaki et al., "Infrared Spectroscopic Evidence for Protonated Water Clusters Forming Nanoscale Cages," Science Magazine, 304:1134-1137, Apr. 29, 2004.
Moe et al., "Remarkable Aliphatic Hydroxylation by the Diiron Enzyme Toluene 4-Monooxygenase in reactions with Radical or Cation Diagnostic Probes Norcarane, 1,1-Dimethylcyclopropane, and 1,1-Diethylcyclopropane," American Chemical Society, 43:15688-15701, Jul. 1, 2004.
Morris, "The physiological causes of contact lens complications," Optometry Today;28-33, Dec. 3, 1999.
Murga et al., "Activation of Akt/Protein Kinase B by G Protein-coupled Receptors," The Journal of Biological Chemistry 273(30):19080-19085, especially abstract p. 19085, col. 1, paragraph 3, 1998.
Neuman, et al., "Optical Trapping," Review of Scientific Instruments 75(9):2787-2809, Sep. 2004.

(56) References Cited

OTHER PUBLICATIONS

Nguyen et al., "Neuroprotection by NGF and BDGF Against Neurotoxin-Exerted Apoptotic Death in Neural Stem Cells Are Mediated Through Trk Receptors, Activating PI3-Kinase and MAPK Pathways," Neurochemical Research 34(5):942-951, especially abstract, p. 943, col. 1, paragraphs 2-3, 2009.

NIH (National Institute of Health, National Heart, Lung and Blood Institute), "What are the Signs and Symptoms of Cystic Fibrosis?" Downloaded from http://www.nhlbi.nih.gov/health/health-topics/topics/cf/signs.html on Jan. 1, 2014.

Nozaki et al., "New enhancers for the chemiluminescent peroxidase catalyzed chemiluminescent oxidation of pyrogallol and purpurogallin," Journal of Biolumin Chemilumin 10:151-156, 1995.

Ohgaki et al., "Physiochemical approach to nanobubble solutions," Chemical Engineering Science 65:1296-1300, 2010.

Paik et al., "Electrons in Finite-Sized Water Cavities: Hydration Dynamics Observed in Real Time," Science Express, 306(5696):672-675, Sep. 16, 2004.

Pan et al., "Role of the Rho GTPas in Bradykinin-Stimulated Nuclear Factor-kB Activation and IL-1B Gene Expression in Cultured Human Epithelial Cells," J. Immunol. 160:3038-3045, The Scripps Researh Institue. La Jolla, 1998.

Park, et al., "Nitric oxide regulates nitric oxide synthase-2 gene expression by inhibiting NF-KB binding to DNA," Biochem J. 322:609-613, abstract, 1997.

Patent Office of the Russian Federation, Official Action, Application No. 2004133560/15(036500), original in Russian plus English translation, 6 pages, Jan. 27, 2006.

Pronated Water Clusters in Nature, "Protonated Water Clusters in Interstellar Clouds, the Upper Atmosphere and Biomolecules," http://pro3.chem.pitt.edu/richard/prot_clust_nature.html, 1 page, retrieved Oct. 29, 2004.

Rivera et al., "Current Concepts in Antimicrobial Therapy Against Select Gram-Positive Organisms: Methicillin-Resistant *Staphylococcus aureus*, Penicillin-Resistant Pneumococci, and Vancomycin-Resistant Enterococci," Symposium on Antimicrobial therapy, Mayo Clin. Proc. 86(12):1230-1243, published Dec. 2011.

Rutgeerts et al., "Review article: the limitations of corticosteroid therapy in Crohn's disease," Aliment Pharmacol. Ther. 15(10):1515-1525, abstract, Oct. 2001.

Sagel et al., "Induced sputum matrix metalloproteinase-9 correlates with lung function and airway inflammation in children with cystic fibrosis," Pediatr. Pulmon. 39(3):224-232, Mar. 2005.

Salzman et al., "Nitric oxide dilates tight junctions and depletes ATP in cultured Caco-2BBe intestinal epithelial monolayers," AJP-Gastrointestinal and Liver Physiology 268(2):361-G373, Abstract, 1995.

Schmidt et al., "A role for Rho in receptor- and G protein-stimulated phospholipase C. Reduction in phosphatidylinositol 4,5-bisophosphate by Clostridium difficile toxin B.," Naunyn Schmiedebergs Arch Pharmacol 354(2):87-94, abstract only, Jul. 1996.

Science Week (1) Chemistry: On Protonated Water Clusters, points made by Zwier-Science (2004) 204:1119; (2) On Water Structure, points made by Head-Gordon et al.-Chem. Rev (2002) 102:2651; (3) Liquid Water: Current Research Problems, points made by Keutsch et al.-Proc. Nat. Acad. Sci. (2001) 98:10533.

Shin et al., "Infrared Signature of Structures Associated with the H+(H2O)n (n=6 to 27) Clusters, Science Magazine," 304:1137-1140, May 21, 2004.

Singh et al., "Benzimidazolone Activators of Chloride Secretion: Potential Therapeutics for Cystic Fibrosis and Chronic Obstructive Pulmonary Disease," J. Pharmacol. and Experimental Therapeutics 296(2):600-611, 2001.

Stoll et al., "Inflammation and Atherosclerosis Novel Insights into Plaque Formation and Destabilization," American Stroke Association through the American Journal of Heart Association 37:1923-1932, Jul. 2006.

Suslick, "Sonochemistry," Science Magazine 247:1439-1445, Mar. 23, 1990.

Torr, "Conversion between Torr and atm," http://antoine.frostburg.edu/chem/senese/101/solutions/faq/predicting-DO.shtml, downloaded Dec. 12, 2013.

Tristani-Firouzi et al., "Oxygen-induced constriction of rabbit ductus arteriosus via inhibition of a 4-aminopyridine-, voltage-sensitive potassium channel," J. Clin Invest 98:1959-1965, 1996.

Valmori et al., "Human ROR-gt+ TH17 cells preferentially differentiate from naive FOXP3=Treg in the presence of lineagespecific polarizing factor," Proceedings of the National Academy of Science 45:19402-19407, 2010.

Wang, "Radical Clocks: Molecular Stopwatches for timing Radical Reactions," 65-72, Apr. 27, 2006.

Warheit et al., "Development of a respiratory Allergy model in male Brown Norway rats": Pulmonary immune and gene expression studies, Ann. Occup. Hyg., 46:362-364, 2002.

Watson, U.S. Appl. No. 13/097,565, filed Apr. 29, 2011.

Watson, U.S. Appl. No. 13/126,117, filed Jul. 19, 2011.

Wojciak-Stothard et al., "Rac and Rho play opposing roles in the regulation of hypoxia/reoxygenation-induced permeability changes in pulmonary artery endothelial cells," Am J of Lung Cell Mol Physiol 288:L749-L760, 2005.

Wood et al., U.S. Appl. No. 12/861,179, filed Aug. 23, 2010.

Wood et al., U.S. Appl. No. 12/945,703, filed Nov. 12, 2010.

Wood et al., U.S. Appl. No. 13/016,659, filed Jan. 28, 2011.

Wood et al., U.S. Appl. No. 13/028,058, filed Feb. 15, 2011.

Wronski et al., "Interfacial area in a reactor with helicoidal flow for the twophase gas-liquid system," Chemical Engineering Journal 105:71-79, 2005.

(1) Wunderlich et al. "In vivo observation of oxygen-supersaturated water in the human mouth and stomach", Magnetic Resonance Imaging, 22(4): 551-556, 2004; (2) Divino et al. "Injection of highly supersaturated oxygen solutions without nucleation", Journal of Biomechanical Engineering, 124(6): 676-683, 2002; (3) 02 Canada Water, Product Information from 02 Canada Water, Inc., http://www.ocanadawater.com/BeverageDiffusion.html; (4) FBC Technologies "O2 x-Box (R)Super Oxygenation Process", http://www.fbctech.com/oxbox.htm, http://www.lsbu.ac.uk/water/anmlous.html; (5) Wayne State University Press Researcher Discovers Potential Approach to Hyperoxygenate Blood, Wayne State University Press Release, Apr. 4, 2006 (4 pages).

Ziegler et al., "Thymic stromal lymphopoietin in normal and pathogenic T cell development and function," Nature Immunology 7(7):709-714, Jul. 2006.

Ziegler, "The role of thymic stromal lymphopoietin (TSLP) in allergic disorders," Current Opinion in Immunology 22(6):795-799, Dec. 2010.

Zwier, "The structure of protonated water clusters," Science Magazine 304(5674):1119-1120, Apr. 29, 2004.

Akbar, "Expression of the TRPV1 receptor differs in quiescent inflammatory bowel disease with or without abdominal pain," Gut 59:767-774 (doi:10.1136/gut.2009.194449), 2010.

Andrews, "Determination of minimum inhibitory concentrations," Journal of Antimicrobial Chemotherapy vol. 48 (suppl. S1), pp. 5-16, 2001.

Baird et al., "Creatine-Kinase- and Exercise-Related Muscle Damage Implications for Muscle Performance and Recovery," Journal of Nutrition and Metabolism, 2012:1-13, Sep. 28, 2011.

Baker et al. "Mutations in progranulin cause tau-negative frontotemporal dementia linked to chromosome 17", Nature, 442(24):916-919, Aug. 2006.

Bates et al., "The use and misuse of Penh in animal models of lung disease," American Journal of Respiratory Cell and Molecular Biology 31(3):373-4, Sep. 2004.

Berger et al., "Antimyelin Antibodies as a Predicator of Clinically Definite Multiple Sclerosis after a First Demyelinating Event," The New England Journal of Medicine 349(2):139-145, Jul. 10, 2003.

Boedker et al., "Budesonide epimer R, LAU-8080 and phenyl butyl nitrone synergistically repress cyclooxygenase-2 induction in [IL-1β+Aβ42]-stressed human neural cells," Neuroscience Letters, 380:176-180, 2005.

(56) References Cited

OTHER PUBLICATIONS

Boundless, "Lung Capacity and Volume," Boundless Anatomy and Physiology, Boundless, from https://www.boundless.com/physiology/textbooks/boundless-anatomy-and-physiology-textbook/the-respiratory-system-22/lung-volumes-and-capacities-209/lung-capacity-and-volume-1029-9200, downloaded Jun. 22, 2015.
Breitner et al., "Extended results of the Alzheimer's disease anti-inflammatory prevention trial (ADAPT)," Alzheimers Dement. 7(4):402-411, published Jul. 2011.
Bulakbasi et al., "Massive Lower Gastrointestinal Hemorrhage from the Surgical Anastomosis in Patients with Multiorgan Trauma: Treatment by Subselective Embolization with Polyvinyl Alcohol Particles," CardioVascular and Interventional Radiology 22:461-467, 1999.
Caro et al., "Healing and Relapse Rates in Gastroesophageal Reflux Disease Treated with the Newer Proton-Pump Inhibitors Lansoprazole, Rabeprazole, and Pantoprazole Compared with Omeprazole, Ranitidine, and Placebo: Evidence from Randomized Clinical Trials," Clinical Therapeutics 23(7):998-1017, 2001.
Cheng et al., HCl-acativated neural and epithelial vanilloid receptors (TRPV1) in cat esophageal mucosa, American Journal Physiol Gastrointest Liver Physiol 297:G135-G143, 2009.
Chu et al., "Urokinase-type plasminogen activator, receptor, and inhibitor correlating with gelatinase-B (MMP-9) contribute to inflammation in gouty arthritis of the knee," The Journal of Rhuematology 33(2):311-317, Feb. 2006.
Corrigan, "Eotaxin and asthma: some answers, more questions," Clinical and Experimental Immunology 1999 116:1-3.
Cotman et al., "Exercise builds brain health: key roles of growth factor cascades and inflammation," Trends in Neurosciences, 30(9):464-472, published online Aug. 31, 2007.
Cross, "Can Probiotics Help GERD?" http://www.livestrong.com/article/474546-can-probiotics-help-gerd/, Apr. 5, 2012.
Degre, "Cytokines and bacterial infections," Institute of Microbiology, Rikshospitalet, University of Oslo, Norway, Biotherapy 8:219-228, 1996.
Fletcher et al., "T cells in multiple sclerosis and experimental autoimmune encephalomyelitis," Clinical and Experimental Immunology 162:1-11, 2010.
Gabbey, "What are Anaerobic Infections?," Anaerobic Infections/Definition and Patient Education, published Jun. 18, 2013, downloaded on Nov. 29, 2014, from http://www.healthline.com/health/anaerobic-infections, 3 pages.
Glass et al., "Mechanism Underlying Inflammation on Neurodegeneration," Cell 140(6):918-934, Mar. 19, 2010.
Godoy et al., "Central and systemic IL-I exacerbates neurodegeneration and motor symptoms in a model of Parkinson's disease," Brain 131:1880-1894, 2008.
Guarino et al., "Increased TRPV1 gene expression in esophageal mucosa of patients with non-erosive and erosive reflux disease," Neurogastroenterol Motil 22:746-e219, 2010.
Harari et al., "NF-kB and innate immunity in ischemic stroke," National Institute of Health Public Access Author Manuscript, published in final edited form as Ann New York Academy of Science 1207: 32-40, Oct. 2010.
Hardy et al. "The Amyloid Hypothesis of Alzheimer's Disease: Progress and Problems on the Road to Therapeutics," Science 297:353-356, Jul. 19, 2002.
Hedbom et al., "Molecular aspects of pathogenesis in osteoarthritis: the role of inflammation," Cellular and Molecular Life Sciences 59(1):45-53, Jan. 2002.
Holub et al, "Cytokines and Chemokines as Biomarkers of Community-Acquired Bacterial Infection," Mediators of Inflammation, vol. 2013, Article ID 190145, published after Mar. 26, 2013, by Hindawi publishing production, 7 pages.
Hong-Qi et al., "Current advances in the treatment of Alzheimer's disease: focused on considerations targeting AB and tau," Translational Neurodegeneration 1:21(http://www.translationalneurodegeneration.com/content/1/1/21), 12 pages, Oct. 30, 2012.

Hubbard et al., "Cell signalling diversity of the Gqalpha family of heterotrimeric G proteins," Cellular Signalling 18(2):135-150, Sep. 22, 2005.
Kemp et al., "Once-daily budesonide inhalation suspension for the treatment of persistent asthma in infants and young children," Annals of Allergy, Asthma, & Immunology, Sep. 1999, 83(3):231-239.
Khasnavis et al., "Protection of Dopaminergic Neurons in a Mouse Model of Parkinson's Disease by a Physically-Modified Saline Containing Charge-Stabilized Nanobubbles," The Journal of Neuroimmune Pharmacology, Oct. 11, 2013, 15 pages.
Khasnavis et al., "Suppression of Nuclear Factor-KB Activation and Inflammation in Microglia by Physically Modified Saline," The Journal of BioloQical Chemistry, Aug. 24, 2012, 287(35):29529-29542.
Knobloch et al., "Dendritic spine loss and synaptic alterations in Alzheimer's disease," Mol Neurobiol 37:73-82, 2008.
Kroeze et al., "G-protein-coupled receptors at a glance," Journal of Cell Science at a Glance, 114:4867-4869, 2003.
Lambertsen et al., "Inflammatory cytokines in experimental and human stroke," Journal of Cerebral Blood Flow & Metabolism 32:1677-1698, 2012.
Lassmann, "Hypoxia-like tissue injury as a component of multiple sclerosis lesions," J. Neurol. Sci. 206(2):187-191 (abstract, p. 190, paragraph 3), Feb. 15, 2003.
Lee et al., "Tau phosphorylation in Alzheimer's disease: pathogen or protector?," Trends in Molecular Medicine 11(4):164-169, Apr. 2005.
Licalzi et al., "Effect of hemorrhagic hypotension and hypoventilation on lower esophageal sphincter pressure," Annals of Surgery 192(1):53-57, p. 55, para 6-p. 56, para 1, (Document entitled "Licalzi PubMed" included to establish publication date.), Jul. 1980.
Lundblad et al., "A reevaluation of the validity of unrestrained plethysmography in mice," J. Appl. Physiol. 93:1198-1207, 2002.
Martin et al., "Cognitive Function Over Time in the Alzheimer's Disease Anti-inflammatory Prevention Trial (ADAPT)," Arch Neurol. 65(7):896-905, Jul. 14, 2008.
Masters et al., "Anti-inflammatory drugs fall short in Alzheimer's disease," Nature Medicine Community Corner 14(9):916, Sep. 2008.
Merriam-Webster, "Electrokinetic" word definition extracted from online dictionary http://www.merriam-webster.com/dictionary/electrokinetic, Sep. 23, 2014, 1 page.
Modi et al., "A Physically-Modified Saline Suppresses Neuronal Apoptosis, Attenuates Tau Phosphorylation and Protects Memory in an Animal Model of Alzheimer's Disease," PLOS ONE, www.plosone.org, Aug. 2014: 9(8):e103606, 16 pages.
Mondal et al., "Protection of Tregs, Suppression of Th1 and Th17 Cells, and Amelioration of Experimental Allergic Encephalomyelitis by a Physically-Modified Saline," PloS One, Dec. 2012, 7(12)e51869, 18 pages.
Murray et al., "Exacerbation of CNS inflammation and neurodegeneration by systemic LPS treatment is independent of circulating IL-1β and Il-6," Journal of Neuroinflammation 8:50, May 17, 2011.
Nickols et al., "Development of allosteric modulators of GPCRs for treatment of CNS disorders," Neurobiology of Disease 61:55-71, available online Sep. 27, 2013.
NIH (National Institute of Health, National Heart, Lung and Blood Institute), "What is Atherosclerosis?" http://www.nhlbi.nih.gov/health/health-topics/topics/atherosclerosis, published Jul. 1, 2011, retrieved on Dec. 18, 2013.
NINDS, "What is Corticobasal Degeneration?," Corticobasal Degeneration Information Page: National Institute of Neurological Disorders and Stroke (NINDS), retrieved on Jan. 9, 2015, from http://www.ninds.nih.gov/disorders/corticobasal_degeneration/corticobasal_degeneration.htm.
NINDS, "What is progressive supranuclear palsy?," Progressive Supranuclear Palsy Fact Sheet: National Institute of Neurological Disorders and Stroke (NINDS), retrieved Jan. 9, 2015, from http://www.ninds.nih.gov/disorders/psp/detail_psp.htm.
Ostrowski et al., "Pro- and anti-inflammatory cytokine balance in strenuous exercise in humans," The Journal of Physiology, Feb. 15, 1999, 515(1):287-291.

(56) References Cited

OTHER PUBLICATIONS

Partridge, "Bacteria 'cause Asthma'," BBC News Health 2001, retrieved May 28, 2014, from http://news.bbc.co.uk/2/hi/health/1372007.stm, 3 pages.

Peles et al., "Differential Effects of TRPV1 Antagonists in Acid-induced Excitation of Esophageal Vagal Afferent Fibers of Rats," Neuroscience 2009 161(2):515-525 (doi:10.1016/j.neuroscience.2009.03.040).

Petersen et al., "The anti-inflammatory effect of exercise," J. Appl. Physiol, 98:1154-1162, Apr. 2005.

Piantadosi, "Oxygenated" water and athletic performance, Br. J. Sports Med., Sep. 2006, 40(9):740, published online Jul. 19, 2006.

Planas et al., "Signalling pathways mediating inflammatory responses in brain ischaemia," International Symposium on Neurodegeneration and Neuroprotection, Biochemical Society Transactions 34(6):1267-1270, 2006.

Present et al., "Infliximab for the Treatment of Fistulas in Patients with Crohn's Disease," The New England Journal of Medicine 340(18):1398-1405, May 6, 1999.

Sanchez-Pernaute et al., "Selective COX-2 inhibition prevents progressive dopamine neuron degeneration in a rat model of Parkinson's disease," Journal of Neuroinflammation 1(6):1-11, 2004.

Silverman et al., "Inhibition of Daptomycin by Pulmonary Surfactant: In Vitro Modeling and Clinical Impact," Journal of Infectious Diseases, Jun. 15, 2005, 191:214952 (published electronically May 5, 2005).

Sjogren et al., "Increased intrathecal inflammatory activity in frontotemporal dementia: pathophysiological implications," J. Neurol. Neurosurg. Psychiatry 75:1107-1111, 2004.

Sun et al., "Role of G protein-coupled receptors in inflammation," Acta Pharmacologica Sinica, 2012, 33:342-350.

Taylor, "Regulation of intestinal epithelial gene expression in hypoxia," Kidney Int. 66(2):528-531, abstract; p. 530, paragraph 3 (Document entitled "Taylor Ingenta" included to establish publication date), Aug. 2004.

Teronen et al., Annals of the New York Academy of Sciences 878:453-465, Jun. 1999.

Torre, "Is Alzheimer's disease a neurodegenerative or a vascular disorder? Data, dogma, and dialectics," Neurology 3:184-190, Mar. 2004.

Van Winsen et al., "Sensitivity to glucocorticoids is decreased in relapsing remitting multiple sclerosis," J. Clin. Endocrinol. Metab. 90(2):734-740, abstract, Feb. 2005.

Venken et al., "Disturbed regulatory T cell homeostasis in multiple sclerosis," Trends in Molecular Medicine, 16(2):58-68, Feb. 2010.

Vignali et al., "How regulatory T cells work," Nature Review—Immunology Jul. 2008, 8:523-532.

Viviani et al., "Cytokines and neuronal channels: A molecular basis for age-related decline of neuronal function?," Experimental Gerontology 46:199-206, 2011.

Vliet et al., "Nitric oxide: a pro-inflammatory mediator in lung disease?", Respiratory Research 1:67-72, Aug. 15, 2000.

Watson et al., U.S. Appl. No. 12/258,210, filed Oct. 24, 2008.

Watson et al., U.S. Appl. No. 12/256,774, filed Oct. 23, 2008.

Watson et al., U.S. Appl. No. 12/257,224, filed Oct. 23, 2008.

Watson et al., U.S. Appl. No. 12/257,607, filed Oct. 24, 2008.

Watson et al., U.S. Appl. No. 12/259,101, filed Oct. 27, 2008.

Watson et al., U.S. Appl. No. 61/373,652, filed Aug. 13, 2010 (unpublished).

Whittaker et al., "Matrix Metalloproteinases and their Inhibitors—Current Status and Future Challenges," Celltransmissions 7(1):3-12, 2001.

Yasuda et al., "Modulation of hypoglossal motoneuron excitability by NK1 receptor activation in neonatal mice in vitro," Journal of Physiology 534(2):447-464, published Jan. 5, 2001.

Zhao et al., "Expression of Matrix Metalloproteinase-9 mRNA in Osteoporotic Bone Tissues," Journal of Tongii Medical University 17(1):28-31, Mar. 1997.

Zozulya et al., "The Role of Regulatory T Cells in Multiple Sclerosis," Nature Clinical Practice Neurology 4(7):384-398, Jun. 24, 2008.

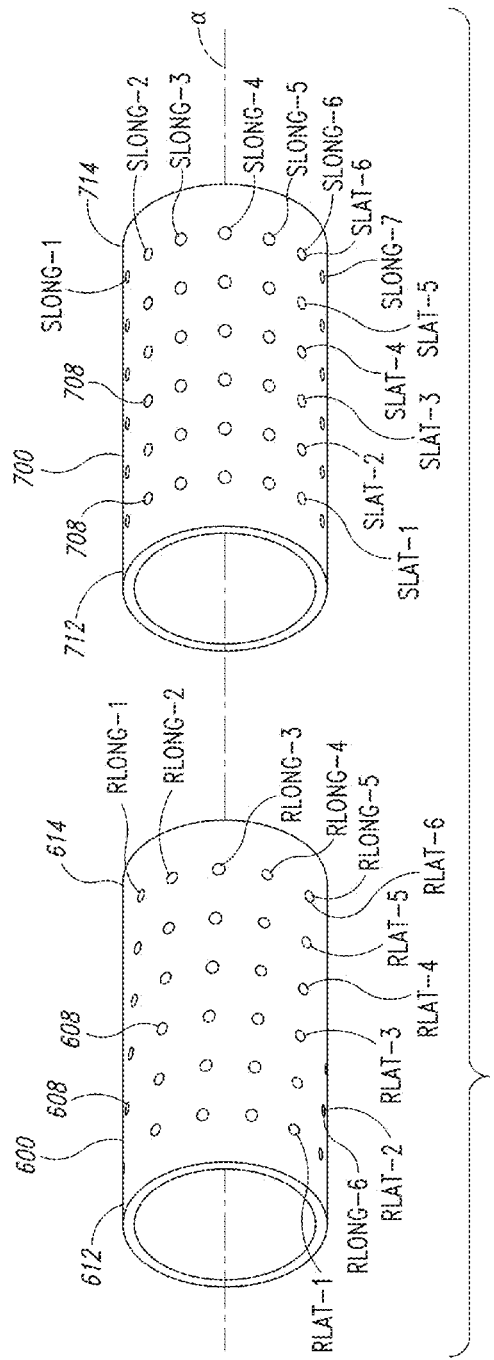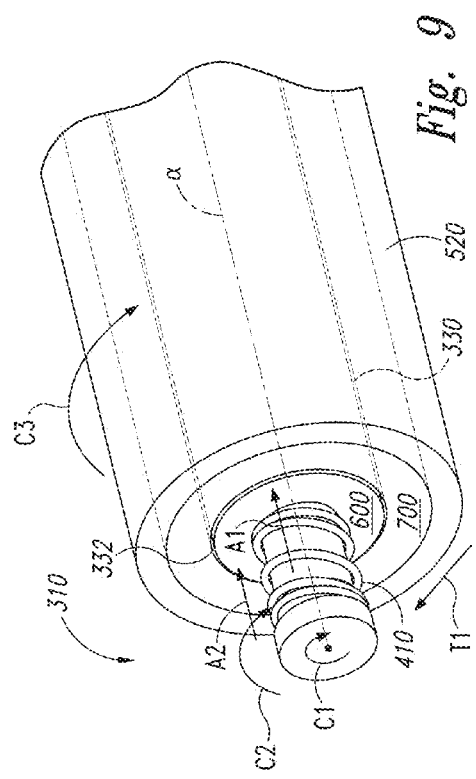

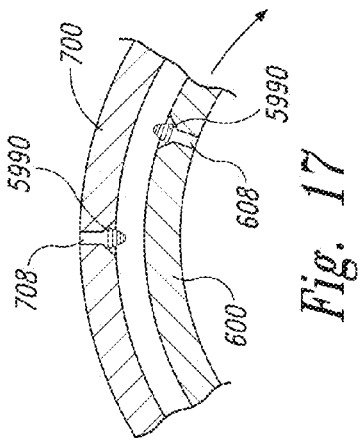
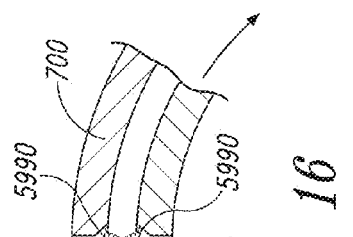
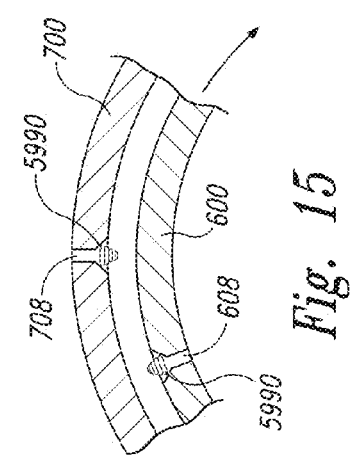
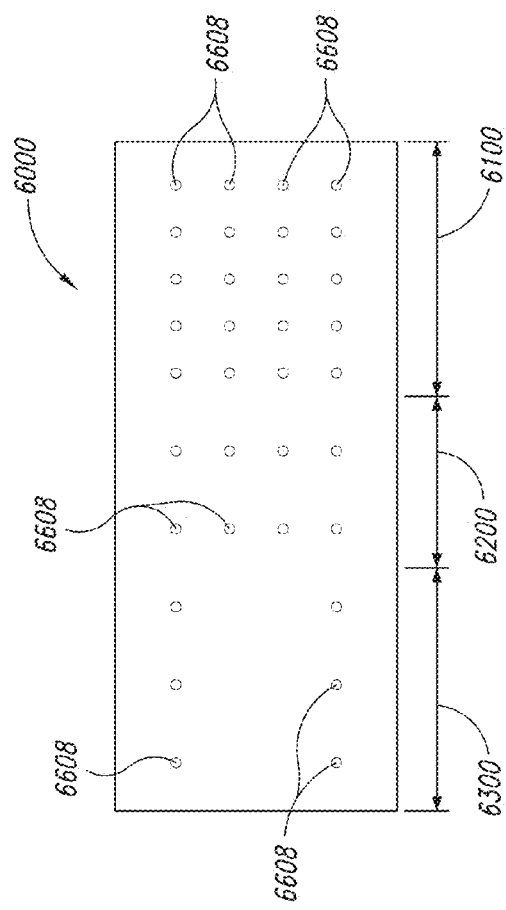

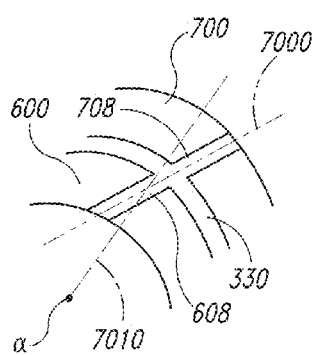
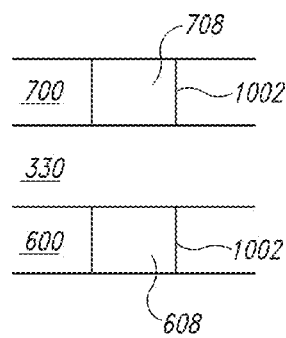
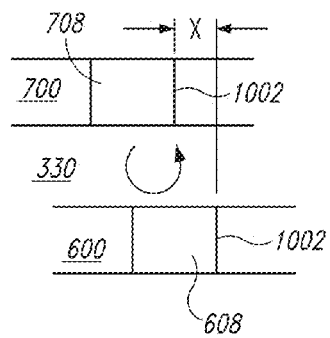
Fig. 19　　　Fig. 20　　　Fig. 21
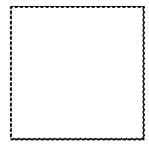
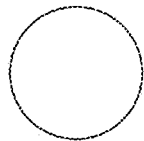
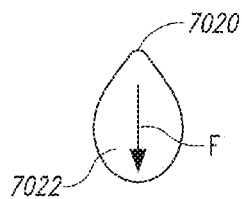
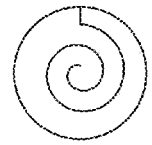
Fig. 22　　Fig. 23　　Fig. 24　　Fig. 25
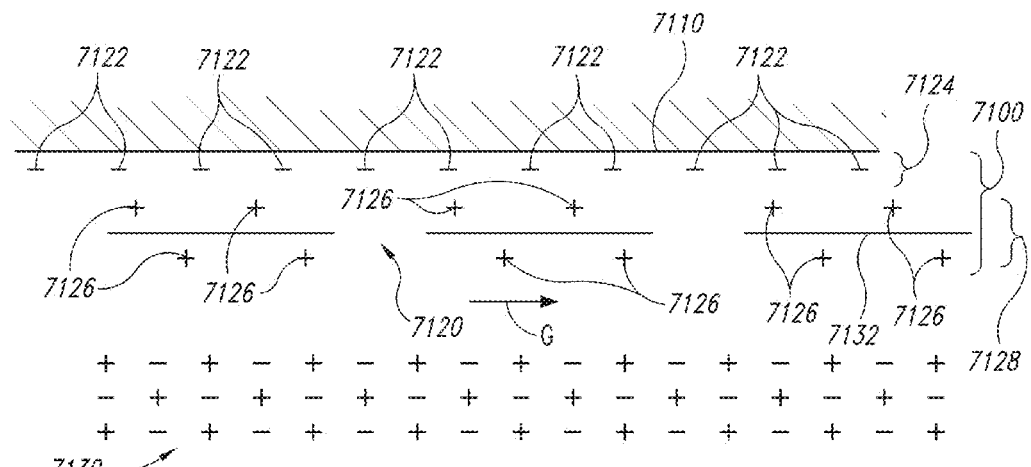
Fig. 26

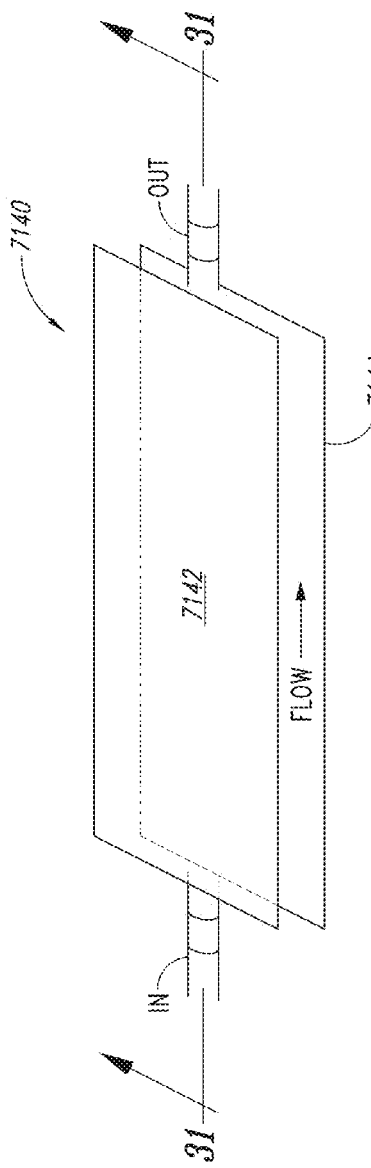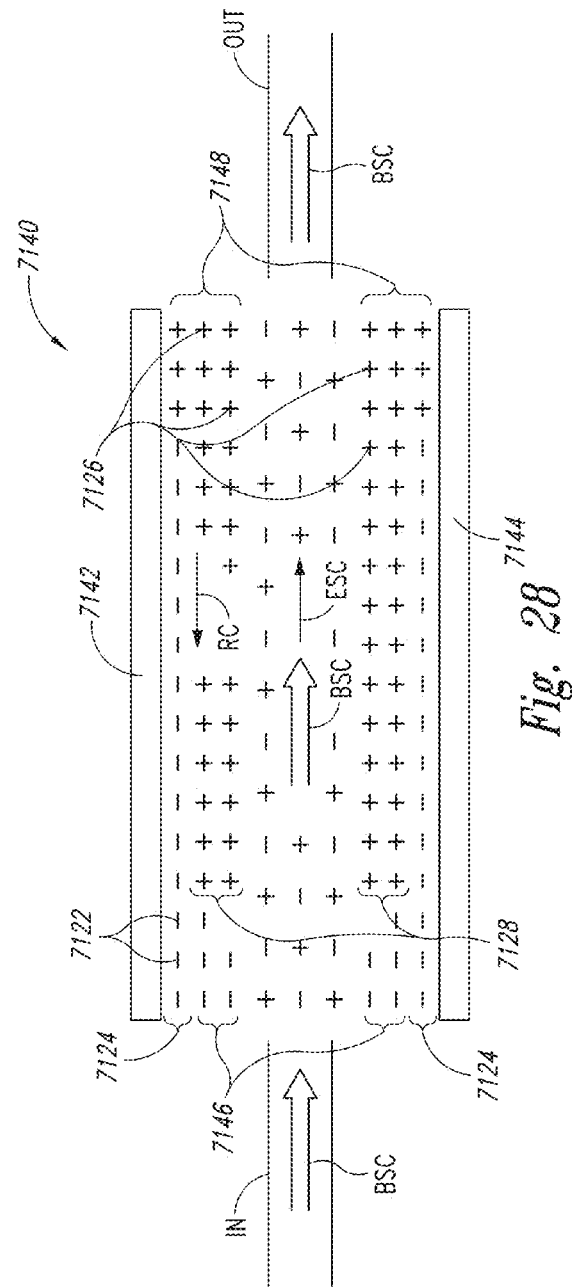

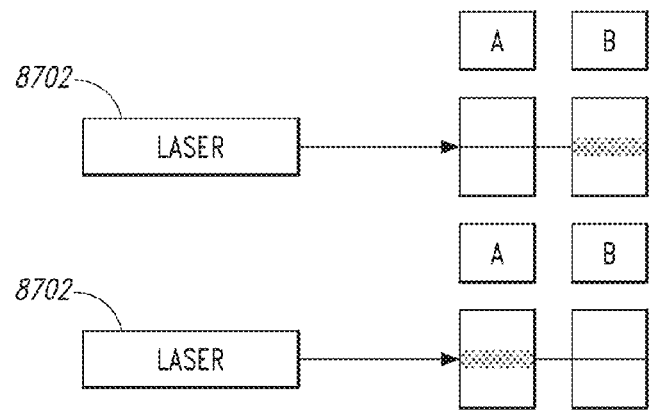
*Fig. 37A*
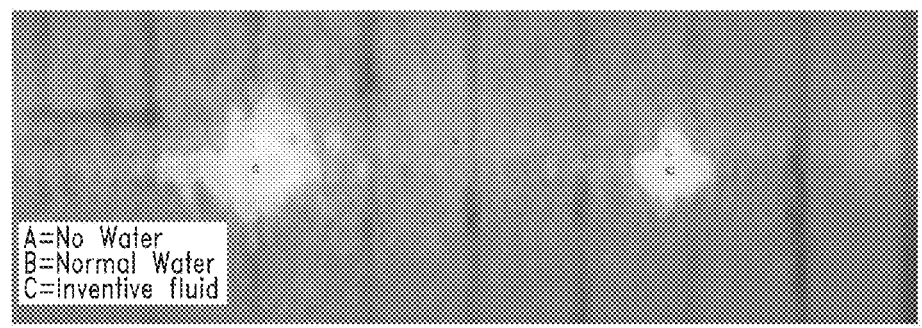
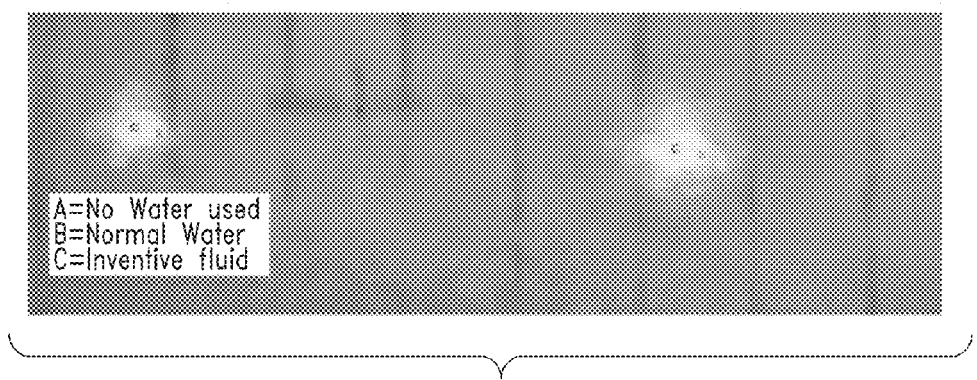
*Fig. 37B*

Control one day post wounding showing epidermal/dermal thickening and loss of contour Experimental with inventive fluid one day post wounding showing normal epidermal/dermal thickness and normal contour Control day four showing 600 micron epidermal spur Experimental day four with inventive fluid showing 1200 micron epidermal spur Control day 16 showing less differentiated epidermis with loss of epidermal/dermal contour Experimental day 16 with inventive fluid showing more differentiated epidermis with more normal epidermal/dermal contour

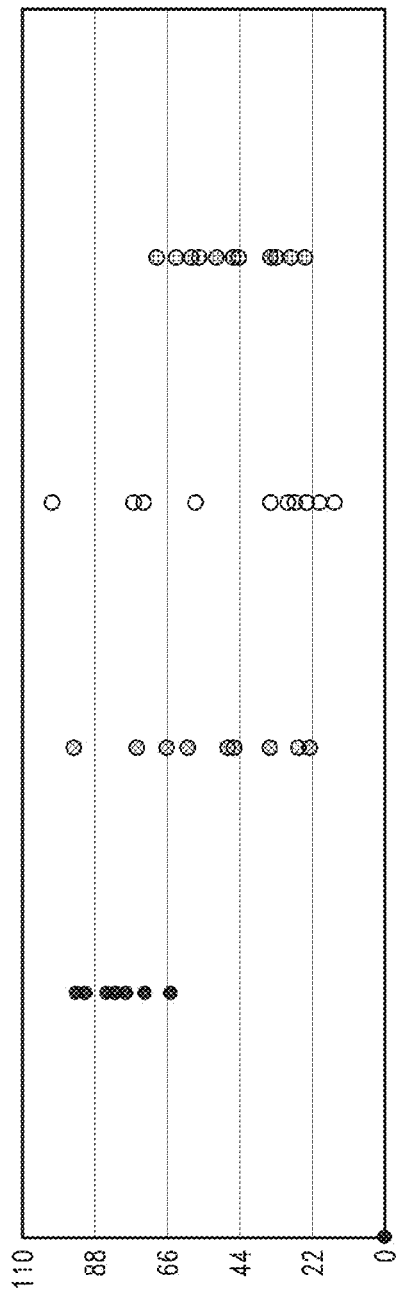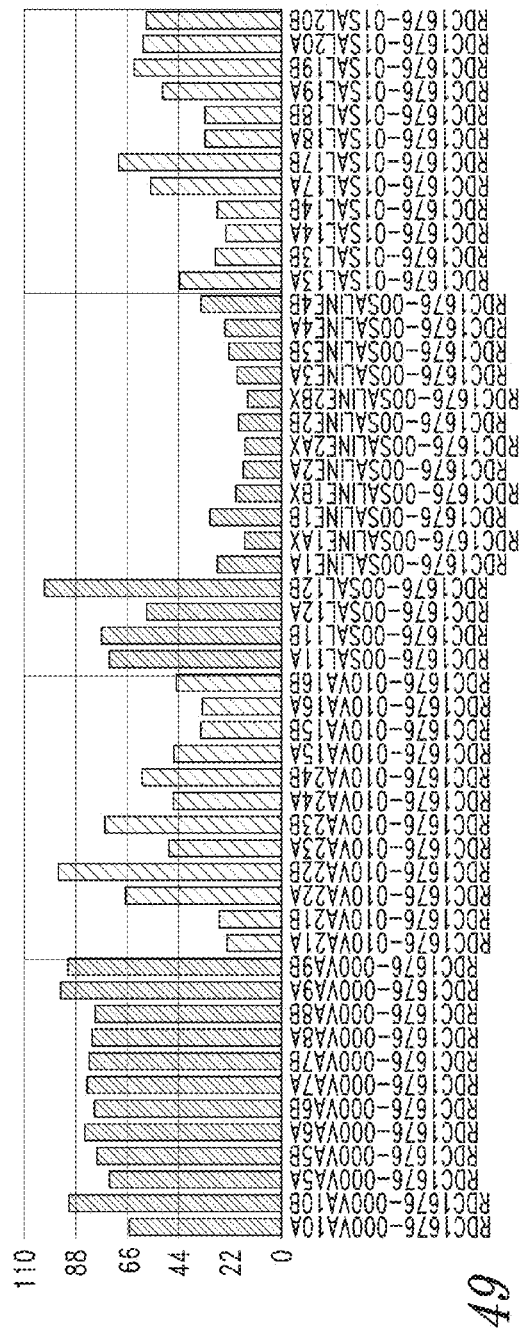
Fig. 49

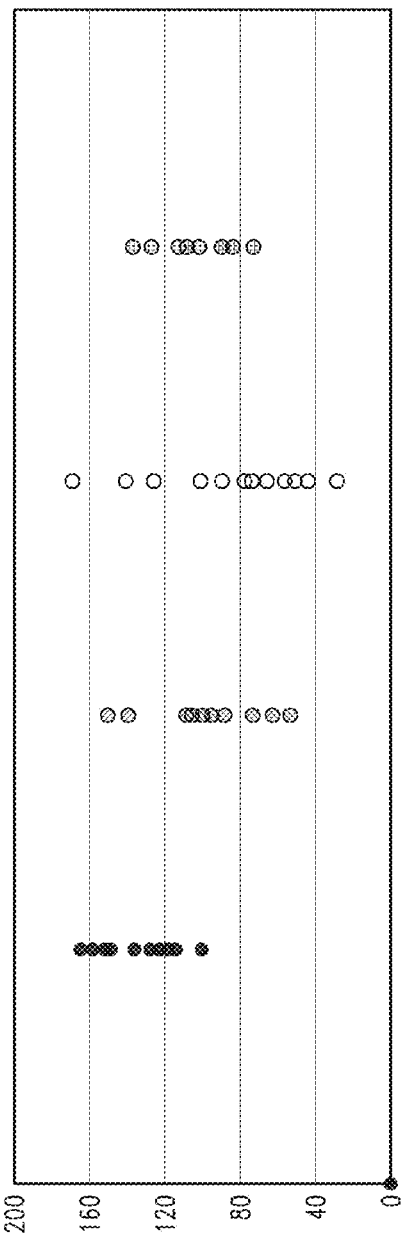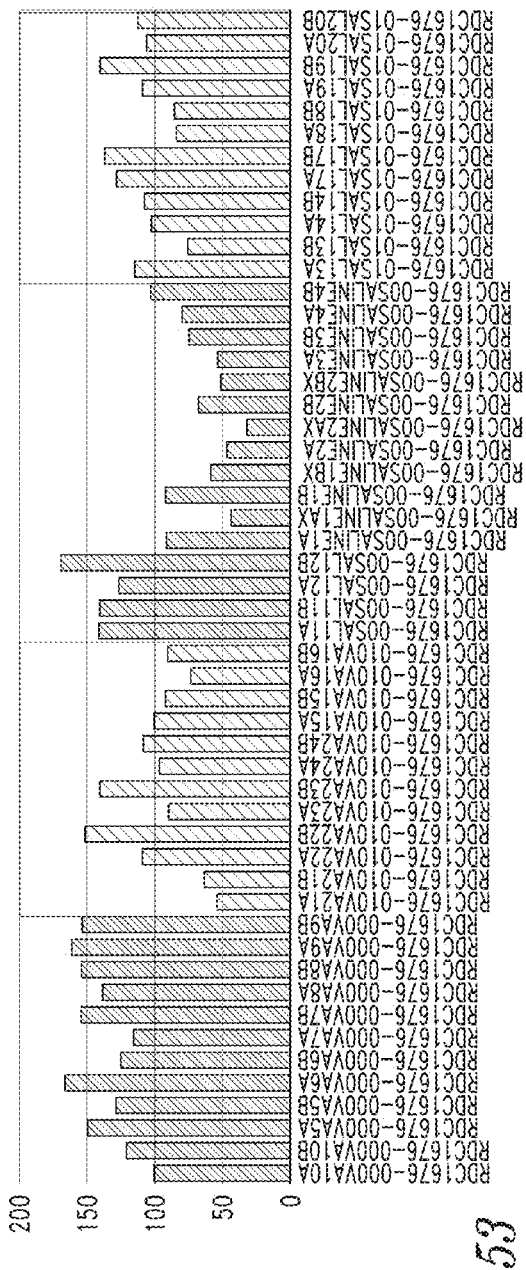
Fig. 53

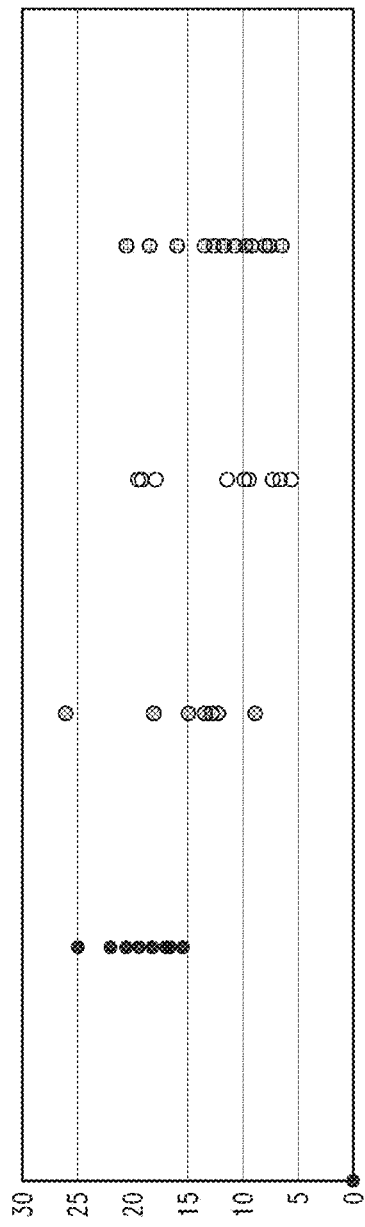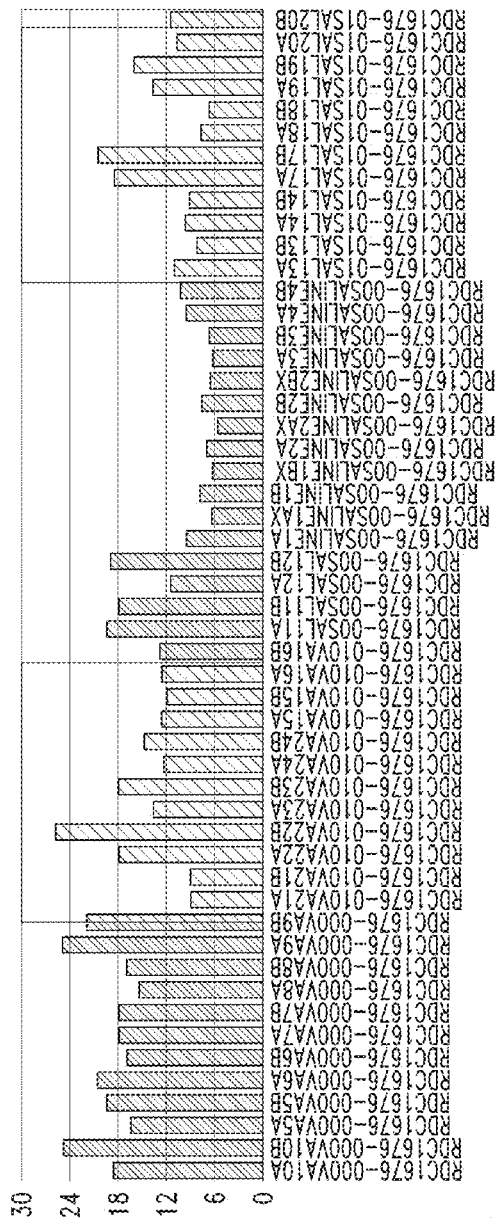
Fig. 54

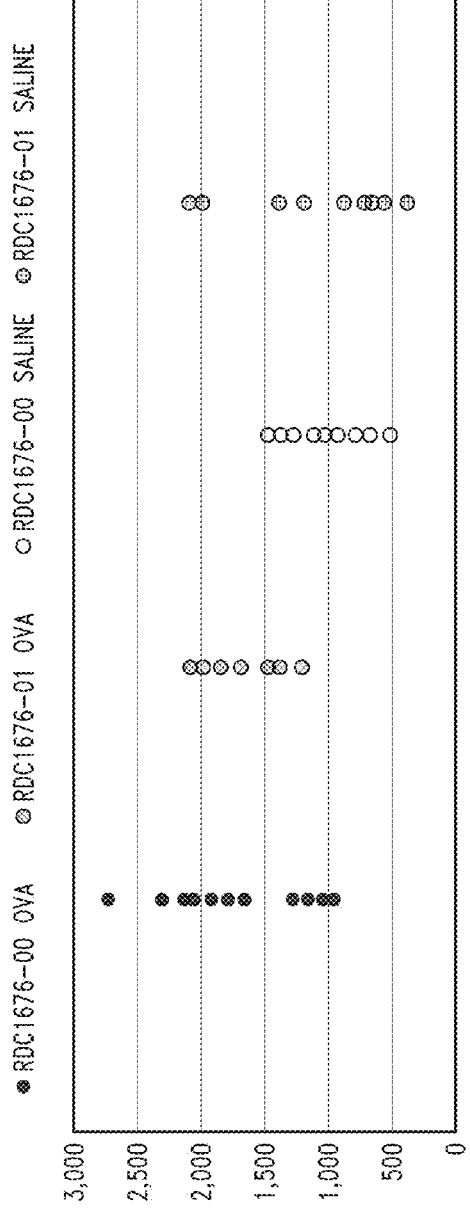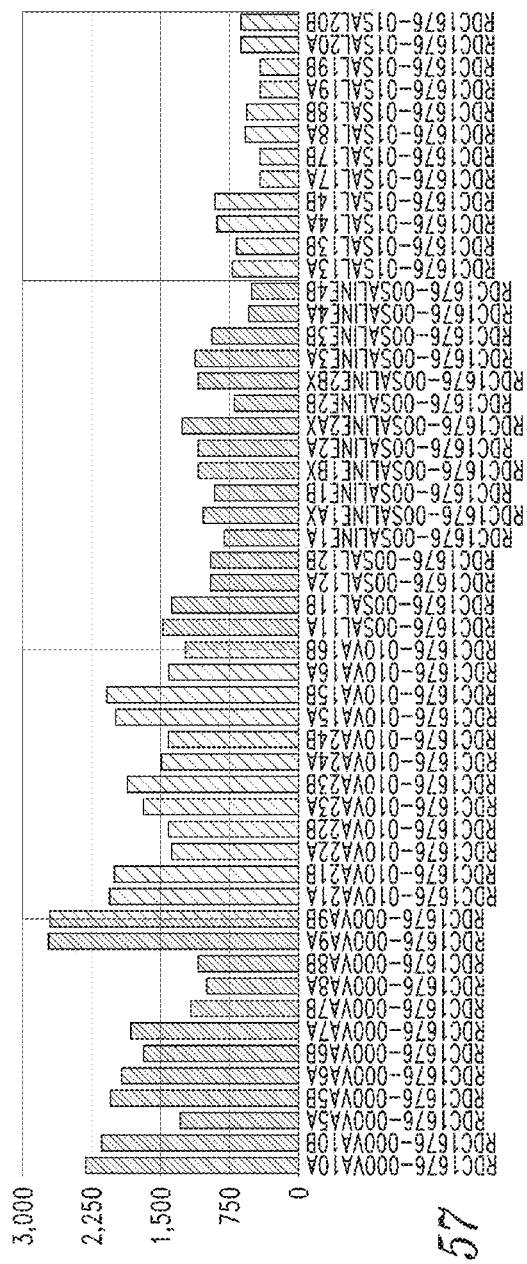
Fig. 57

Albuterol = 0

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: synthetic MOG 35-55 sequence
<220> FEATURE:
<221> NAME/KEY: VARIANT
<222> LOCATION: 13
<223> OTHER INFORMATION: Xaa = Ornithine

<400> SEQUENCE: 1

Met Glu Val Gly Trp Tyr Arg Ser Pro Phe Ser Arg Xaa Val His Leu
 1               5                  10                  15

Tyr Arg Asn Gly Lys
            20
```

METHODS OF WOUND CARE AND TREATMENT

CROSS-REFERENCE TO RELATED APPLICATIONS

This application is a continuation of U.S. patent application Ser. No. 12/431,704, filed Apr. 28, 2009 and entitled METHODS OF WOUND CARE AND TREATMENT (issuing on Dec. 31, 2013 as U.S. Pat. No. 8,617,616), which is a continuation-in-part of U.S. patent application Ser. No. 11/978,137, filed Oct. 25, 2007 and entitled METHODS OF WOUND CARE AND TREATMENT (issued on Dec. 3, 2013 as U.S. Pat. No. 8,597,689), which claims priority to U.S. Provisional Patent Application Ser. No. 60/862,904, filed Oct. 25, 2006 and entitled DIFFUSER/EMULSIFIER, 60/862,953, filed Oct. 25, 2006 and entitled METHOD OF THERAPEUTIC TREATMENTS OF EYES AND OTHER HUMAN TISSUES USING AN OXYGENATED SOLUTION, 60/862,955, filed Oct. 25, 2006 and entitled OXYGENATED SALINE SOLUTION, 60/862,959, filed Oct. 25, 2006 and entitled WOUND TREATMENT WITH INFUSION MATERIALS, and 60/982,387, filed Oct. 24, 2007 and entitled MIXING DEVICE, and wherein U.S. patent application Ser. No. 12/431,704 additionally claims priority to U.S. Provisional Patent Application Ser. No. 61/048,433, filed Apr. 28, 2008 and entitled METHODS OF WOUND CARE AND TREATMENT, all of which are incorporated by reference herein in their entirety.

FIELD OF THE INVENTION

Particular aspects relate generally to treating a wound to a surface tissue or a symptom thereof. Disclosed herein are electrokinetically-altered fluids (including gas-enriched (e.g., oxygen enriched) electrokinetically-altered fluids) as disclosed herein for modulation of at least one of cellular membrane potential and cellular membrane conductivity, regulating or modulating intracellular signal transduction by modulation of at least one of cellular membranes, membrane potential, and membrane proteins such as membrane receptors, including but not limited to G protein coupled receptors. Particular aspects relate to treating at least one disease or condition or symptom thereof associated with general wound care and treatment. In particular embodiments, the fluids are electrokinetically-altered oxygen-enriched fluids. Adjunctive and combination therapy embodiments are encompassed.

BACKGROUND OF THE INVENTION

Wound care is desirable in order to improve health and appearance of the outer epidermis, as well as underlying dermal and other tissues. Wounds, either injury induced (such as cuts, abrasions, blisters, etc.), or surgically induced (such as surgical incisions, astomies, etc.) require localized treatment to remedy the affected area and prevent further dermal damage. If wounds are not properly treated, further dermal irritation can result, including secondary infections and further discomfort to the subject.

Improper wound care and/or wound healing result in greater than 100 billion dollars per year, and may require antibiotic use, hospitalizations, and great pain or discomfort to the subject. Present methods of therapeutic wound care are inadequate and routinely include washing with soap and water and/or applying an antiseptic, but still may lead to infection and/or improper wound healing and repair. Thus, novel therapeutic methods and compositions for wound care and wound healing are needed.

SUMMARY OF THE INVENTION

Particular aspects provide methods for treating a wound to a surface tissue or a symptom thereof, comprising administering to a subject in need thereof a therapeutically effective amount of an electrokinetically-altered aqueous fluid comprising an ionic aqueous solution of charge-stabilized oxygen-containing nanostructures substantially having an average diameter of less than about 100 nanometers and stably configured in the ionic aqueous fluid in an amount sufficient to provide, upon contact of a living cell by the fluid, modulation of at least one of cellular membrane potential and cellular membrane conductivity, wherein a wound to a surface tissue or a symptom thereof is treated. Additional aspects provide for wherein treating the wound comprises treating to decrease scarring in the wound to the surface tissue, wherein scarring is reduced. In further aspects, the electrokinetically-altered aqueous fluid further increases the level of chemokines at the wound.

In certain aspects, treating the wound comprises treating to increase or decrease nitric oxide production or degradation in the wound to the surface tissue, wherein an increased or decreased level of nitric oxide is afforded. In additional aspects, the electrokinetically-altered aqueous fluid is contacted to the wound by means of a wound dressing. Particular aspects provide for the electrokinetically-altered aqueous fluid accelerates epidermal or dermal layering.

According to additional aspects, the electrokinetically-altered aqueous fluid increases cellular migration of at least one type of cell to the wound. In further aspects, the type of cellular migration or proliferation comprises at least one cell selected from the group consisting of: keratinocytes, fibroblasts, epidermal cells, dermal cells, epithelial cells, mast cells, neutrophils, lymphocytes, and macrophages. In certain aspects, the electrokinetically-altered aqueous fluid accelerates neoangiogenesis of blood vessels or lymphatic vessels. In further aspects, the electrokinetically-altered aqueous fluid increases collagen deposition at the wound.

Particular aspects provide for the electrokinetically-altered aqueous fluid reduces growth of at least one microbe in the wound. In further aspects, the microbe comprises *Pseudomonas*. In yet further aspects, the charge-stabilized oxygen-containing nanostructures are the major charge-stabilized gas-containing nanostructure species in the fluid. In additional aspects, the percentage of dissolved oxygen molecules present in the fluid as the charge-stabilized oxygen-containing nanostructures is a percentage selected from the group consisting of greater than: 0.01%, 0.1%, 1%, 5%; 10%; 15%; 20%; 25%; 30%; 35%; 40%; 45%; 50%; 55%; 60%; 65%; 70%; 75%; 80%; 85%; 90%; and 95%.

Particular aspects provide for the total dissolved oxygen is substantially present in the charge-stabilized oxygen-containing nanostructures. In additional aspects, the charge-stabilized oxygen-containing nanostructures substantially have an average diameter of less than a size selected from the group consisting of: 90 nm; 80 nm; 70 nm; 60 nm; 50 nm; 40 nm; 30 nm; 20 nm; 10 nm; and less than 5 nm. In yet further aspects, the ionic aqueous solution comprises a saline solution. Additional aspects provide for the fluid is superoxygenated. In certain aspects, the fluid comprises a form of solvated electrons.

Particular aspects provide for alteration of the electrokinetically altered aqueous fluid comprises exposure of the fluid to hydrodynamically-induced, localized electrokinetic effects. In further aspects, exposure to the localized electrokinetic effects comprises exposure to at least one of voltage pulses and current pulses. In yet further aspects, the exposure of the fluid to hydrodynamically-induced, localized electrokinetic effects, comprises exposure of the fluid to electrokinetic effect-inducing structural features of a device used to generate the fluid. In certain aspects, the wound to a surface tissue or the symptom thereof comprises at least one wound type selected from the group consisting of lacerations, abrasions, rupture, puncture wounds, chemical, thermal, or radiation-induced burns, cuts, scrapes, incisions, blisters, diabetic ulcers, bedsores or pressure ulcers, skin grafts, and surgical wounds. Particular aspects provide for the wound to a surface tissue or the symptom thereof comprises at least one of diabetic ulcers, bedsores or pressure ulcers, skin grafts, and surgical wounds. In additional aspects, the wound to a surface tissue or the symptom thereof comprises diabetic ulcers, and bedsores or pressure ulcers. In further aspects, the at least one symptom is related to at least one condition selected from the group consisting of epidmeral or dermal layering, cellular migration, collagen deposition at the wound, neoangiogenesis at the wound, elastin deposition at the wound, inflammation at the wound, expression of proteoglycans or glycosaminoglycans, cellular proliferation, and hyaluronic acid concentration at the wound.

Particular aspects provide for the electrokinetically altered aqueous fluid modulates localized or cellular levels of nitric oxide. Further aspects provide for the electrokinetically altered aqueous fluid promotes a localized decrease at the site of administration of at least one cytokine selected from the group consisting of: IL-1 beta, IL-8, TNF-alpha, and TNF-beta. In certain aspects, the invention further comprises a synergistic or non-synergistic inhibition or reduction in inflammation by simultaneously or adjunctively treating the subject with another anti-inflammatory agent. In further aspects, said other anti-inflammatory agent comprises a steroid or glucocorticoid steroid. In yet further aspects, said steroid comprises a glucocorticoid steroid.

Certain aspects provide for the invention further comprising combination therapy, wherein at least one additional therapeutic agent is administered to the patient. According to additional aspects, the one additional therapeutic agent is selected from the group consisting of anti-microbial agents, antifungal agents, and antibiotic agents. In further aspects, at least one additional therapeutic agent is selected from the group consisting of: ciclosporin, hyaluronic acid, carmellose, macrogol(s), dextran and hyprolose, sodium and calcium, sodium and povidone, hypromellose, carbomer, amikacin, gentamicin, kanamycin, neomycin, netilmicin, streptomycin, tobramycin, paromomycin, geldanamycin, herimycin, loracarbef, ertapenem, imipenem/cilastatin, meropenem, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, peperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, tinidazole, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, teronazole, terbinafine, amorolfine, naftifine, butenafine, anidulafungin, caspofungin, micafungin, ciclopirox, flucytosine, griseofulvin, Gentian violet, haloprogin, tolnaftate, undecylenic acid, and combinations thereof. In yet further aspects, at least one additional therapeutic agent is a TSLP and/or TSLPR antagonist. In certain aspects, TSLP and/or TSLPR antagonist is selected from the group consisting of neutralizing antibodies specific for TSLP and the TSLP receptor, soluble TSLP receptor molecules, and TSLP receptor fusion proteins, including TSLPR-immunoglobulin Fc molecules or polypeptides that encode components of more than one receptor chain.

Particular aspects provide for modulation of at least one of cellular membrane potential and cellular membrane conductivity comprises altering of a conformation, ligand binding activity, or a catalytic activity of a membrane associated protein. In further aspects, the membrane associated protein comprises at least one selected from the group consisting of receptors, transmembrane receptors, ion channel proteins, intracellular attachment proteins, cellular adhesion proteins, integrins, etc. According to certain aspects, the transmembrane receptor comprises a G-Protein Coupled Receptor (GPCR). According to further aspects, the G-Protein Coupled Receptor (GPCR) interacts with a G protein a subunit. According to yet further aspects, the G protein a subunit comprises at least one selected from the group consisting of $G\alpha_s$, $G\alpha_i$, $G\alpha_q$, and $G\alpha_{12}$. In further aspects, the at least one G protein a subunit is $G\alpha_q$. According to certain aspects, modulating cellular membrane conductivity, comprises modulating whole-cell conductance. In further aspects, modulating whole-cell conductance, comprises modulating at least one of linear and non-linear voltage-dependent contribution of the whole-cell conductance. In yet further aspects, modulation of at least one of cellular membrane potential and cellular membrane conductivity comprises modulation of a calcium dependent cellular messaging pathway or system.

Particular aspects provide for modulation of at least one of cellular membrane potential and cellular membrane conductivity comprises modulation of phospholipase C activity. According to further aspects, modulation of at least one of cellular membrane potential and cellular membrane conductivity comprises modulation of adenylate cyclase (AC) activity. In certain aspects, modulation of at least one of cellular membrane potential and cellular membrane conductivity comprises modulation of intracellular signal transduction associated with at least one condition or symptom selected from the group consisting of epidmeral or dermal layering, cellular migration, collagen deposition at the wound, neoangiogenesis at the wound, elastin deposition at the wound, inflammation at the wound, expression of proteoglycans or glycosaminoglycans, cellular proliferation, and hyaluronic acid concentration at the wound. Particular aspects provide for comprising administration to a cell network or layer, and further comprising modulation of an intercellular junction therein. In further aspects, the intracellular junction comprises at least one selected from the group consisting of tight junctions, gap junctions, zona adherins and desmasomes. In yet further aspects, the cell network or layers comprises at least one selected from the group consisting of epithelial cell layer or network. In certain aspects, the electrokinetically-altered aqueous fluid is oxygenated, and wherein the oxygen in the fluid is present in an amount of at least 8 ppm, at least 15, ppm, at least 25 ppm, at least 30 ppm, at least 40 ppm, at least 50 ppm, or at least 60 ppm oxygen at atmospheric pressure.

Particular aspects provide for the electrokinetically altered aqueous fluid comprises at least one of a form of solvated electrons, and electrokinetically modified or charged oxygen species. Particular aspects further provide for the form of solvated electrons or electrokinetically modified or charged oxygen species are present in an amount of at least 0.01 ppm, at least 0.1 ppm, at least 0.5 ppm, at least 1 ppm, at least 3 ppm, at least 5 ppm, at least 7 ppm, at least 10 ppm, at least 15 ppm, or at least 20 ppm. According to additional aspects, the electrokinetically-altered aqueous fluid comprises a form of solvated electrons stabilized, at least in part, by molecular oxygen. In further aspects, the ability to modulation of at least one of cellular membrane potential and cellular membrane conductivity persists for at least two, at least three, at least four, at least five, at least 6, at least 12 months, or longer periods, in a closed gas-tight container.

BRIEF DESCRIPTION OF THE DRAWINGS

FIG. 8 is a perspective view of a rotor and a stator of the mixing device of FIG. 2.

FIG. 9 is a perspective view of an inside of a first chamber of the mixing device of FIG. 2.

FIG. 15 is a cross-sectional view of the mixing chamber of the mixing device of FIG. 2 taken through a plane orthogonal to the axis of rotation depicting a rotary flow pattern caused by cavitation bubbles when a through-hole of the rotor approaches (but is not aligned with) an aperture of the stator.

FIG. 16 is a cross-sectional view of the mixing chamber of the mixing device of FIG. 2 taken through a plane orthogonal to the axis of rotation depicting a rotary flow pattern caused by cavitation bubbles when the through-hole of the rotor is aligned with the aperture of the stator.

FIG. 17 is a cross-sectional view of the mixing chamber of the mixing device of FIG. 2 taken through a plane orthogonal to the axis of rotation depicting a rotary flow pattern caused by cavitation bubbles when a through-hole of the rotor that was previously aligned with the aperture of the stator is no longer aligned therewith.

FIG. 18 is a side view of an alternate embodiment of a rotor.

FIG. 19 is an enlarged fragmentary cross-sectional view taken through a plane orthogonal to an axis of rotation of the rotor depicting an alternate configuration of through-holes formed in the rotor and through-holes formed in the stator.

FIG. 20 is an enlarged fragmentary cross-sectional view taken through a plane passing through and extending along the axis of rotation of the rotor depicting a configuration of through-holes formed in the rotor and through-holes formed in the stator.

FIG. 21 is an enlarged fragmentary cross-sectional view taken through a plane passing through and extending along the axis of rotation of the rotor depicting an alternate offset configuration of through-holes formed in the rotor and through-holes formed in the stator.

FIG. 22 is an illustration of a shape that may be used to construct the through-holes of the rotor and/or the apertures of the stator.

FIG. 23 is an illustration of a shape that may be used to construct the through-holes of the rotor and/or the apertures of the stator.

FIG. 24 is an illustration of a shape that may be used to construct the through-holes of the rotor and/or the apertures of the stator.

FIG. 25 is an illustration of a shape that may be used to construct the through-holes of the rotor and/or the apertures of the stator.

FIG. 26 is an illustration of an electrical double layer ("EDL") formed near a surface.

FIG. 27 is a perspective view of a model of the inside of the mixing chamber.

FIG. 28 is a cross-sectional view of the model of FIG. 27.

FIGS. 37A and B illustrate Rayleigh scattering effects of an oxygen-enriched fluid.

FIG. 38 illustrates the cytokine profile of a mitogenic assay in the presence of a gas-enriched fluid and deionized control fluid.

FIGS. 49-58 show the results of whole blood sample evaluations of cytokines.

FIGS. 69-75 shows studies where the Bradykinin B2 membrane receptor was immobilized onto aminopropylsilane (APS) biosensor. The Sample plate set up was as designated in FIG. 69 and the binding of Bradykinin to the immobilized receptor was assessed according to the sample set up as designated in FIG. 71. Results of Bradykinin binding are shown in FIG. 72. Bradykinin binding to the receptor was further titrated according to the set-up as designated in FIG. 73. As indicated in FIG. 74, Bradykinin binding to the B2 receptor was concentration dependent, and binding affinity was increased in the proprietary gas-enriched saline fluid of the instant disclosure compared to normal saline. Stabilization of Bradykinin binding to the B2 receptor is shown in FIG. 75.

DETAILED DESCRIPTION

Figure 1:
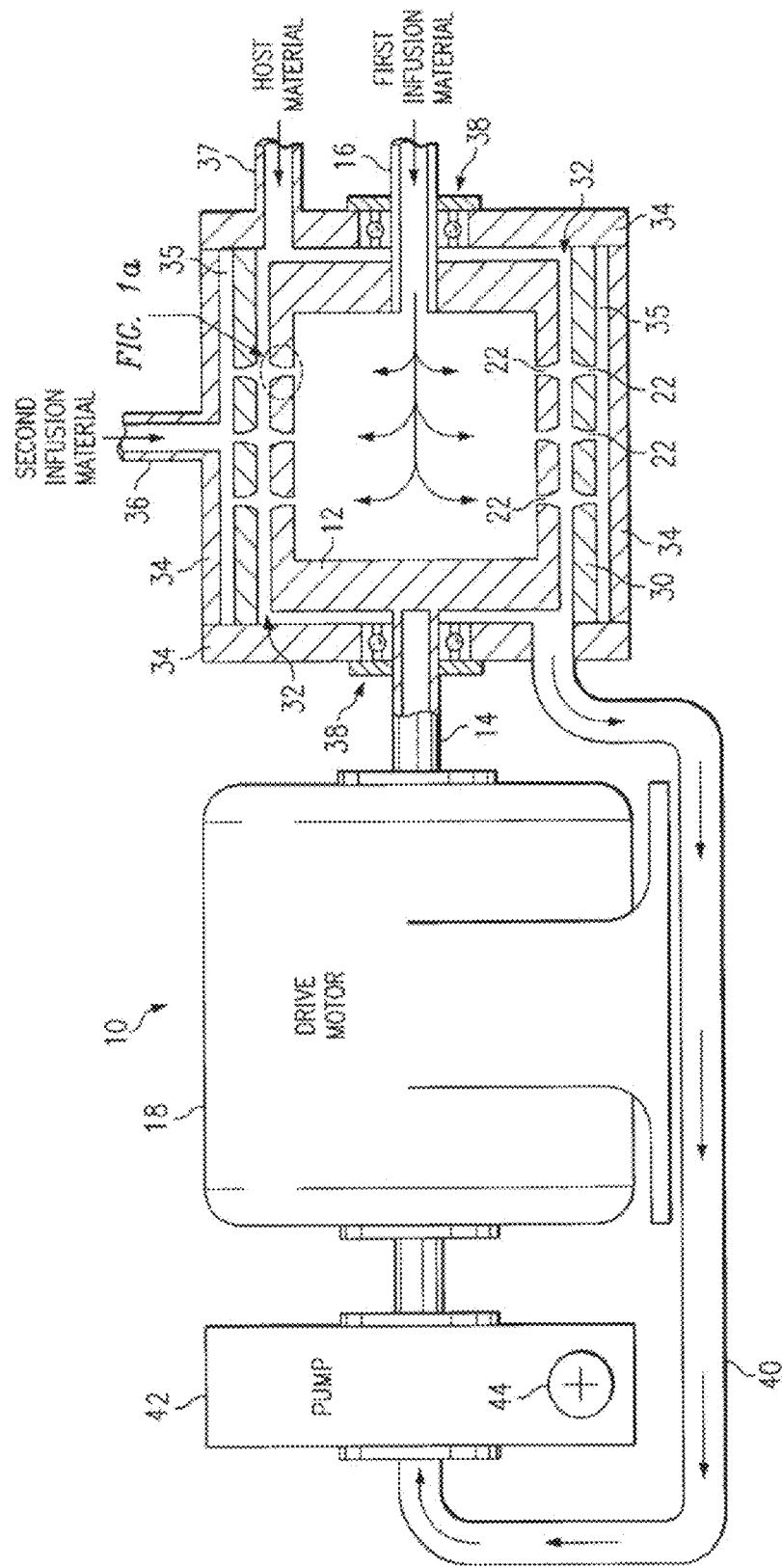
FIG. 1 is a partial cross-section, partial block diagram of a prior art mixing device.

The present invention includes compositions and methods for promoting proper wound healing and/or wound care. The compositions and/or methods disclosed herein may be used on a variety of wounds, wherein a wound is a break in the skin or other tissue or organ, such as lacerations, cuts, scrapes, blisters, abrasions, burns, diabetic ulcers, bedsores, surgical wounds, and other wounds. Healing is a biological response to the injury that occurs typically with some scarring (with the exception of bone wounds). Thus, one of the objects of proper wound care is to minimize the possibility of infection and/or scarring.

The present medical practice is typically to wash or irrigate the wound with a stream of sterile saline, soap and water, providone/iodine, and/or other antiseptic antibiotic or anesthetic solutions. Typically, irrigating fluid is splashed onto the wound surface with an amount of force sufficient to dislodge dirt, debris, bacteria or dead tissue. The goal of wound irrigation is to remove debris and bacteria from the wound while minimizing injury to the normal tissue around the wound. This is difficult for deep penetrating wounds, such as those associated with a puncture wound from a stick or those from an animal bite. In the case of deep puncture wounds, and especially animal bites, it is especially important to thoroughly clean the wound due to the debris and microbial introduction deep into the tissue. These types of wounds typically require daily care under the present modes of wound care. Additionally, chronic wounds are common in subjects who are confined to a bed, wheelchair, or are otherwise sedentary or immobile, who have a nerve and/or blood circulation disorder or condition that impairs wound healing (such as those suffering from diabetes, cancer, HIV/AIDS, peripheral neuropathy, immunosuppression, sickle cell anemia, those who are or have been receiving steroids and/or chemotherapy drugs, those who are advanced in age, and others).

In certain situations, it may be necessary to suture the wound. If the wound requires sutures (stitches, staples, skin glue, tape, etc.), it may be cleansed, sutured, and dressed with bandages.

The present inventive compositions and/or methods may further be utilized for dressing treatment and/or wound irrigation. In certain embodiments, the wound irrigation may be applied under a pressure. In certain embodiments the wound irrigation pressure comprises about 2 psi, about 5 psi, about 8 psi, about 10 psi, about 12 psi, about 15 psi, about 18 psi, about 20 psi, or any value therebetween.

In certain embodiments, the gas-enriched fluid compositions and/or methods of the present invention relate to treating wound dressings. Wound dressings remove excess exudate from the wound, keeps the wound moist, and prevents dehydration, which can increase the rate of wound healing. In the treatment of wounds, antibiotics and/or antiseptics may be incorporated into dressings. In some particular embodiments, the wound dressing incorporates a biologically and/or chemically active substance (such as a cosmetic and/or therapeutic agent) in a separate phase which is disbursed in a continuous phase upon applying and/or over time. In this manner, the biologically and/or chemically active substance can be applied directly to the wound by way of the dressing. Application of the biologically and/or chemically active substance can be delivered continuous, all at once, or intermittent over time by way of the wound dressing.

In the case of occlusive dressings for wounds such as pressure sores (including bedsores), ulcers, or other wounds that may be persistent or chronic, the dressing may be applied that contains both an inner contact layer and an outer protecting layer. In certain embodiments, the inner layer or barrier layer, contains water absorptive material such as hydrocolloids, which allows fluid from the wound to be absorbed and making it possible to keep the dressing in place for at least several days.

In certain embodiments, the gas-enriched fluid compositions and/or methods of the present invention promote wound healing and/or reduce scarring, and/or reduce infection in wounds. In certain embodiments, the gas-enriched fluid compositions and/or methods of the present invention increase extracellular matrix deposition and/or production; increase collagen deposition and/or production; hylauronic acid deposition and/or production; and/or elastin deposition and/or production. In other embodiments, the gas-enriched fluid compositions and/or methods of the present invention promote proliferation, differentiation, and/or apoptosis of epithelial cells, keratinocytes, connective tissue, and/or muscle cells or other related cells of a wound.

The gas-enriched compositions and/or methods disclosed herein may promote any one or more stages of wound healing, including decreasing bleeding, increasing narrowing of blood vessels and/or clot formation, release of various chemical substances into the wound; increase angiogenesis, increase epithelialization of the wound, increase production of proteins related to wound healing, increase remodeling and/or proliferation and/or migration of epithelial cells and/or keratinocytes.

Electrokinetically-Generated Fluids:

"Electrokinetically generated fluid," as used herein, refers to Applicants' inventive electrokinetically-generated fluids generated, for purposes of the working Examples herein, by the exemplary Mixing Device described in detail herein (see also US200802190088 and WO2008/052143, both incorporated herein by reference in their entirety). The electrokinetic fluids, as demonstrated by the data disclosed and presented herein, represent novel and fundamentally distinct fluids relative to prior art non-electrokinetic fluids, including relative to prior art oxygenated non-electrokinetic fluids (e.g., pressure pot oxygenated fluids and the like). As disclosed in various aspects herein, the electrokinetically-generated fluids have unique and novel physical and biological properties including, but not limited to the following:

In particular aspects, the electrokinetically altered aqueous fluid comprise an ionic aqueous solution of charge-stabilized oxygen-containing nanostructures substantially having an average diameter of less than about 100 nanometers and stably configured in the ionic aqueous fluid in an amount sufficient to provide, upon contact of a living cell by the fluid, modulation of at least one of cellular membrane potential and cellular membrane conductivity.

In particular aspects, electrokinetically-generated fluids refers to fluids generated in the presence of hydrodynamically-induced, localized (e.g., non-uniform with respect to the overall fluid volume) electrokinetic effects (e.g., voltage/current pulses), such as device feature-localized effects as described herein. In particular aspects said hydrodynamically-induced, localized electrokinetic effects are in combination with surface-related double layer and/or streaming current effects as disclosed and discussed herein.

In particular aspects, the electrokinetically altered aqueous fluids are suitable to modulate $^{13}$C-NMR line-widths of reporter solutes (e.g., Trehelose) dissolved therein. NMR line-width effects are in indirect method of measuring, for example, solute 'tumbling' in a test fluid as described herein in particular working Examples.

In particular aspects, the electrokinetically altered aqueous fluids are characterized by at least one of: distinctive square wave voltametry peak differences at any one of −0.14V, −0.47V, −1.02V and −1.36V; polarographic peaks at −0.9 volts; and an absence of polarographic peaks at −0.19 and −0.3 volts, which are unique to the electrokinetically generated fluids as disclosed herein in particular working Examples.

In particular aspects, the electrokinetically altered aqueous fluids are suitable to alter cellular membrane conductivity (e.g., a voltage-dependent contribution of the whole-cell conductance as measure in patch clamp studies disclosed herein).

In particular aspects, the electrokinetically altered aqueous fluids are oxygenated, wherein the oxygen in the fluid is present in an amount of at least 15, ppm, at least 25 ppm, at least 30 ppm, at least 40 ppm, at least 50 ppm, or at least 60 ppm dissolved oxygen at atmospheric pressure. In particular aspects, the electrokinetically altered aqueous fluids have less than 15 ppm, less that 10 ppm of dissolved oxygen at atmospheric pressure, or approximately ambient oxygen levels.

In particular aspects, the electrokinetically altered aqueous fluids are oxygenated, wherein the oxygen in the fluid is present in an amount between approximately 8 ppm and approximately 15 ppm, and in this case is sometimes referred to herein as "Solas."

In particular aspects, the electrokinetically altered aqueous fluid comprises at least one of solvated electrons (e.g., stabilized by molecular oxygen), and electrokinetically modified and/or charged oxygen species, and wherein in certain embodiments the solvated electrons and/or electrokinetically modified or charged oxygen species are present in an amount of at least 0.01 ppm, at least 0.1 ppm, at least 0.5 ppm, at least 1 ppm, at least 3 ppm, at least 5 ppm, at least 7 ppm, at least 10 ppm, at least 15 ppm, or at least 20 ppm.

In particular aspects, the electrokinetically altered aqueous fluids are suitable to alter cellular membrane structure or function (e.g., altering of a conformation, ligand binding activity, or a catalytic activity of a membrane associated protein) sufficient to provide for modulation of intracellular signal transduction, wherein in particular aspects, the membrane associated protein comprises at least one selected from the group consisting of receptors, transmembrane receptors (e.g., G-Protein Coupled Receptor (GPCR), TSLP receptor, beta 2 adrenergic receptor, bradykinin receptor, etc.), ion channel proteins, intracellular attachment proteins, cellular adhesion proteins, and integrins. In certain aspects, the effected G-Protein Coupled Receptor (GPCR) interacts with a G protein a subunit (e.g., $G\alpha_s$, $G\alpha_i$, $G\alpha_q$, and $G\alpha_{12}$).

In particular aspects, the electrokinetically altered aqueous fluids are suitable to modulate intracellular signal transduction, comprising modulation of a calcium dependent cellular messaging pathway or system (e.g., modulation of phospholipase C activity, or modulation of adenylate cyclase (AC) activity).

In particular aspects, the electrokinetically altered aqueous fluids are characterized by various biological activities (e.g., regulation of cytokines, receptors, enzymes and other proteins and intracellular signaling pathways) described in the working Examples and elsewhere herein.

In particular aspects, the electrokinetically altered aqueous fluids display synergy with metformin as shown in working Examples herein.

In particular aspects, the electrokinetically altered aqueous fluids reduce DEP-induced TSLP receptor expression in bronchial epithelial cells (BEC) as shown in working Examples herein.

In particular aspects, the electrokinetically altered aqueous fluids inhibit the DEP-induced cell surface-bound MMP9 levels in bronchial epithelial cells (BEC) as shown in working Examples herein.

In particular aspects, the biological effects of the electrokinetically altered aqueous fluids are inhibited by *diphtheria* toxin, indicating that beta blockade, GPCR blockade and Ca channel blockade affects the activity of the electrokinetically altered aqueous fluids (e.g., on regulatory T cell function) as shown in working Examples herein.

In particular aspects, the physical and biological effects (e.g., the ability to alter cellular membrane structure or function sufficient to provide for modulation of intracellular signal transduction) of the electrokinetically altered aqueous fluids persists for at least two, at least three, at least four, at least five, at least 6 months, or longer periods, in a closed container (e.g., closed gas-tight container).

Inventive Gas-Enriched Fluids and Solutions:

Diffusing or enriching a fluid with another fluid may result in a solution or suspension of the two fluids. In particular, enriching a liquid with a gas (e.g., oxygen) may be beneficial for certain applications, including therapeutic treatments. As utilized herein, "fluid," may generally refer to a liquid, a gas, a vapor, a mixture of liquids and/or gases, or any combination thereof, for any particular disclosed embodiment.

Furthermore, in certain embodiments a "liquid" may generally refer to a pure liquid or may refer to a gel, sol, emulsion, fluid, colloid, dispersion, or mixture, as well as any combination thereof; any of which may vary in viscosity.

In particular preferred embodiments, the dissolved gas comprises oxygen. In other particular embodiments, the dissolved gas comprises nitric oxide. In other particular embodiments, the gas comprises ambient air.

There are several art-recognized methods of gas-enriching fluids (such as oxygenating water). For example, a turbine aeration system can release air near a set of rotating blades of an impeller, which mixes the air or oxygen with the water, or water can be sprayed into the air to increase its oxygen content. Additionally, other systems on the market inject air or oxygen into the water and subject the water/gas to a large scale vortex. Naturally occurring levels of oxygen in water are typically no more than 10 ppm (parts per million), which is considered to be a level of 100% dissolved oxygen. Tests on certain devices have shown that under ideal conditions, the device can attain upwards of approximately 20 ppm, or twice the natural oxygen levels of water. In certain embodiments, the oxygen level may be even higher.

Particular embodiments provided herein relate to a diffuser-processed therapeutic fluid as defined herein, comprising: a fluid host material; an infusion material diffused into the host material; and optionally, at least one therapeutic agent dispersed in the host material, wherein the infusion material comprises oxygen micro-bubbles in the host fluid, wherein the majority of the micro-bubbles are less than 0.2 microns, or preferably less than 0.1 microns in size. In certain embodiments, the dissolved oxygen level in the infused fluid host material may be maintained at greater than about 30 ppm at atmospheric pressure for at least 13 hours. In other particular embodiments, the dissolved oxygen level in the infused fluid host material may be maintained at greater than 40 ppm at atmospheric pressure for at least 3 hours.

In additional embodiments, the infused fluid host material further comprises a saline solution. In further embodiments, the infused fluid host material maintains a dissolved oxygen level of at least about 20 ppm to about 40 ppm for a period of at least 100 days, preferably at least 365 days within a sealed container at atmospheric pressure. In certain embodiments, the infused fluid host material may have a dissolved oxygen level of at least 50 ppm at atmospheric pressure.

In certain embodiments, the infused fluid host material exhibits Rayleigh scattering for a laser beam shining therethrough for a selected period of time after the oxygen has been diffused into therein.

Table 1 illustrates various partial pressure measurements taken in a healing wound treated with an oxygen-enriched saline solution and in samples of the gas-enriched oxygen-enriched saline solution of the present invention.

TABLE 1

TISSUE OXYGEN MEASUREMENTS
Probe Z082BO
In air: 171 mmHg 23° C.

| Column | Partial Pressure (mmHg) |
|---|---|
| B1 | 32-36 |
| B2 | 169-200 |
| B3 | 20-180* |
| B4 | 40-60 |

*wound depth minimal, majority >150, occasional 20 s

In certain embodiments disclosed herein, a gas-enriched fluid of the present invention provides a cosmetic and/or therapeutic wound care benefit. Certain embodiments disclosed herein relate to a cosmetic and/or therapeutic composition comprising a gas-enriched fluid of the present invention, and optionally at least one additional therapeutic agent, such as a pharmaceutical drug, a metal, a peptide, a polypeptide, a protein, a nucleotide, a carbohydrate or glycosylated protein, a fat (including oils or waxes), or other agent that prevents or alleviates at least one symptom of a condition or disease associated with wounds or wound healing.

Compositions and methods are disclosed for treating a wound in any particular organ and/or tissues in need thereof by administering an effective amount of a composition comprising a gas-enriched fluid. As used herein, "treat," "treating," "treatment," and any and all derivations thereof refer to using the compositions of the present invention either prophylactically to conditions or diseases related to wounds and/or wound healing, or cosmetically or therapeutically to ameliorate an existing condition or disease related to improper wound healing, or to increase proper wound healing. In one particular embodiment, the gas-enriched fluid of the present invention inhibits microbial growth. In another particular embodiment, the gas-enriched fluid of the present invention promotes apoptosis.

Microbial infections, particularly of *Staphlycoccus, Streptococcus, yeast, Serratia, E. coli, Pseudomonas aeruginosa,* and other microbial infections, can cause devastating infections in wounds. Thus, in certain embodiments, the gas-enriched fluid compositions and/or methods of the present invention include anti-microbial agents, such as antifungal, antibiotic, or other anti-microbial agents. Some examples of anti-microbial agents that may be utilized with the gas-enriched fluid compositions and/or methods include, but are not limited to, amikacin, gentamicin, kanamycin, neomycin, netilmicin, streptomycin, tobramycin, paromomycin, geldanamycin, herimycin, loracarbef, ertapenem, imipenem/cilastatin, meropenem, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, peperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, tinidazole, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, teronazole, terbinafine, amorolfine, naftifine, butenafine, anidulafungin, caspofungin, micafungin, ciclopirox, flucytosine, griseofulvin, Gentian violet, haloprogin, tolnaftate, undecylenic acid, and others.

In some embodiments, the composition further comprises an inert and physiologically-acceptable carrier or diluent, enzymes, anti-microbial agents (anti-bacterial agents, anti-fungal agents, etc.), vasoconstrictors (such as epinephrine, naphazoline hydrochloride, tetrahydrozoline, etc.), acids (such as boric acid, hydrochloric acid, etc.), bases (such as sodium hydroxide, etc.), salts (such as sodium, potassium, calcium, etc.), polymers, alcohols (such as polyvinyl alcohol), cellulose or starch, dextrose, mannose, sucrose, or other carbohydrates; glycoproteins, proteins, polypeptides or peptides, colors, fragrances, preservatives (such as edentate disodium, chlorhexidine gluconate, etc.), or a mixture thereof. In other related embodiments, the composition further comprises an active pharmaceutical drug or therapeutic drug substance or an active cosmetic substance. In one particular embodiment, the pharmaceutical or therapeutic drug comprises an antihistamine, such as pheniramine maleate.

Gas-enriched fluids produced in accordance with the disclosed invention may also be used to decontaminate or wash away contaminants from a tissue, intact and/or ex vivo. In certain embodiments, higher levels of gas (e.g., oxygen) in the fluid (e.g., water) may provide for additional benefits when cleaning and/or decontaminating wounds.

Particular embodiments provided herein relate to a diffuser-processed gas-enriched fluid as defined herein, comprising: a fluid host material; an infusion material diffused into the host material; and optionally, at least one cosmetic and/or therapeutic agent dispersed in the host material. In certain embodiments, the infusion material comprises oxygen micro-bubbles in the host fluid, wherein the majority of the micro-bubbles are less than 0.2 microns, or preferably less than 0.1 microns in size.

In certain embodiments, the dissolved oxygen level in the infused fluid host material may be maintained at greater than 30 parts per million at atmospheric pressure for at least 13 hours. In other particular embodiments, the dissolved oxygen level in the infused fluid host material may be maintained at greater than 40 ppm at atmospheric pressure for at least 3 hours. In further embodiments, the infused fluid host material maintains a dissolved oxygen level of at least 20 ppm for a period of at least 100 days, preferably 365 days within a sealed container at atmospheric pressure. In certain embodiments, the infused fluid host material may have a dissolved oxygen level of at least 50 parts per million at atmospheric pressure.

In certain embodiments, the infused fluid host material exhibits Rayleigh scattering for a laser beam shining therethrough for a selected period of time after the oxygen has been diffused therein.

By using the diffuser device described herein with respect to exemplary embodiments illustrated in the corresponding figures, an output fluid may be achieved having a gas diffused therein that has a number of characteristics and provides a number of advantages for use as a therapeutic composition. Solutions have been created using freshwater, saline, distilled, deionized, double distilled, and/or double distilled deionized water, oxygen, nitrogen and other components. Experiments have indicated that oxygen bubbles produced within saline solution are generally no greater than approximately 0.1 micron in size.

Wound Healing Activity of the Inventive Gas-Enriched Fluids and Solutions:

According to certain aspects of the present invention, the gas-enriched fluids and/or solutions disclosed herein have anti-inflammatory properties and effects, and can be used as anti-inflammatory agents for the treatment of subjects afflicted by diseases or disorders relating to inflammation. FIG. 38 shows the experimental results of cytokine profiles in stimulated lymphocytes from a healthy blood donor. As can be seen in FIG. 38, the inventive oxygen-enriched fluid (water) affected a down regulation of particular cytokines, especially IL-6, IL-8, and IL-1 β.

Increased production of pro-inflammatory cytokines has been implicated in the pathogenesis of numerous inflammatory and autoimmune diseases. Secretion of TNFα is a primary event in the initiation of the inflammatory cascade (Brennan F. M., et. al. *Lancet,* 1989, 2:244-7; Haworth C, et. al. *Eur. J. Immunol.* 1991, 21:2575-2579) and directly contributes to the initiation and maintenance of inflammatory and autoimmune diseases. Other pro-inflammatory cytokines also play a role, including interleukin 1β (IL-1β), IL-6, IL-8, IL-12 nitric oxide, IFN-γ and GM-CSF, while anti-inflammatory cytokines such as IL-10 may reduce disease. Cells of the immune system, macrophages in particular, secrete many of these cytokines in response to activating stimuli.

A variety of cell types are involved in the inflammatory process. Overproduction of TNFα by monocytes, macrophages and other immune cells is a key element in the pathogenesis of a multitude of diseases. Macrophages and T-cells in particular play a central role in the initiation and maintenance of the immune response. Once activated by pathological or immunogenic stimuli, macrophages respond by releasing a host of cytokines, including TNF-α, IL-1β, IL-8, IL-12, nitric oxide (NO), IL-6, GM-CSF, G-CSF, M-CSF and others. T-cells release IL-2, IL-4, INF-γ, and other inflammatory cytokines. These cytokines activate other immune cells and some can also act as independent cytotoxic agents. Excessive release of macrophage and T-cell derived inflammatory mediators can particularly lead to damage of normal cells and surrounding tissues.

Pro-inflammatory cytokines have been implicated in HIV-AIDS, and other viral infections including the cytomegalovirus, influenza virus and the herpes family of viruses. TNFα enhances the basal activity of the major immediate early enhancer/promoter of human cytomegalovirus and may play a role in reactivation of latent HCMV infection in premonocytic cells (Prosch S., et. al. *Virology* 1995, 208:197-206).

Additionally, a number of inflammatory cytokines contribute to mortality in patients suffering from sepsis or endotoxic shock. For example, TNFα and IL-1β have a well-established central role in sepsis, septic shock and endotoxic shock. Increased levels of these cytokines are associated with fever, hypotension and shock (Smith J. W. et. al. *J. Clin. Oncol.* 1992, 10:1141-1152; Chapman P. B., et. al. *J. Clin. Oncol.* 1987, 5:1942-1951) together with the induction of gene expression for phospholipase A2 (Gronich J., et. al. *J. Clin. Invest.* 1994, 93:1224-1233) and NO synthase.

The induction of NO from smooth muscle cells mediates decreased mean arterial pressure and systemic vascular resistance during septic shock, suggesting a fundamental role for NO. Thus, therapies that target downregulatory effects on IL-8, IL-1β, and NO could be beneficial in the treatment of inflammatory diseases or disorders, including sepsis, septic shock, and endotoxic shock.

Overproduction of TNFα contributes to the clinical features of numerous autoimmune diseases such as diabetes and rheumatoid arthritis. Systemic lupus erythematosus (SLE) is also precipitated by increased IL-1β and TNFα levels. Within lupus patients, serum C-reactive protein, IL-1.beta and TNFα levels were higher than in controls, suggesting that an increased inflammatory response plays a role in the disease (Liou L. B. *Clin. Exp. Rheumatol.* 2001, 19:515-523). A study of patients with one form of SLE, neuropsychiatric lupus erythematosus (NPLE), showed that the number of peripheral blood mononuclear cells expressing mRNA for TNFα as well as the cerebrospinal fluid level of NO metabolites correlated with NPLE disease severity (Svenungsson E., et al. *Ann. Rheum. Dis.* 2001, 60:372-9).

IL-1 and TNFα play a central role in various acute as well as chronic responses in animal models. Additionally, IL-11, IFNα and IFNβ may also up-regulate inflammatory reactions. Conversely, several cytokines may be involved in down-regulation of inflammatory responses (i.e. IL-4, IL-10, IL-13, among others). As set forth in Example 1, cells contacted with the inventive gas-enriched fluid showed an increase in IFN-γ levels with T3 antigen than in the control culture media with T3 antigen, while IL-8 was lower in the inventive gas-enriched culture media with T3 antigen than in the control culture media with T3 antigen. Additionally, IL-6, IL-8, and TNF-α levels were lower in the inventive gas-enriched media with PHA, than in the control media with PHA, while IL-1β levels were lower in the inventive gas-enriched fluid with PHA when compared with control media with PHA. In the inventive gas-enriched media alone, IFN-γ levels were higher than in control media. These results are consistent with an anti-inflammatory microenvironment.

NO is recognized as a mediator and regulator of inflammatory responses. It possesses cytotoxic properties toward pathogens, but can also have deleterious effects on the subject's own tissues. (Korhonen et al., *Curr Drug Targets Inflamm Allergy* 4(4): 471-9, 2005). NO reacts with soluble guanylate cyclase to form cyclic guanosine monophosphate (cGMP), which mediates many of the effects of NO. NO can also interact with molecular oxygen and superoxide anion to produce reactive oxygen species that can modify various cellular functions. These indirect effects of NO have a significant role in inflammation, where NO is produced in high amounts by inducible NO synthase (iNOS) and reactive oxygen species are synthesized by activated inflammatory cells.

NO can be produced by keratinocytes, fibroblasts, endothelial cells, and possibly others. Some of the vascular actions of NO include vasodilation, inhibiting platelet adhesion to the vascular endothelium, inhibiting leukocyte adhesion to the vascular endothelium, and scavenging superoxides. (Shah et al., *Env. Health Persp. v.* 106 (5): 1139-1143.)

Furthermore, inhibition of NO synthesis has been shown to delay wound contraction, alter collagen organization, and alter neoepidermis thickness. (Amadeu and Costa, *J. Cutan. Pathol.* 33: 465-473, 2006.) Mast cell migration and angiogenesis in wounds is also affected by inhibition of NO. (Id.) Without being bound to any particular theory of mechanism, in certain embodiments the inventive gas-enriched fluids may be modulating localized and/or cellular NO production, or degradation, consistent with the spectrum of wound healing effects illustrated in the Examples section disclosed herein. Due to variable pathways of regulation, in certain embodiments, the inventive gas-enriched fluid may increase NO production and/or retard NO degradation, whereas in other certain embodiments, the inventive gas-enriched fluid may decrease NO production and/or hasten NO degradation.

Specifically, wounds treated with oxygen-enriched saline solution showed an increase in wound healing at days 4 through 11, and between days 3 and 11, the new epidermis in wounds treated with the oxygen-enriched saline solution migrated at two to four times as fast as the epidermis of the wounds treated with the normal saline solution, as set forth in Example 8 herein. The study also showed that between 15 and 22 days, wounds treated by the oxygen-enriched saline solution differentiated at a more rapid rate as evidenced by the earlier formation of more mature epidermal layers. At all stages, the thickening that occurs in the epidermis associated with normal healing did not occur within the wounds treated by the oxygen-enriched saline solution.

Thus, in accordance with this spectrum of wound healing effects, but without wishing to be bound by any particular theory, it is believed that the oxygen-enriched saline solution may modulate the localized and/or cellular level of NO within the wounds. NO modulates growth factors, collagen deposition, inflammation, mast cell migration, epidermal thickening, and neovascularization in wound healing. Furthermore, nitric oxide is produced by an inducible enzyme that is regulated by oxygen.

In the case of mast cell migration, differences also occurred in early and late migration for the oxygen-enriched solution. This is consistent with what is known in the art regarding inhibition of NO synthesis (Amadeu and Costa, *J. Cutan Pathol* 33: 465-473, 2006).

Referring now to FIG. 41A through 41F, various illustrations compare the wound healing results of the porcine epidermal tissues with or without oxygen-enriched saline solution. As can be seen, the healing of the control wound and of the wound using the oxygen-enriched saline solution was followed for days 1, 4 and 16.

Figure 41A:
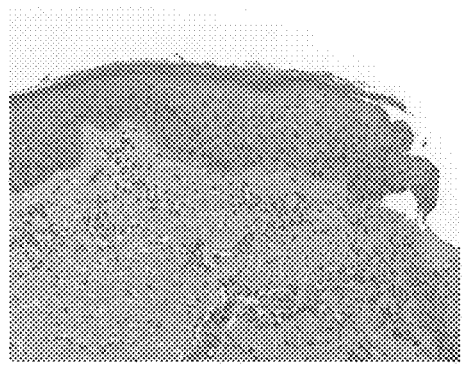
FIGS. 41A through 41F show histological cross-sections of dermal and epidermal in vivo wound healing.
Figure 41B:

FIG. 41A illustrates the wound healing for the control wound on day 1. As can be seen, the wound shows epidermal/dermal thickening and a loss of contour. FIG. 41B illustrates the wound healing on day 1 for the wound treated using the oxygen-enriched saline solution. The wound shows normal epidermal/dermal thickness and normal contouring is typical on a new wound.

Figure 41C:
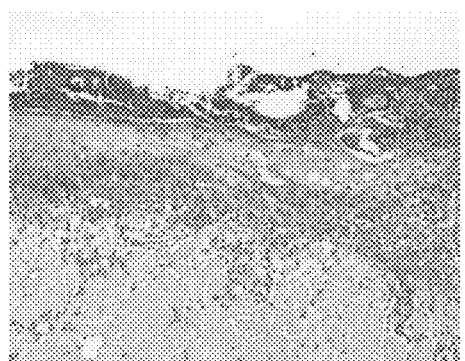
Figure 41D:
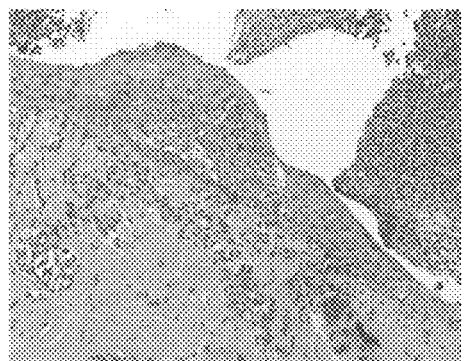

Referring now to FIGS. 41C and 41D, there are illustrated the wound healing for the control wound on day 4 and the wound healing for the wound treated with the oxygen-enriched saline solution on day 4. For the control wound illustrated in FIG. 41C, the wound shows a 600 micron epidermal spur. In the wound treated with the oxygen-enriched saline solution in FIG. 41D, there is illustrated a 1200 micron epidermal spur. Thus, in the first 4 days of the experiment, the epidermal spur created in the wound treated using the oxygen-enriched saline solution shows an epidermal growth rate of twice of that of the wound that was not treated with the oxygen-enriched saline solution.

Figure 41E:
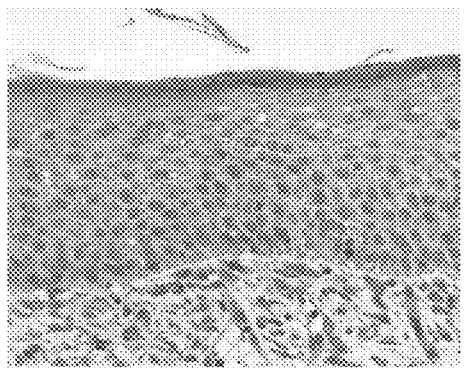
Figure 41F:
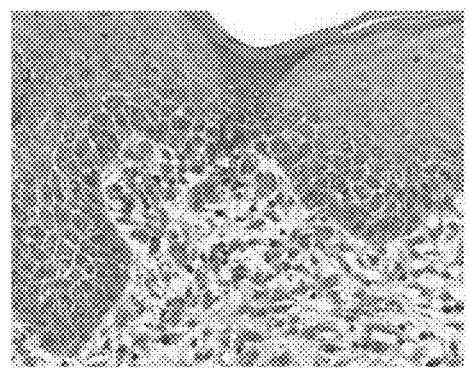
Figure 42:
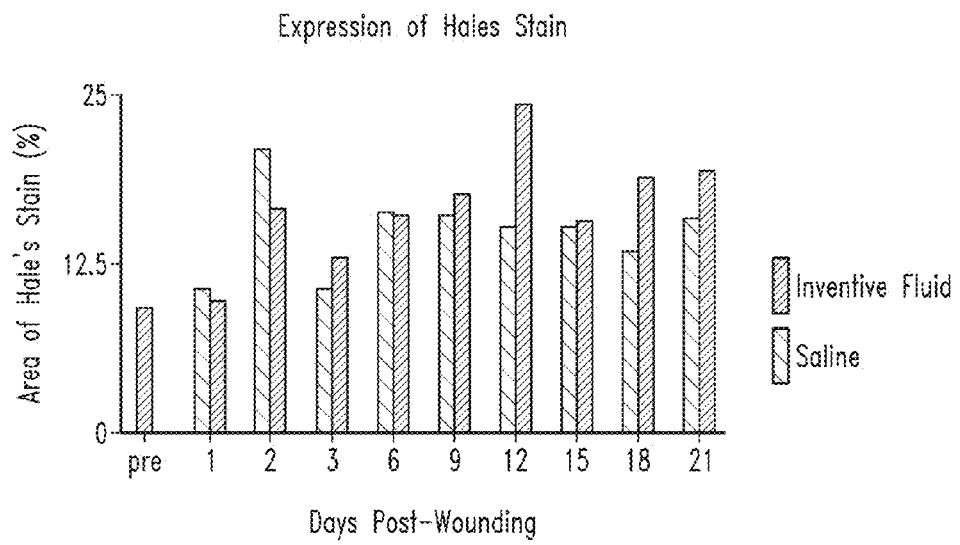
FIG. 42 illustrates the expression of Hale's stain in treated and control healing wounds, used to detect acid mucopolysaccharides, such as hyaluronic acid.
Figure 43:
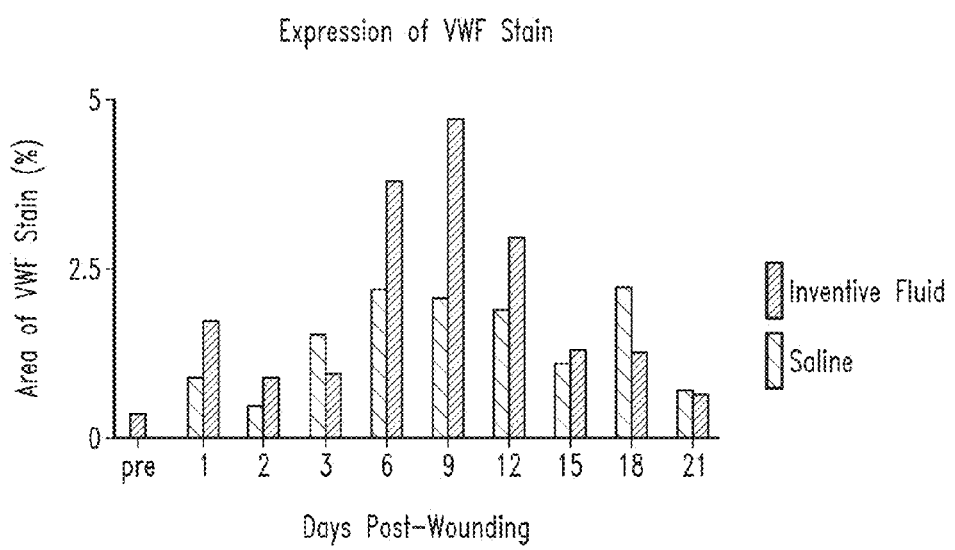
FIG. 43 illustrates the expression of von Willebrand's Factor stain used to detect angiogenesis in treated and control healing wounds.

Referring now to FIG. 41E, there is illustrated the control wound at day 16. The wound shows less differentiated epidermis with loss of epidermal/dermal contour than that illustrated by the wound treated with the oxygen-enriched saline solution illustrated in FIG. 41F. FIG. 41F shows more differentiated epidermis and more normal epidermal/dermal contouring in the wound.

In the first two phases of the inflammatory process, the foreign body is either destroyed, for example, if the foreign body is an organism, or the tissue around it is loosened, for example, if it is a splinter. In the healing phase, the inflammation begins to subside; individual blood vessels and vascular patterns become normal once again; and repair of the wound commences. The three main events in the repair process are (1) formation of new connective tissue by proliferating fibroblasts; (2) regeneration of epithelium; and (3) outgrowth of new capillaries.

Even before the inflammation subsides, fibroblasts begin moving into the injured area from the surrounding normal tissue, where they usually exist in a dormant state. They migrate by an amoeboid movement along strands of fibrin and distribute themselves throughout the healing area. Once fixed into position in the injured tissue, they begin to synthesize collagen and secrete this protein, which arranges itself into fibers. The fibers orient themselves with their longitudinal axes in the direction of the greatest stress. As the collagen bundles grow in firmness, the fibroblasts gradually degenerate and attach closely to the bundles, and the injured area transforms into scar tissue.

Simultaneously with scar tissue formation, the intact epidermal cells on the edge of the wound begin to proliferate and move, as one sheet, toward the center of the injured area. As the inflammation subsides, a need for a direct supply of blood arises, and angiogenesis occurs at the wound site.

Inflammation is a complex process that involves multiple cell types. For example, mast cells release mediators that trigger an early phase of vasodilation, accompanied by the separation of endothelial cells and exposure of collagen fibers in the subendothelial layer. Fibers in the intercellular gaps that form in blood vessels trap platelets and trigger the release of mediators from these cells.

In addition to platelets, the exposed collagen fibers also interact with proteins of the plasma that filter through the pores of the dilated vessel wall, including the triggering factor of the blood-clotting cascade, increased vasodilation, increased blood vessel permeability, and chemotaxis.

Additionally, the complement cascade can be activated by several stimuli: the injured blood vessels, the proteolytic enzymes released by the damaged cells, the membrane components of any participating bacteria, and antigen-antibody complexes. Some of the activated complement components act as chemotactic factors, responsible for the influx of leukocytes into the inflamed area, while others facilitate phagocytosis and participate in cell lysis.

In addition, it is believed that the inventive gas-enriched fluids or solutions may also regulate at least one cytokine involved in at least one aspect of inflammation, the cytokine(s) including, but not limited to MAF (macrophage activating factor), MMIF (macrophage migration inhibition factor), MCF (macrophage chemotactic factor), LMIF (leukocyte migration inhibition factor), HRFs (histamine releasing factors), TF (transfer factors), interleukins (IL-1, IL-2, IL-3, IL-4, IL-5, IL-6, IL-7, IL-8, IL-9, IL-10, IL-11, IL-12, IL-13, IL-14, IL-15, etc.), TNF-$\alpha$, TNF-$\beta$, interferons (IFN-$\alpha$, IFN-$\beta$, IFN-$\gamma$, IFN-$\zeta$, IFN-$\delta$, etc.), G-CSF (granulocyte colony stimulating factor), GM-CSF (granulocyte-macrophage CSF), M-CSF (macrophage CSF), multi-CSF (IL-3), fibroblast growth factor (aFGF, bFGF), EGF (epidermal growth factor), NGF (nerve growth factor), PDGF (platelet-derived growth factor), VEGF (vascular endothelial growth factor), transforming growth factors (TGF-$\alpha$, TGF-$\beta$, etc.), NAP-2 (neutrophil-activating protein 2), PF-4 (platelet factor 4), thromboglobulin, MCP-1 (monocyte chemoattractant protein 1), MCP-3, MIP-1$\alpha$, MIP-1$\beta$-+ (macrophage inflammatory proteins), RANTES (regulated upon activation normal T expressed and presumably secreted chemokine), HSPs (heat shock proteins), GRPs (glucose-regulated proteins), ubiquitin, and others.

Thus, in certain embodiments, the gas-enriched fluids and/or therapeutic compositions may increase production and/or secretion of anti-inflammatory molecules or cytokines or decrease the degradation of anti-inflammatory molecules or cytokines, thereby alleviating or preventing at least one symptom of inflammation. In other embodiments, the gas-enriched fluids and/or therapeutic compositions of the present invention may decrease production and/or secretion of pro-inflammatory molecules or cytokines or increase the degradation of pro-inflammatory molecules or cytokines, thereby alleviating or preventing at least one symptom of inflammation.

Previous studies had shown a critical role of anti-MOG antibodies in augmentation of demyelination and worsening of EAE (experimental autoimmune encephalomyelitis), an animal model system for the human autoimmune disorder of rheumatoid arthritis. (Linington, et al. 1992. *J. Neuroimmunol.* 40:219-224). Additionally, antibodies against MOG have been implicated in the pathogenesis of multiple sclerosis. (Berger et al. *N. Engl. J. Med.* 2003 Jul. 10; 349(2):139-45).

Figure 48:
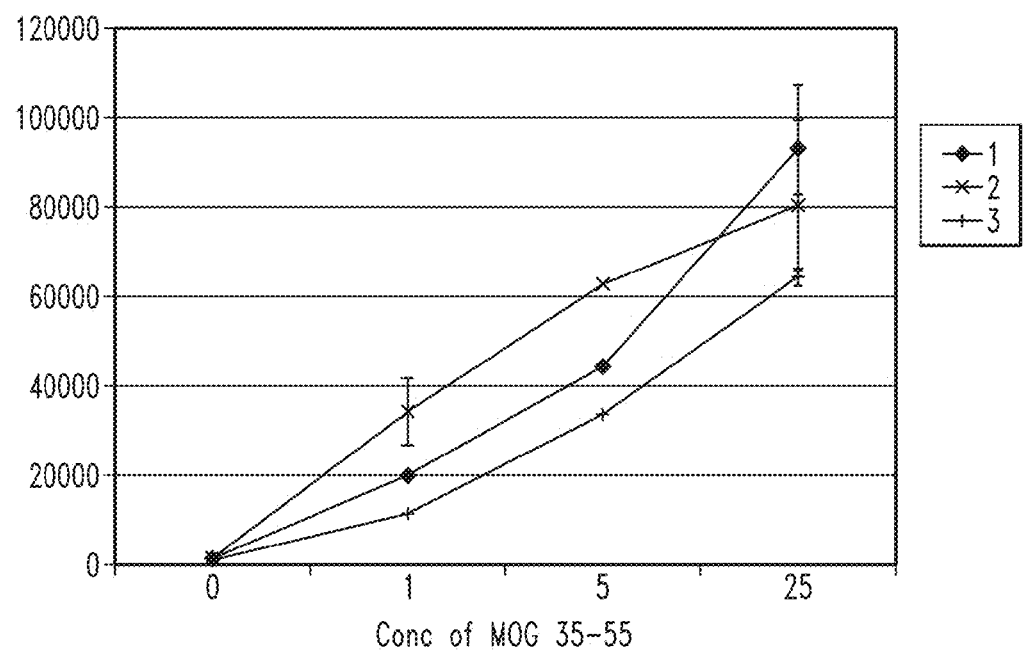
FIG. 48 illustrates the results of contacting splenocytes with MOG in the presence of pressurized pot oxygenated fluid (1), inventive gas-enriched fluid (2), or control deionized fluid (3).

As set forth in FIG. 48 and Example 12, the inventive gas-enriched fluid of the present invention amplifies the lymphocyte response to an antigen for which an animal was previously primed. As indicated in FIG. 48, lymphocyte proliferation was greater for response to MOG challenge when cultured in fluid reconstituted with the inventive gas-enriched fluid comprising solvated electrons, when compared with pressurized, oxygenated fluid (pressure pot) or control deionized fluid.

Bubble Size Measurements

Experimentation was performed to determine a size of the bubbles of gas diffused within the fluid by the mixing device 100. While experiments were not performed to measure directly the size of the bubbles, experiments were performed that established that the bubble size of the majority of the gas bubbles within the fluid was smaller than 0.1 microns. In other words, the experiments determined a size threshold value below which the sizes of the majority of bubbles fall.

This size threshold value or size limit was established by passing the output material 102 formed by processing a fluid and a gas in the mixing device 100 through a 0.22 filter and a 0.1 micron filter. In performing these tests, a volume of the first material 110, in this case, a fluid, and a volume of the second material 120, in this case, a gas, were passed through the mixing device 100 to generate a volume of the output material 102 (i.e., a fluid having a gas diffused therein). Sixty milliliters of the output material 102 was drained into a 60 ml syringe. The DO level of the fluid within the syringe was then measured using an Orion 862a. The Orion 862a is capable of measuring DO levels within a fluid. The fluid within the syringe was injected through a 0.22 micron filter into a 50 ml beaker. The filter comprised the Milipor Millex GP50 filter. The DO level of the material in the 50 ml beaker was then measured. The experiment was performed three times to achieve the results illustrated in Table 2 below.

TABLE 2

| DO levels | |
| --- | --- |
| DO IN SYRINGE | DO AFTER 0.22 MICRON FILTER |
| 42.1 ppm | 39.7 ppm |
| 43.4 ppm | 42.0 ppm |
| 43.5 ppm | 39.5 ppm |

As can be seen, the DO levels measured within the syringe and the DO levels measured within the 50 ml beaker were not changed drastically by passing the output material 102 through the 0.22 micron filter. The implication of this experiment is that the bubbles of dissolved gas within the output material 102 are not larger than 0.22 microns otherwise there would be a significantly greater reduction in the DO levels in the output material 102 passed through the 0.22 micron filter.

A second test was performed in which the 0.1 micron filter was substituted for the 0.22 micron filter. In this experiment, saline solution was processed with oxygen in the mixing device 100 and a sample of the output material 102 was collected in an unfiltered state. The DO level of the unfiltered sample was 44.7 ppm. The output material 102 was filtered using the 0.1 micron filter and two additional samples were collected. The DO level of the first sample was 43.4 ppm. The DO level of the second sample was 41.4 ppm. Then, the filter was removed and a final sample was taken from the unfiltered output material 102. The final sample had a DO level of 45.4 ppm. These results were consistent with those seen using the Millipore 0.2 micron filter. These results lead to the conclusion that there is a trivial reduction in the DO levels of the output material 102 passed through the 0.1 micron filter providing an indication that the majority of the bubbles in the processed saline solution are no greater than 0.1 micron in size.

As appreciated in the art, the double-layer (interfacial) (DL) appears on the surface of an object when it is placed into a liquid. This object, for example, might be that of a solid surface (e.g., rotor and stator surfaces), solid particles, gas bubbles, liquid droplets, or porous body. In the mixing device 100, bubble surfaces represent a significant portion of the total surface area present within the mixing chamber that may be available for electrokinetic double-layer effects. Therefore, in addition to the surface area and retention time aspects discussed elsewhere herein, the relatively small bubble sizes generated within the mixer 100 compared to prior art devices 10, may also contribute, at least to some extent, to the overall electrokinetic effects and output fluid properties disclosed herein. Specifically, in preferred embodiments, as illustrated by the mixer 100, all of the gas is being introduced via apertures on the rotor (no gas is being introduced through stator apertures. Because the rotor is rotating at a high rate (e.g., 3,400 rpm) generating substantial shear forces at and near the rotor surface, the bubble size of bubbles introduced via, and adjacent to the spinning rotor surface apertures would be expected to be substantially (e.g., 2 to 3-times smaller) smaller than those introduced via and near the stationary stator. The average bubble size of the prior art device 10 may, therefore, be substantially larger because at least half of the gas is introduced into the mixing chamber from the stationary stator apertures. Because the surface area of a sphere surface varies with $r^2$, any such bubble component of the electrokinetic surface area of the mixing device 100 may be substantially greater than that of the prior art diffusion device 10.

Compositions Comprising Hydrated (Solvated) Electrons Imparted to the Inventive Compositions by the Inventive Processes:

In certain embodiments as described herein (see under "Double-layer"), the gas-enriched fluid is generated by the disclosed electromechanical processes in which molecular oxygen is diffused or mixed into the fluid and may operate to stabilize charges (e.g., hydrated (solvated) electrons) imparted to the fluid. Without being bound by theory or mechanism, certain embodiments of the present invention relate to a oxygen-enriched fluid (output material) comprising charges (e.g., hydrated (solvated) electrons) that are added to the materials as the first material is mixed with oxygen in the inventive mixer device to provide the combined output material. According to particular aspects, these hydrated (solvated) electrons (alternately referred to herein as 'solvated electrons') are stabilized in the inventive solutions as evidenced by the persistence of assayable effects mediated by these hydrated (solvated) electrons. Certain embodiments may relate to hydrated (solvated) electrons and/or water-electron structures, clusters, etc. (See, for example, Lee and Lee, *Bull. Kor. Chem. Soc.* 2003, v. 24, 6; 802-804; 2003).

*Horseradish peroxidase* (HRP) effects. *Horseradish peroxidase* (HRP) is isolated from horseradish roots (*Amoracia rusticana*) and belongs to the ferroprotoporphyrin group (Heme group) of peroxidases. HRP readily combines with hydrogen peroxide or other hydrogen donors to oxidize the pyrogallol substrate. Additionally, as recognized in the art, HRP facilitates auto-oxidative degradation of indole-3-acetic acid in the absence of hydrogen peroxide (see, e.g., Heme Peroxidases, H. Brian Dunford, Wiley-VCH, 1999, Chapter 6, pages 112-123, describing that auto-oxidation involves a highly efficient branched-chain mechanism; incorporated herein by reference in its entirety). The HRP reaction can be measured in enzymatic activity units, in which Specific activity is expressed in terms of pyrogallol units. One pyrogallol unit will form 1.0 mg purpurogallin from pyrogallol in 20 sec at pH 6.0 at 20° C. This purpurogallin (20 sec) unit is equivalent to approx. 18 µM units per min at 25° C.

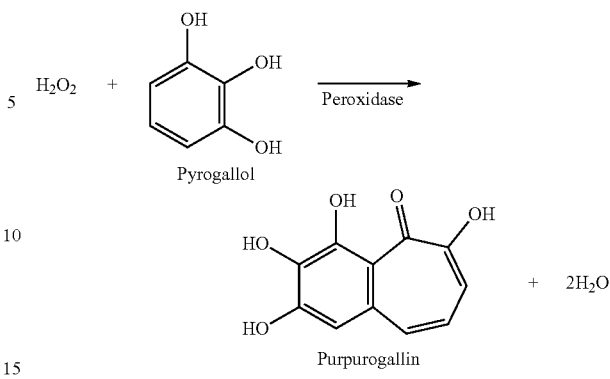

It is known that *Horseradish peroxidase* enzyme catalyzes the auto-oxidation of pyrogallol by way of facilitating reaction with the molecular oxygen in a fluid. (Khajehpour et al., *PROTEINS: Struct, Funct, Genet.* 53: 656-666 (2003)). It is also known that oxygen binds the heme pocket of *horseradish peroxidase* enzyme through a hydrophobic pore region of the enzyme (between Phe68 and Phe142), whose conformation likely determines the accessibility of oxygen to the interior. According to particular aspects, and without being bound by mechanism, because surface charges on proteins are known in the protein art to influence protein structure, the solvated electrons present in the inventive gas-enriched fluid may act to alter the conformation of the *horseradish peroxidase* such that greater oxygen accessibility may result. The greater accessibility of oxygen to the prosthetic heme pocket of the *horseradish peroxidase* enzyme may in turn allow for increased HRP reactivity, when compared with prior art oxygenated fluids (pressure-pot, fine-bubbled).

In any event, according to particular aspects, production of output material using the inventive methods and devices comprises a process involving: an interfacial double layer that provides a charge gradient; movement of the materials relative to surfaces pulling charge (e.g., electrons) away from the surface by virtue of a triboelectric effect, wherein the flow of material produces a flow of solvated electrons. Moreover, according to additional aspects, and without being bound by mechanism, the orbital structure of diatomic oxygen creates charge imbalances (e.g., the two unpaired electrons affecting the hydrogen bonding of the water) in the hydrogen bonding arrangement within the fluid material (water), wherein electrons are solvated and stabilized within the imbalances.

Several chemical tests of the inventive oxygen-enriched fluid for the presence of hydrogen peroxide were conducted as described below, and none of these tests were positive (sensitivity of 0.1 ppm hydrogen peroxide). Thus, the inventive oxygen-enriched fluid of the instant application contain no, or less than 0.1 ppm hydrogen peroxide.

According to particular aspects, despite the absence of hydrogen peroxide, the inventive combination of oxygen-enrichment and solvated electrons imparted by the double-layer effects and configuration of the presently claimed devices may act to alter the conformation and/or heme group accessibility of the *horseradish peroxidase.*

Glutathione Peroxidase Study:

The inventive oxygen-enriched output fluid material was tested for the presence of hydrogen peroxide by testing the reactivity with glutathione peroxidase using a standard assay (Sigma). Briefly, glutathione peroxidase enzyme cocktail was constituted in deionized water and the appropriate buffers. Water samples were tested by adding the enzyme cocktail and inverting. Continuous spectrophotometric rate determination was made at $A_{340}$ nm, and room temperature (25 degrees Celsius). Samples tested were: 1. deionized water (negative control), 2. inventive oxygen-enriched fluid at low concentration, 3. inventive oxygen-enriched fluid at high concentration, 4. hydrogen peroxide (positive control). The hydrogen peroxide positive control showed a strong reactivity, while none of the other fluids tested reacted with the glutathione.

Device for Generating Gas-Enriched Fluids or Solutions

Description Of The Related Art:

FIG. 1 provides a partial block diagram, partial cross-sectional view of a prior art device 10 for diffusing or emulsifying one or two gaseous or liquid materials ("infusion materials") into another gaseous or liquid material ("host material") reproduced from U.S. Pat. No. 6,386,751, incorporated herein by reference in its entirety. The device 10 includes a housing configured to house a stator 30 and a rotor 12. The stator 30 encompasses the rotor 12. A tubular channel 32 is defined between the rotor 12 and the stator 30. The generally cylindrically shaped rotor 12 has a diameter of about 7.500 inches and a length of about 6.000 inches providing a length to diameter ratio of about 0.8.

The rotor 12 includes a hollow cylinder, generally closed at both ends. A gap exists between each of the first and second ends of the rotor 12 and a portion of the housing 34. A rotating shaft 14 driven by a motor 18 is coupled to the second end of the rotor 12. The first end of the rotor 12 is coupled to an inlet 16. A first infusion material passes through the inlet 16 and into the interior of the rotor 12. The first infusion material passes from the interior of the rotor 12 and into the channel 32 through a plurality of openings 22 formed in the rotor 12.

The stator 30 also has openings 22 formed about its circumference. An inlet 36 passes a second infusion material to an area 35 between the stator 30 and the housing 34. The second infusion material passes out of the area 35 and into the channel 32 through openings 22.

An external pump (not shown) is used to pump the host material into a single inlet port 37. The host material passes through a single inlet port 37 and into the channel 32 where it encounters the first and second infusion materials, which enter the channel 32 through openings 22. The infusion materials may be pressurized at their source to prevent the host material from passing through openings 22.

The inlet port 37, is configured and positioned such that it is located along only a relatively small portion (<about 5%) of the annular inlet channel 32, and is substantially parallel to the axis of rotation of the rotor 12 to impart an axial flow toward a portion of the channel 32 into the host material.

Unfortunately, before entering the tubular channel 32, the host material must travel in tortuous directions other than that of the axial flow (e.g., including in directions substantially orthogonal thereto) and down into and between the gap formed between the first end of the rotor 12 and the housing 34 (i.e., down a portion of the first end of the rotor adjacent to the inlet 16 between the end of the rotor 12 and the housing 34). The non-axial and orthogonal flow, and the presence of the host material in the gap between the first end of the rotor 12 and the housing 34 causes undesirable and unnecessary friction. Further, it is possible for a portion of the host material to become trapped in eddy currents swirling between the first end of the rotor and the housing. Additionally, in the device 10, the host material must negotiate at least two right angles to enter any aspect of the annual of the annular inlet of the tubular channel 32.

A single outlet port 40 is formed in the housing 34. The combined host material and infusion material(s) exit the channel 32 via the outlet 40. The outlet port 40, which is also located along only a limited portion (<about 5%) of the annular outlet of tubular channel 32, is substantially parallel to the axis of rotation of the rotor 12 to impart or allow for an axial flow of the combined materials away from the limited portion of the annular outlet of tubular channel 32 into the outlet port 40. An external pump 42 is used to pump the exiting fluid through the outlet port 40.

Unfortunately, before exiting the channel 32, a substantial portion of the exiting material must travel in a tortuous direction other than that of the axial flow (e.g., including in directions substantially orthogonal thereto) and down into and between the gap formed between the second end of the rotor 12 and the housing 34 (i.e., down a portion of the second end of the rotor adjacent to the shaft 14 between the end of the rotor 12 and the housing 34). As mentioned above, the non-axial and orthogonal flow, and the presence of the host material in the other gap between the end (in this case, the second end) of the rotor 12 and the housing 34 causes additional undesirable and unnecessary friction. Further, it is possible for a portion of the host material to become trapped in eddy currents swirling between the second end of the rotor and the housing. Additionally, in the device 10, a substantial portion of the exiting combined material must negotiate at least two right angles as it exits form the annular exit of the tubular channel 32 into the outlet port 40.

As is apparent to those of ordinary skill in the art, the inlet port 37 imparts only an axial flow to the host material. Only the rotor 21 imparts a circumferential flow into the host material. Further, the outlet port 40 imparts or provides for only an axial flow into the exiting material. Additionally, the circumferential flow velocity vector is imparted to the material only after it enters the annular inlet 37 of the tubular channel 32, and subsequently the circumferential flow vector must be degraded or eliminated as the material enters the exit port 40. There is, therefore, a need for a progressive circumferential acceleration of the material as it passes in the axial direction through the channel 32, and a circumferential deceleration upon exit of the material from the channel 32. These aspects, in combination with the tortuous path that the material takes from the inlet port 37 to the outlet port 40, create a substantial friction and flow resistance over the path that is accompanied by a substantial pressure differential (26 psi, at 60 gallons/min flow rate) between the inlet 37 and outlet 40 ports, and these factors, inter alia, combine to reduce the overall efficiency of the system.

Figure 2:
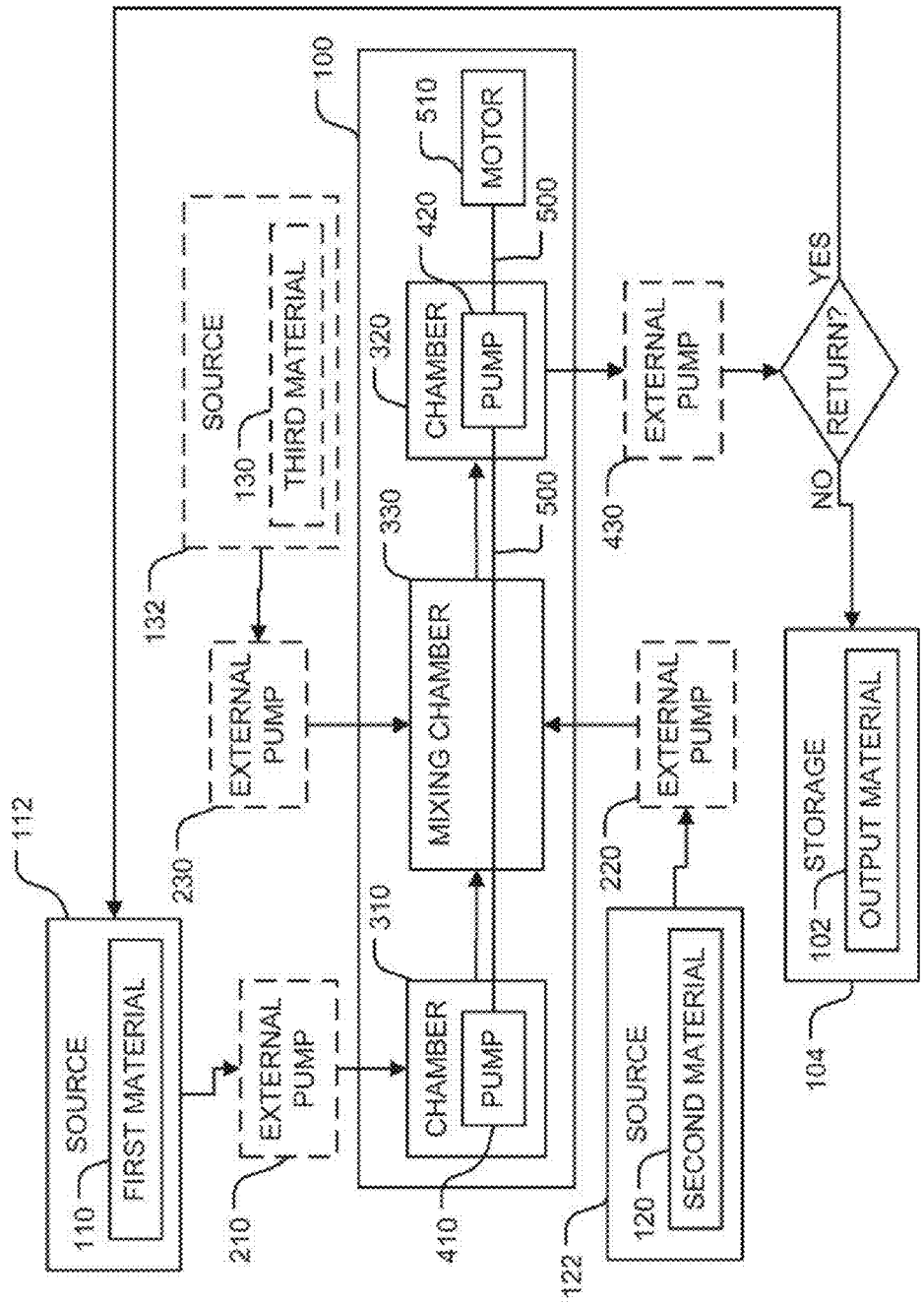
FIG. 2 is block diagram of an exemplary embodiment of a mixing device.

Electrokinetically Oxygen-Enriched Aqueous Fluids and Solutions:

FIG. 2 provides a block diagram illustrating some of the components of a mixing device 100 and the flow of material into, within, and out of the device. The mixing device 100 combines two or more input materials to form an output material 102, which may be received therefrom into a storage vessel 104. The mixing device 100 agitates the two or more input materials in a novel manner to produce an output material 102 having novel characteristics. The output material 102 may include not only a suspension of at least one of the input materials in at least one of the other input materials (e.g., emulsions) but also a novel combination (e.g., electrostatic combinations) of the input materials, a chemical compound resulting from chemical reactions between the input materials, combinations having novel electrostatic characteristics, and combinations thereof.

The input materials may include a first material 110 provided by a source 112 of the first material, a second material 120 provided by a source 122 of the second material, and optionally a third material 130 provided by a source 132 of the third material. The first material 110 may include a liquid, such as water, saline solution, chemical suspensions, polar liquids, non-polar liquids, colloidal suspensions, cell growing media, and the like. In some embodiments, the first material 110 may include the output material 102 cycled back into the mixing device 100. The second material 120 may consist of or include a gas, such as oxygen, nitrogen, carbon dioxide, carbon monoxide, ozone, sulfur gas, nitrous oxide, nitric oxide, argon, helium, bromine, and combinations thereof, and the like. In preferred embodiments, the gas is or comprises oxygen. The optional third material 130 may include either a liquid or a gas. In some embodiments, the third material 130 may be or include the output material 102 cycled back into the mixing device 100 (e.g., to one or more of the pumps 210, 220 or 230, and/or into the chamber 310, and/or 330).

Optionally, the first material 110, the second material 120, and the optional third material 130 may be pumped into the mixing device 100 by an external pump 210, an external pump 220, and an external pump 230, respectively. Alternatively, one or more of the first material 110, the second material 120, and the optional third material 130 may be stored under pressure in the source 112, the source 122, and the source 132, respectively, and may be forced into the mixing device 100 by the pressure. The invention is not limited by the method used to transfer the first material 110, the second material 120, and optionally, the third material 130 into the mixing device 100 from the source 112, the source 122, and the source 132, respectively.

The mixing device 100 includes a first chamber 310 and a second chamber 320 flanking a mixing chamber 330. The three chambers 310, 320, and 330 are interconnected and form a continuous volume.

The first material 110 is transferred into the first chamber 310 and flows therefrom into the mixing chamber 330. The first material 110 in the first chamber 310 may be pumped into the first chamber 310 by an internal pump 410. The second material 120 is transferred into the mixing chamber 330. Optionally, the third material 130 may be transferred into the mixing chamber 330. The materials in the mixing chamber 330 are mixed therein to form the output material 102. Then, the output material 102 flows into the second chamber 320 from which the output material 102 exits the mixing device 100. The output material 102 in the mixing chamber 330 may be pumped into the second chamber 320 by an internal pump 420. Optionally, the output material 102 in the second chamber 320 may be pumped therefrom into the storage vessel 104 by an external pump 430 (e.g., alone or in combination with the internal pump 410 and/or 420).

In particular aspects, a common drive shaft 500 powers both the internal pump 410 and the internal pump 420. The drive shaft 500 passes through the mixing chamber 330 and provides rotational force therein that is used to mix the first material 110, the second material 120, and optionally, the third material 130 together. The drive shaft 500 is powered by a motor 510 coupled thereto.

Figure 3:
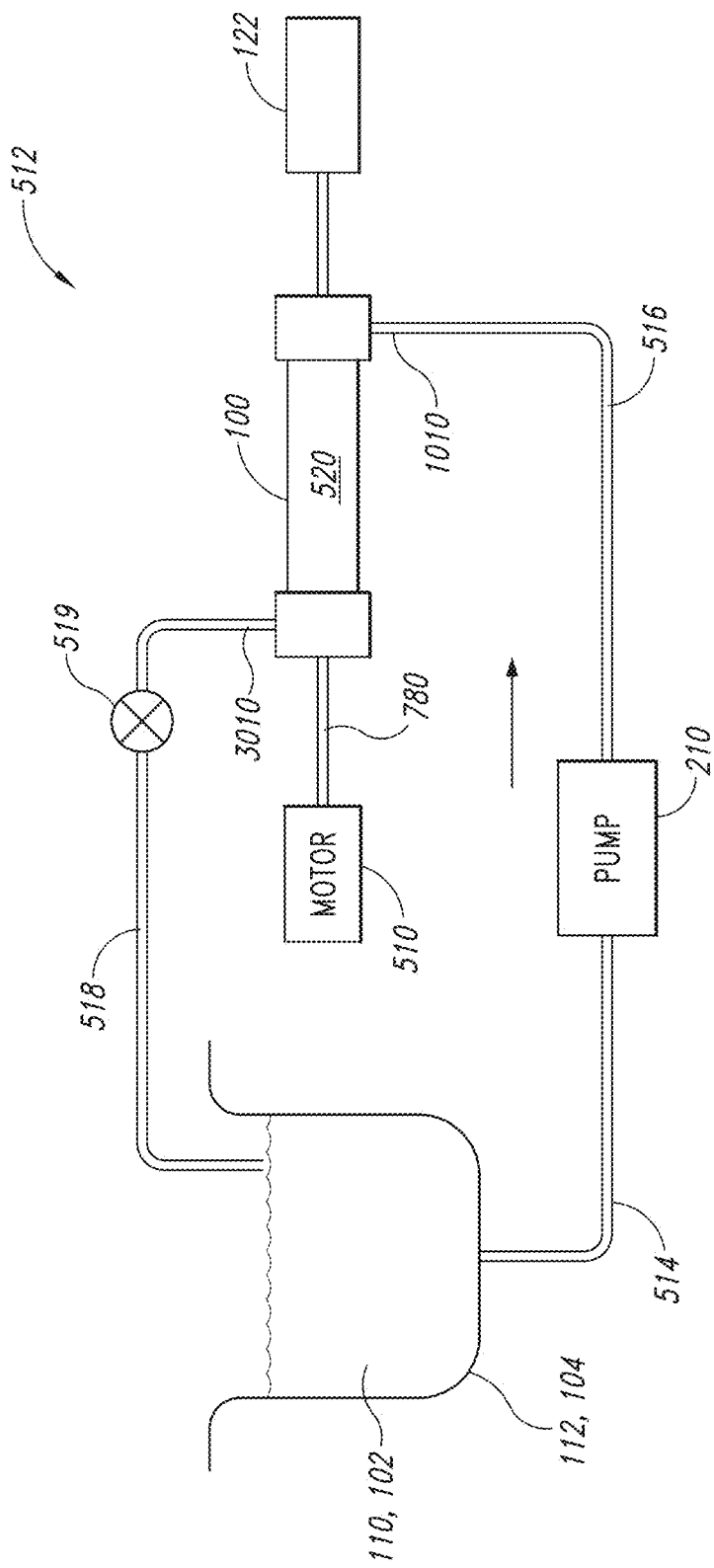
FIG. 3 is an illustration of an exemplary system for delivering a first material to the mixing device of FIG. 2.

FIG. 3 provides a system 512 for supplying the first material 110 to the mixing device 100 and removing the output material 102 from the mixing device 100. In the system 512, the storage vessel 104 of the output material 102 and the source 112 of the first material 110 are combined. The external pump 210 is coupled to the combined storage vessel 104 and source 112 by a fluid conduit 514 such as hose, pipe, and the like. The external pump 210 pumps the combined first material 110 and output material 102 from the combined storage vessel 104 and source 112 through the fluid conduit 514 and into a fluid conduit 516 connecting the external pump 210 to the mixing device 100. The output material 102 exits the mixing device 100 through a fluid conduit 518. The fluid conduit 518 is coupled to the combined storage vessel 104 and source 112 and transports the output material 102 exiting the mixing device 100 to the combined storage vessel 104 and source 112. The fluid conduit 518 includes a valve 519 that establishes an operating pressure or back pressure within the mixing device 100.

Referring to FIGS. 2, 4-9, and 11, a more detailed description of various components of an embodiment of the mixing device 100 will be provided. The mixing device 100 is scalable. Therefore, dimensions provided with respect to various components may be used to construct an embodiment of the device or may be scaled to construct a mixing device of a selected size.

Figure 4:
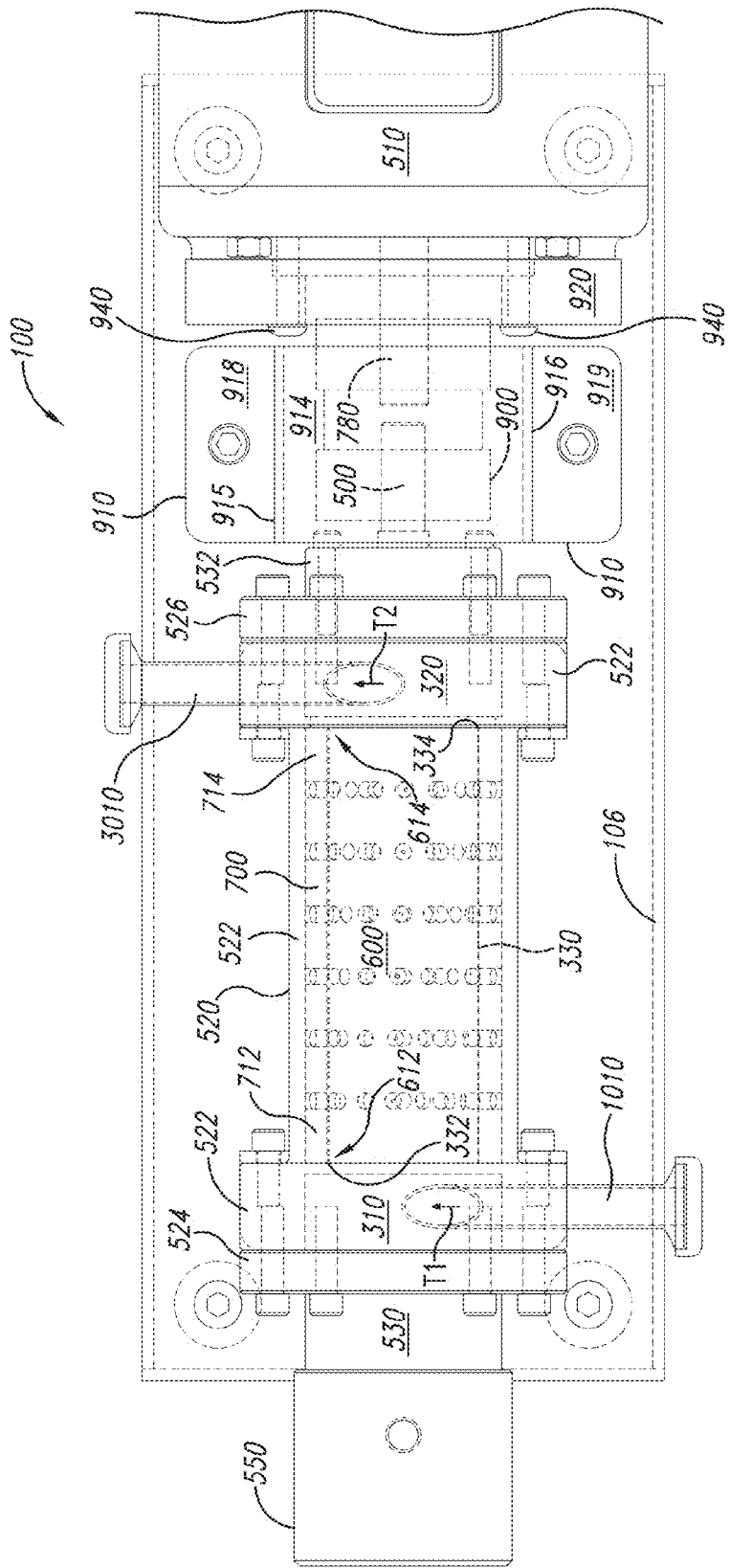
FIG. 4 is a fragmentary partial cross-sectional view of a top portion of the mixing device of FIG. 2.

Turning to FIG. 4, the mixing device 100 includes a housing 520 that houses each of the first chamber 310, the mixing chamber 330, and the second chamber 320. As mentioned above, the mixing device 100 includes the drive shaft 500, which rotates during operation of the device. Therefore, the mixing device 100 may vibrate or otherwise move. Optionally, the mixing device 100 may be coupled to a base 106, which may be affixed to a surface such as the floor to maintain the mixing device 100 in a substantially stationary position.

The housing 520 may be assembled from two or more housing sections. By way of example, the housing 520 may include a central section 522 flanked by a first mechanical seal housing 524 and a second mechanical seal housing 526. A bearing housing 530 may be coupled to the first mechanical seal housing 524 opposite the central section 522. A bearing housing 532 may be coupled to the second mechanical seal housing 526 opposite the central section 522. Optionally, a housing section 550 may be coupled to the bearing housings 530.

Figure 5:
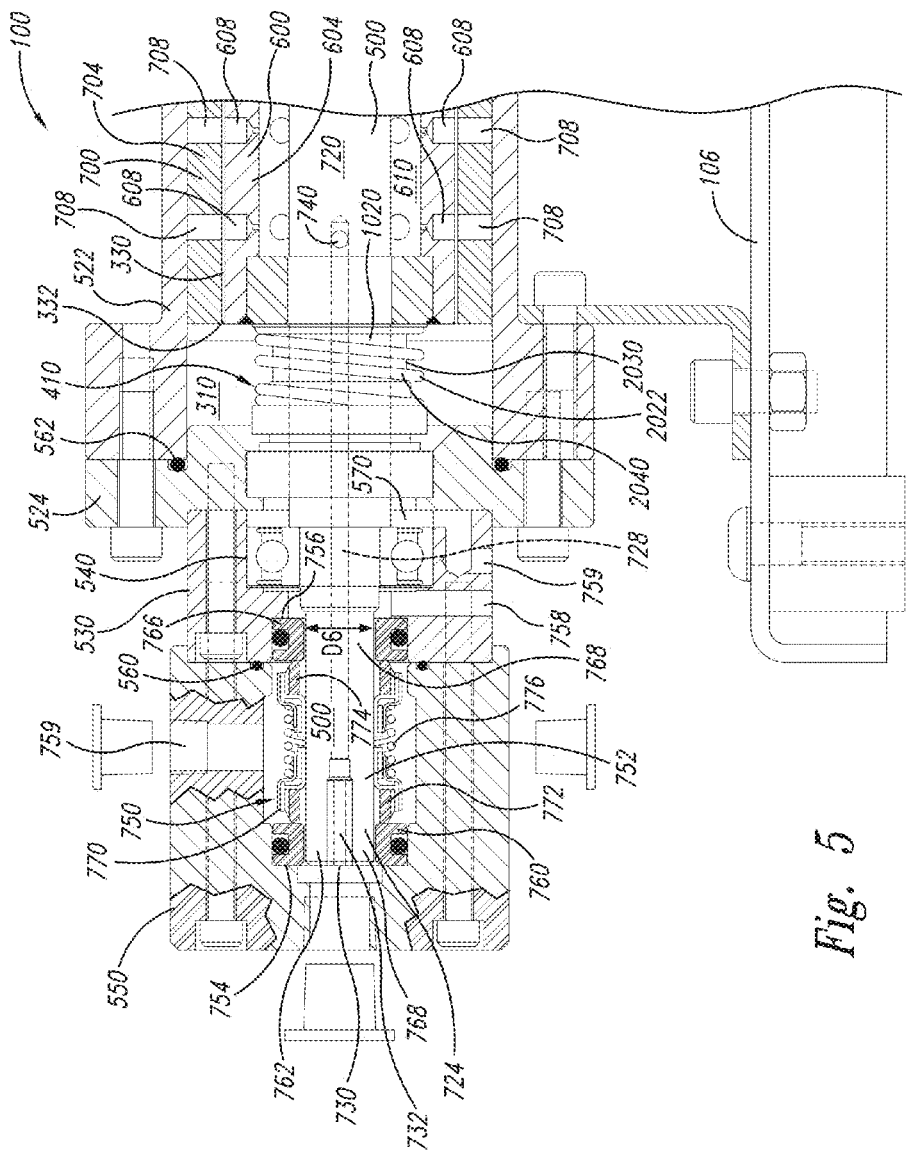
FIG. 5 is a fragmentary cross-sectional view of a first side portion of the mixing device of FIG. 2.
Figure 6:
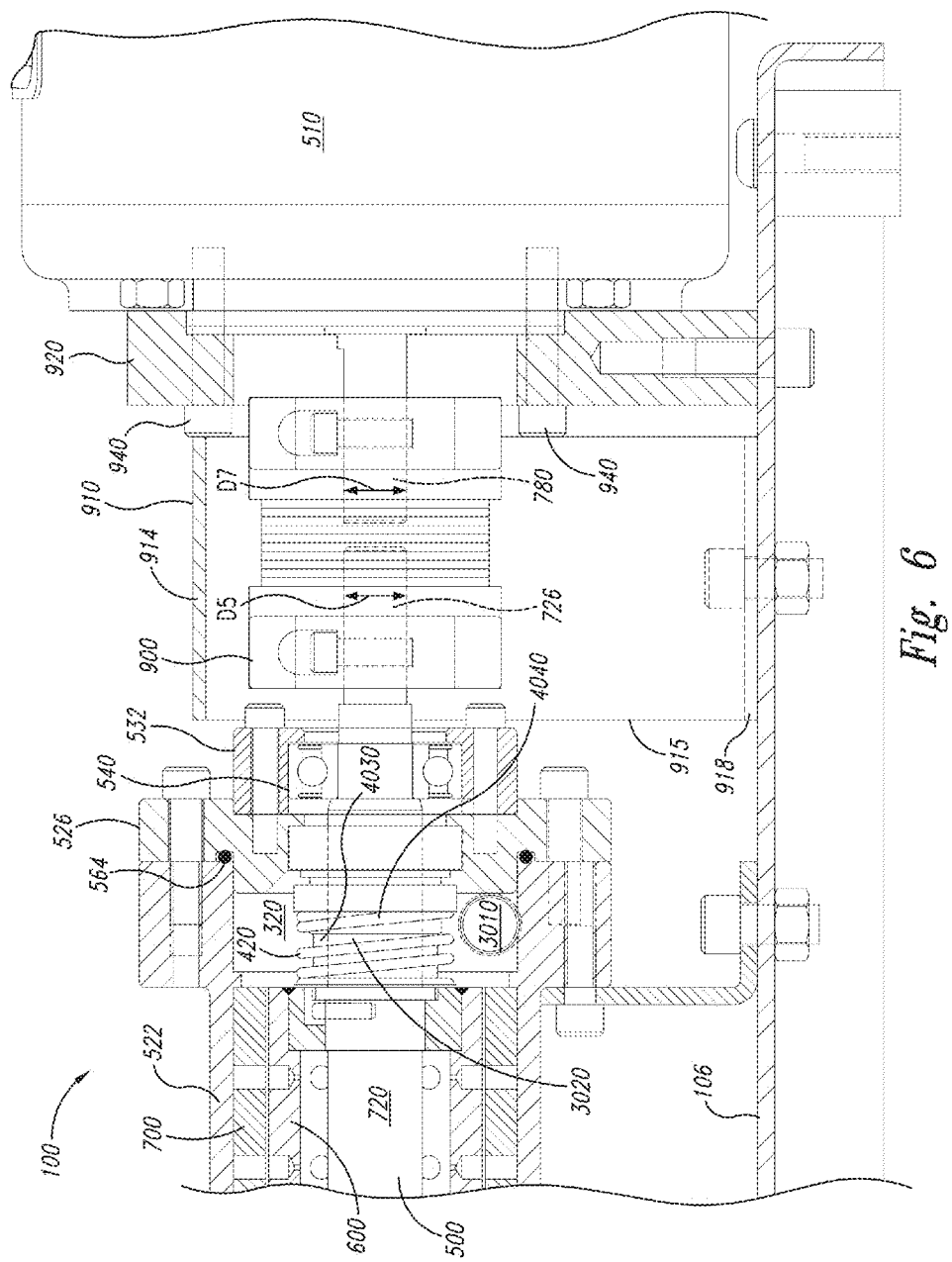
FIG. 6 is a fragmentary cross-sectional view of a second side portion of the mixing device of FIG. 2.

Each of the bearing housings 530 and 532 may house a bearing assembly 540 (see FIGS. 5 and 6). The bearing assembly 540 may include any suitable bearing assembly known in the art including a model number "202SZZST" manufactured by SKF USA Inc, of Kulpsville, Pa., operating a website at www.skf.com.

Seals may be provided between adjacent housing sections. For example, o-ring 560 (see FIG. 5) may be disposed between the housing section 550 and the bearing housing 530, o-ring 562 (see FIG. 5) may be disposed between the first mechanical seal housing 524 and the central section 522, and o-ring 564 (see FIG. 6) may be disposed between the second mechanical seal housing 526 and the central section 522.

Mixing Chamber 330

Figure 7:
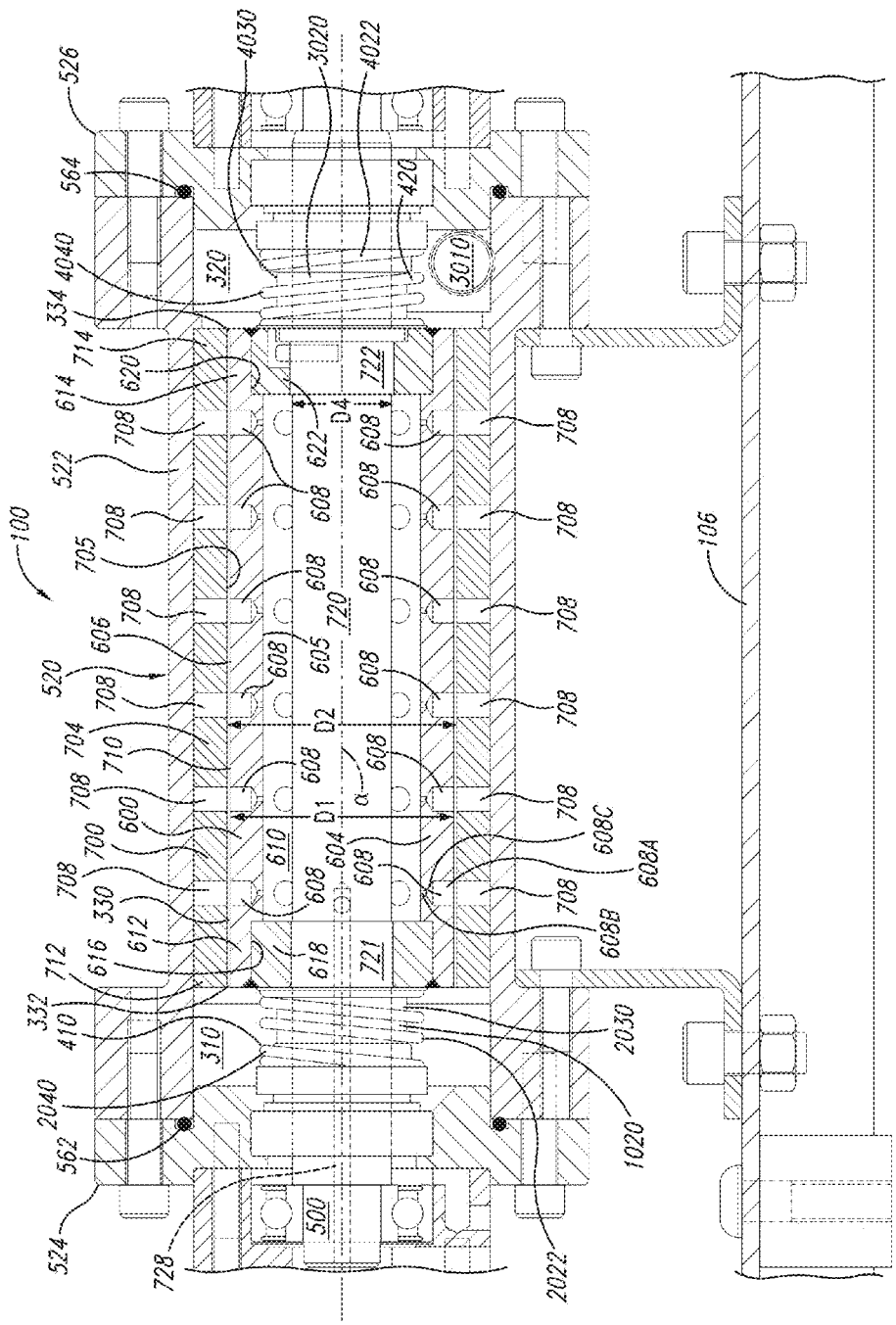
FIG. 7 is a fragmentary cross-sectional view of a side portion of the mixing device of FIG. 2 located between the first side portion of FIG. 5 and the second side portion of FIG. 6.

Turning now to FIG. 7, the mixing chamber 330 is disposed inside the central section 522 of the housing 520 between the first mechanical seal housing 524 and the second mechanical seal housing 526. The mixing chamber 330 is formed between two components of the mixing device 100, a rotor 600 and a stator 700. The rotor 600 may have a sidewall 604 with an inside surface 605 defining a generally hollow inside portion 610 and an outside surface 606. The sidewall 604 may be about 0.20 inches to about 0.75 inches thick. In some embodiments, the sidewall 604 is about 0.25 inches thick. However, because the mixing device 100 may be scaled to suit a particular application, embodiments of the device having a sidewall 604 that is thicker or thinner than the values provided are within the scope of the present teachings. The sidewall 604 includes a first end portion 612 and a second end portion 614 and a plurality of through-holes 608 formed between the first end portion 612 and the second end portion 614. Optionally, the outside surface 606 of the sidewall 604 may include other features such as apertures, projections, textures, and the like. The first end portion 612 has a relieved portion 616 configured to receive a collar 618 and the second end portion 614 has a relieved portion 620 configured to receive a collar 622.

The rotor 600 is disposed inside the stator 700. The stator 700 has a sidewall 704 with an inside surface 705 defining a generally hollow inside portion 710 into which the rotor 600 is disposed. The sidewall 704 may be about 0.1 inches to about 0.3 inches thick. In some embodiments, the sidewall 604 is about 1.5 inches thick. The stator 700 may be non-rotatably coupled to the housing 520 in a substantially stationary position. Alternatively, the stator 700 may integrally formed with the housing 520. The sidewall 704 has a first end portion 712 and a second end portion 714. Optionally, a plurality of apertures 708 are formed in the sidewall 704 of the stator 700 between the first end portion 712 and the second end portion 714. Optionally, the inside surface 705 of the sidewall 704 may include other features such as through-holes, projections, textures, and the like.

The rotor 600 rotates with respect to the stationary stator 700 about an axis of rotation "α" in a direction indicated by arrow "C3" in FIG. 9. Each of the rotor 600 and the stator 700 may be generally cylindrical in shape and have a longitudinal axis. The rotor 600 has an outer diameter "D1" and the stator 700 may have an inner diameter "D2." The diameter "D1" may range, for example, from about 0.5 inches to about 24 inches. In some embodiments, the diameter "D1" is about 3.04 inches. In some embodiments, the diameter "D1" is about 1.7 inches. The diameter "D2," which is larger than the diameter "D1," may range from about 0.56 inches to about 24.25 inches. In some embodiments, the diameter "D2" is about 4 inches. Therefore, the mixing chamber 330 may have a ring-shaped cross-sectional shape that is about 0.02 inches to about 0.125 inches thick (i.e., the difference between the diameter "D2" and the diameter "D1"). In particular embodiments, the mixing chamber 330 is about 0.025 inches thick. The channel 32 between the rotor 12 and the stator 34 of prior art device 10 (see FIG. 1) has a ring-shaped cross-sectional shape that is about 0.09 inches thick. Therefore, in particular embodiments, the thickness of the mixing chamber 330 is less than about one third of the channel 32 of the prior art device 10.

The longitudinal axis of the rotor 600 may be aligned with its axis of rotation "α." The longitudinal axis of the rotor 600 may be aligned with the longitudinal axis of the stator 700. The rotor 600 may have a length of about 3 inches to about 6 inches along the axis of rotation "α." In some embodiments, the rotor 600 may have a length of about 5 inches along the axis of rotation "α." The stator 700 may have a length of about 3 inches to about 6 inches along the axis of rotation "α." In some embodiments, the stator 700 may have a length of about 5 inches along the axis of rotation "α."

While the rotor 600 and the stator 700 have been depicted as having a generally cylindrical shape, those of ordinary skill in the art appreciate that alternate shapes may be used. For example, the rotor 600 and the stator 700 may be conically, spherically, arbitrarily shaped, and the like. Further, the rotor 600 and the stator 700 need not be identically shaped. For example, the rotor 600 may be cylindrically shaped and the stator 700 rectangular shaped or vise versa.

The apertures 708 of the stator 700 and the through-holes 608 depicted in FIGS. 4-7 are generally cylindrically shaped. The diameter of the through-holes 608 may range from about 0.1 inches to about 0.625 inches. The diameter of the apertures 708 may range from about 0.1 inches to about 0.625 inches. One or more of apertures 708 of the stator 700 may have a diameter that differs from the diameters of the other apertures 708. For example, the apertures 708 may increase in diameter from the first end portion 712 of the stator 700 to the second end portion 714 of the stator 700, the apertures 708 may decrease in diameter from the first end portion 712 of the stator 700 to the second end portion 714 of the stator 700, or the diameters of the apertures 708 may vary in another manner along the stator 700. One or more of through-holes 608 of the rotor 600 may have a diameter that differs from the diameters of the other through-holes 608. For example, the through-holes 608 may increase in diameter from the first end portion 612 of the rotor 600 to the second end portion 614 of the rotor 600, the through-holes 608 may decrease in diameter from the first end portion 612 of the rotor 600 to the second end portion 614 of the rotor 600, or the diameters of the through-holes 608 may vary in another manner along the rotor 600.

As described below with reference to alternate embodiments, the apertures 708 and the through-holes 608 may have shapes other than generally cylindrical and such embodiments are within the scope of the present invention. For example, the through-holes 608 may include a narrower portion, an arcuate portion, a tapered portion, and the like. Referring to FIG. 7, each of the through-holes 608 includes an outer portion 608A, a narrow portion 608B, and a tapered portion 608C providing a transition between the outer portion 608A and the narrow portion 608B. Similarly, the apertures 708 may include a narrower portion, an arcuate portion, a tapered portion, and the like.

FIG. 8 provides a non-limiting example of a suitable arrangement of the apertures 708 of the stator 700 and the through-holes 608 of the rotor 600. The apertures 708 of the stator 700 may be arranged in substantially parallel lateral rows "SLAT-1" through "SLAT-6" substantially orthogonal to the axis of rotation "α." The apertures 708 of the stator 700 may also be arranged in substantially parallel longitudinal rows "SLONG-1" through "SLONG-7" substantially parallel with the axis of rotation "α." In other words, the apertures 708 of the stator 700 may be arranged in a grid-like pattern of orthogonal rows (i.e., the lateral rows are orthogonal to the longitudinal rows) having the longitudinal rows "SLONG-1" through "SLONG-7" substantially parallel with the axis of rotation "α."

Like the apertures 708 of the stator 700, the through-holes 608 of the rotor 600 may be arranged in substantially parallel lateral rows "RLAT-1" through "RLAT-6" substantially orthogonal to the axis of rotation "α." However, instead of being arranged in a grid-like pattern of orthogonal rows, the through-holes 608 of the rotor 600 may also be arranged in substantially parallel rows "RLONG-1" through "RLONG-7" that extend longitudinally along a helically path. Alternatively, the through-holes 608 of the rotor 600 may also be arranged in substantially parallel rows "RLONG-1" through "RLONG-7" that extend longitudinally at an angle other than parallel with the axis of rotation "α."

The apertures 708 of the stator 700 and the through-holes 608 of the rotor 600 may be configured so that when the rotor 600 is disposed inside the stator 700 the lateral rows "SLAT-1" to "SLAT-6" at least partially align with the lateral rows "RLAT-1" to "RLAT-6," respectively. In this manner, as the rotor 600 rotates inside the stator 700, the through-holes 608 pass by the apertures 708.

The through-holes 608 in each of the lateral rows "RLAT-1" to "RLAT-6" may be spaced apart laterally such that all of the through-holes 608 in the lateral row align, at least partially, with the apertures 708 in a corresponding one of the lateral rows "SLAT-1" to "SLAT-6" of the stator 700 at the same time. The longitudinally extending rows "RLONG-1" through "RLONG-6" may be configured such that the through-holes 608 in the first lateral row "RLAT-1" in each of the longitudinally extending rows passes completely by the apertures 708 of the corresponding lateral row "SLAT-1" before the through-holes 608 in the last lateral row "RLAT-6" begin to partially align with the apertures 708 of the corresponding last lateral row "SLAT-6" of the stator 700.

While, in FIG. 8, six lateral rows and six longitudinally extending rows have been illustrated with respect to the rotor 600 and six lateral rows and seven longitudinally extending rows have been illustrated with respect stator 700, it is apparent to those of ordinary skill in the art that alternate numbers of lateral rows and/or longitudinal rows may be used with respect to the rotor 600 and/or stator 700 without departing from the present teachings.

To ensure that only one pair of openings between corresponding lateral rows will be coincident at any one time, the number of apertures 708 in each of the lateral rows "SLAT-1" to "SLAT-6" on the stator 700 may differ by a predetermined number (e.g., one, two, and the like) the number of through-holes 608 in each of the corresponding lateral rows "RLAT-1" to "RLAT-6" on the rotor 600. Thus, for example, if lateral row "RLAT-1" has twenty through-holes 608 evenly spaced around the circumference of rotor 600, the lateral row "SLAT-1" may have twenty apertures 708 evenly spaced around the circumference of stator 700.

Returning to FIG. 7, the mixing chamber 330 has an open first end portion 332 and an open second end portion 334. The through-holes 608 formed in the sidewall 604 of the rotor 600 connect the inside portion 610 of the rotor 600 with the mixing chamber 330.

The rotor 600 is rotated inside the stator 700 by the drive shaft 500 aligned with the axis of rotation "α" of the rotor 600. The drive shaft 500 may be coupled to the first end portion 612 and the second end portion 614 of the rotor 600 and extend through its hollow inside portion 610. In other words, a portion 720 of the drive shaft 500 is disposed in the hollow inside portion 610 of the rotor 600.

The collar 618 is configured to receive a portion 721 of the drive shaft 500 disposed in the hollow inside portion 610 and the collar 622 is configured to receive a portion 722 of the drive shaft 500 disposed in the hollow inside portion 610.

The portion 721 has an outer diameter "D3" that may range from about 0.5 inches to about 2.5 inches. In some embodiments, the diameter "D3" is about 0.625 inches. The portion 722 has an outer diameter "D4" that may be substantially similar to the diameter "D3," although, this is not required. The diameter "D4" may range from about 0.375 inches to about 2.5 inches.

The rotor 600 may be non-rotationally affixed to the portion 721 and the portion 722 of the drive shaft 500 by the collar 618 and the collar 622, respectively. By way of example, each of the collars 618 and 622 may be installed inside relieved portions 616 and 620, respectively. Then, the combined rotor 600 and collars 618 and 622 may be heated to expand them. Next, the drive shaft 500 is inserted through the collars 618 and 622 and the assembly is allowed to the cool. As the collars 618 and 622 shrink during cooling, they tighten around the portions 722A and 722B of the drive shaft 500, respectively, gripping it sufficiently tightly to prevent the drive shaft 500 from rotating relative to the rotor 600. The collar 618, which does not rotate with respect to either the portion 721 or the relieved portion 616, translates the rotation of the drive shaft 500 to the first end portion 612 the rotor 600.

The collar 622, which does not rotate with respect to either the portion 722 or the relieved portion 620, translates the rotation of the drive shaft 500 to the second end portion 614 of the rotor 600. The drive shaft 500 and the rotor 600 rotate together as a single unit.

The drive shaft 500 may have a first end portion 724 (see FIG. 5) and a second end portion 726 (see FIG. 6). The first end portion 724 may have a diameter "D5" of about 0.5 inches to about 1.75 inches. In particular embodiments, the diameter "D5" may be about 1.25 inches. The second end portion 726 may have a diameter "D6" that may be substantially similar to diameter "D5."

The second material 120 may be transported into the mixing chamber 330 through one of the first end portion 724 and the second end portion 726 of the rotating drive shaft 500. The other of the first end portion 724 and the second end portion 726 of the drive shaft 500 may be coupled to the motor 510. In the embodiment depicted in FIGS. 5 and 6, the second material 120 is transported into the mixing chamber 330 through the first end portion 724 and the second end portion 726 of the drive shaft 500 is coupled to the motor 510.

Turning to FIG. 5, the drive shaft 500 may have a channel 728 formed therein that extends from first end portion 724 into the portion 720 disposed in the inside portion 610 of the rotor 600. The channel 728 has an opening 730 formed in the first end portion 724. When the mixing device 100 is operating, the second material 120 is introduced into the channel 728 through the opening 730.

A valve 732 may be disposed inside a portion of the channel 728 located in the first end portion 724 of the drive shaft 500. The valve 732 may restrict or otherwise control the backward flow of the second material 120 from inside the hollow inside portion 610 through the channel 728 and/or the forward flow of the second material 120 into the channel 728. The valve 732 may include any valve known in the art including a check valve. A suitable check valve includes a part number "CKFA1876205A," free flow forward check valve, manufactured by The Lee Company USA having an office in Bothell, Wash. and operating a website at www.theleeco.com.

The drive shaft 500 may include an aperture 740 located in the inside portion 610 of the rotor 600 that connects the channel 728 with the inside portion 610 of the rotor 600. While only a single aperture 740 is illustrated in FIG. 5, it is apparent to those of ordinary skill in the art that multiple apertures may be used to connect the channel 728 with the inside portion 610 of the rotor 600.

Referring to FIG. 2, optionally, the external pump 220 may pump the second material 120 into the mixing device 100. The pump 220 may include any suitable pump known in the art. By way of non-limiting example, the pump 220 may include any suitable pump known in the art including a diaphragm pump, a chemical pump, a peristaltic pump, a gravity fed pump, a piston pump, a gear pump, a combination of any of the aforementioned pumps, and the like. If the second material 120 is a gas, the gas may be pressurized and forced into the opening 730 formed in the first end portion 724 of the drive shaft 500 by releasing the gas from the source 122.

The pump 220 or the source 122 is coupled to the channel 728 by the valve 732. The second material 120 transported inside the channel 728 exits the channel 728 into the inside portion 610 of the rotor 600 through the aperture 740. The second material 120 subsequently exits the inside portion 610 of the rotor 600 through the through-holes 608 formed in the sidewall 608 of the rotor 600.

Referring to FIG. 5, the mixing device 100 may include a seal assembly 750 coupled to the first end portion 724 of the drive shaft 500. The seal assembly 750 is maintained within a chamber 752 defined in the housing 520. The chamber 752 has a first end portion 754 spaced across the chamber from a second end portion 756. The chamber 752 also includes an input port 758 and an output port 759 that provide access into the chamber 752. The chamber 752 may be defined by housing section 550 and the bearing housing 530. The first end portion 754 may be formed in the housing section 550 and the second end portion 756 may be adjacent to the bearing housing 530. The input port 758 may be formed in the bearing housing 530 and the output port 759 may be formed in the housing section 550.

The seal assembly 750 includes a first stationary seal 760 installed in the first end portion 754 of the chamber 752 in the housing section 550 and the bearing housing 530. The first stationary seal 760 extends around a portion 762 of the first end portion 724 of the drive shaft 500. The seal assembly 750 also includes a second stationary seal 766 installed in the second end portion 756 of the chamber 752 in the bearing housing 530. The second stationary seal 766 extends around a portion 768 of the first end portion 724 of the drive shaft 500.

The seal assembly 750 includes a rotating assembly 770 that is non-rotatably coupled to the first end portion 724 of the drive shaft 500 between the portion 762 and the portion 768. The rotating assembly 770 rotates therewith as a unit. The rotating assembly 770 includes a first seal 772 opposite a second seal 774. A biasing member 776 (e.g., a spring) is located between the first seal 772 and the second seal 774. The biasing member 776 biases the first seal 772 against the first stationary seal 760 and biases the second seal 774 against the second stationary seal 766.

A cooling lubricant is supplied to the chamber 752 and around rotating assembly 770. The lubricant enters the chamber 752 through the input port 758 and exits the chamber 752 through output port 759. The lubricant may lubricate the bearing assembly 540 housed by the bearing housing 530. A chamber 570 may be disposed between the bearing housing 530 and the mechanical seal housing 524. The bearing housing 530 may also include a second input port 759 connected to the chamber 570 into which lubricant may be pumped. Lubricant pumped into the chamber 570 may lubricate the bearing assembly 540. The seal assembly 750 may significantly, if not greatly, reduce frictional forces within this portion of the device caused by the rotation of the rotor 600 and may increase the active life of the seals 770. The seals may include surfaces constructed using silicon carbide.

Referring to FIG. 9, as the rotor 600 rotates about the axis of rotation "α" in the direction indicated by arrow "C1," the rotor expels the second material 120 into the mixing chamber 330. The expelled bubbles, droplets, particles, and the like of the second material 120 exit the rotor 600 and are imparted with a circumferential velocity (in a direction indicated by arrow "C3") by the rotor 600. The second material 120 may forced from the mixing chamber 330 by the pump 220 (see FIG. 2), the centrifugal force of the rotating rotor 600, buoyancy of the second material 120 relative to the first material 110, and a combination thereof.

Motor 510

Returning to FIG. 6, the second end portion 726 of the drive shaft 500 may be coupled to a rotating spindle 780 of a motor 510 by a coupler 900. The spindle 780 may have a generally circular cross-sectional shape with a diameter "D7" of about 0.25 inches to about 2.5 inches. In particular embodiments, the diameter "D7" may be about 0.25 inches to about 1.5 inches. While in the embodiment depicted in FIG. 6, the diameter "D5" of the first end portion 724 of the drive shaft 500 is substantially equal to the diameter "D7" and the spindle 780, embodiments in which one of the diameter "D5" and the diameter "D7" is larger than the other are within the scope of the present invention.

Referring also to FIG. 4, it may be desirable to cover or shield the coupler 900. In the embodiment illustrated in FIGS. 4 and 6, a drive guard 910 covers the coupler 900. The drive guard 910 may be generally U-shaped having a curved portion 914 flanked by a pair of substantially linear portions 915 and 916. The distal end of each of the substantially linear portions 915 and 916 of the drive guard 910 may have a flange 918 and 919, respectively. The drive guard 910 may be fastened by each of its flanges 918 and 919 to the base 106.

The motor 510 may be supported on the base 106 by a support member 920. The support member 920 may be coupled to the motor 510 near the spindle 780. In the embodiment depicted, the support member 920 includes a through-hole through which the spindle 780 passes. The support member 920 may be coupled to the motor 510 using any method known in the art, including bolting the support member 920 to the motor 510 with one or more bolts 940.

The coupler 900 may include any coupler suitable for transmitting a sufficient amount of torque from the spindle 780 to the drive shaft 500 to rotate the rotor 600 inside to the stator 700. In the embodiment illustrated in FIGS. 4 and 6, the coupler 900 is a bellows coupler. A bellows coupler may be beneficial if the spindle 780 and the drive shaft 500 are misaligned. Further, the bellows coupler may help absorb axial forces exerted on the drive shaft 500 that would otherwise be translated to the spindle 780. A suitable bellows coupler includes a model "BC32-8-8-A," manufactured by Ruland Manufacturing Company, Inc. of Marlborough, Mass., which operates a website at www.ruland.com.

The motor 510 may rotate the rotor 600 at about 0.1 revolutions per minute ("rpm") to about 7200 rpm. The motor 510 may include any motor suitable for rotating the rotor 600 inside to the stator 700 in accordance with the present teachings. By way of non-limiting example, a suitable motor may include a one-half horsepower electric motor, operating at 230/460 volts and 3450 per minute ("rpm"). A suitable motor includes a model "C4T34NC4C" manufactured by LEESON Electric Corporation of Grafton, Wis., which operates a website at www.leeson.com.

First Chamber 310

Turning to FIGS. 4 and 7, the first chamber 320 is disposed inside the central section 522 of the housing 520 between the first mechanical seal housing 524 and the first end portions 612 and 712 of the rotor 600 and the stator 700, respectively. The first chamber 310 may be annular and have a substantially circular cross-sectional shape. The first chamber 310 and the mixing chamber 330 form a continuous volume. A portion 1020 of the drive shaft 500 extends through the first chamber 310.

As may best be viewed in FIG. 4, the first chamber 310 has an input port 1010 through which the first material 110 enters the mixing device 100. The first material 110 may be pumped inside the first chamber 310 by the external pump 210 (see FIG. 2). The external pump 210 may include any pump known in the art for pumping the first material 110 at a sufficient rate to supply the first chamber 310.

The input port 1010 is oriented substantially orthogonally to the axis of rotation "α." Therefore, the first material 110 enters the first chamber 310 with a velocity tangential to the portion 1020 of the drive shaft 500 extending through the first chamber 310. The tangential direction of the flow of the first material 110 entering the first chamber 310 is identified by arrow "T1." In the embodiment depicted in FIGS. 4 and 7, the input port 1010 may be offset from the axis of rotation "α." As is apparent to those of ordinary skill in the art, the direction of the rotation of the drive shaft 500 (identified by arrow "C1" in FIG. 9), has a tangential component. The input port 1010 is positioned so that the first material 110 enters the first chamber 310 traveling in substantially the same direction as the tangential component of the direction of rotation of the drive shaft 500.

The first material 110 enters the first chamber 310 and is deflected by the inside of the first chamber 310 about the portion 1020 of the drive shaft 500. In embodiments wherein the first chamber 310 has a substantially circular cross-sectional shape, the inside of the first chamber 310 may deflect the first material 110 in a substantially circular path (identified by arrow "C2" in FIG. 9) about the portion 1020 of the drive shaft 500. In such an embodiment, the tangential velocity of the first material 110 may cause it to travel about the axis of rotation "α" at a circumferential velocity, determined at least in part by the tangential velocity.

Once inside the first chamber 310, the first material 110 may be pumped from the first chamber 310 into the mixing chamber 330 by the pump 410 residing inside the first chamber 310. In embodiments that include the external pump 210 (see FIG. 2), the external pump 210 may be configured to pump the first material 110 into the first chamber 310 at a rate at least as high as a rate at which the pump 410 pumps the first material 110 from the first chamber 310.

The first chamber 310 is in communication with the open first end portion 332 of the mixing chamber 330 and the first material 110 inside the first chamber 310 may flow freely into the open first end portion 332 of the mixing chamber 330. In this manner, the first material 110 does not negotiate any corners or bends between the mixing chamber 330 and the first chamber 310. In the embodiment depicted, the first chamber 310 is in communication with the entire open first end portion 332 of the mixing chamber 330. The first chamber 310 may be filled completely with the first material 110.

The pump 410 is powered by the portion 1020 of the drive shaft 500 extending through the first chamber 310. The pump 410 may include any pump known in the art having a rotating pump member 2022 housed inside a chamber (i.e., the first chamber 310) defined by a stationary housing (i.e., the housing 520). Non-limiting examples of suitable pumps include rotary positive displacement pumps such as progressive cavity pumps, single screw pumps (e.g., Archimedes screw pump), and the like.

The pump 410 depicted in FIGS. 7 and 9, is generally referred to as a single screw pump. In this embodiment, the pump member 2022 includes a collar portion 2030 disposed around the portion 1020 of the drive shaft 500. The collar portion 2030 rotates with the portion 1020 of the drive shaft 500 as a unit. The collar portion 2030 includes one or more fluid displacement members 2040. In the embodiment depicted in FIGS. 7 and 9, the collar portion 2030 includes a single fluid displacement member 2040 having a helical shape that circumscribes the collar portion 2030 along a helical path.

Referring to FIG. 9, the inside of the first chamber 310 is illustrated. The pump 410 imparts an axial flow (identified by arrow "A1" and arrow "A2") in the first material 110 inside the first chamber 310 toward the open first end portion 332 of the mixing chamber 330. The axial flow of the first material 110 imparted by the pump 410 has a pressure that may exceed the pressure obtainable by the external pump of the prior art device 10 (see FIG. 1).

The pump 410 may also be configured to impart a circumferential flow (identified by arrow "C2") in the first material 110 as it travels toward the open first end portion 332 of the mixing chamber 330. The circumferential flow imparted in the first material 110 before it enters the mixing chamber 330 causes the first material 110 to enter the mixing chamber 330 already traveling in the desired direction at an initial circumferential velocity. In the prior art device 10 depicted in FIG. 1, the first material 110 entered the channel 32 of the prior art device 10 without a circumferential velocity. Therefore, the rotor 12 of the prior art device 10 alone had to impart a circumferential flow into the first material 110. Because the first material 110 is moving axially, in the prior art device 10, the first material 110 traversed at least a portion of the channel 32 formed between the rotor 12 and the stator 30 at a slower circumferential velocity than the first material 110 traverses the mixing chamber 330 of the mixing device 100. In other words, if the axial velocity of the first material 110 is the same in both the prior art device 10 and the mixing device 100, the first material 110 may complete more revolutions around the rotational axis "α" before traversing the axial length of the mixing chamber 330, than it would complete before traversing the axial length of the channel 32. The additional revolutions expose the first material 110 (and combined first material 110 and second material 120) to a substantially larger portion of the effective inside surface 706 (see FIG. 7) of the stator 700.

In embodiments including the external pump 210 (see FIG. 2), the circumferential velocity imparted by the external pump 210 combined with the input port 1010 being oriented according to the present teachings, may alone sufficiently increase the revolutions of the first material 110 (and combined first material 110 and second material 120) about the rotational axis "α." Further, in some embodiments, the circumferential velocity imparted by the pump 210 and the circumferential velocity imparted by the pump 410 combine to achieve a sufficient number of revolutions of the first material 110 (and combined first material 110 and second material 120) about the rotational axis "α." As is appreciated by those of ordinary skill in the art, other structural elements such as the cross-sectional shape of the first chamber 310 may contribute to the circumferential velocity imparted by the pump 210, the pump 410, and a combination thereof.

Figure 10:
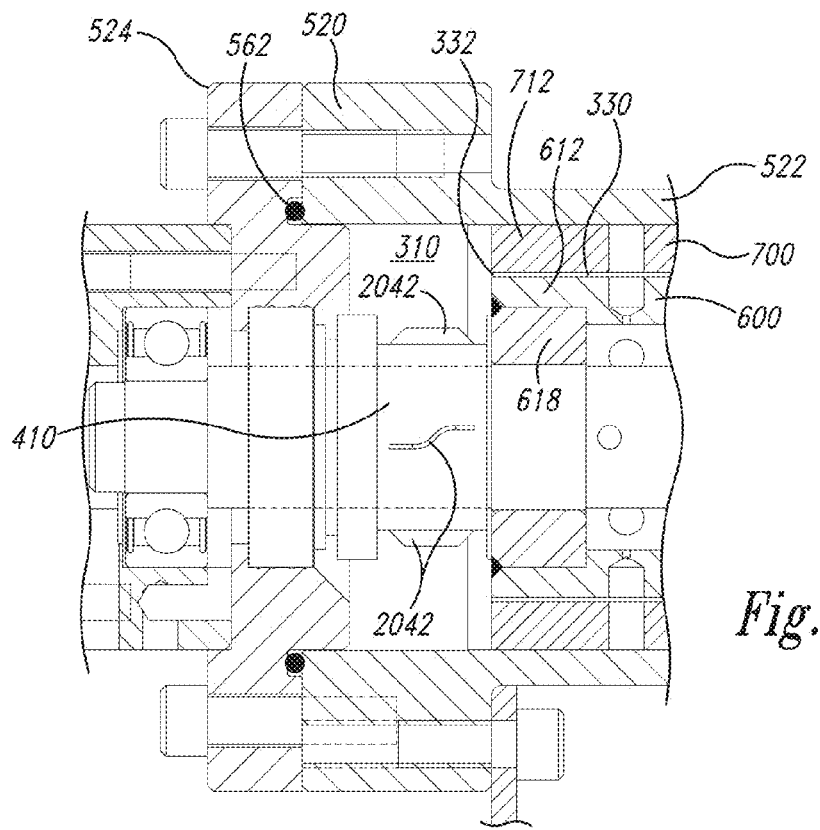
FIG. 10 is a fragmentary cross-sectional view of the inside of a first chamber of the mixing device of FIG. 2 including an alternate embodiment of the pump 410.

In an alternate embodiment depicted in FIG. 10, the pump 410 may include one or more vanes 2042 configured to impart a circumferential flow in the first material 110 as it travels toward the open first end portion 332 of the mixing chamber 330.

Second Chamber 320

Turning now to FIGS. 4 and 7, the second chamber 320 is disposed inside the central section 522 of the housing 520 between the second mechanical seal housing 526 and the second end portions 614 and 714 of the rotor 600 and the stator 700, respectively. The second chamber 320 may be substantially similar to the first chamber 310, however, instead of the input port 1010, the second chamber 320 may include an output port 3010. A portion 3020 of the drive shaft 500 extends through the second chamber 320.

The second chamber 320 and the mixing chamber 330 form a continuous volume. Further, the first chamber 310, the mixing chamber 330, and the second chamber 320 form a continuous volume. The first material 110 flows through the mixing device 100 from the first chamber 310 to the mixing chamber 330 and finally to the second chamber 320. While in the mixing chamber 330, the first material 110 is mixed with the second material 120 to form the output material 102. The output material 102 exits the mixing device 100 through the output port 3010. Optionally, the output material 102 may be returned to the input port 1010 and mixed with an additional quantity of the second material 120, the third material 130, or a combination thereof.

The output port 3010 is oriented substantially orthogonally to the axis of rotation "α" and may be located opposite the input port 1010 formed in the first chamber 310. The output material 102 enters the second chamber 320 from the mixing chamber 330 having a circumferential velocity (in the direction indicated by arrow "C3" in FIG. 9) imparted thereto by the rotor 600. The circumferential velocity is tangential to the portion 3020 of the drive shaft 500 extending through the second chamber 320. In the embodiment depicted in FIGS. 4, 6, and 7, the output port 3010 may be offset from the axis of rotation "α." The output port 3010 is positioned so that the output material 102, which enters the second chamber 320 traveling in substantially the same direction in which the drive shaft 500 is rotating (identified in FIG. 9 by arrow "C1"), is traveling toward the output port 3010.

The output material 102 enters the second chamber 320 and is deflected by the inside of the second chamber 320 about the portion 3020 of the drive shaft 500. In embodiments wherein the second chamber 320 has a substantially circular cross-sectional shape, the inside of the second chamber 320 may deflect the output material 102 in a substantially circular path about the portion 3020 of the drive shaft 500.

Referring to FIG. 2, optionally, the output material 102 may be pumped from inside the second chamber 320 by the external pump 430. The external pump 430 may include any pump known in the art for pumping the output material 102 at a sufficient rate to avoid limiting throughput of the mixing device 100. In such an embodiment, the external pump 430 may introduce a tangential velocity (in a direction indicated by arrow "T2" in FIGS. 4 and 11) to at least a portion of the output material 102 as the external pump 430 pumps the output material 102 from the second chamber 320. The tangential velocity of the portion of the output material 102 may cause it to travel about the axis of rotation "α" at a circumferential velocity, determined in part by the tangential velocity.

Pump 420

Turning to FIGS. 6 and 7, the pump 420 residing inside the second chamber 320 may pump the output material 102 from the second chamber 320 into the output port 3010 and/or from the mixing chamber 330 into the second chamber 320. In embodiments that include the external pump 430, the external pump 430 may be configured to pump the output material 102 from the second chamber 320 at a rate at least as high as a rate at which the pump 420 pumps the output material 102 into the output port 3010.

The second chamber 320 is in communication with the open second end portion 334 of the mixing chamber 330 and the output material 102 inside the mixing chamber 330 may flow freely from the open second end portion 334 into the second chamber 320. In this manner, the output material 102 does not negotiate any corners or bends between the mixing chamber 330 and the second chamber 320. In the embodiment depicted, the second chamber 320 is in communication with the entire open second end portion 334 of the mixing chamber 330. The second chamber 320 may be filled completely with the output material 102.

The pump 420 is powered by the portion 3020 of the drive shaft 500 extending through the second chamber 320. The pump 420 may be substantially identical to the pump 410. Any pump described above as suitable for use as the pump 410 may be used for the pump 420. While the pump 410 pumps the first material 110 into the mixing chamber 330, the pump 420 pumps the output material 102 from the mixing chamber 330. Therefore, both the pump 410 and the pump 420 may be oriented to pump in the same direction.

As is appreciated by those of ordinary skill in the art, the first material 110 may differ from the output material 102. For example, one of the first material 110 and the output material 102 may be more viscous than the other. Therefore, the pump 410 may differ from the pump 420. The pump 410 may be configured to accommodate the properties of the first material 110 and the pump 420 may be configured to accommodate the properties of the output material 102.

The pump 420 depicted in FIGS. 6 and 7, is generally referred to as a single screw pump. In this embodiment, the pump member 4022 includes a collar portion 4030 disposed around the portion 3020 of the drive shaft 500. The collar portion 4030 rotates with the portion 3020 of the drive shaft 500 as a unit. The collar portion 4030 includes one or more fluid displacement members 4040. The collar portion 4030 includes a single fluid displacement member 4040 having a helical shape that circumscribes the collar portion 4030 along a helical path.

Figure 11:
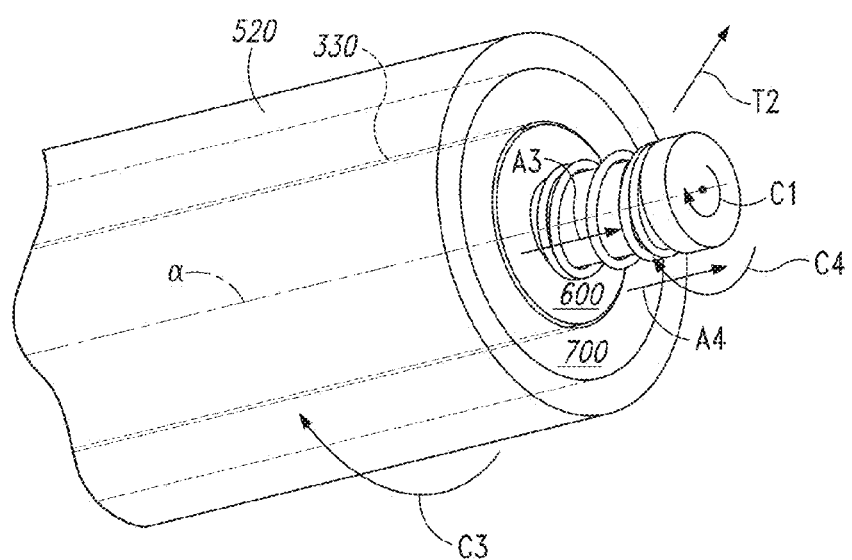
FIG. 11 is a perspective view of an inside of a second chamber of the mixing device of FIG. 2.

Referring to FIG. 11, the inside of the second chamber 320 is illustrated. The pump 420 imparts an axial flow (identified by arrow "A3" and arrow "A4") in the output material 102 inside the second chamber 320 away from the open second end portion 334 of the mixing chamber 330.

The pump 420 may be configured to impart a circumferential flow (identified by arrow "C4") in the output material 102 as it travels away from the open second end portion 334 of the mixing chamber 330. The circumferential flow imparted in the output material 102 may help reduce an amount of work required by the rotor 600. The circumferential flow also directs the output material 102 toward the output port 3010.

In an alternate embodiment, the pump 420 may have substantially the same configuration of the pump 410 depicted in FIG. 10. In such an embodiment, the one or more vanes 2042 are configured to impart a circumferential flow in the output material 102 as it travels away from the open second end portion 334 of the mixing chamber 330.

As is apparent to those of ordinary skill, various parameters of the mixing device 100 may be modified to obtain different mixing characteristics. Exemplary parameters that may be modified include the size of the through-holes 608, the shape of the through-holes 608, the arrangement of the through-holes 608, the number of through-holes 608, the size of the apertures 708, the shape of the apertures 708, the arrangement of the apertures 708, the number of apertures 708, the shape of the rotor 600, the shape of the stator 700, the width of the mixing chamber 330, the length of the mixing chamber 330, rotational speed of the drive shaft 500, the axial velocity imparted by the internal pump 410, the circumferential velocity imparted by the internal pump 410, the axial velocity imparted by the internal pump 420, the circumferential velocity imparted by the internal pump 420, the configuration of disturbances (e.g., texture, projections, recesses, apertures, and the like) formed on the outside surface 606 of the rotor 600, the configuration of disturbances (e.g., texture, projections, recesses, apertures, and the like) formed on the inside surface 706 of the stator 700, and the like.

Alternate Embodiment

Figure 12:
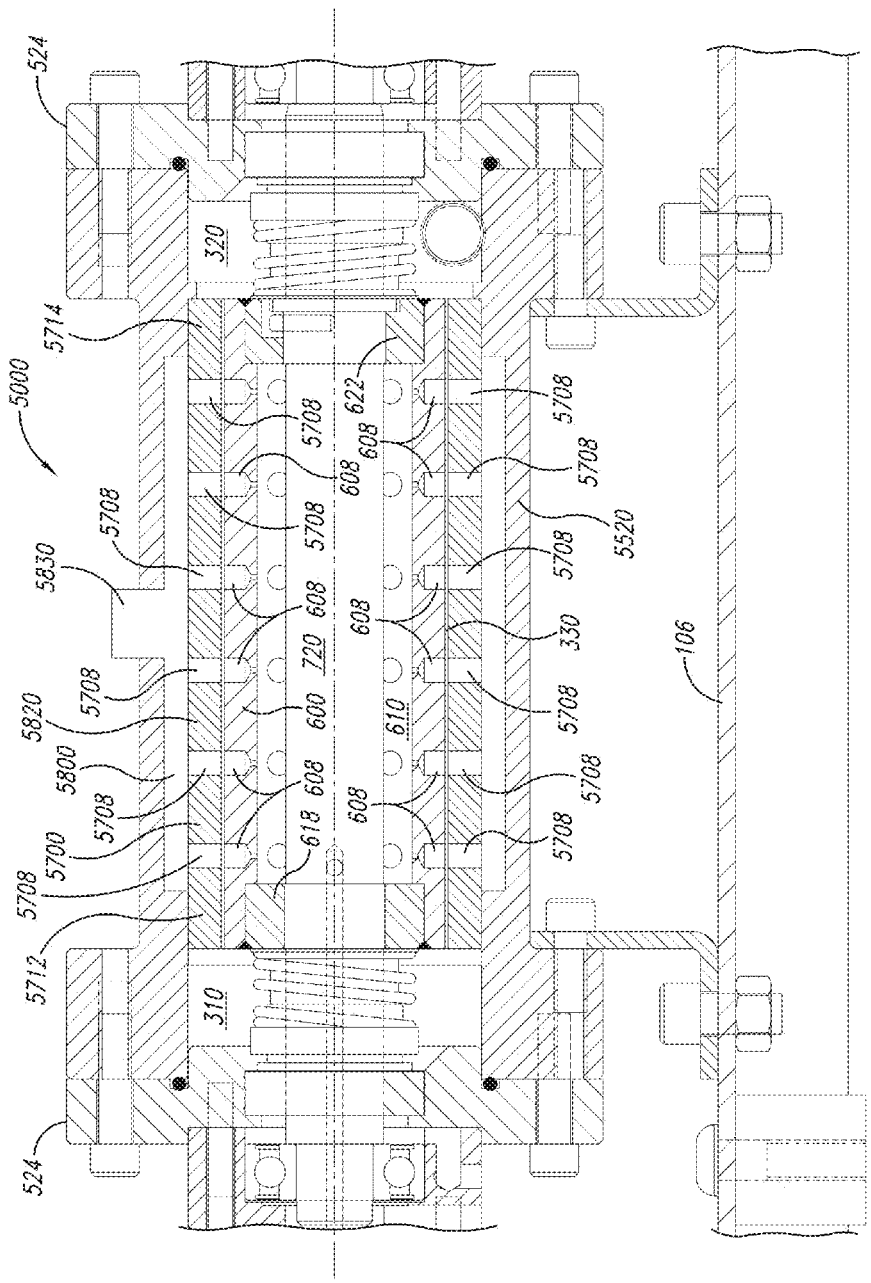
FIG. 12 is a fragmentary cross-sectional view of a side portion of an alternate embodiment of the mixing device.

Referring to FIG. 12, a mixing device 5000 is depicted. The mixing device 5000 is an alternate embodiment of the mixing device 100. Identical reference numerals have been used herein to identify components of the mixing device 5000 that are substantially similar corresponding components of the mixing device 100. Only components of the mixing device 5000 that differ from the components of the mixing device 100 will be described.

The mixing device 5000 includes a housing 5500 for housing the rotor 600 and the stator 5700. The stator 5700 may be non-rotatably couple by its first end portion 5712 and its second end portion 5714 to the housing 5500. A chamber 5800 is defined between the housing 5500 and a portion 5820 of the stator 5700 flanked by the first end portion 5712 and the second end portion 5714. The housing 5500 includes an input port 5830 which provides access into the chamber 5800. The input port 5830 may be oriented substantially orthogonally to the axis of rotation "α." however, this is not a requirement.

The stator 5700 includes a plurality of through-holes 5708 that connect the chamber 5800 and the mixing chamber 330 (defined between the rotor 600 and the stator 5700). An external pump 230 may be used to pump the third material 130 (which may be identical to the second material 120) into the chamber 5800 via the input port 5830. The third material 130 pumped into the chamber 5800 may enter the mixing chamber 330 via the through-holes 5708 formed in the stator 5700. The third material 130 may forced from the channel 5800 by the pump 230, buoyancy of the third material 130 relative to the first material 110, and a combination thereof. As the rotor 600 rotates, it may also draw the third material 130 from the channel 5800 into the mixing chamber 330. The third material 130 may enter the mixing chamber 330 as bubbles, droplets, particles, and the like, which are imparted with a circumferential velocity by the rotor 600.

Alternate Embodiment

Figure 13:
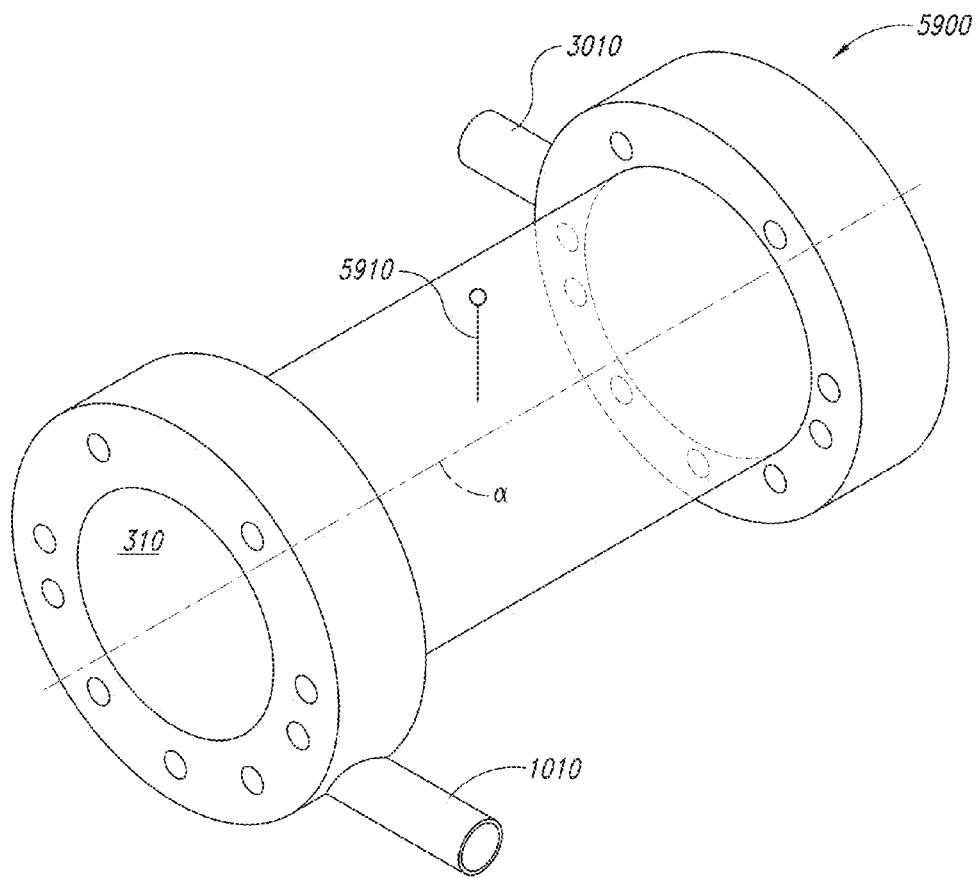
FIG. 13 is a perspective view of an alternate embodiment of a central section of the housing for use with an alternate embodiment of the mixing device.
Figure 14:
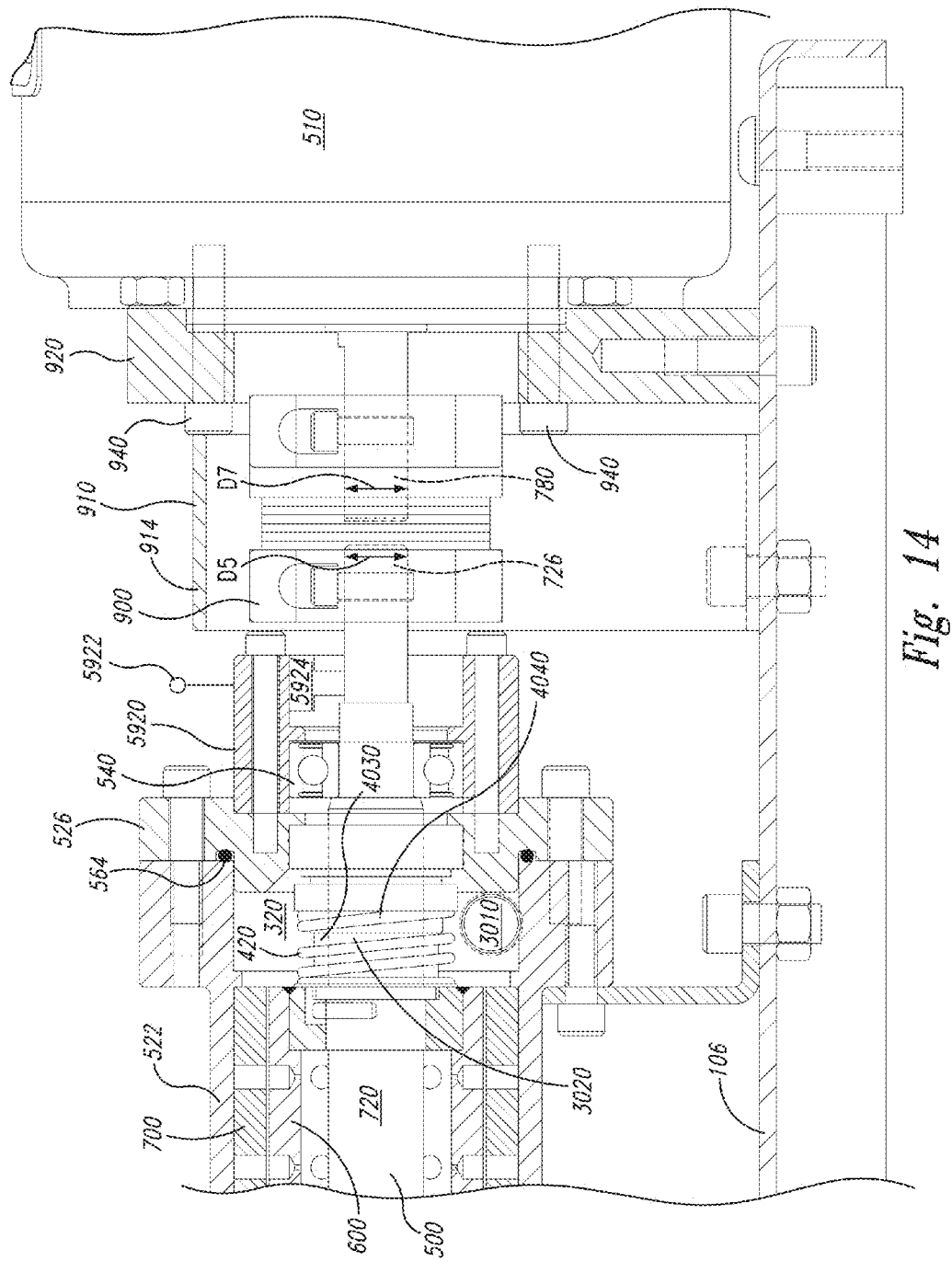
FIG. 14 is a fragmentary cross-sectional view of an alternate embodiment of a bearing housing for use with an alternate embodiment of the mixing device.

An alternate embodiment of the mixing device 100 may be constructed using a central section 5900 depicted in FIG. 13 and a bearing housing 5920 depicted in FIG. 14. FIG. 13 depicts the central section 5900 having in its interior the stator 700 (see FIG. 7). Identical reference numerals have been used herein to identify components associated with the central section 5900 that are substantially similar corresponding components of the mixing device 100. Only components of the central section 5900 that differ from the components of the central section 522 will be described. The central section 5900 and the stator 700 are both constructed from a conductive material such as a metal (e.g., stainless steel). The input port 1010 and the output port 3010 are both constructed from a nonconductive material such as plastic (e.g., PET, Teflon, nylon, PVC, polycarbonate, ABS, Delrin, polysulfone, etc.).

An electrical contact 5910 is coupled to the central section 5900 and configured to deliver a charge to thereto. The central section 5900 conducts an electrical charge applied to the electrical contact 5910 to the stator 700. In further embodiments, the central section 5900 may be constructed from a nonconductive material. In such embodiments, the electrical contact 5910 may pass through the central section 5900 and coupled to the stator 700. The electric charge applied by the electrical contact 5910 to the stator 700 may help facilitate redox or other chemical reactions inside the mixing chamber 330.

Optionally, insulation (not shown) may be disposed around the central section 5900 to electrically isolate it from the environment. Further, insulation may be used between the central section 5900 and the first and second mechanical seals 524 and 526 that flank it to isolate it electrically from the other components of the mixing device.

Turning now to FIG. 14, the bearing housing 5920 will be described. The bearing housing 5920 is disposed circumferentially around the portion 726 of the drive shaft 500. An electrical contact 5922 is coupled to the bearing housing 5920. A rotating brush contact 5924 provides an electrical connection between the drive shaft 500 and the electrical contact 5922.

In this embodiment, the drive shaft 500 and the rotor 600 are both constructed from a conductive material such as a metal (e.g., stainless steel). The bearing housing 5920 may be constructed from either a conductive or a nonconductive material. An electrical charge is applied to the drive shaft 500 by the electrical contact 5922 and the rotating brush contact 5924. The electrical charge is conducted by the drive shaft 500 to the rotor 600.

The alternate embodiment of the mixing device 100 constructed using the central section 5900 depicted in FIG. 13 and the bearing housing 5920 depicted in FIG. 14 may be operated in at least two ways. First, the electrical contacts 5910 and 5922 may be configured not to provide an electrical charge to the stator 700 and the rotor 600, respectively. In other words, neither of the electrical contacts 5910 and 5922 are connected to a current source, a voltage source, and the like.

Alternatively, the electrical contacts 5910 and 5922 may be configured to provide an electrical charge to the stator 700 and the rotor 600, respectively. For example, the electrical contacts 5910 and 5922 may be coupled to a DC voltage source (not shown) supplying a steady or constant voltage across the electrical contacts 5910 and 5922. The negative terminal of the DC voltage source may be coupled to either of the electrical contacts 5910 and 5922 and the positive terminal of the DC voltage source may be coupled to the other of the electrical contacts 5910 and 5922. The voltage supplied across the electrical contacts 5910 and 5922 may range from about 0.0001 volts to about 1000 volts. In particular embodiments, the voltage may range from about 1.8 volts to about 2.7 volts. By way of another example, a pulsed DC voltage having a duty cycle of between about 1% to about 99% may be used.

While the above examples of methods of operating the mixing device apply a DC voltage across the electrical contacts 5910 and 5922, as is apparent to those of ordinary skill in the art, a symmetrical AC voltage or non symmetrical AC voltage having various shapes and magnitudes may be applied across the electrical contacts 5910 and 5922 and such embodiments are within the scope of the present invention.

Mixing Inside the Mixing Chamber 330

As mentioned above, in the prior art device 10 (shown in FIG. 1), the first material 110 entered the channel 32 between the rotor 12 and the stator 30 via a single limited input port 37 located along only a portion of the open second end of the channel 32. Likewise, the output material 102 exited the channel 32 via a single limited output port 40 located along only a portion of the open first end of the channel 32. This arrangement caused undesirable and unnecessary friction. By replacing the single limited inlet port 37 and the single limited outlet port 40 with the chambers 310 and 320, respectively, friction has been reduced. Moreover, the first material 110 does not negotiate a corner before entering the mixing chamber 330 and the output material 102 does not negotiate a corner before exiting the mixing chamber 330. Further, the chambers 310 and 320 provide for circumferential velocity of the material prior to entering, and after exiting the channel 32.

Accordingly, pressure drop across the mixing device 100 has been substantially reduced. In the embodiments depicted in FIGS. 2, 4-9, and 11, the pressure drop between the input port 1010 and the output port 3010 is only approximately 12 psi when the mixing device 100 is configured to produce about 60 gallons of the output material 102 per minute. This is an improvement over the prior art device 10 depicted in FIG. 1, which when producing about 60 gallons of output material per minute was at least 26 psi. In other words, the pressure drop across the mixing device 100 is less than half that experienced by the prior art device 10.

According to additional aspects, the inclusion of pumps 410 and 420, which are powered by the drive shaft 500, provides a configuration that is substantially more efficient in mixing materials and that requires less energy than the external pumps used in the prior art.

Micro-Cavitation

During operation of the mixing device 100, the input materials may include the first material 110 (e.g., a fluid) and the second material 120 (e.g., a gas). The first material 110 and the second material 120 are mixed inside the mixing chamber 330 formed between the rotor 600 and the stator 700. Rotation of the rotor 600 inside the stator 700 agitates the first material 110 and the second material 120 inside the mixing chamber 330. The through-holes 608 formed in the rotor 600 and/or the apertures 708 formed in the stator 700 impart turbulence in the flow of the first material 110 and the second material 120 inside the mixing chamber 330.

Without being limited by theory, the efficiency and persistence of the diffusion of the second material 120 into the first material 110 is believed to be caused in part by micro-cavitation, which is described in connection with FIGS. 15-17. Whenever a material flows over a smooth surface, a rather laminar flow is established with a thin boundary layer that is stationary or moving very slowly because of the surface tension between the moving fluid and the stationary surface. The through-holes 608 and optionally, the apertures 708, disrupt the laminar flow and can cause localized compression and decompression of the first material 110. If the pressure during the decompression cycle is low enough, voids (cavitation bubbles) will form in the material. The cavitation bubbles generate a rotary flow pattern 5990, like a tornado, because the localized area of low pressure draws the host material and the infusion material, as shown in FIG. 15. When the cavitation bubbles implode, extremely high pressures result. As two aligned openings (e.g., one of the apertures 708 and one of the through-holes 608) pass one another, a succession (shock wave) occurs, generating significant energy. The energy associated with cavitation and succession mixes the first material 110 and the second material 120 together to an extremely high degree, perhaps at the molecular level.

The tangential velocity of the rotor 600 and the number of openings that pass each other per rotation may dictate the frequency at which the mixing device 100. It has been determined that operating the mixing device 100 within in the ultrasonic frequency range can be beneficial in many applications. It is believed that operating the mixing device 100 in the ultrasonic region of frequencies provides the maximum succession shock energy to shift the bonding angle of the fluid molecule, which enables it to transport an additional quantity of the second material 120 which it would not normally be able to retain. When the mixing device 100 is used as a diffuser, the frequency at which the mixing device 100 operates appears to affect the degree of diffusion, leading to much longer persistence of the second material 120 (infusion material) in the first material 110 (host material).

Referring now to FIG. 15, an alternate embodiment of the rotor 600, rotor 6000 is provided. The cavitations created within the first material 110 in the mixing chamber 330 may be configured to occur at different frequencies along the length of the mixing chamber 330. The frequencies of the cavitations may be altered by altering the number and/or the placement of the through-holes 6608 along the length of the rotor 600. Each of the through-holes 6608 may be substantially similar to the through-holes 608 (discussed above).

By way of non-limiting example, the rotor 6000 may be subdivided into three separate exemplary sections 6100, 6200, and 6300. The through-holes 6608 increase in density from the section 6100 to the section 6200, the number of holes in the section 6100 being greater than the number of holes in the section 6200. The through-holes 6608 also increase in density from the section 6200 to the section 6300, the number of holes in the section 6200 being greater than the number of holes in the section 6300. Each of the sections 6100, 6200, and 6300 create successions within their particular area at a different frequency due to the differing numbers of through-holes 6608 formed therein.

By manufacturing the rotor 6000 with a desired number of through-holes 6608 appropriately arranged in a particular area, the desired frequency of the successions within the mixing chamber 330 may be determined. Similarly, the desired frequency of the cavitations may be determined by a desired number of apertures 708 appropriately arranged in a particular area upon the stator 700 within which the rotor 600 rotates. Further, the desired frequency (or frequencies) of the successions within the mixing chamber 330 may be achieved by selecting both a particular number and arrangement of the apertures 708 formed in the stator 700 and a particular number and arrangement of the through-holes 608 formed in the rotor 600.

FIGS. 19-21, depict various alternative arrangements of the apertures 708 formed in the stator 700 and the through-holes 608 formed in the rotor 600 configured to achieve different results with respect to the cavitations created. FIG. 19 illustrates a configuration in which the apertures 708 and the through-holes 608 are aligned along an axis 7000 that is not parallel with any line (e.g., line 7010) drawn through the axis of rotation "α" of the rotor 600. In other words, if the rotor 600 has a cylindrical shape, the axis 7000 does not pass through the center of the rotor 600. Thus, the first material 110 within the mixing chamber 330 will not be oriented perpendicularly to the compressions and decompressions created by the apertures 708 and the through-holes 608. The compressions and decompressions will instead have a force vector that has at least a component parallel to the circumferential flow (in the direction of arrow "C3" of FIG. 9) of first material 110 within the mixing chamber 330.

Relative alignment of the apertures 708 and the through-holes 608 may also affect the creation of cavitations in the mixing chamber 330. FIG. 20 illustrates an embodiment in which the apertures 708 are in registration across the mixing chamber 330 with the through-holes 608. In this embodiment, rotation of the rotor 600 brings the through-holes 608 of the rotor into direct alignment with the apertures 708 of the stator

700. When in direct alignment with each other, the compressive and decompressive forces created by the apertures 708 and the through-holes 608 are directly aligned with one another.

In the embodiment depicted in FIG. 21, the apertures 708 and the through-holes 608 are offset by an offset amount "X" along the axis of rotation "α.". By way of non-limiting example, the offset amount "X" may be determined as a function of the size of the apertures 708. For example, the offset amount "X" may be approximately equal to one half of the diameter of the apertures 708. Alternatively, the offset amount "X" may be determined as a function of the size of the through-holes 608. For example, the offset amount "X" may be approximately equal to one half of the diameter of the through-holes 608. If features (e.g., recesses, projections, etc.) other than or in addition to the through-holes 608 and the apertures 708 are included in either the rotor 600 or the stator 700, the offset amount "X" may be determined as a function of the size of such features. In this manner, the compressive and decompressive forces caused by the apertures 708 of the stator 700 and the through-holes 608 of the rotor 600 collide at a slight offset causing additional rotational and torsional forces within the mixing chamber 330. These additional forces increase the mixing (e.g., diffusive action) of the second material 120 into the first material 110 within the mixing chamber 330.

Referring now to FIGS. 22-25, non-limiting examples of suitable cross-sectional shapes for the apertures 708 and the through-holes 608 are provided. The cross-sectional shape of the apertures 708 and/or the through-holes 608 may be square as illustrated in FIG. 22, circular as illustrated in FIG. 23, and the like.

Various cross-sectional shapes of apertures 708 and/or the through-holes 608 may be used to alter flow of the first material 110 as the rotor 600 rotates within the stator 700. For example, FIG. 24 depicts a teardrop cross-sectional shape having a narrow portion 7020 opposite a wide portion 7022. If the through-holes 608 have this teardrop shape, when the rotor 600 is rotated (in the direction generally indicated by the arrow "F"), the forces exerted on the first material 110, the second material 120, and optionally the third material 130 within the mixing chamber 330 increase as the materials pass from the wide portion 7022 of the teardrop to the narrow portion 7020.

Additional rotational forces can be introduced into the mixing chamber 330 by forming the apertures 708 and/or the through-holes 608 with a spiral configuration as illustrated in FIG. 25. Material that flows into and out of the apertures 708 and/or the through-holes 608 having the spiral configuration experience a rotational force induced by the spiral configuration. The examples illustrated in FIGS. 22-25 are provided as non-limiting illustrations of alternate embodiments that may be employed within the mixing device 100. By application of ordinary skill in the art, the apertures 708 and/or the through-holes 608 may be configured in numerous ways to achieve various successive and agitative forces appropriate for mixing materials within the mixing chamber 330.

Double Layer Effect

The mixing device 100 may be configured to create the output material 102 by complex and non-linear fluid dynamic interaction of the first material 110 and the second material 120 with complex, dynamic turbulence providing complex mixing that further favors electrokinetic effects (described below). The result of these electrokinetic effects may be observed within the output material 102 as charge redistributions and redox reactions, including in the form of solublized electrons that are stabilized within the output material.

Ionization or dissociation of surface groups and/or adsorption of ions from a liquid cause most solid surfaces in contact with the liquid to become charged. Referring to FIG. 26, an electrical double layer ("EDL") 7100 forms around exemplary surface 7110 in contact with a liquid 7120. In the EDL 7100, ions 7122 of one charge (in this case, negatively charged ions) adsorb to the surface 7120 and form a surface layer 7124 typically referred to as a Stern layer. The surface layer 7124 attracts counterions 7126 (in this case, positively charged ions) of the opposite charge and equal magnitude, which form a counterion layer 7128 below the surface layer 7124 typically referred to as a diffuse layer. The counterion layer 7128 is more diffusely distributed than the surface layer 7124 and sits upon a uniform and equal distribution of both ions in the bulk material 7130 below. For OH— and H+ ions in neutral water, the Gouy-Chapman model would suggest that the diffuse counterion layer extends about one micron into the water.

According to particular aspects, the electrokinetic effects mentioned above are caused by the movement of the liquid 7120 next to the charged surface 7110. Within the liquid 7120 (e.g., water, saline solution, and the like), the adsorbed ions 7122 forming the surface layer 7124 are fixed to the surface 7120 even when the liquid 7120 is in motion (for example, flowing in the direction indicated by arrow "G"); however, a shearing plane 7132 exists within the diffuse counterion layer 7128 spaced from the surface 7120. Thus, as the liquid 7120 moves, some of the diffuse counterions 7126 are transported away from the surface 7120, while the absorbed ions 7122 remain at the surface 7120. This produces a so-called 'streaming current.'

Within the mixing chamber 330, the first material 110, the second material 120, and optionally, the third material 130 are subject to an electromagnetic field created by the inside surface 705 of the stator 700 and/or the outside surface 606 of the rotor 600, a voltage between the inside surface 705 and the outside surface 606, and/or an electrokinetic effect (e.g., streaming current) caused by at least one EDL formed in the first material 110. The at least one EDL may be introduced into the first material 110 by at least one of the inside surface 705 of the stator 700 and the outside surface 606 of the rotor 600.

Movement of the first material 110 through the mixing chamber 330 relative to surface disturbances (e.g., the through-holes 608 and apertures 708) creates cavitations in the first material 110 within the mixing chamber 330, which may diffuse the second material 120 into the first material 110. These cavitations may enhance contact between of the first material 110 and/or the second material 120 with the electric double layer formed on the inside surface 705 of the stator 700 and/or the electric double layer formed on the outside surface 606 of the rotor 600. Larger surface to volume ratios of the mixing chamber, an increased dwell time of the combined materials within the mixing chamber, and further in combination with a small average bubble size (and hence substantially greater bubble surface area) provide for effectively imparting EDL-mediated effects to the inventive output materials.

In embodiments in which the inside surface 705 and the outside surface 606 are constructed from a metallic material, such as stainless steel, the motion of the liquid 7120 and/or the streaming current(s) facilitate redox reactions involving $H_2O$, OH—, H+, and $O_2$ at the inside surface 705 and the outside surface 606.

Referring to FIG. 27, without being limited by theory, it is believed a section 7140 of the mixing chamber 330 between the inside surface 705 and the outside surface 606 the may be modeled as a pair of parallel plates 7142 and 7144. If the first material 110 is a liquid, the first material 110 enters the section 7140 through an inlet "IN" and exits the section 7140 through an outlet "OUT." The inlet "IN" and the outlet "OUT" restrict the flow into and out of the section 7140.

Referring to FIG. 28, the area between the parallel plates 7142 and 7144 has a high surface area to volume ratio. Hence, a substantial portion of the counterion layer 7128 (and counterions 7126) may be in motion as the first material 110 moves between the plates 7142 and 7144. The number of counterions 7126 in motion may exceed the number allowed to enter the section 7140 by the inlet "IN" and the number allowed to exit the section 7140 by the outlet "OUT." The inlet "IN" and the outlet "OUT" feeding and removing the first material 110 from the section 7140, respectively, have far less surface area (and a lower surface area to volume ratio) than the parallel plates 7142 and 7144 and thereby reduce the portion of the counterions 7126 in motion in the first material 110 entering and leaving the section 7140. Therefore, entry and exit from the section 7140 increases the streaming current locally. While a background streaming current (identified by arrow "BSC") caused by the flowing first material 110 over any surface is always present inside the mixing device 100, the plates 7142 and 7144 introduce an increased "excess" streaming current (identified by arrow "ESC") within the section 7140.

Without a conductive return current (identified by arrow "RC") in the plates 7142 and 7144 in the opposite direction of the flow of the first material 110, an excess charge 7146 having the same sign as the adsorbing ions 7122 would accumulate near the inlet "IN," and an excess charge 7148 having the same sign as the counterion 7126 would accumulate near the at outlet "OUT." Because such accumulated charges 7146 and 7148, being opposite and therefore attracted to one another, cannot build up indefinitely the accumulated charges seek to join together by conductive means. If the plates 7142 and 7144 are perfectly electrically insulating, the accumulated charges 7146 and 7148 can relocate only through the first material 110 itself. When the conductive return current (identified by arrow "RC") is substantially equivalent to the excess streaming current (identified by arrow "ESC") in the section 7140, a steady-state is achieved having zero net excess streaming current, and an electrostatic potential difference between the excess charge 7146 near the inlet "IN," and the excess charge 7148 near the outlet "OUT" creating a steady-state charge separation therebetween.

The amount of charge separation, and hence the electrostatic potential difference between the excess charge 7146 near the inlet "IN," and the excess charge 7148 near the outlet "OUT," depends on additional energy per unit charge supplied by a pump (e.g., the rotor 600, the internal pump 410, and/or the external pump 210) to "push" charge against the opposing electric field (created by the charge separation) to produce the a liquid flow rate approximating a flow rate obtainable by a liquid without ions (i.e., ions 7122 and 7126). If the plates 7142 and 7144 are insulators, the electrostatic potential difference is a direct measure of the EMF the pump (e.g., the rotor 600, the internal pump 410 and/or the external pump 210) can generate. In this case, one could measure the electrostatic potential difference using a voltmeter having a pair of leads by placing one of the leads in the first material 110 near the inlet "IN," and the other lead in the first material 110 near the outlet "OUT."

With insulating plates 7142 and 7144, any return current is purely an ion current (or flow of ions), in that the return current involves only the conduction of ions through the first material 110. If other conductive mechanisms through more conductive pathways are present between the excess charge 7146 near the inlet "IN," and the excess charge 7148 near the outlet "OUT," the return current may use those more conductive pathways. For example, conducting metal plates 7142 and 7144 may provide more conductive pathways; however, these more conductive pathways transmit only an electron current and not the ion current.

As is appreciated by those of ordinary skill, to transfer the charge carried by an ion to one or more electrons in the metal, and vise versa, one or more oxidation-reduction reactions must occur at the surface of the metal, producing reaction products.

Assuming the first material 110 is water ($H_2O$) and the second material 120 is oxygen ($O_2$), a non-limiting example of a redox reaction, which would inject negative charge into the conducting plates 7142 and 7144 includes the following known half-cell reaction:

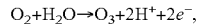

$O_2 + H_2O \rightarrow O_3 + 2H^+ + 2e^-$,

Again, assuming the first material 110 is water ($H_2O$) and the second material 120 is oxygen ($O_2$), a non-limiting example of a redox reaction includes the following known half-cell reaction, which would remove negative charge from the conducting plates 7142 and 7144 includes the following known half-cell reaction:

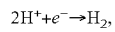

$2H^+ + e^- \rightarrow H_2$,

With conducting metal plates 7142 and 7144, most of the return current is believed to be an electron current, because the conducting plates 7142 and 7144 are more conductive than the first material 110 (provided the redox reactions are fast enough not to be a limiting factor). For the conducting metal plates 7142 and 7144, a smaller charge separation accumulates between the inlet "IN" and the outlet "OUT," and a much smaller electrostatic potential exists therebetween. However, this does not mean that the EMF is smaller.

As described above, the EMF is related to the energy per unit charge the pump provides to facilitate the flow of the first material 110 against the opposing electric field created by the charge separation. Because the electrostatic potential is smaller, the pump may supply less energy per unit charge to cause the first material 110 to flow. However, the above example redox reactions do not necessarily occur spontaneously, and thus may require a work input, which may be provided by the pump. Therefore, a portion of the EMF (that is not reflected in the smaller electrostatic potential difference) may be used to provide the energy necessary to drive the redox reactions.

In other words, the same pressure differentials provided by the pump to push against the opposing electric field created by the charge separation for the insulating plates 7142 and 7144, may be used both to "push" the charge through the conducting plates 7142 and 7144 and drive the redox reactions.

Figure 29:
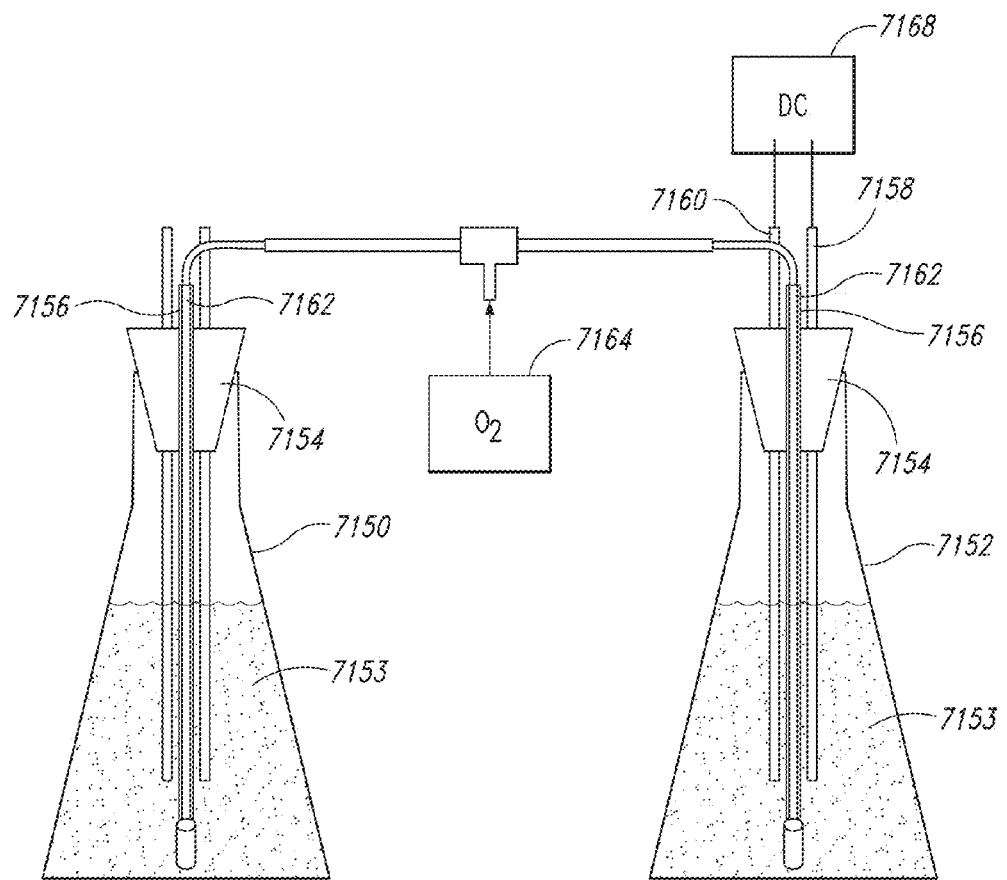
FIG. 29 is an illustration of an experimental setup.

Referring to FIG. 29, an experimental setup for an experiment conducted by the inventors is provided. The experiment included a pair of substantially identical spaced apart 500 ml standard Erlenmeyer flasks 7150 and 7152, each containing a volume of deionized water 7153. A rubber stopper 7154 was inserted in the open end of each of the flasks 7150 and 7152. The stopper 7154 included three pathways, one each for a hollow tube 7156, a positive electrode 7158, and a negative electrode 7160. With respect to each of the flasks 7150 and 7152, each of the hollow tube 7156, the positive electrode 7158, and the negative electrode 7160 all extended from outside the flask, through the stopper 7154, and into the deionized water 7153 inside the flask. The positive electrode 7158 and the negative electrode 7160 were constructed from stainless steel. The hollow tubes 7156 in both of the flasks 7150 and 7152 had an open end portion 7162 coupled to a common oxygen supply 7164. The positive electrode 7158 and the negative electrode 7160 inserted into the flask 7152 where coupled to a positive terminal and a negative terminal, respectively, of a DC power supply 7168. Exactly the same sparger was used in each flask.

Oxygen flowed through the hollow tubes 7156 into both of the flasks 7150 and 7152 at a flow rate (Feed) of about 1 SCFH to about 1.3 SCFH (combined flow rate). The voltage applied across the positive electrode 7158 and the negative electrode 7160 inserted into the flask 7152 was about 2.55 volts. This value was chosen because it is believed to be an electrochemical voltage value sufficient to affect all oxygen species. This voltage was applied continuously over three to four hours during which oxygen from the supply 7164 was bubbled into the deionized water 7153 in each of the flasks 7150 and 7152.

Testing of the deionized water 7153 in the flask 7150 with HRP and pyrogallol gave an HRP-mediated pyrogallol reaction activity, consistent with the properties of fluids produced with the alternate rotor/stator embodiments described herein. The HRP optical density was about 20% higher relative to pressure-pot or fine-bubbled solutions of equivalent oxygen content. The results of this experiment indicate that mixing inside the mixing chamber 330 involves a redox reaction. According to particular aspects, the inventive mixing chambers provide for output materials comprising added electrons that are stabilized by either oxygen-rich water structure within the inventive output solutions, or by some form of oxygen species present due to the electrical effects within the process.

Additionally, the deionized water 7153 in both of the flasks 7150 and 7152 was tested for both ozone and hydrogen peroxide employing industry standard colorimetric test ampoules with a sensitivity of 0.1 ppm for hydrogen peroxide and 0.6 ppm for ozone. There was no positive indication of either species up to the detection limits of those ampoules.

Dwell Time

Dwell time is an amount of time the first material 110, the second material 120, and optionally the third material 130 spend in the mixing chamber 330. The ratio of the length of the mixing chamber 330 to the diameter of the mixing chamber 330 may significantly affect dwell time. The greater the ratio, the longer the dwell time. As mentioned in the Background Section, the rotor 12 of the prior art device 10 (see FIG. 1) had a diameter of about 7.500 inches and a length of about 6.000 inches providing a length to diameter ratio of about 0.8. In contrast, in particular embodiments, the length of the mixing chamber 330 of the mixing device 100 is about 5 inches and the diameter "D1" of the rotor 600 is about 1.69 inches yielding a length to diameter ratio of about 2.95.

Dwell time represents the amount of time that the first material 110, the second material 120, and optionally the third material 130 are able to interact with the electrokinetic phenomena described herein. The prior art device 10 is configured to produce about 60 gallons of the output material 102 per minute and the mixing device 100 is configured to produce about 0.5 gallons of the output material 102 per minute, the prior art device 10 (see FIG. 1) had a fluid dwell time of about 0.05 seconds, whereas embodiments of the mixing device 100 have a substantially greater (about 7-times greater) dwell time of about 0.35 seconds. This longer dwell time allows the first material 110, the second material 120, and optionally the third material 130 to interact with each other and the surfaces 606 and 705 (see FIG. 7) inside the mixing chamber 330 for about 7-times longer than was possible in the prior art device 10. In additional embodiments, the dwell time is at least 1.5-times, at least 2-times, at least 3-times, at least 4-times, at least 5-times, at least 6-times, at least 7-times or greater, than was possible in the prior art device 10.

With reference to Table 3 below, the above dwell times were calculated by first determining the flow rate for each device in gallons per second. In the case of the prior art device 10 was configured to operate at about 60 gallons of output material per minute, while the mixing device 100 is configured to operate over a broader range of flow rate, including at an optimal range of bout 0.5 gallons of output material per minute. The flow rate was then converted to cubic inches per second by multiplying the flow rate in gallons per second by the number of cubic inches in a gallon (i.e., 231 cubic inches). Then, the volume (12.876 cubic inches) of the channel 32 of the prior art device 10 was divided by the flow rate of the device (231 cubic inches/second) to obtain the dwell time (in seconds) and the volume (0.673 cubic inches) of the mixing chamber 330 of the mixing device 100 was divided by the flow rate (1.925 cubic inches/second) of the device (in cubic inches per second) to obtain the dwell time (in seconds).

TABLE 3

Inventive device can accommodate a range of dwell times, including a substantially increased (e.g., 7-times) dwell time relative to prior art devices.

| Device | Flow Rate Gallons/ Minute | Flow Rate Gallons/ Second | Flow Rate Cubic Inches/ Second | Volume Mixing Chamber (Cubic Inches) | Dwell Time (Seconds) |
|---|---|---|---|---|---|
| Prior art device 10 | 60 | 1.000 | 231.000 | 12.876 | 0.056 |
| Mixing device 100 | 2 | 0.033 | 7.700 | 0.673 | 0.087 |
| Mixing device 100 | 0.5 | 0.008 | 1.925 | 0.673 | 0.350 |

Rate of Infusion

Particular aspects of the mixing device 100 provide an improved oxygen infusion rate over the prior art, including over prior art device 10 (see FIG. 1). When the first material 110 is water and the second material 120 is oxygen, both of which are processed by the mixing device 100 in a single pass (i.e., the return block of FIG. 2 is set to "NO") at or near 20° Celsius, the output material 102 has a dissolved oxygen level of about 43.8 parts per million. In certain aspects, an output material having about 43.8 ppm dissolved oxygen is created in about 350 milliseconds via the inventive flow through the inventive non pressurized (non-pressure pot) methods. In contrast, when the first material 110 (water) and the second material 120 (oxygen) are both processed in a single pass at or near 20° Celsius by the prior art device 10, the output material had dissolved oxygen level of only 35 parts per million in a single pass of 56 milliseconds.

Output Material 102

When the first material 110 is a liquid (e.g., freshwater, saline, GATORADE®, and the like) and the second material 120 is a gas (e.g., oxygen, nitrogen, and the like), the mixing device 100 may diffuse the second material 120 into the first material 110. The following discusses results of analyses performed on the output material 102 to characterize one or more properties of the output material 102 derived from having been processed by the mixing device 100.

When the first material 110 is saline solution and the second material 120 is oxygen gas, experiments have indicated that a vast majority of oxygen bubbles produced within the saline solution are no greater than 0.1 micron in size.

Decay of Dissolved Oxygen Levels

Figure 30:
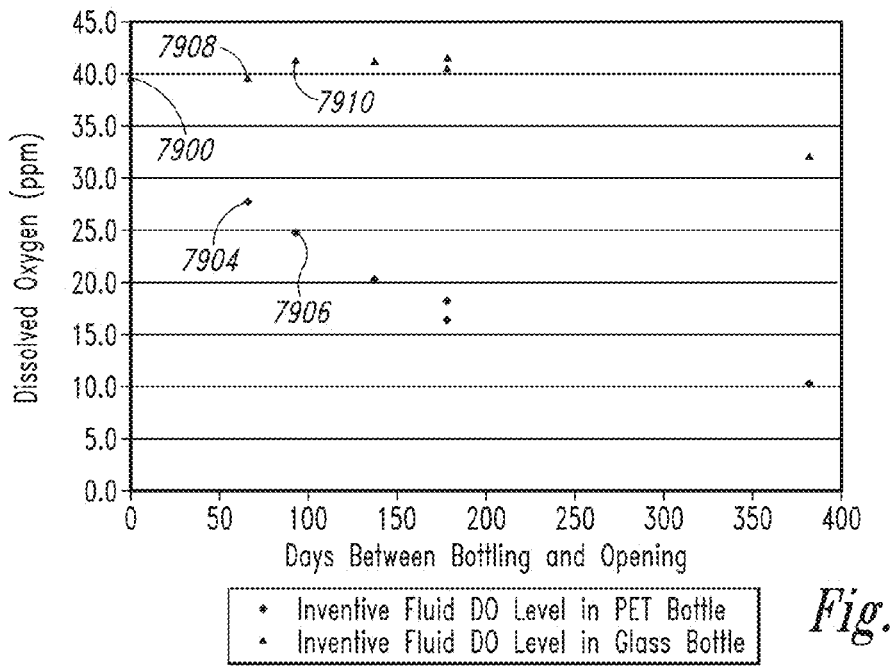
FIG. 30 illustrates dissolved oxygen levels in water processed with oxygen in the mixing device of FIG. 2 and stored a 500 ml thin walled plastic bottle and a 1,000 ml glass bottle each capped at 65° Fahrenheit.

Referring now to FIG. 30, there is illustrated the DO levels in water processed with oxygen in the mixing device 100 and stored in a 500 ml thin-walled plastic bottle and a 1000 ml glass bottle. Each of the bottles was capped and stored at 65 degrees Fahrenheit. Point 7900 is the DO level at bottling. Line 7902 illustrates the Henry's Law equilibrium state (i.e., the amount of dissolved oxygen that should be within the water at 65 degrees Fahrenheit), which is a DO level of slightly less than 10 ppm. Points 7904 and 7906 represent the DO levels within the water in the plastic bottle at 65 days and 95 days respectively. As can be seen at point 7904, when the plastic bottle is opened approximately 65 days after bottling, the DO level within the water is approximately 27.5 ppm. When the bottle is opened approximately 95 days after bottling, as indicated at point 7906, the DO level is approximately 25 ppm. Likewise, for the glass bottle, the DO level is approximately 40 ppm at 65 days as indicated at point 7908 and is approximately 41 ppm at 95 days as illustrated at point 7910. Thus, FIG. 27 indicates the DO levels within both the plastic bottle and the glass bottle remain relatively high at 65 degrees Fahrenheit.

Referring now to FIG. 30, there is illustrated the DO levels in water enriched with oxygen in the mixing device 100 and stored in a 500 ml thin-walled plastic bottle and a 1000 ml glass bottle out to at least 365 days. Each of the bottles was capped and stored at 65 degrees Fahrenheit. As can be seen in the Figure, the DO levels of the oxygen-enriched fluid remained fairly constant out to at least 365 days.

Figure 31:
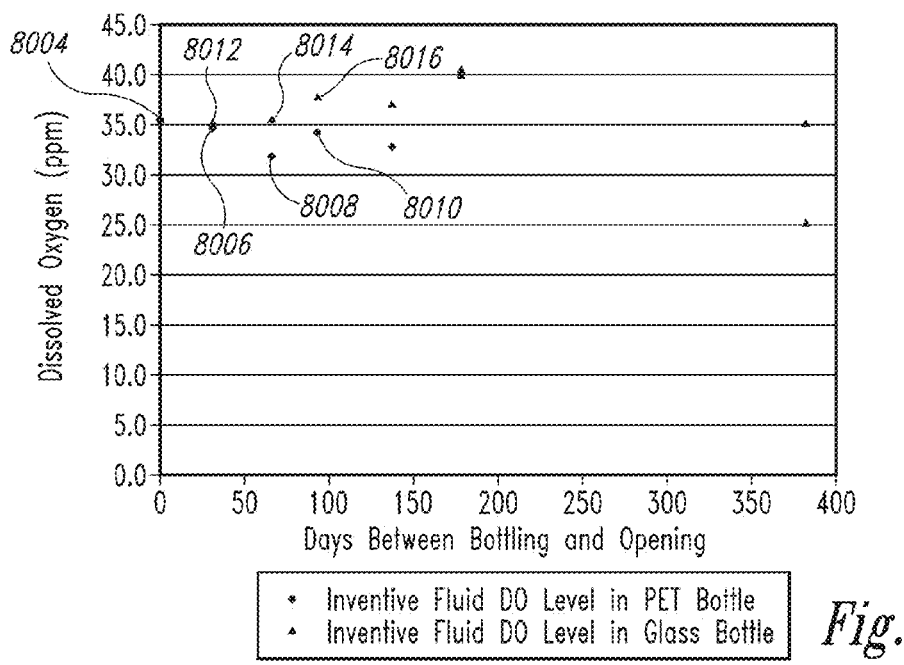
FIG. 31 illustrates dissolved oxygen levels in water processed with oxygen in the mixing device of FIG. 2 and stored in a 500 ml plastic thin walled bottle and a 1,000 ml glass bottle both refrigerated at 39° Fahrenheit.
Figure 32:
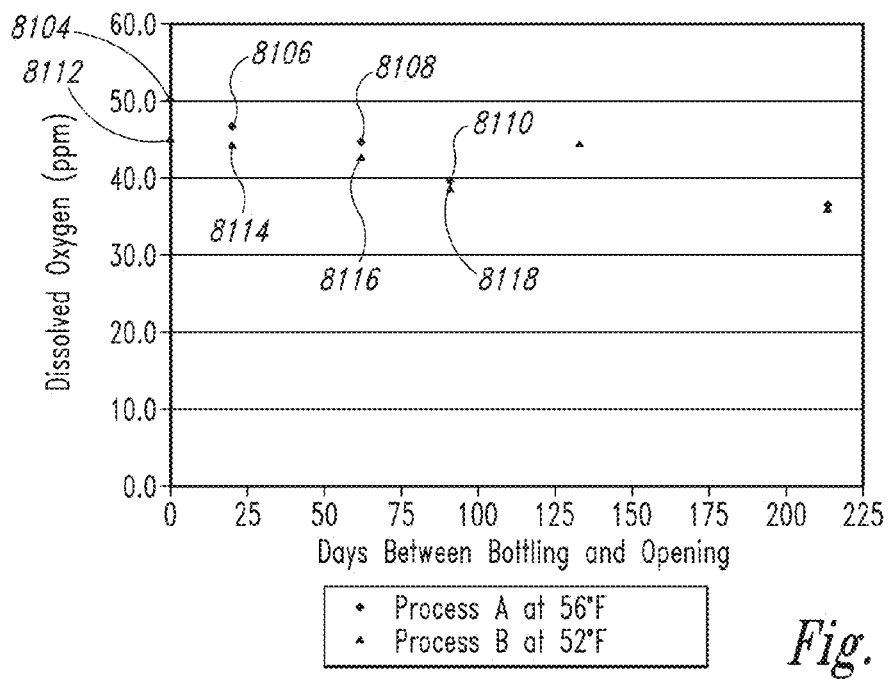
FIG. 32 illustrates the dissolved oxygen retention of a 500 ml beverage fluid processed with oxygen in the mixing device of FIG. 2.

Referring to FIG. 31, there is illustrated the DO levels in water enriched with oxygen in the mixing device 100 and stored in a 500 ml plastic thin-walled bottle and a 1000 ml glass bottle. Both bottles were refrigerated at 39 degrees Fahrenheit. Again, DO levels of the oxygen-enriched fluid remained steady and decreased only slightly out to at least 365 days.

Molecular Interactions

Conventionally, quantum properties are thought to belong to elementary particles of less than $10^{-10}$ meters, while the macroscopic world of our everyday life is referred to as classical, in that it behaves according to Newton's laws of motion.

Recently, molecules have been described as forming clusters that increase in size with dilution. These clusters measure several micrometers in diameter, and have been reported to increase in size non-linearly with dilution. Quantum coherent domains measuring 100 nanometers in diameter have been postulated to arise in pure water, and collective vibrations of water molecules in the coherent domain may eventually become phase locked to electromagnetic field fluctuations, providing for stable oscillations in water, providing a form of 'memory' in the form of excitation of long lasting coherent oscillations specific to dissolved substances in the water that change the collective structure of the water, which may in turn determine the specific coherent oscillations that develop. Where these oscillations become stabilized by magnetic field phase coupling, the water, upon dilution may still carry 'seed' coherent oscillations. As a cluster of molecules increases in size, its electromagnetic signature is correspondingly amplified, reinforcing the coherent oscillations carried by the water.

Despite variations in the cluster size of dissolved molecules and detailed microscopic structure of the water, a specificity of coherent oscillations may nonetheless exist. One model for considering changes in properties of water is based on considerations involved in crystallization.

Figure 36:
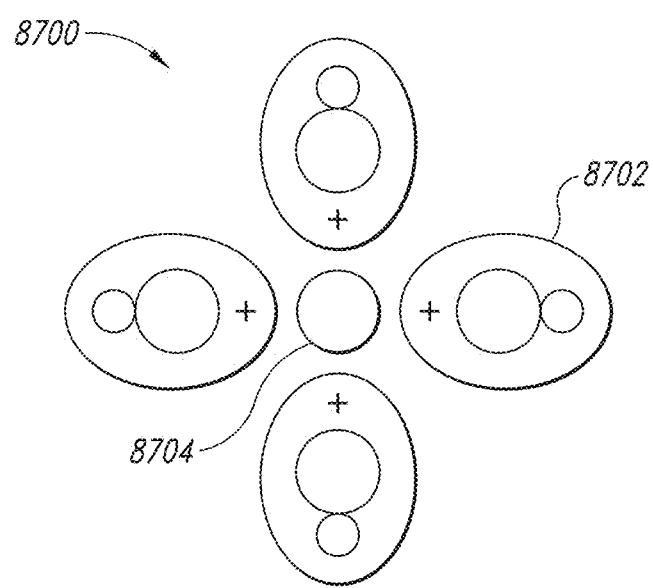
FIG. 36 is an illustration of an exemplary nanocage.
Figure 36:
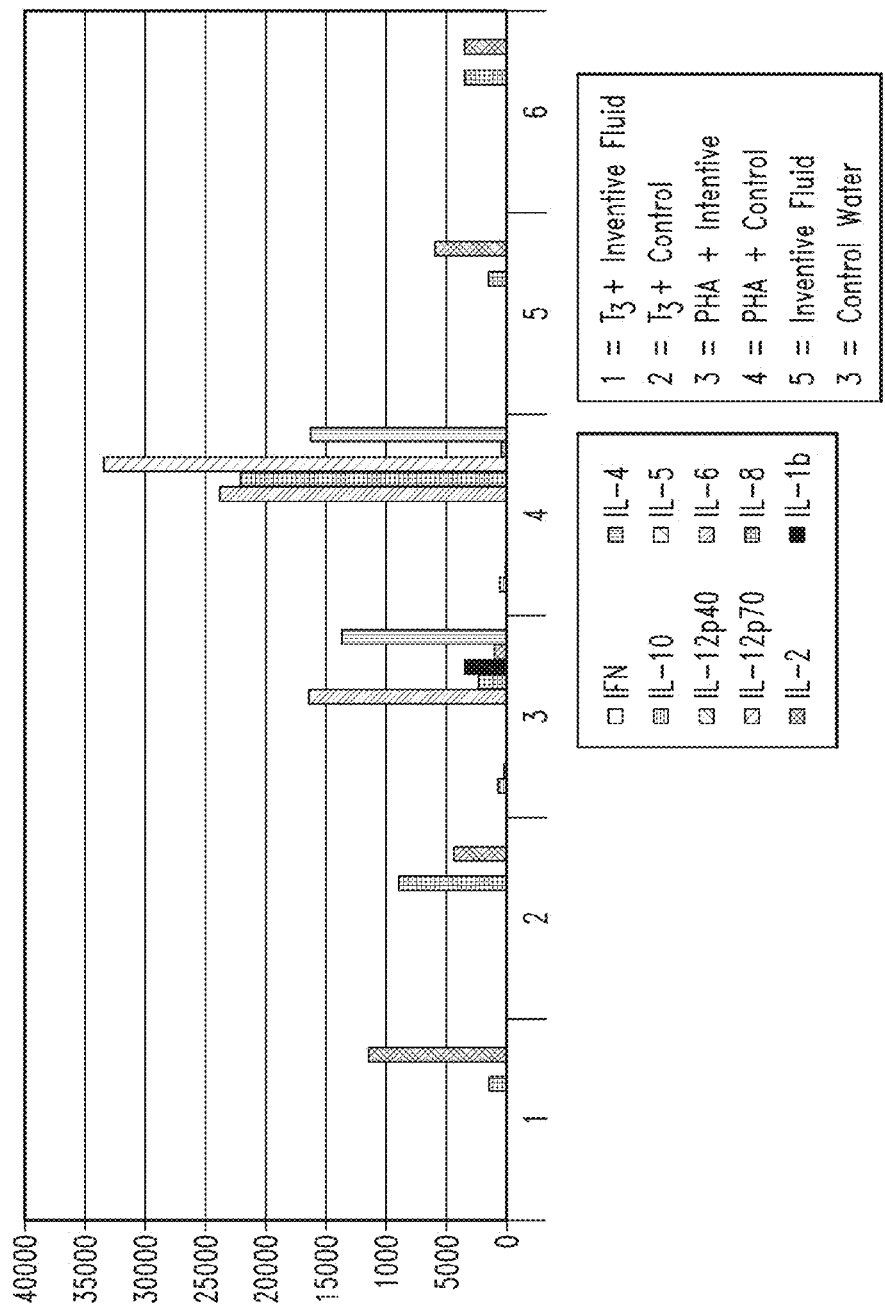

With reference to FIG. 36, a simplified protonated water cluster forming a nanoscale cage 8700 is shown. A protonated water cluster typically takes the form of $H^+(H_2O)_n$. Some protonated water clusters occur naturally, such as in the ionosphere. Without being bound by any particular theory, and according to particular aspects, other types of water clusters or structures (clusters, nanocages, etc.) are possible, including structures comprising oxygen and stabilized electrons imparted to the inventive output materials. Oxygen atoms 8704 may be caught in the resulting structures 8700. The chemistry of the semi-bound nanocage allows the oxygen 8704 and/or stabilized electrons to remain dissolved for extended periods of time. Other atoms or molecules, such as medicinal compounds, can be caged for sustained delivery purposes. The specific chemistry of the solution material and dissolved compounds depend on the interactions of those materials.

Fluids processed by the mixing device 100 have been shown via experiments to exhibit different structural characteristics that are consistent with an analysis of the fluid in the context of a cluster structure.

Water processed through the mixing device 100 has been demonstrated to have detectible structural differences when compared with normal unprocessed water. For example, processed water has been shown to have more Rayleigh scattering than is observed in unprocessed water. In the experiments that were conducted, samples of processed and unprocessed water were prepared (by sealing each in a separate bottle), coded (for later identification of the processed sample and unprocessed sample), and sent to an independent testing laboratory for analysis. Only after the tests were completed were the codes interpreted to reveal which sample had been processed by the mixing device 100.

At the laboratory, the two samples were placed in a laser beam having a wavelength of 633 nanometers. The fluid had been sealed in glass bottles for approximately one week before testing. With respect to the processed sample, Sample B scattered light regardless of its position relative to the laser source. However, Sample A did not. After two to three hours following the opening of the bottle, the scattering effect of Sample B disappeared. These results imply the water exhibited a memory causing the water to retain its properties and dissipate over time. These results also imply the structure of the processed water is optically different from the structure of the unprocessed fluid. Finally, these results imply the optical effect is not directly related to DO levels because the DO level at the start was 45 ppm and at the end of the experiment was estimated to be approximately 32 ppm.

Charge-Stabilized Nanostructures (e.g., Charge Stabilized Oxygen-Containing Nanostructures):

As described herein above under "Double Layer Effect," "Dwell Time," "Rate of Infusion," and "Bubble size Measurements," the mixing device 100 creates, in a matter of milliseconds, a unique non-linear fluid dynamic interaction of the first material 110 and the second material 120 with complex, dynamic turbulence providing complex mixing in contact with an effectively enormous surface area (including those of the device and of the exceptionally small gas bubbles of less that 100 nm) that provides for the novel electrokinetic effects described herein. Additionally, feature-localized electrokinetic effects (voltage/current) were demonstrated herein (see working Example 20) using a specially designed mixing device comprising insulated rotor and stator features.

As well-recognized in the art, charge redistributions and/or solvated electrons are known to be highly unstable in aqueous solution. According to particular aspects, Applicants' electrokinetic effects (e.g., charge redistributions, including, in particular aspects, solvated electrons) are surprisingly stabilized within the output material (e.g., saline solutions, ionic solutions). In fact, as described herein, the stability of the properties and biological activity of the inventive electrokinetic fluids (e.g., RNS-60 or Solas) can be maintained for months in a gas-tight container, indicating involvement of dissolved gas (e.g., oxygen) in helping to generate and/or maintain, and/or mediate the properties and activities of the inventive solutions. Significantly, as described in the working Examples herein, the charge redistributions and/or solvated electrons are stably configured in the inventive electrokinetic ionic aqueous fluids in an amount sufficient to provide, upon contact with a living cell (e.g., mammalian cell) by the fluid, modulation of at least one of cellular membrane potential and cellular membrane conductivity (see, e.g., cellular patch clamp working Examples 23 and 24).

As described herein under "Molecular Interactions," to account for the stability and biological compatibility of the inventive electrokinetic fluids (e.g., electrokinetic saline solutions), Applicants have proposed that interactions between the water molecules and the molecules of the substances (e.g., oxygen) dissolved in the water change the collective structure of the water and provide for nanoscale cage clusters, including nanostructures comprising oxygen and/or stabilized electrons imparted to the inventive output materials. Without being bound by mechanism, and according to the properties and activities described herein, the configuration of the nanostructures in particular aspects is such that they: comprise (at least for formation and/or stability and/or biological activity) dissolved gas (e.g., oxygen); enable the electrokinetic fluids (e.g., RNS-60 or Solas saline fluids) to modulate (e.g., impart or receive) charges and/or charge effects upon contact with a cell membrane or related constituent thereof; and in particular aspects provide for stabilization (e.g., carrying, harboring, trapping) solvated electrons in a biologically-relevant form.

According to particular aspects, and as supported by the present disclosure, in ionic or saline (e.g., standard saline, NaCl) solutions, the inventive nanostructures comprise charge stabilized nanostrutures (e.g., average diameter less that 100 nm) that may comprise at least one dissolved gas molecule (e.g., oxygen) within a charge-stabilized hydration shell. According to additional aspects, and as described elsewhere herein, the charge-stabilized hydration shell may comprise a cage or void harboring the at least one dissolved gas molecule (e.g., oxygen). According to further aspects, by virtue of the provision of suitable charge—stabilized hydration shells, the charge-stabilized nanostructure and/or charge-stabilized oxygen containing nano-structures may additionally comprise a solvated electron (e.g., stabilized solvated electron).

Without being bound by mechanism or particular theory, after the present priority date, charge-stabilized microbubbles stabilized by ions in aqueous liquid in equilibrium with ambient (atmospheric) gas have been proposed (Bunkin et al., *Journal of Experimental and Theoretical Physics,* 104:486-498, 2007; incorporated herein by reference in its entirety). According to particular aspects of the present invention, Applicants' novel electrokinetic fluids comprise a novel, biologically active form of charge-stabilized oxygen-containing nanostructures, and may further comprise novel arrays, clusters or associations of such structures.

According to the charge-stabilized microbubble model, the short-range molecular order of the water structure is destroyed by the presence of a gas molecule (e.g., a dissolved gas molecule initially complexed with a nonadsorptive ion provides a short-range order defect), providing for condensation of ionic droplets, wherein the defect is surrounded by first and second coordination spheres of water molecules, which are alternately filled by adsorptive ions (e.g., acquisition of a 'screening shell of $Na^+$ ions to form an electrical double layer) and nonadsorptive ions (e.g., $Cl^-$ ions occupying the second coordination sphere) occupying six and 12 vacancies, respectively, in the coordination spheres. In under-saturated ionic solutions (e.g., undersaturated saline solutions), this hydrated 'nucleus' remains stable until the first and second spheres are filled by six adsorptive and five nonadsorptive ions, respectively, and then undergoes Coulomb explosion creating an internal void containing the gas molecule, wherein the adsorptive ions (e.g., $Na^+$ ions) are adsorbed to the surface of the resulting void, while the nonadsorptive ions (or some portion thereof) diffuse into the solution (Bunkin et al., supra). In this model, the void in the nanostructure is prevented from collapsing by Coulombic repulsion between the ions (e.g., $Na^+$ ions) adsorbed to its surface. The stability of the void-containing nanostrutures is postulated to be due to the selective adsorption of dissolved ions with like charges onto the void/bubble surface and diffusive equilibrium between the dissolved gas and the gas inside the bubble, where the negative (outward electrostatic pressure exerted by the resulting electrical double layer provides stable compensation for surface tension, and the gas pressure inside the bubble is balanced by the ambient pressure. According to the model, formation of such microbubbles requires an ionic component, and in certain aspects collision-mediated associations between particles may provide for formation of larger order clusters (arrays) (ld).

The charge-stabilized microbubble model suggests that the particles can be gas microbubbles, but contemplates only spontaneous formation of such structures in ionic solution in equilibrium with ambient air, is uncharacterized and silent as to whether oxygen is capable of forming such structures, and is likewise silent as to whether solvated electrons might be associated and/or stabilized by such structures.

According to particular aspects, the inventive electrokinetic fluids comprising charge-stabilized nanostructures and/or charge-stabilized oxygen-containing nanostructures are novel and fundamentally distinct from the postulated non-electrokinetic, atmospheric charge-stabilized microbubble structures according to the microbubble model. Significantly, this conclusion is in unavoidable, deriving, at least in part, from the fact that control saline solutions do not have the biological properties disclosed herein, whereas Applicants' charge-stabilized nanostructures provide a novel, biologically active form of charge-stabilized oxygen-containing nanostructures.

According to particular aspects of the present invention, Applicants' novel electrokinetic device and methods provide for novel electrokinetically-altered fluids comprising significant quantities of charge-stabilized nanostructures in excess of any amount that may or may not spontaneously occur in ionic fluids in equilibrium with air, or in any non-electrokinetically generated fluids. In particular aspects, the charge-stabilized nanostructures comprise charge-stabilized oxygen-containing nanostructures. In additional aspects, the charge-stabilized nanostrutures are all, or substantially all charge-stabilized oxygen-containing nanostructures, or the charge-stabilized oxygen-containing nanostructures the major charge-stabilized gas-containing nanostructure species in the electrokinetic fluid.

According to yet further aspects, the charge-stabilized nanostructures and/or the charge-stabilized oxygen-containing nanostructures may comprise or harbor a solvated electron, and thereby provide a novel stabilized solvated electron carrier. In particular aspects, the charge-stabilized nanostructures and/or the charge-stabilized oxygen-containing nanostructures provide a novel type of electride (or inverted electride), which in contrast to conventional solute electrides having a single organically coordinated cation, rather have a plurality of cations stably arrayed about a void or a void containing an oxygen atom, wherein the arrayed sodium ions are coordinated by water hydration shells, rather than by organic molecules. According to particular aspects, a solvated electron may be accommodated by the hydration shell of water molecules, or preferably accommodated within the nanostructure void distributed over all the cations. In certain aspects, the inventive nanostructures provide a novel 'super electride' structure in solution by not only providing for distribution/stabilization of the solvated electron over multiple arrayed sodium cations, but also providing for association or partial association of the solvated electron with the caged oxygen molecule(s) in the void—the solvated electron distributing over an array of sodium atoms and at least one oxygen atom. According to particular aspects, therefore, 'solvated electrons' as presently disclosed in association with the inventive electrokinetic fluids, may not be solvated in the traditional model comprising direct hydration by water molecules. Alternatively, in limited analogy with dried electride salts, solvated electrons in the inventive electrokinetic fluids may be distributed over multiple charge-stabilized nanostructures to provide a 'lattice glue' to stabilize higher order arrays in aqueous solution.

In particular aspects, the inventive charge-stabilized nanostructures and/or the charge-stabilized oxygen-containing nanostructures are capable of interacting with cellular membranes or constituents thereof, or proteins, etc., to mediate biological activities. In particular aspects, the inventive charge-stabilized nanostructures and/or the charge-stabilized oxygen-containing nanostructures harboring a solvated electron are capable of interacting with cellular membranes or constituents thereof, or proteins, etc., to mediate biological activities.

In particular aspects, the inventive charge-stabilized nanostructures and/or the charge-stabilized oxygen-containing nanostructures interact with cellular membranes or constituents thereof, or proteins, etc., as a charge and/or charge effect donor (delivery) and/or as a charge and/or charge effect recipient to mediate biological activities. In particular aspects, the inventive charge-stabilized nanostructures and/or the charge-stabilized oxygen-containing nanostructures harboring a solvated electron interact with cellular membranes as a charge and/or charge effect donor and/or as a charge and/or charge effect recipient to mediate biological activities.

In particular aspects, the inventive charge-stabilized nanostructures and/or the charge-stabilized oxygen-containing nanostructures are consistent with, and account for the observed stability and biological properties of the inventive electrokinetic fluids, and further provide a novel electride (or inverted electride) that provides for stabilized solvated electrons in aqueous ionic solutions (e.g., saline solutions, NaCl, etc.).

In particular aspects, the charge-stabilized oxygen-containing nanostructures substantially comprise, take the form of, or can give rise to, charge-stabilized oxygen-containing nanobubbles. In particular aspects, charge-stabilized oxygen-containing clusters provide for formation of relatively larger arrays of charge-stabilized oxygen-containing nanostructures, and/or charge-stabilized oxygen-containing nanobubbles or arrays thereof. In particular aspects, the charge-stabilized oxygen-containing nanostructures can provide for formation of hydrophobic nanobubbles upon contact with a hydrophobic surface (see elsewhere herein under EXAMPLE 25).

In particular aspects, the charge-stabilized oxygen-containing nanostructures substantially comprise at least one oxygen molecule. In certain aspects, the charge-stabilized oxygen-containing nanostructures substantially comprise at least 1, at least 2, at least 3, at least 4, at least 5, at least 10 at least 15, at least 20, at least 50, at least 100, or greater oxygen molecules. In particular aspects, charge-stabilized oxygen-containing nanostructures comprise or give rise to nanobubles (e.g., hydrophobid nanobubbles) of about 20 nm×1.5 nm, comprise about 12 oxygen molecules (e.g., based on the size of an oxygen molecule (approx 0.3 nm by 0.4 nm), assumption of an ideal gas and application of n=PV/RT, where P=1 atm, R=0.082 057 l·atm/mol·K; T=295K; V=pr²h=4.7×10⁻²² L, where r=10×10⁻⁹ m, h=1.5×10⁻⁹ m, and n=1.95×10⁻²² moles).

In certain aspects, the percentage of oxygen molecules present in the fluid that are in such nanostructures, or arrays thereof, having a charge-stabilized configuration in the ionic aqueous fluid is a percentage amount selected from the group consisting of greater than: 0.1%; 1%; 2%; 5%; 10%; 15%; 20%; 25%; 30%; 35%; 40%; 45%; 50%; 55%; 60%; 65%; 70%; 75%; 80%; 85%; 90%; and greater than 95%. Preferably, this percentage is greater than about 5%, greater than about 10%, greater than about 15% f, or greater than about 20%. In additional aspects, the substantial size of the charge-stabilized oxygen-containing nanostructures, or arrays thereof, having a charge-stabilized configuration in the ionic aqueous fluid is a size selected from the group consisting of less than: 100 nm; 90 nm; 80 nm; 70 nm; 60 nm; 50 nm; 40 nm; 30 nm; 20 nm; 10 nm; 5 nm; 4 nm; 3 nm; 2 nm; and 1 nm. Preferably, this size is less than about 50 nm, less than about 40 nm, less than about 30 nm, less than about 20 nm, or less than about 10 nm.

In certain aspects, the inventive electrokinetic fluids comprise solvated electrons. In further aspects, the inventive electrokinetic fluids comprises charge-stabilized nanostructures and/or charge-stabilized oxygen-containing nanostructures, and/or arrays thereof, which comprise at least one of: solvated electron(s); and unique charge distributions (polar, symmetric, asymmetric charge distribution). In certain aspects, the charge-stabilized nanostructures and/or charge-stabilized oxygen-containing nanostructures, and/or arrays thereof, have paramagnetic properties.

By contrast, relative to the inventive electrokinetic fluids, control pressure pot oxygenated fluids (non-electrokinetic fluids) and the like do not comprise such charge-stabilized biologically-active nanostructures and/or biologically-active charge-stabilized oxygen-containing nanostructures and/or arrays thereof, capable of modulation of at least one of cellular membrane potential and cellular membrane conductivity.

Systems for Making Gas-Enriched Fluids:

The presently disclosed system and methods allow gas (e.g., oxygen) to be enriched stably at a high concentration with minimal passive loss. This system and methods can be effectively used to enrich a wide variety of gases at heightened percentages into a wide variety of fluids. By way of example only, deionized water at room temperature that typically has levels of about 2-3 ppm (parts per million) of dissolved oxygen can achieve levels of dissolved oxygen ranging from at least about 5 ppm, at least about 10 ppm, at least about 15 ppm, at least about 20 ppm, at least about 25 ppm, at least about 30 ppm, at least about 35 ppm, at least about 40 ppm, at least about 45 ppm, at least about 50 ppm, at least about 55 ppm, at least about 60 ppm, at least about 65 ppm, at least about 70 ppm, at least about 75 ppm, at least about 80 ppm, at least about 85 ppm, at least about 90 ppm, at least about 95 ppm, at least about 100 ppm, or any value greater or therebetween using the disclosed systems and/or methods. In accordance with a particular exemplary embodiment, oxygen-enriched water may be generated with levels of about 30-60 ppm of dissolved oxygen.

Table 4 illustrates various partial pressure measurements taken in a healing wound treated with an oxygen-enriched saline solution and in samples of the gas-enriched oxygen-enriched saline solution of the present invention.

TABLE 4

TISSUE OXYGEN MEASUREMENTS
Probe Z082BO
In air: 171 mmHg 23° C.

| Column | Partial Pressure (mmHg) |
|---|---|
| B1 | 32-36 |
| B2 | 169-200 |
| B3 | 20-180* |
| B4 | 40-60 |

*wound depth minimal, majority >150, occasional 20 s

Using a gas-enriching diffusion system in accordance with the present disclosure it is possible to significantly increase the amount of dissolved gas in most liquids. The system and method allows gas (e.g., oxygen) to be dissolved stably at a high concentration with minimal passive loss. This system and method can be effectively used to incorporate a wide variety of gases at heightened percentages into a wide variety of fluids. By way of example only, a de-ionized water sample at room temperature that typically has levels of about 2-3 ppm (parts per million) of dissolved oxygen can achieve levels of dissolved oxygen ranging from about 8-70 ppm using the disclosed gas-enriching system and/or methods. In accordance with a disclosed embodiment, a gas-enriched fluid may be generated with levels of about 30-60 ppm of dissolved gas (e.g., oxygen).

Methods of Treatment:

The term "treating" refers to, and includes, reversing, alleviating, inhibiting the progress of, or preventing a disease, disorder or condition, or one or more symptoms thereof; and "treatment" and "therapeutically" refer to the act of treating, as defined herein.

A "therapeutically effective amount" is any amount of any of the compounds utilized in the course of practicing the invention provided herein that is sufficient to reverse, alleviate, inhibit the progress of, or prevent a disease, disorder or condition, or one or more symptoms thereof.

Cosmetic and/or Therapeutic Application and Administration:

In particular exemplary embodiments, the gas-enriched fluid of the present invention may function as a cosmetic and/or therapeutic composition alone or in combination with another cosmetic and/or therapeutic agent such that the therapeutic composition prevents or alleviates at least one symptom of a wound-related disease or condition, or to increase proper wound healing. The therapeutic compositions of the present invention include compositions that are able to be administered to a subject in need thereof. As used herein, "subject," may refer to any living creature, preferably an animal, more preferably a mammal, and even more preferably a human.

In certain embodiments, the composition formulation may also comprise at least one additional agent selected from the group consisting of: carriers, adjuvants, emulsifying agents, suspending agents, sweeteners, flavorings, perfumes, and binding agents.

As used herein, "pharmaceutically acceptable carrier" and "carrier" generally refer to a non-toxic, inert solid, semi-solid or liquid filler, diluent, encapsulating material or formulation auxiliary of any type. Some non-limiting examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In particular aspects, such carriers and excipients may be gas-enriched fluids or solutions of the present invention.

The pharmaceutically acceptable carriers described herein, for example, vehicles, adjuvants, excipients, or diluents, are well-known to those who are skilled in the art. Typically, the pharmaceutically acceptable carrier is chemically inert to the therapeutic agents and has no detrimental side effects or toxicity under the conditions of use. The pharmaceutically acceptable carriers can include polymers and polymer matrices, nanoparticles, microbubbles, and the like.

In addition to the therapeutic gas-enriched fluid of the present invention, the therapeutic composition may further comprise inert diluents such as additional non-gas-enriched water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. As is appreciated by those of ordinary skill, a novel and improved formulation of a particular therapeutic composition, a novel gas-enriched therapeutic fluid, and a novel method of delivering the novel gas-enriched therapeutic fluid may be obtained by replacing one or more inert diluents with a gas-enriched fluid of identical, similar, or different composition. For example, conventional water may be replaced or supplemented by a gas-enriched fluid produced by infusing oxygen into water or deionized water to provide gas-enriched fluid.

Certain embodiments provide for therapeutic compositions comprising a gas-enriched fluid of the present invention, a pharmaceutical composition or other therapeutic agent or a pharmaceutically acceptable salt or solvate thereof, and at least one pharmaceutical carrier or diluent. These pharmaceutical compositions may be used in the prophylaxis and treatment of the foregoing diseases or conditions and in therapies as mentioned above. Preferably, the carrier must be pharmaceutically acceptable and must be compatible with, i.e., not have a deleterious effect upon, the other ingredients in the composition. The carrier may be a solid or liquid and is preferably formulated as a unit dose formulation, for example, a tablet which may contain from 0.05 to 95% by weight of the active ingredient.

While the compositions and/or methods disclosed herein generally relate to topical application, the most suitable means of administration for a particular subject will depend on the nature and severity of the disease or condition being treated or the nature of the therapy being used, as well as the nature of the therapeutic composition or additional therapeutic agent.

In addition to the therapeutic gas-enriched fluid of the present invention, the therapeutic composition may further comprise inert diluents such as additional non-gas-enriched water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. As is appreciated by those of ordinary skill, a novel and improved formulation of a particular therapeutic composition, a novel gas-enriched therapeutic fluid, and a novel method of delivering the novel gas-enriched therapeutic fluid may be obtained by replacing one or more inert diluents with a gas-enriched fluid of identical, similar, or different composition. For example, conventional water may be replaced or supplemented by a gas-enriched fluid produced by mixing oxygen into water or deionized water to provide gas-enriched fluid.

In certain embodiments, the inventive gas-enriched fluid may be combined with one or more therapeutic agents and/or used alone. In particular embodiments, incorporating the gas-enriched fluid may include replacing one or more solutions known in the art, such as deionized water, saline solution, and the like with one or more gas-enriched fluid, thereby providing an improved therapeutic composition for delivery to the subject.

Certain embodiments provide for therapeutic compositions comprising a gas-enriched fluid of the present invention, a pharmaceutical composition or other therapeutic agent or a pharmaceutically acceptable salt or solvate thereof, and at least one pharmaceutical carrier or diluent. These pharmaceutical compositions may be used in the prophylaxis and treatment of the foregoing diseases or conditions and in therapies as mentioned above. Preferably, the carrier must be pharmaceutically acceptable and must be compatible with, i.e., not have a deleterious effect upon, the other ingredients in the composition. The carrier may be a solid or liquid and is preferably formulated as a unit dose formulation, for example, a tablet which may contain from 0.05 to 95% by weight of the active ingredient.

Possible administration routes include oral, sublingual, buccal, parenteral (for example subcutaneous, intramuscular, intra-arterial, intraperitoneally, intracisternally, intravesically, intrathecally, or intravenous), rectal, topical including transdermal, intravaginal, intraoccular, intraotical, intranasal, inhalation, and injection or insertion of implantable devices or materials.

Administrative Routes:

Most suitable means of administration for a particular subject will depend on the nature and severity of the disease or condition being treated or the nature of the therapy being used, as well as the nature of the therapeutic composition or additional therapeutic agent. In certain embodiments, oral or topical administration is preferred.

Formulations suitable for oral administration may be provided as discrete units, such as tablets, capsules, cachets, syrups, elixirs, chewing gum, "lollipop" formulations, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Formulations suitable for transmucosal methods, such as by sublingual or buccal administration include lozenges patches, tablets, and the like comprising the active compound and, typically a flavored base, such as sugar and acacia or tragacanth and pastilles comprising the active compound in an inert base, such as gelatin and glycerine or sucrose acacia.

Formulations suitable for parenteral administration typically comprise sterile aqueous solutions containing a predetermined concentration of the active gas-enriched fluid and possibly another therapeutic agent; the solution is preferably isotonic with the blood of the intended recipient. Additional formulations suitable for parenteral administration include formulations containing physiologically suitable co-solvents and/or complexing agents such as surfactants and cyclodextrins. Oil-in-water emulsions may also be suitable for formulations for parenteral administration of the gas-enriched fluid. Although such solutions are preferably administered intravenously, they may also be administered by subcutaneous or intramuscular injection.

Formulations suitable for urethral, rectal or vaginal administration include gels, creams, lotions, aqueous or oily suspensions, dispersible powders or granules, emulsions, dissolvable solid materials, douches, and the like. The formulations are preferably provided as unit-dose suppositories comprising the active ingredient in one or more solid carriers forming the suppository base, for example, cocoa butter. Alternatively, colonic washes with the gas-enriched fluids of the present invention may be formulated for colonic or rectal administration.

Formulations suitable for topical, intraoccular, intraotic, or intranasal application include ointments, creams, pastes, lotions, pastes, gels (such as hydrogels), sprays, dispersible powders and granules, emulsions, sprays or aerosols using flowing propellants (such as liposomal sprays, nasal drops, nasal sprays, and the like) and oils. Suitable carriers for such formulations include petroleum jelly, lanolin, polyethyleneglycols, alcohols, and combinations thereof. Nasal or intranasal delivery may include metered doses of any of these formulations or others. Likewise, intraotic or intraocular may include drops, ointments, irritation fluids and the like.

Formulations of the invention may be prepared by any suitable method, typically by uniformly and intimately admixing the gas-enriched fluid optionally with an active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and a gas-enriched fluid of the present invention.

Suitable formulations for administration by inhalation include fine particle dusts or mists which may be generated by means of various types of metered dose pressurized aerosols, nebulisers, or insufflators. In particular, powders or other compounds of therapeutic agents may be dissolved or suspended in a gas-enriched fluid of the present invention.

For pulmonary administration via the mouth, the particle size of the powder or droplets is typically in the range 0.5-10 µM, preferably 1-5 µM, to ensure delivery into the bronchial tree. For nasal administration, a particle size in the range 10-500 µM is preferred to ensure retention in the nasal cavity.

Metered dose inhalers are pressurized aerosol dispensers, typically containing a suspension or solution formulation of a therapeutic agent in a liquefied propellant. In certain embodiments, as disclosed herein, the gas-enriched fluids of the present invention may be used in addition to or instead of the standard liquefied propellant.

During use, these devices discharge the formulation through a valve adapted to deliver a metered volume, typically from 10 to 150 µL, to produce a fine particle spray containing the therapeutic agent and the gas-enriched fluid. Suitable propellants include certain chlorofluorocarbon compounds, for example, dichlorodifluoromethane, trichlorofluoromethane, dichlorotetrafluoroethane and mixtures thereof.

The formulation may additionally contain one or more co-solvents, for example, ethanol surfactants, such as oleic acid or sorbitan trioleate, anti-oxidants and suitable flavoring agents. Nebulisers are commercially available devices that transform solutions or suspensions of the active ingredient into a therapeutic aerosol mist either by means of acceleration of a compressed gas (typically air or oxygen) through a narrow venturi orifice, or by means of ultrasonic agitation. Suitable formulations for use in nebulisers consist of another therapeutic agent in a gas-enriched fluid and comprising up to 40% w/w of the formulation, preferably less than 20% w/w. In addition, other carriers may be utilized, such as distilled water, sterile water, or a dilute aqueous alcohol solution, preferably made isotonic with body fluids by the addition of salts, such as sodium chloride. Optional additives include preservatives, especially if the formulation is not prepared sterile, and may include methyl hydroxy-benzoate, anti-oxidants, flavoring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

In addition to the ingredients specifically mentioned above, the formulations of the present invention may include other agents known to those skilled in the art, having regard for the type of formulation in issue. For example, formulations suitable for oral administration may include flavoring agents and formulations suitable for intranasal administration may include perfumes.

The therapeutic compositions of the invention can be administered by any conventional method available for use in conjunction with pharmaceutical drugs, either as individual therapeutic agents or in a combination of therapeutic agents.

A suitable dose is that which will result in a concentration of the cosmetic and/or therapeutic composition in a subject which is known to affect the desired response. The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.0001 to 1000 milligrams (mg) per kilogram (kg) of body weight, with the preferred dose being 0.01 to about 30 mg/kg. According to certain aspects daily dosage of active ingredient may be 0.00001 liters to 10 liters, with the preferred dose being from about 0.0001 liters to 1 liter.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

Ointments, pastes, foams, occlusions, creams and gels also can contain excipients, such as starch, tragacanth, cellulose derivatives, silicones, bentonites, silica acid, and talc, or mixtures thereof. Powders and sprays also can contain excipients such as lactose, talc, silica acid, aluminum hydroxide, and calcium silicates, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such as nitrogen, carbon dioxide, or other inert gases. In addition, microspheres or nanoparticles may be employed with the gas-enriched therapeutic compositions or fluids of the present invention in any of the routes required to administer the therapeutic compounds to a subject.

The injection-use formulations can be presented in unit-dose or multi-dose sealed containers, such as ampules and vials, and can be stored in a freeze-dried (lyophilized) condition requiring only the addition of the sterile liquid excipient, or gas-enriched fluid, immediately prior to use. Extemporaneous injection solutions and suspensions can be prepared from sterile powders, granules, and tablets. The requirements for effective pharmaceutical carriers for injectable compositions are well known to those of ordinary skill in the art. See, for example, Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include lozenges comprising a gas-enriched fluid of the invention and optionally, an additional therapeutic and a flavor, usually sucrose and acacia or tragacanth; pastilles comprising a gas-enriched fluid and optional additional therapeutic agent in an inert base, such as gelatin and glycerin, or sucrose and acacia; and mouth washes or oral rinses comprising a gas-enriched fluid and optional additional therapeutic agent in a suitable liquid carrier; as well as creams, emulsions, gels and the like.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to a subject, especially an animal, particularly a human, in the context of the present invention should be sufficient to effect a therapeutic response in the animal over a reasonable time frame. One skilled in the art will recognize that dosage will depend upon a variety of factors including a condition of the animal, the body weight of the animal, as well as the condition being treated. A suitable dose is that which will result in a concentration of the therapeutic composition in a subject which is known to affect the desired response.

The size of the dose also will be determined by the route, timing and frequency of administration as well as the existence, nature, and extent of any adverse side effects that might accompany the administration of the therapeutic composition and the desired physiological effect.

Formulations suitable for topical application include liquids (aqueous or oil based), ointments, creams, lotions, pastes, gels (such as hydrogels), sprays, dispersible powders and granules, emulsions, sprays or aerosols using flowing propellants (such as liposomal sprays, nasal drops, nasal sprays, and the like) and oils. Suitable carriers for such formulations include petroleum jelly, lanolin, polyethylene glycol (such as PEG 3000, PEG 5000, or other), alcohols, and combinations thereof.

Formulations of the invention may be prepared by any suitable method, typically by uniformly and intimately admixing the gas-enriched fluid optionally with an active compound with liquids or finely divided solid carriers or both, in the required proportions and then, if necessary, shaping the resulting mixture into the desired shape.

Ointments, pastes, foams, occlusions, creams, gels, sols, suspensions, and patches also can contain excipients, such as starch, tragacanth, cellulose derivatives, silicones, bentonites, silica acid, and talc, or mixtures thereof. Powders and sprays also can contain excipients such as lactose, talc, silica acid, aluminum hydroxide, and calcium silicates, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the fluid, usually with an inert carrier gas, and passing the pressurized gas through a small orifice. Sprays can additionally contain customary propellants, such as nitrogen, carbon dioxide, or other inert gases. In addition, microspheres or nanoparticles may be employed with the gas-enriched therapeutic compositions or fluids of the present invention in any of the routes required to administer the compounds to a subject.

The topical formulations can be presented in unit-dose or multi-dose sealed containers, such as ampules and vials, and can be stored in a freeze-dried (lyophilized) condition requiring only the addition of the sterile liquid excipient, or gas-enriched fluid, immediately prior to use. Extemporaneous fluids, and/or suspensions can be prepared from sterile powders, granules, and tablets.

The dose administered to a subject, especially an animal, particularly a human, in the context of the present invention should be sufficient to effect a cosmetic and/or therapeutic response in the animal over a reasonable time frame. One skilled in the art will recognize that dosage will depend upon a variety of factors including a condition of the animal, the body weight of the animal, the desired outcome, as well as the condition being treated. A suitable dose is that which will result in a concentration of the cosmetic and/or therapeutic composition in a subject which is known to affect the desired response.

The size of the dose also will be determined by the route, timing and frequency of administration as well as the existence, nature, and extent of any adverse side effects that might accompany the administration of the therapeutic composition and the desired physiological effect.

The gas-enriched fluids of the present invention may be used to improve existing drug delivery compositions and methods. The diffuser processed fluids may be formulated, alone or together with one or more therapeutic agents, in suitable dosage unit formulations. In various embodiments, these formulations may include conventional non-toxic pharmaceutically acceptable carriers, adjuvants, emulsifying and suspending agents, sweetening, flavoring, perfuming agents, and vehicles appropriate for the particular route taken into the body of the subject.

As used herein, the terms "pharmaceutically acceptable carrier" and "carrier" mean a non-toxic, inert solid, semi-solid or liquid filler, diluent, encapsulating material or formulation auxiliary of any type. Some non-limiting examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In particular aspects, such carriers and excipients or are themselves diffuser processed fluids.

In certain embodiments, the gas-enriched fluid disclosed herein may comprise a wetting, irrigation or soaking fluid to apply to organs, such as the skin, or into which organs and/or tissues may be placed. One or more therapeutic agents may be dissolved in the gas-enriched fluid or placed in the tissue before wetting, irrigating or soaking it in the gas-enriched fluid. The gas-enriched fluid may also be applied to the skin or other organ or tissue in combination with a preexisting medication, thereby creating a gas-enriched therapeutic fluid, to increase the efficacy of the medication. The gas-enriched fluid may also be used to dissolve a powder, thereby creating a gas-enriched therapeutic fluid and drug delivery method. Alternatively, the inventive gas-enriched fluid may comprise infused ingredients of these patches, gels, creams, lotions, ointments, pastes, solutions, sprays, aqueous or oily suspensions, emulsions, and the like.

Topical drug delivery, including drug delivery by administration to the skin or mucosal membranes is also within the scope of this invention. Particular aspects provide for therapeutic wound care products for delivery to the skin or to a portion thereof, or to any bodily location of a wound. For example, the gas-enriched diffuser processed fluid may comprise ointments, drops, therapeutic solutions, irrigation fluids, pharmaceuticals (prescription and over the counter drops and other medications, steroid drops, carteol, a non-selective beta blocker, vitamins), and the like. For example, the gas-enriched fluid may replace common carriers such as saline and water.

Enhancing Biological Tissue Growth:

In other related embodiments, the gas-enriched fluid compositions and/or methods described herein can be used in relation to enhancing biological cell and/or tissue growth of cell (including stem cells), tissue and organ cultures, whether naturally occurring, or genetically modified. In addition, gas-enriched fluid compositions and/or methods disclosed herein can be used for artificial blood and surgical procedures requiring artificial blood (such as coronary bypass surgery and shock-trauma procedures). Similarly, oxygen-rich solutions may be used to perfuse one or more solid organs, such as liver, kidney, heart, eye, hand, foot, brain, and others after harvesting and prior to (e.g. in transit) and during transplantation. Use of gas-enriched (particularly oxygen-enriched) fluids in accordance with the disclosed embodiments may lead to longer storage time and more successful transplant rates.

In particular embodiments, the gas-enriched fluid may be used In certain embodiments, storing, transporting, infusing, delivering, and or transplanting organs with the gas-enriched fluid of the invention may provide for more successful preservation and/or transplantation of organs and/or tissues, due to decreased inflammation, decreased necrosis, and or increased cellular function. In addition, the gas-enriched fluid of the present invention may be delivered intravenously to a subject, including a human patient. It is possible to oxygenate plasma for use in a subject (human body or other animal) which may have application in the treatment of cancer or other medical conditions or disorders. It may also be useful to oxygenate plasma to preserve it when stored for extended periods of time.

In other embodiments, hydrotherapy or topical application of gas-enriched or oxygen-enriched solution, it is possible for the subject to receive an increased blood oxygen level and would thereby lead to a healthier, subject with increased energy and vitality.

EXAMPLES

Example 1

Dissolved Oxygen Stability

As indicated in FIG. 30, there is illustrated the dissolved oxygen levels in a 500 ml thin-walled plastic bottle and a 1000 ml glass bottle which were each capped and stored at 65 degrees Fahrenheit.

As can be seen, when the plastic bottle is opened approximately 65 days after bottling, the dissolved oxygen level within the water is approximately 27.5 ppm. When a second bottle is opened at approximately 95 days after bottling, the dissolved oxygen level is approximately 25 ppm. Likewise, for the glass bottle, the dissolved oxygen level is approximately 40 ppm at 65 days and is approximately 41 ppm at 95 days. Thus, this chart indicates that the dissolved oxygen levels within both plastic and glass bottles are maintained at relatively high rates at 65° Fahrenheit when the oxygen is diffused within the fluid using the described system and method.

Example 2

Decayed Oxygen Content in Balanced Salt Solution

Figure 33:
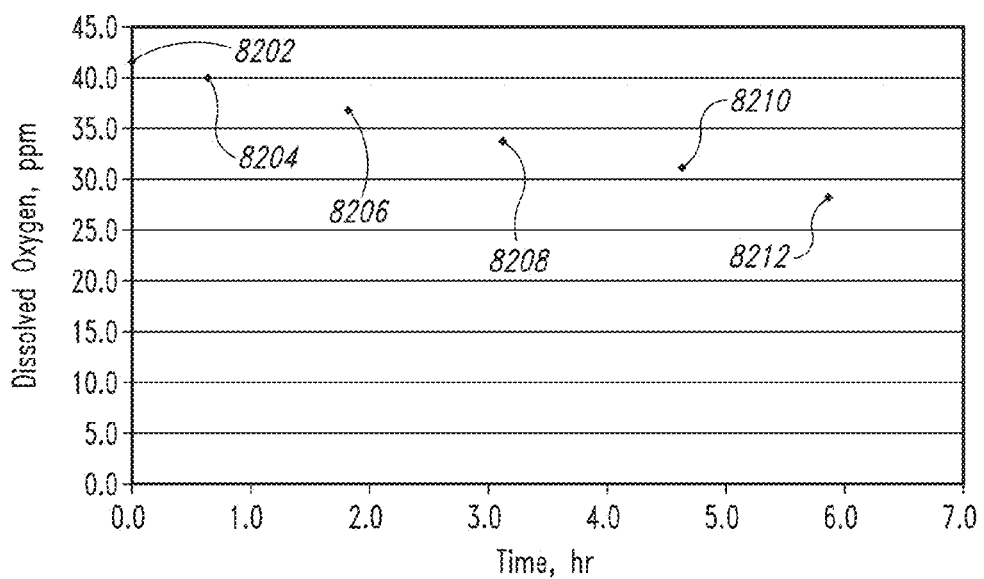
FIG. 33 illustrates the dissolved oxygen retention of a 500 ml braun balanced salt solution processed with oxygen in the mixing device of FIG. 2.

FIG. 33 illustrates the dissolved oxygen retention of a 500 ml balanced salt solution that originally had a dissolved oxygen level of 5 ppm. Following enrichment of the solution at standard temperature and pressure with the diffuser of the present invention, the dissolved oxygen level was approximately 41 ppm. The solution was kept in an amber glass bottle. After an hour, the dissolved oxygen level was 40 ppm; 36 ppm after two hours; 34 ppm after three hours; and slightly more than 30 ppm after approximately four and a half hours. The final measurement was taken shortly before six hours, at which point the dissolved oxygen level was approximately 28 ppm.

Example 3

Microbubble Size

Experiments were performed with a gas-enriched fluid by using the diffuser of the present invention in order to determine a gas microbubble size limit. The microbubble size limit was established by passing the gas enriched fluid through 0.22 and 0.1 micron filters. In performing these tests, a volume of fluid passed through the diffuser of the present invention and generated a gas-enriched fluid. Sixty milliliters of this fluid was drained into a 60 ml syringe. The dissolved oxygen level of the fluid within the syringe was then measured by Winkler titration. The fluid within the syringe was injected through a 0.22 micron Millipore Millex GP50 filter and into a 50 ml beaker. The dissolved oxygen rate of the material in the 50 ml beaker was then measured. The experiment was performed three times to achieve the results illustrated in Table 5 below.

TABLE 5

| DO IN SYRINGE | DO AFTER 0.22 MICRON FILTER |
| --- | --- |
| 42.1 ppm | 39.7 ppm |
| 43.4 ppm | 42.0 ppm |
| 43.5 ppm | 39.5 ppm |

As can be seen, the dissolved oxygen levels that were measured within the syringe and the dissolved oxygen levels within the 50 ml beaker were not significantly changed by passing the diffused material through a 0.22 micron filter, which implies that the microbubbles of dissolved gas within the fluid are not larger than 0.22 microns.

A second test was performed in which a batch of saline solution was enriched with the diffuser of the present invention and a sample of the output solution was collected in an unfiltered state. The dissolved oxygen level of the unfiltered sample was 44.7 ppm. A 0.1 micron filter was used to filter the oxygen-enriched solution from the diffuser of the present invention and two additional samples were taken. For the first sample, the dissolved oxygen level was 43.4 ppm. For the second sample, the dissolved oxygen level was 41.4 ppm. Finally, the filter was removed and a final sample was taken from the unfiltered solution. In this case, the final sample had a dissolved oxygen level of 45.4 ppm. These results were consistent with those in which the Millipore 0.22 micron filter was used. Thus, the majority of the gas bubbles or microbubbles within the saline solution are approximately less than 0.1 microns in size.

Example 4

Sparging Effects

Figure 34:
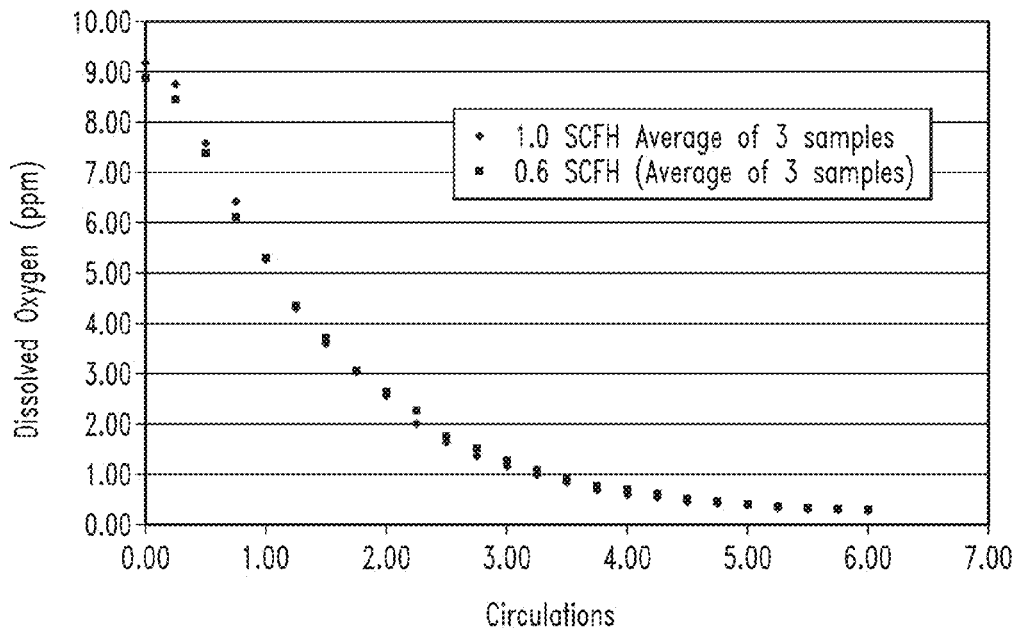
FIG. 34 illustrates a further experiment wherein the mixing device of FIG. 2 is used to sparge oxygen from water by processing the water with nitrogen in the mixing device of FIG. 2.
Figure 35:
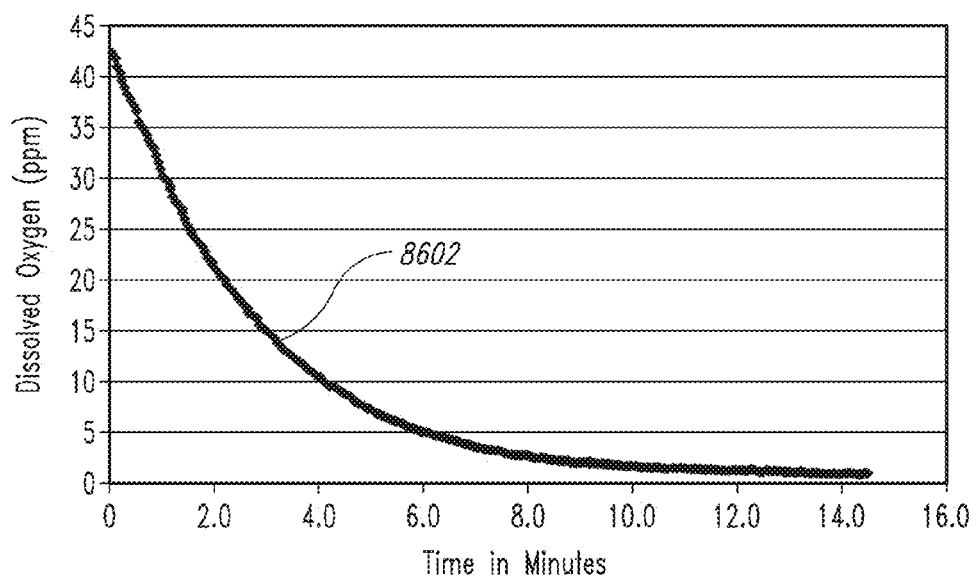
FIG. 35 illustrates the sparging of oxygen from water by the mixing device of FIG. 2 at standard temperature and pressure.

FIGS. 34 and 35 illustrate the sparging effects of the diffuser of the present invention on a fluid passing therethrough. The sparging of oxygen-enriched water occurred in an 8 gallon tank at standard temperature and pressure. As indicated, initially the oxygen-enriched water had a dissolved oxygen level of approximately 42 ppm. After 2 minutes of running through the diffuser, the nitrogen had sparged the oxygen-enriched water such that the dissolved oxygen level was then slightly more than 20 ppm. At 6 minutes, the dissolved oxygen level was approximately 6 ppm. The dissolved oxygen level of the oxygen-enriched water reached a minimum value slightly greater than zero (0) at approximately 14 minutes after the beginning of the process. These figures illustrate the manner in which nitrogen may be diffused into water to sparge the oxygen from the water. However, any gas could be used within any fluid to sparge one gas from the other and diffuse the other gas into the fluid. The same experiment could utilize any host fluid material, and any fluid infusion material.

Example 5

Rayleigh Effects

Fluids processed through the diffuser device described herein exhibit differences within the structure of the water when compared with normal unprocessed water. Gas-enriched water made by embodiments disclosed herein has been shown to have more Rayleigh scattering compared to unprocessed water.

In experiments conducted, samples of gas-enriched and non-enriched water were prepared and sent for optical analysis. The purpose of these tests was to determine whether there are any gross optical differences between normal (unprocessed) deionized water and water enriched by the diffuser device of the present invention.

The two samples, were coded to maintain their identities in secrecy, and only after the tests were completed were the samples identified. The two samples were placed in a laser beam of 633 nanometers according to the diagram illustrated in FIG. 37A. Sample B, which was gas-enriched fluid according to certain embodiments disclosed herein, exhibited scattered light regardless of its position relative to the laser source. The Sample B fluid had been sealed in glass bottles for approximately one week. After two to three hours of opening the bottle, the scattering effect disappeared. Thus, the structure of the gas-enriched fluid is optically different from the structure of the unprocessed fluid. The optical effect is not directly related to dissolved oxygen levels since the dissolved oxygen level at the start was approximately 45 ppm and at the end of the experiment was estimated to be approximately 32 ppm. Results are shown in FIG. 37B.

Example 6

Generation of Solvated Electrons

Additional evidence has also suggested that the enriching process generated by the diffuser device of the present invention results in solvated electrons within the gas-enriched fluid. Due to the results of the polarographic dissolved oxygen probes, it is believed that the diffused fluid exhibits an electron capture effect and thus the fluid may include solvated electrons within the gas-enriched material.

There are two fundamental techniques for measuring dissolved oxygen levels electrically: galvanic measuring techniques and polarographic measurements. Each process uses an electrode system wherein the dissolved oxygen levels within the solution being tested react with a cathode of the probe to produce a current. Dissolved oxygen level sensors consist of two electrodes, an anode and a cathode, which are both immersed in electrolyte within the sensor body. An oxygen permeable membrane separates the anode and cathode from the solution being tested. Oxygen diffuses across the membrane and interacts with the internal components of the probe to produce an electrical current. The cathode is a hydrogen electrode and carries negative potential with respect to the anode. The electrolyte solution surrounds the electrode pair and is contained by the membrane. When no oxygen is present, the cathode is polarized by hydrogen and resists the flow of current. When oxygen passes through the membrane, the cathode is depolarized and electrons are consumed. The cathode electrochemically reduces the oxygen to hydroxyl ions according to the following equation:

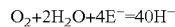

$$O_2 + 2H_2O + 4E^- = 4OH^-$$

When performing dissolved oxygen level measurements of a gas-enriched solution according to the systems of the present invention, an overflow condition has been repeatedly experienced wherein the dissolved oxygen meter displays a reading that is higher than the meter is capable of reading. However, evaluation of the gas-enriched solution by Winkler Titration indicates lower dissolved oxygen (DO) level for the solution than indicated by the probe. Typically, a DO probe (such as the Orion 862 used in these experiments) has a maximum reading of 60 ppm. However, when the meter is left in gas-enriched water of the present invention, it overflows.

Without wishing to be bound by any particular mechanism of action, the mechanism of the meter responds to electrons where the oxygen reacts. However, according to electron spin resonance, no free ions are present in the fluid. Thus, the fluid presumably contains solvated electrons stabilized by the oxygen species that is also present in the fluid.

Example 7

In Vitro Wound Healing

The effects of a gas-enriched fluid (enriched with oxygen) were tested for the ability of cultured human epidermal keratinocytes to seal a wound.

Human epidermal keratinocytes were isolated from neonatal foreskins that were obtained from routine circumcision and de-identified. Foreskins were washed twice in PBS and incubated in 2.4 U/mL Dispase II in order to separate the dermis from the epidermis. The epidermis was incubated with 0.25% trypsin/1 mM EDTA, neutralized with soy bean trypsin inhibitor, agitated, and passed through a 70 um sieve to separate the cells. Next, the cell suspension was centrifuged and resuspended in cell culture medium (M154) supplemented with 0.07 mM $CaCl_2$, and human keratinocyte growth supplements (0.2% hydrocortisone, 0.2 ng/mL human epidermal growth factor) and penicillin/streptomycin, amphoteracin antibiotic cocktail. The keratinocyte cell suspensions were plated onto uncoated 12-well culture dishes and the medium replaced after 24 hours, and every 48 hours after the initial seeding.

Upon reaching cellular confluence, linear scratches were made with a sterile p1000 pipette tip, which resulted in a uniform cell-free wound. The monolayers were washed several times with Dulbecco's PBS in order to remove any cellular debris. The wound monolayers were then incubated in the following media: i) the complete growth media (as described above in this Example); ii) the complete growth media diluted 1:1 with a sheared version of saline without oxygen (control fluid that was processed using the disclosed diffuser device but without adding a gas); and iii) the complete growth media diluted 1:1 with oxygen-enriched saline. Each study was done in triplicate.

Prior to incubation, the wells were filled with the respective media and sealed by placing a 25×25 mm glass coverslip on top of each well. At 6, 12, 24, and 48 hours post-wounding, oxygen measurements were made, and cultures were imagined.

Figure 40A:
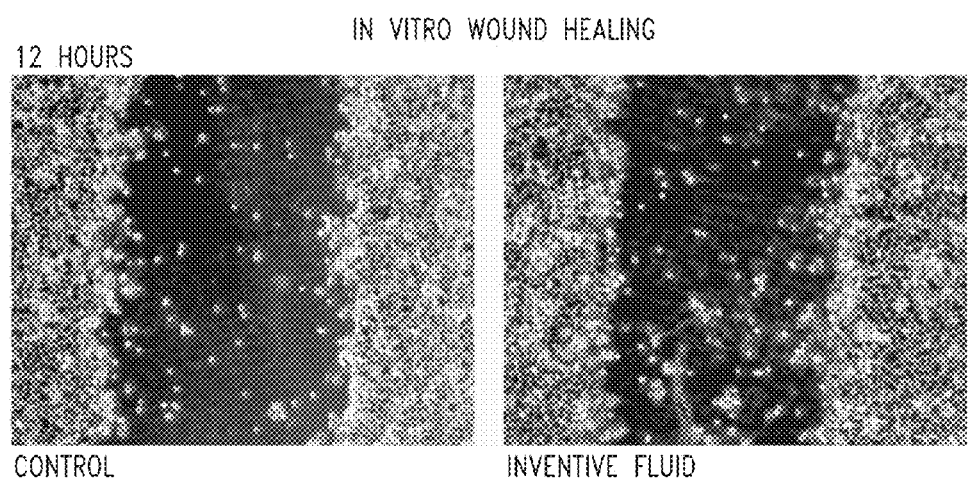
FIGS. 40A and 40B illustrate in vitro healing of wounds using an oxygen-enriched cell culture media and a non-gas-enriched media.
Figure 40B:
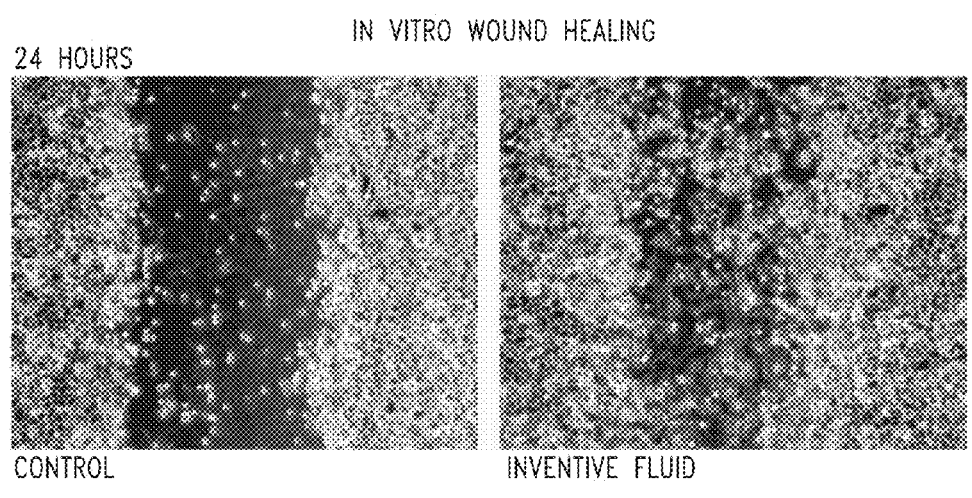
Figure 44:
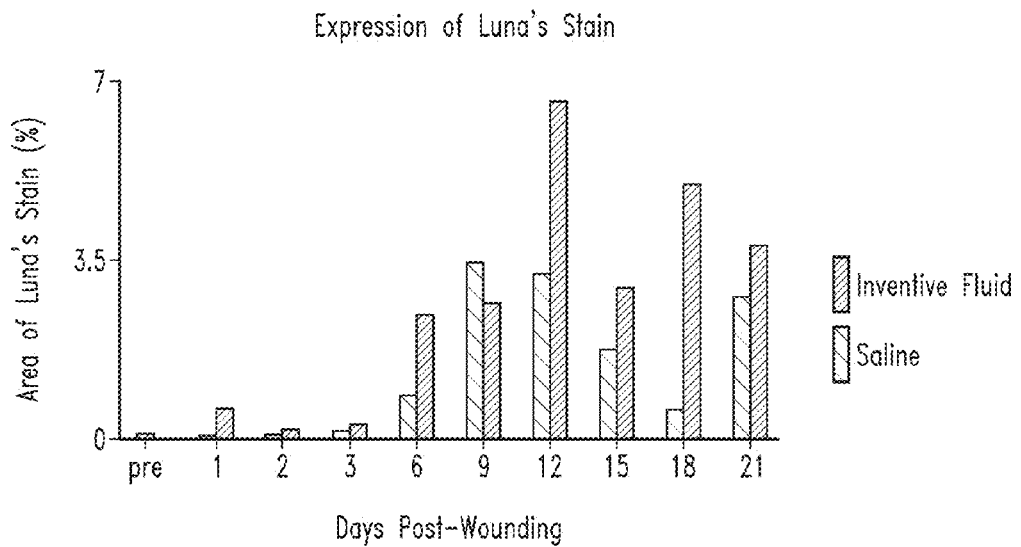
FIG. 44 illustrates the detection of Luna's stain used to detect elastin in treated and control healing wounds.
Figure 45:
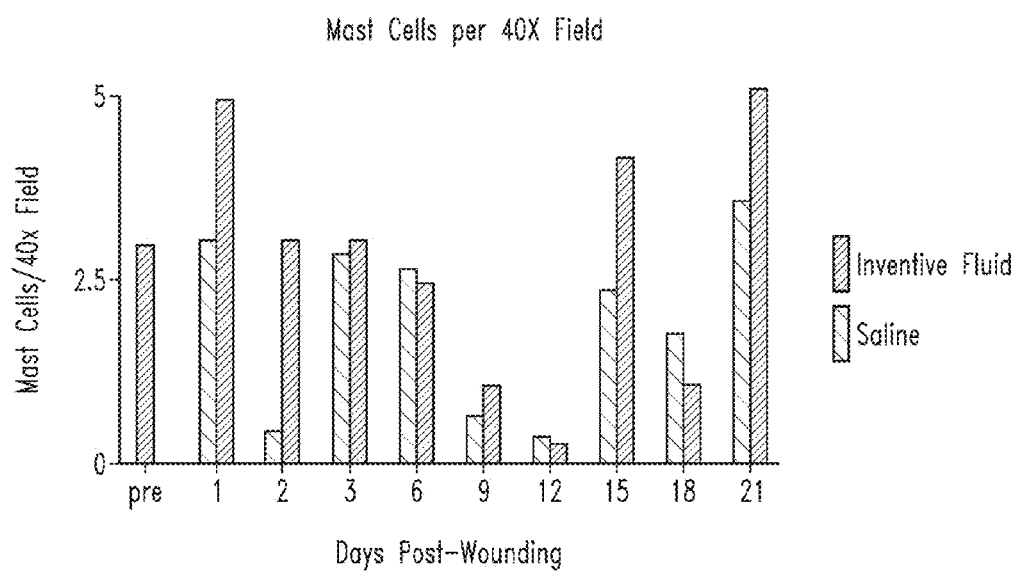
FIG. 45 illustrates the number of mast cells per visual field for treated and control healing wounds.

Six hours post-wounding, the edges of the wounds in the saline and gas-enriched media were more ruffled than those in the media control that was processed with the diffuser device disclosed herein, but without the addition of a gas. Twelve hours post-wounding the edges of the wounds in all three media appeared uneven, with keratinocytes along the borders migrating toward the center of the wounds. Quantification of migrating keratinocytes revealed approximately the same level of keratinocyte migration in the saline and gas-enriched media. Results of the experiment are shown in FIGS. 40A and 44B.

Example 8

Improved Wound Healing

A study was performed to determine the improved healing characteristics of wounds that were exposed to an oxygen-enriched saline solution that was processed according to embodiments disclosed herein. In this experiment, bandages were placed on porcine dermal excision biopsy wounds. The bandages soaked in oxygen-enriched saline solution or a control group of bandages soaked in a saline solution that was not oxygen-enriched. Microscopically, several factors were evaluated by the study including: 1) epidermalization; 2) neovascularization; 3) epidermal differentiation; 4) mast cell migration; and 5) mitosis.

Externally, the wounds appeared to heal at varying rates. The wounds treated with the oxygen-enriched saline solution showed an increase in wound healing at days 4 through 11. However, both wounds seemed to complete healing at approximately the same time. The study showed that between days 3 and 11, the new epidermis in wounds treated with the oxygen-enriched saline solution migrated at two to four times as fast as the epidermis of the wounds treated with the normal saline solution. The study also showed that between 15 and 22 days, the wound treated by the oxygen-enriched saline solution differentiated at a more rapid rate as evidenced by the earlier formation of more mature epidermal layers. At all stages, the thickening that occurs in the epidermis associated with normal healing did not occur within the wounds treated by the oxygen-enriched saline solution.

Without wishing to be bound by any particular theory, it is believed that the oxygen-enriched saline solution may increase the localized level of NO within the wounds. NO modulates growth factors, collagen deposition, inflammation, mast cell migration, epidermal thickening, and neovascularization in wound healing. Furthermore, nitric oxide is produced by an inducible enzyme that is regulated by oxygen.

Thus, while not wishing to be bound to any particular theory, the inventive gas-enriched fluid may stimulate NO production, which is in accordance with the spectrum of wound healing effects seen in these experiments.

The epidermis of the healing pigs experienced earlier differentiation in the oxygen-enriched saline group at days 15 through 22. In the case of mast cell migration, differences also occurred in early and late migration for the oxygen-enriched solution. A conclusive result for the level of mitosis was unascertainable due to the difficulty in staining.

Referring now to FIG. 41A through 41F, various illustrations compare the wound healing results of the porcine epidermal tissues with or without oxygen-enriched saline solution. Thus, the healing of the control wound and of the wound using the oxygen-enriched saline solution was followed for days 1, 4 and 16. FIG. 41A illustrates the wound healing for the control wound on day 1. As can be seen, the wound shows epidermal/dermal thickening and a loss of contour. FIG. 41B illustrates the wound healing on day 1 for the wound treated using the oxygen-enriched saline solution. The wound shows normal epidermal/dermal thickness and normal contouring is typical on a new wound.

Referring now to FIGS. 41C and 41D, there are illustrated the wound healing for the control wound on day 4 and the wound healing for the wound treated with the oxygen-enriched saline solution on day 4. For the control wound illustrated in FIG. 41C, the wound shows a 600 micron epidermal spur. In the wound treated with the oxygen-enriched saline solution in FIG. 41D, there is illustrated a 1200 micron epidermal spur. Thus, in the first 4 days of the experiment, the epidermal spur created in the wound treated using the oxygen-enriched saline solution shows an epidermal growth rate of twice of that of the wound that was not treated with the oxygen-enriched saline solution.

Referring now to FIG. 41E, there is illustrated the control wound at day 16. The wound shows less differentiated epidermis with loss of epidermal/dermal contour than that illustrated by the wound treated with the oxygen-enriched saline solution illustrated in FIG. 41F. FIG. 41F shows more differentiated epidermis and more normal epidermal/dermal contouring in the wound.

Thus, as illustrated with respect to FIGS. 41A through 41F, the wound treated with the oxygen-enriched saline solution shows much greater healing characteristics than the untreated wound and shows a greater differentiated epidermis with more normal epidermal/dermal contour.

Example 9

Glutathione Peroxidase Study

The inventive oxygen-enriched fluid was tested for the presence of hydrogen peroxide by testing the reactivity with glutathione peroxidase using a standard assay (Sigma). Water samples were tested by adding the enzyme cocktail and inverting. Continuous spectrophotometric rate determination was made at $A_{340}$ nm, and room temperature (25 degrees Celsius). Samples tested were: 1. deionized water (negative control), 2. inventive oxygen-enriched fluid at low concentration, 3. inventive oxygen-enriched fluid at high concentration, 4. hydrogen peroxide (positive control). The hydrogen peroxide positive control showed a strong reactivity, while none of the other fluids tested reacted with the glutathione peroxidase.

Example 10

Electrokinetically Generated Superoxygenated Fluids and Solas were Shown to Provide for Synergistic Prolongation Effects (e.g., Suppression of Bronchoconstriction) with Albuterol In Vivo in an Art-Recognized Animal Model of Human Bronchoconstriction (Human Asthma Model)

Experiment 1

In an initial experiment, sixteen guinea pigs were evaluated for the effects of bronchodilators on airway function in conjunction with methacholine-induced bronchoconstriction. Following determination of optimal dosing, each animal was dosed with 50 µg/mL to deliver the target dose of 12.5 µg of albuterol sulfate in 250 µL per animal.

The study was a randomized blocked design for weight and baseline PenH values. Two groups (A and B) received an intratracheal instillation of 250 µL of 50 µg/mL albuterol sulfate in one or two diluents: Group A was deionized water that had passed through the inventive device, without the addition of oxygen, while Group B was inventive gas-enriched water. Each group was dosed intratracheally with solutions using a Penn Century Microsprayer. In addition, the animals were stratified across BUXCO plethysmograph units so that each treatment group is represented equally within nebulizers feeding the plethysmographs and the recording units.

Animals that displayed at least 75% of their baseline PenH value at 2 hours following albuterol administration were not included in the data analyses. This exclusion criteria is based on past studies where the failure to observe bronchoprotection with bronchodilators can be associated with dosing errors. As a result, one animal from the control group was dismissed from the data analyses.

Once an animal had greater than 50% bronchoconstriction, the animal was considered to be not protected. As set forth in Table 6 below, 50% of the Group B animals (shaded) were protected from bronchoconstriction out to 10 hours (at which time the test was terminated).

Experiment 2

A Bronchoconstriction Evaluation of RDC1676 with Albuterol Sulfate in Male Hartley Guinea Pigs An additional set of experiments was conducted using a larger number of animals to evaluate the protective effects of the inventive electrokinetically generated fluids (e.g, RDC1676-00, RDC1676-01, RDC1676-02 and RDC1676-03) against methacholine-induced bronchoconstriction when administered alone or as diluents for albuterol sulfate in male guinea pigs.

Materials:

Guinea Pigs (*Cavia porcellus*) were Hartley albino, Crl: (HA)BR from Charles River Canada Inc. (St. Constant, Quebec, Canada). Weight: Approximately 325±50 g at the onset of treatment. Number of groups was 32, with 7 male animals per group (plus 24 spares form same batch of animals). Diet; All animals had free access to a standard certified pelleted commercial laboratory diet (PMI Certified Guinea Pig 5026; PMI Nutrition International Inc.) except during designated procedures.

Methods:

Route of administration was intratracheal instillation via a Penn Century Microsprayer and methacholine challenge via whole body inhalation. The intratracheal route was selected to maximize lung exposure to the test article/control solution. Whole body inhalation challenge has been selected for methacholine challenge in order to provoke an upper airway hypersensitivity response (i.e., bronchoconstriction).

Duration of Treatment was One Day.

Table 7 shows the experimental design. All animals were subjected to inhalation exposure of methacholine (500 µg/ml), 2 hours following TA/Control administration. All animals received a dose volume of 250 µl. Therefore, albuterol sulfate was diluted (in the control article and the 4 test articles) to concentrations of 0, 25, 50 and 100 µg/ml.

Thirty minutes prior to dosing, solutions of albuterol sulfate of 4 different concentrations (0, 25, 50 and 100 µg/ml) was made up in a I Ox stock (500 µg/mL) in each of these four test article solutions (RDC1676-00, RDC1676-01, RDC1676-02; and RDC1676-03). These concentrations of albuterol sulfate were also made up in non-electrokinetically

TABLE 6

Bronchoconstriction Protection as Measured with Methacholine Challenge

Group A
Percent protection from bronchoconstriction by animal number

| Time (hours) | 1 | 2 | 3 | 4 | 5 | 6 | 7 |
|---|---|---|---|---|---|---|---|
| 0 | 100.00 | 100.00 | 100.00 | 100.00 | 100.00 | 100.00 | 100.00 |
| 2 | 20.81 | 23.82 | 32.89 | 11.56 | 7.91 | 24.95 | 20.15 |
| 6 | 15.67 | 9.96 | 8.53 | 8.40 | 81.66 | 75.60 | 91.97 |
| 10 | 173.92 | 130.34 | 95.45 | 68.14 | 57.85 | 103.95 | 69.03 |

Group B
Percent protection from bronchoconstriction by animal number

| Time (hours) | 1 | 2 | 3 | 4 | 5 | 6 | 7 | 8 |
|---|---|---|---|---|---|---|---|---|
| 0 | 100.00 | 100.00 | 100.00 | 100.00 | 100.00 | 100.00 | 100.00 | 100.00 |
| 2 | 15.85 | 18.03 | 17.88 | 24.09 | 18.59 | 15.18 | 21.33 | 13.33 |
| 6 | 211.57 | 10.96 | 68.79 | 23.72 | 11.09 | 99.00 | 118.26 | 6.95 |
| 10 | 174.54 | 12.87 | 88.16 | 20.40 | 21.45 | 31.60 | 123.47 | 8.46 | generated control fluid (control 1). The dosing solutions were prepared by making the appropriate dilution of each stock solution. All stock and dosing solutions were maintained on ice once prepared. The dosing was completed within one hour after the test/control articles are made. A solution of methacholine (500 µg/ml) was prepared on the day of dosing.

Each animal received an intratracheal instillation of test or control article using a Penn Century microsprayer. Animals were food deprived overnight and were anesthetized using isoflurane, the larynx was visualized with the aid of a laryngoscope (or suitable alternative) and the tip of the microsprayer was inserted into the trachea. A dose volume of 250 µl/animal of test article or control was administered.

The methacholine aerosol was generated into the air inlet of a mixing chamber using aeroneb ultrasonic nebulizers supplied with air from a Buxco bias flow pump. This mixing chamber in turn fed four individual whole body unrestrained plethysmographs, each operated under a slight negative pressure maintained by means of a gate valve located in the exhaust line. A vacuum pump was used to exhaust the inhalation chamber at the required flow rate.

Prior to the commencement of the main phase of the study, 12 spare animals were assigned to 3 groups (n=4/group) to determine the maximum exposure period at which animals may be exposed to methacholine to induce a severe but non-fatal acute bronchoconstriction. Four animals were exposed to methacholine (500 µg/mL) for 30 seconds and respiratory parameters were measured for up to 10 minutes following commencement of aerosol. Methacholine nebulizer concentration and/or exposure time of aerosolization was adjusted appropriately to induce a severe but non-fatal acute/reversible bronchoconstriction, as characterized by an transient increase in penes.

Once prior to test article administration (Day −1) and again at 2, 6, 10, 14, 18, 22 and 26 hours postdose, animals were placed in the chamber and ventilatory parameters (tidal volume, respiratory rate, derived minute volume) and the enhanced pause Penh were measured for a period of 10 minutes using the Buxco Electronics BioSystem XA system, following commencement of aerosol challenge to methacholine. Once animals were within chambers baseline, values were recorded for 1-minute, following which methacholine, nebulizer concentration of 500 ug/mL were aerosoloized for 30 seconds, animals were exposed to the aerosol for further 10 minutes during which time ventilatory paramaters were continuously assessed. Penh was used as the indicator of bronchoconstriction; Penh is a derived value obtained from peak inspiratory flow, peak expiratory flow and time of expiration. Penh=(Peak expiratory flow/Peak inspiratory flow)*(Expiratory time/time to expire 65% of expiratory volume −1).

Animals that did not display a severe acute broncoconstriction during the predose methacholine challenge were replaced. Any animal displaying at least 75% of their baseline PenhPenes value at 2 hours post dose were not included in the data analysis. The respiratory parameters were recorded as 20 second means.

Data considered unphysiological was excluded from further analysis.

Changes in Penh were plotted over a 15 minute period and Penh value was expressed as area under the curve. Numerical data was subjected to calculation of group mean values and standard deviations (as applicable).

TABLE 7

Experimental design; 7 male guinea pigs per group.

| Group ID | Albuterol (0 µg/animal) | Albuterol (6/25 µg/animal) | Albuterol (12.5 µg/animal) | Albuterol (25 µg/animal) |
|---|---|---|---|---|
| 1 (control 1) (ambient oxygen) | 7 males | 7 males | 7 males | 7 males |
| 5 (RDC1676-00) (Solas) | 7 males | 7 males | 7 males | 7 males |
| 6 (RDC1676-01) (20 ppm oxygen) | 7 males | 7 males | 7 males | 7 males |
| 7 (RDC1676-02) (40 ppm oxygen) | 7 males | 7 males | 7 males | 7 males |
| 8 (RDC1676-03) (60 ppm oxygen) | 7 males | 7 males | 7 males | 7 males |

Results:

As shown in FIG. 107A-D, in the absence of Albuterol, administration of the inventive electrokinetically generated fluids had no apparent effect on mean percent baseline PenH values, when measured over a 26 hour period.

Surprisingly, however, as shown in FIG. 108A-D, administration of albuterol (representative data for the 25 µg albuterol/animal groups are shown) formulated in the inventive electrokinetically generated fluids (at all oxygen level values tested; ambient (FIG. 108-A), 20 ppm (FIG. 108-B), 40 ppm (FIG. 108-C) and 60 ppm (FIG. 108-D)) resulted in a striking prolongation of anti-broncoconstrictive effects of albuterol, compared to control fluid. That is, the methacholine results showed a prolongation of the bronchodilation of albuterol out to at least 26 hours. FIGS. 108 A-D shows that there were consistent differences at all oxygen levels between RDC1676 and the normal saline control. Combining all 4 RDC1676 fluids, the p value for the overall treatment difference from normal saline was 0.03.

According to particular aspects of the present invention, therefore, the inventive electrokinetically generated solutions provide for synergistic prolongation effects with Albuterol, thus providing for a decrease in a patient's albuterol usage, enabling more efficient cost-effective drug use, fewer side effects, and increasing the period over which a patient may be treated and responsive to treatment with albuterol.

Example 11

A Cytokine Profile was Determined

Mixed lymphocytes were obtained from a single healthy volunteer donor. Buffy coat samples were washed according to standard procedures to remove platelets. Lymphocytes were plated at a concentration of $2 \times 10^6$ per plate in RPMI media (+50 mm HEPES) diluted with either inventive gas-enriched fluid or distilled water (control). Cells were stimulated with 1 microgram/mL T3 antigen, or 1 microgram/mL phytohemagglutinin (PHA) lectin (pan-T cell activator), or unstimulated (negative control). Following 24-hour incubation, cells were checked for viability and the supernatants were extracted and frozen.

The supernatants were thawed, centrifuged, and tested for cytokine expression using a XMAP® (Luminex) bead lite protocol and platform.

Two million cells were plated into 6 wells of a 24-well plate in full RPMI+50 mm Hepes with either inventive oxygen-enriched fluid (water) (wells 1, 3, and 5) or distilled water (2, 4 and 6) (10×RPMI diluted into water to make 1×). Cells were stimulated with 1 ug/ml T3 antigen (wells 1 and 2) or PHA (wells 3 and 4). Control wells 5 and 6 were not stimulated. After 24 hours, cells were checked for viability and supernatants were collected and frozen. Next, the supernatants were thawed and spun at 8,000 g to pellet. The clarified supernatants were assayed for the cytokines listed using a LUMINEX BEAD LITE™ protocol and platform. The numerical data is tabulated in Table 8, and the corresponding bar graphs are depicted in FIG. 38. Notably, IFN-γ level was higher in the inventive gas-enriched culture media with T3 antigen than in the control culture media with T3 antigen, while IL-8 was lower in the inventive gas-enriched culture media with T3 antigen than in the control culture media with T3 antigen. Additionally, IL-6, IL-8, and TNF-α levels were lower in the inventive gas-enriched media with PHA, than in the control media with PHA, while IL-1β levels were lower in the inventive gas-enriched fluid with PHA when compared with control media with PHA. In the inventive gas-enriched media alone, IFN-γ levels were higher than in control media.

inflammatory cytokines (IL-1β, TNF-α, IL-6, and GM-CSF), chemokines (IL-8, MIP-1α, RANTES, and Eotaxin), inflammatory enzymes (iNOS, COX-2, and MMP-9), allergen responses (MHC class II, CD23, B7-1, and B7-2), and Th2 cytokines (IL-4, IL-13, and IL-5) tested were reduced in test fluid versus control fluid. By contrast, anti-inflammatory cytokines (e.g., IL1R-α, TIMPs) tested were increased in test fluid versus control fluid.

To expand on these data, Applicants used an art recognized model system involving ovalbumin sensitization, for assessing allergic hypersensitivity reactions. The end points studied were particular cytologic and cellular components of the reaction as well as serologic measurements of protein and LDH. Cytokine analysis was performed, including analysis of Eotaxin, IL-1A, IL-1B, KC, MCP-1, MCP-3, MIP-1A, RANTES, TNF-A, and VCAM.

Briefly, male Brown Norway rats were injected intraperitoneally with 0.5 mL Ovalbumin (OVA) Grade V (A5503-1G,

TABLE 8

| Sample | IFN | Il-10 | Il-12p40 | Il-12p70 | Il-2 | Il-4 | Il-5 | Il-6 | Il-8 | Il-ib | IP-10 | TNFa |
|---|---|---|---|---|---|---|---|---|---|---|---|---|
| 1 | 0 | 0 | 0 | 2.85 | 0 | 0 | 7.98 | 20.3 | 1350 | 7.56 | 11500 | 15.5 |
| 2 | 0 | 0 | 0 | 3.08 | 0 | 0 | 8 | 15.2 | 8940 | 3.68 | 4280 | 7.94 |
| 3 | 0 | 581 | 168 | 3.15 | 0 | 0 | 8 | 16400 | 2200 | 3280 | 862 | 13700 |
| 4 | 0 | 377 | 56.3 | 4.22 | 0 | 0 | 8.08 | 23800 | 22100 | 33600 | 558 | 16200 |
| 5 | 0 | 0 | 0 | 2.51 | 0 | 0 | 7.99 | 24 | 1330 | 7.33 | 5900 | 8.55 |
| 6 | 0 | 0 | 0 | 2.77 | 0 | 0 | 8 | 5.98 | 3210 | 4.68 | 3330 | 0 |

Example 12

Myelin Oligodendrocyte Glycoprotein (MOG)

As set forth in FIG. 48, lymphocyte proliferation in response to MOG antigenic peptide was increased when cultured in the presence of the inventive gas-enriched fluid when compared to pressurized, oxygenated fluid (pressure pot) or deionized control fluid. Thus, the inventive gas-enriched fluid amplifies the lymphocyte proliferative response to an antigen to which the cells were previously primed.

Myelin oligodendrocyte glycoprotein peptide 35-55 (MOG 35-55) (M-E-V-G-W-Y-R-S-P-F-S-R-O-V-H-L-Y-R-N-G-K) (SEQ ID NO:1; see publication US20080139674, incorporated by reference herein, including for purposes of this SEQ ID NO:1) corresponding to the known mouse sequence was synthesized. Next, $5 \times 10^5$ spleen cells were removed from MOG T cell receptor transgenic mice previously immunized with MOG, and were cultured in 0.2 ml TCM fluid reconstituted with inventive gas-enriched fluid, pressurized oxygenated water (pressure pot water) or with control deionized water. Splenocytes were cultured with MOG p35-55 for 48 or 72 hours, respectively. Cultures were pulsed with 1Ci [3H]-thymidine and harvested 16 hours later. Mean cpm of [3H] thymidine incorporation was calculated for triplicate cultures. Results are shown in FIG. 48.

Example 13

Cytokine Expression

In particular aspects, human mixed lymphocytes were stimulated with T3 antigen or PHA in inventive electrokinetic fluid, or control fluid, and changes in IL-1β, IL-2, IL-4, IL-5, IL-6, IL-7, IL-8, IL-10, IL-12(p40), IL-12(p70), IL-13, IL-17, Eotaxin, IFN-γ, GM-CSF, MIP-1β, MCP-1, G-CSF, FGFb, VEGF, TNF-α, RANTES, Leptin, TNF-β, TFG-β, and NGF were evaluated. As can be seen from FIG. 38, pro- Sigma) in solution (2.0 mg/mL) containing aluminum hydroxide (Al(OH)$_3$) (200 mg/mL) once each on days 1, 2, and 3. The study was a randomized 2×2 factorial arrangement of treatments (4 groups). After a two week waiting period to allow for an immune reaction to occur, the rats were either exposed or were treated for a week with either RDC1676-00 (sterile saline processed through the Revalesio proprietary device), and RDC1676-01 (sterile saline processed through the Revalesio proprietary device with additional oxygen added). At the end of the 1 week of treatment for once a day, the 2 groups were broken in half and 50% of the rats in each group received either Saline or OVA challenge by inhalation.

Specifically, fourteen days following the initial serialization, 12 rats were exposed to RDC 1676-00 by inhalation for 30 minutes each day for 7 consecutive days. The air flow rate through the system was set at 10 liters/minute. A total of 12 rats were aligned in the pie chamber, with a single port for nebulized material to enter and evenly distribute to the 12 sub-chambers of the Aeroneb.

Fifteen days following initial sensitization, 12 rats were exposed to RDC 1676-01 by ultrasonic nebulization for 30 minutes each day for 7 consecutive days. The air flow was also set for 10 liters/minute, using the same nebulizer and chamber. The RDC 1676-00 was nebulized first and the Aeroneb chamber thoroughly dried before RDC 1676-01 was nebulized.

Approximately 2 hours after the last nebulization treatment, 6 rats from the RDC 1676-00 group were re-challenged with OVA (1% in saline) delivered by intratracheal instillation using a Penn Century Microsprayer (Model 1A-1B). The other 6 rats from the RDC 1676-00 group were challenged with saline as the control group delivered by way of intratracheal instillation. The following day, the procedure was repeated with the RDC 1676-01 group.

Twenty four hours after re-challenge, all rats in each group were euthanized by overdose with sodium pentobarbital. Whole blood samples were collected from the inferior venacava and placed into two disparate blood collection tubes: Qiagen PAXgene™ Blood RNA Tube and Qiagen PAXgene™ Blood DNA Tube. Lung organs were processed to obtain bronchoalveolar lavage (BAL) fluid and lung tissue for RT-PCR to assess changes in markers of cytokine expression known to be associated with lung inflammation in this model. A unilateral lavage technique was be employed in order to preserve the integrity of the 4 lobes on the right side of the lung. The left "large" lobe was lavaged, while the 4 right lobes were tied off and immediately placedinot TRI-zol™, homogenized, and sent to the lab for further processing.

BAL Analysis.

Lung lavage was collected and centrifuged for 10 minutes at 4° C. at 600-800 g to pellet the cells. The supernatants were transferred to fresh tubes and frozen at −80° C. Bronchial lavage fluid ("BAL") was separated into two aliquots. The first aliquot was spun down, and the supernatant was snap frozen on crushed dry ice, placed in −80° C., and shipped to the laboratory for further processing. The amount of protein and LDH present indicates the level of blood serum protein (the protein is a serum component that leaks through the membranes when it's challenged as in this experiment) and cell death, respectively. The proprietary test side showed slight less protein than the control.

The second aliquot of bronchial lavage fluid was evaluated for total protein and LDH content, as well as subjected to cytological examination. The treated group showed total cells to be greater than the saline control group. Further, there was an increase in eosinophils in the treated group versus the control group. There were also slightly different polymorphonuclear cells for the treated versus the control side.

Blood Analysis.

Whole blood was analyzed by transfer of 1.2-2.0 mL blood into a tube, and allowing it to clot for at least 30 minutes. The remaining blood sample (approximately 3.5-5.0 mL) was saved for RNA extraction using TRI-zol™ or PAXgene™. Next, the clotted blood sample was centrifuged for 10 minutes at 1200 g at room temperature. The serum (supernatant) was removed and placed into two fresh tubes, and the serum was stored at −80° C.

For RNA extraction utilizing Tri-Reagent (TB-126, Molecular Research Center, Inc.), 0.2 mL of whole blood or plasma was added to 0.75 mL of TRI Reagent BD supplemented with 20 µL of 5N acetic acid per 0.2 mL of whole blood or plasma. Tubes were shaken and stored at −80° C. Utilizing PAXgene™, tubes were incubated for approximately two hours at room temperature. Tubes were then placed on their side and stored in the −20° C. freezer for 24 hours, and then transferred to −80° C. for long term storage.

Luminex Analysis.

By Luminex platform, a microbead analysis was utilized as a substrate for an antibody-related binding reaction which is read out in luminosity units and can be compared with quantified standards. Each blood sample was run as 2 samples concurrently. The units of measurement are luminosity units and the groups are divided up into OVA challenged controls, OVA challenged treatment, and saline challenged treatment with proprietary fluid.

For Agilant gene array data generation, lung tissue was isolated and submerged in TRI Reagent (TR118, Molecular Research Center, Inc.). Briefly, approximately 1 mL of TRI Reagent was added to 50-100 mg of tissue in each tube. The samples were homogenized in TRI Reagent, using glass-Teflon™ or Polytron™ homogenizer. Samples were stored at −80° C.

Blood Samples:

FIGS. 49-58 show the results of whole blood sample evaluations.

Exemplary FIG. 49 shows the basic luminosity data presentation format for the blood sample data. Letters designating the identity of the measured cytokine (in this case KC) are at the top right of each data figure. The data is presented both as data points (upper graph) and bar graphs (lower graph) of the individual samples. In either case, the graphs are divided, from left to right, in four groups. The first 2 groups (RDC1676-00 OVA and RDC1676-01 OVA, respectively) were those that were re-challenged with OVA by inhalation, whereas the last two groups (RDC1676-00 OVA and RDC1676-01 OVA, respectively) where those that were re-challenged with saline control only. Again, the suffix 00 represents saline treatment and suffix 01 represents inventive electrokinetic fluid treated groups.

Each blood sample was split into 2 samples and the samples were run concurrently. The units of measure are units of luminosity and the groups, going from left to right are: OVA challenged controls; OVA challenged inventive electrokinetic fluid treatment; followed by saline challenged saline treatment; and saline challenged inventive electrokinetic fluid treatment. To facilitate review, both the RDC1676-01 groups are highlighted with gray shaded backdrops, whereas the control saline treatment groups have unshaded backdrops.

Generally, in comparing the two left groups, while the spread of the RDC1676-01 group data is somewhat greater, particular cytokine levels in the RDC1676-01 group as a whole are less than the samples in the control treated group; typically about a 30% numerical difference between the 2 groups. Generally, in comparing the right-most two groups, the RDC1676-01 group has a slightly higher numerical number compared to the RDC1676-00 group.

Figure 50:
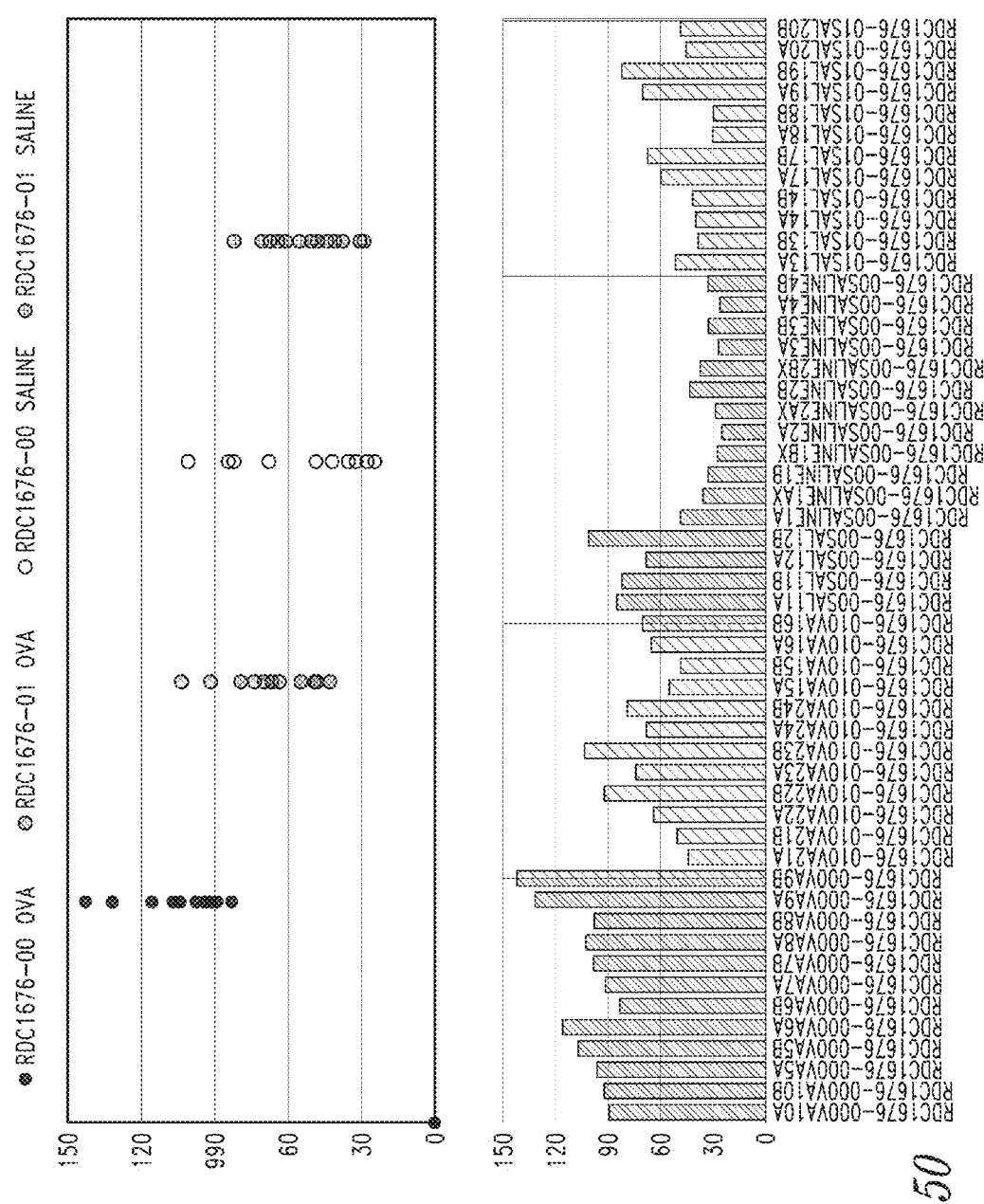

FIG. 50 shows analysis of RANTES (IL-8 super family) in blood sample data according to particular exemplary aspects. Luminosity units for the leftmost two groups (the OVA challenged groups) indicate that generally values in the RDC1676-01 treated group were less than the RDC1676-00 control group as shown by the dot plot in the upper graph portion which again shows a 30-35% differential between the two groups, whereas in the saline only exposed groups the cytokine level values where roughly the same, or perhaps slightly increased in the RDC1676-01 treated group.

Figure 51:
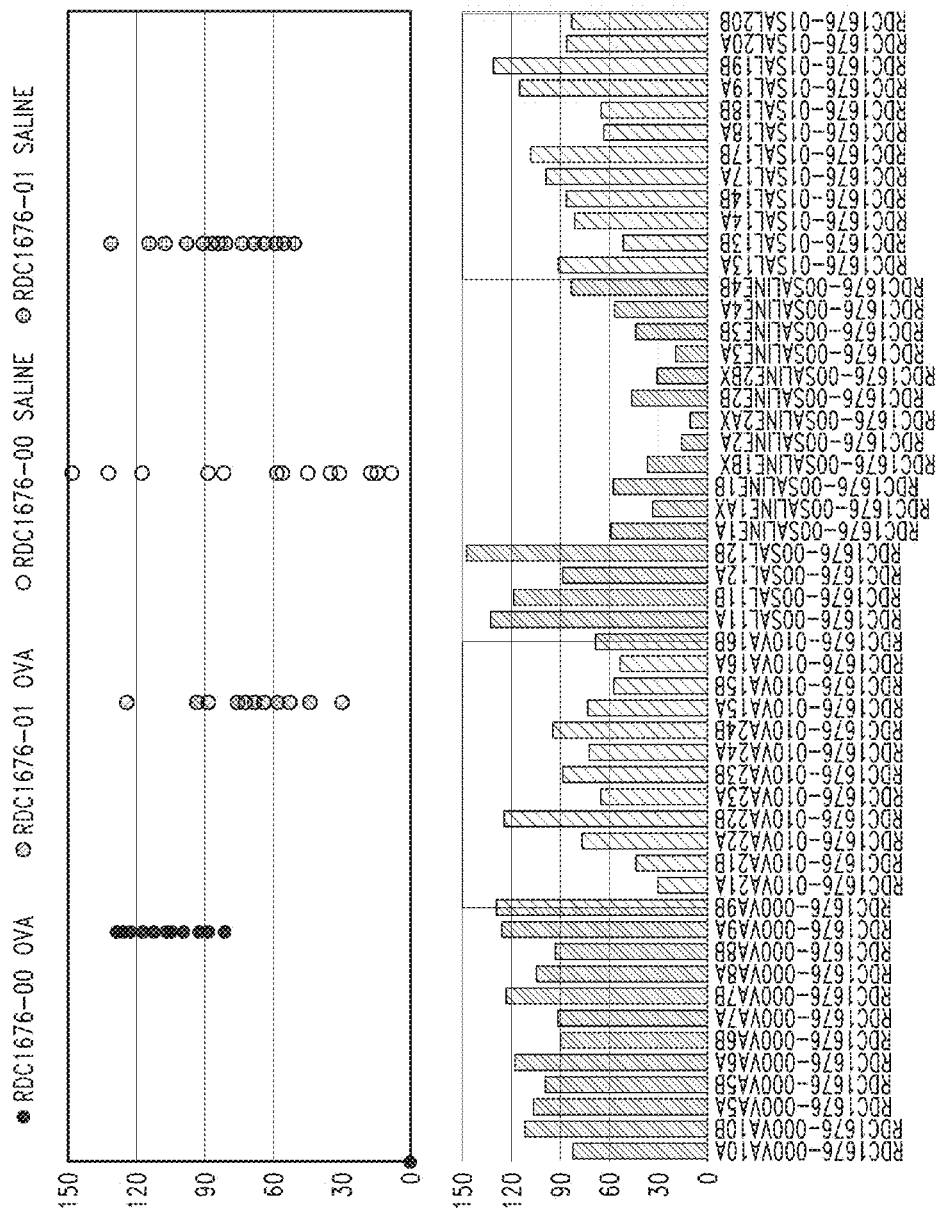

FIG. 51 shows analysis of MCP-1 in blood sample data according to particular exemplary aspects. Luminosity units for the leftmost two groups (the OVA challenged groups) indicate that generally values in the RDC1676-01 treated group were less than the RDC1676-00 control group as shown by the dot plot in the upper graph portion, whereas in the saline only exposed groups the cytokine level values where roughly the same, or perhaps slightly increased in the RDC1676-01 treated group.

Figure 52:
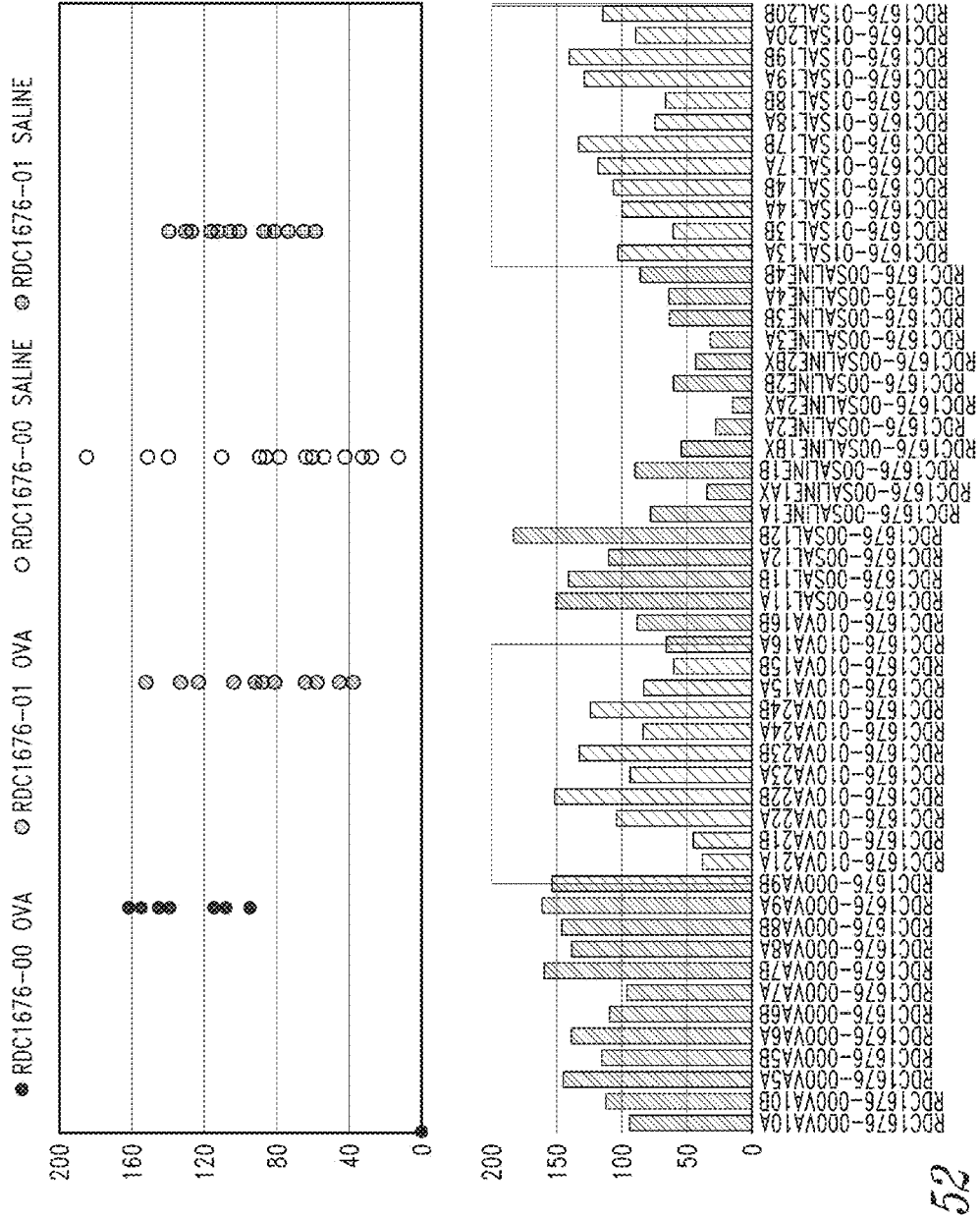

FIG. 52 shows analysis of TNF alpha in blood sample data according to particular exemplary aspects. Luminosity units for the leftmost two groups (the OVA challenged groups) indicate that generally values in the RDC1676-01 treated group were less than the RDC1676-00 control group as shown by the dot plot in the upper graph portion, whereas in the saline only exposed groups the cytokine level values where roughly the same, or perhaps slightly increased in the RDC1676-01 treated group.

FIG. 53 shows analysis of MIP-1 alpha in blood sample data according to particular exemplary aspects. Luminosity units for the leftmost two groups (the OVA challenged groups) indicate that generally values in the RDC1676-01 treated group were less than the RDC1676-00 control group as shown by the dot plot in the upper graph portion, whereas in the saline only exposed groups the cytokine level values where roughly the same, or perhaps slightly increased in the RDC1676-01 treated group.

FIG. 54 shows analysis of IL-1 alpha in blood sample data according to particular exemplary aspects. Luminosity units for the leftmost two groups (the OVA challenged groups) indicate that generally values in the RDC1676-01 treated group were less than the RDC1676-00 control group as shown by the dot plot in the upper graph portion, whereas in the saline only exposed groups the cytokine level values where roughly the same, or perhaps slightly increased in the RDC1676-01 treated group.

Figure 55:
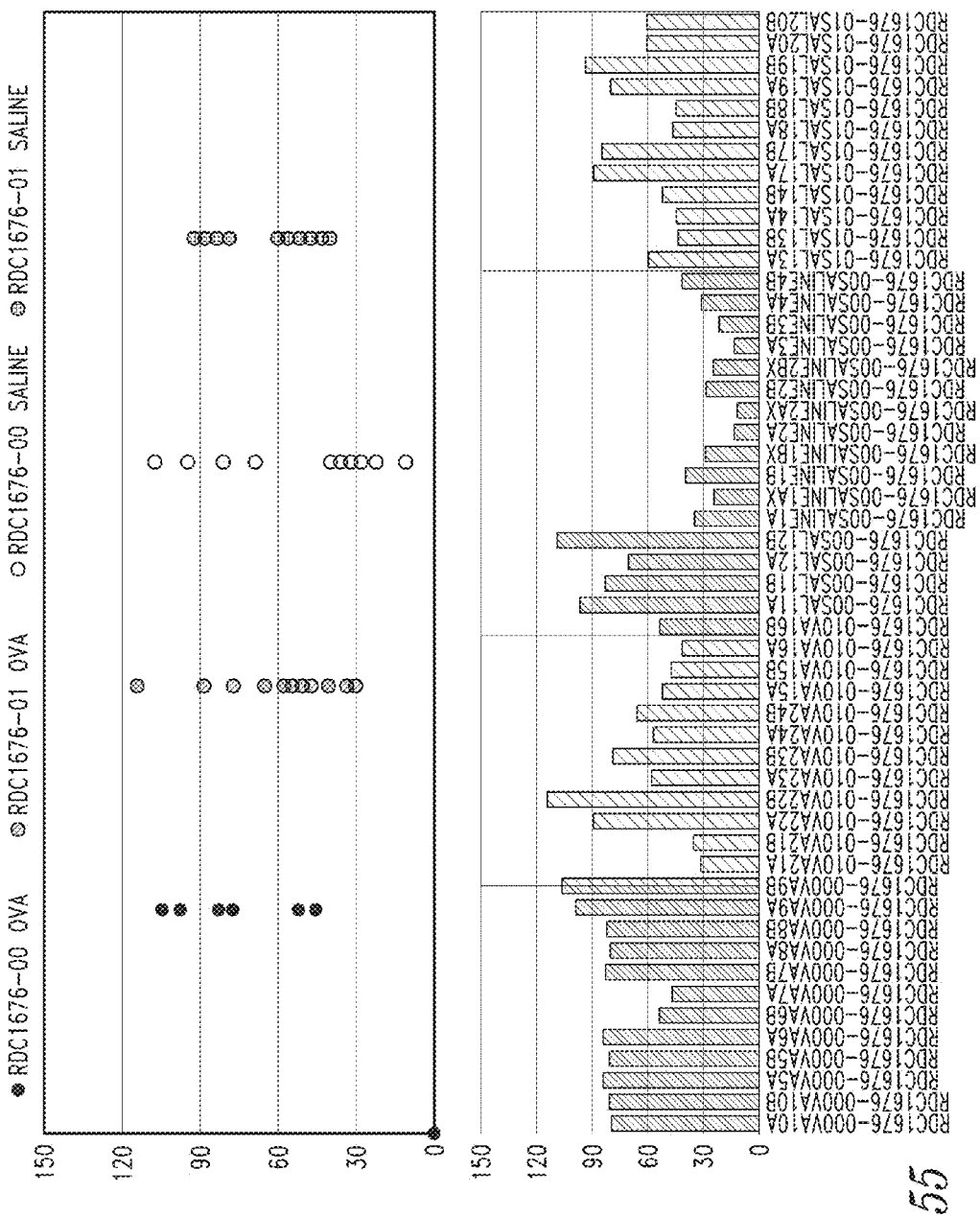

FIG. 55 shows analysis of Vcam in blood sample data according to particular exemplary aspects. Luminosity units for the leftmost two groups (the OVA challenged groups) indicate that generally values in the RDC1676-01 treated group were less than the RDC1676-00 control group as shown by the dot plot in the upper graph portion, whereas in the saline only exposed groups the cytokine level values where roughly the same, or perhaps slightly increased in the RDC1676-01 treated group.

Figure 56:
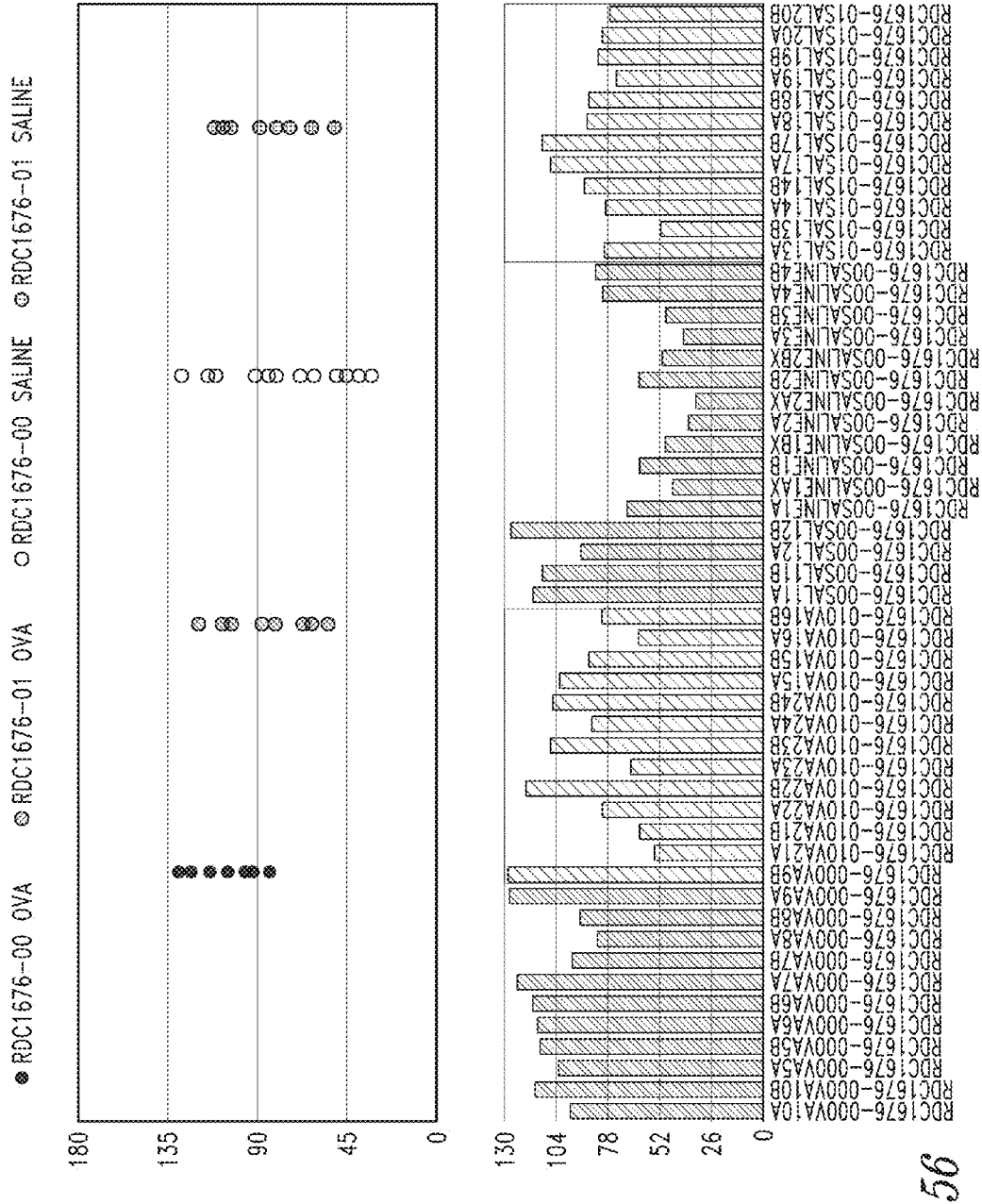

FIG. 56 shows analysis of IL-1 beta in blood sample data according to particular exemplary aspects. Luminosity units for the leftmost two groups (the OVA challenged groups) indicate that generally values in the RDC1676-01 treated group were less than the RDC1676-00 control group as shown by the dot plot in the upper graph portion, whereas in the saline only exposed groups the cytokine level values where roughly the same, or perhaps slightly increased in the RDC1676-01 treated group.

Figure 58:
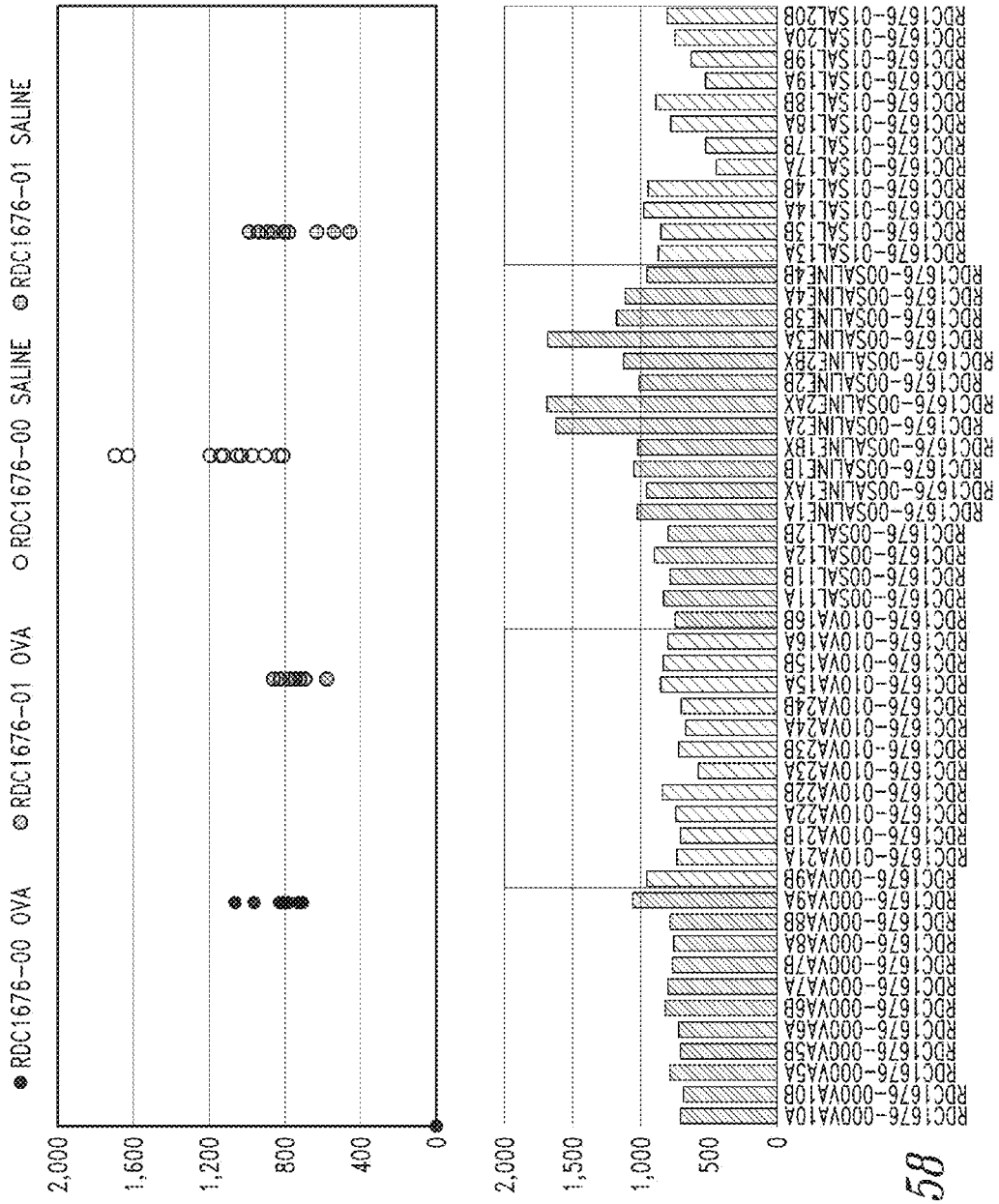

FIGS. 57 and 58 show analysis of Eotaxin and MCP-3, respectively, in blood sample data according to particular exemplary aspects. In each case, luminosity units for the leftmost two groups (the OVA challenged groups) indicate that generally values in the RDC1676-01 treated group were less than the RDC1676-00 control group as shown by the dot plot in the upper graph portion, whereas in the saline only exposed groups the cytokine level values where roughly the same, or perhaps slightly increased in the RDC1676-01 treated group.

Bronchial Lavage Samples:

FIGS. 59-68 show the corresponding results of bronchoalveolar lavage fluid (BAL) sample evaluations.

Figure 59:
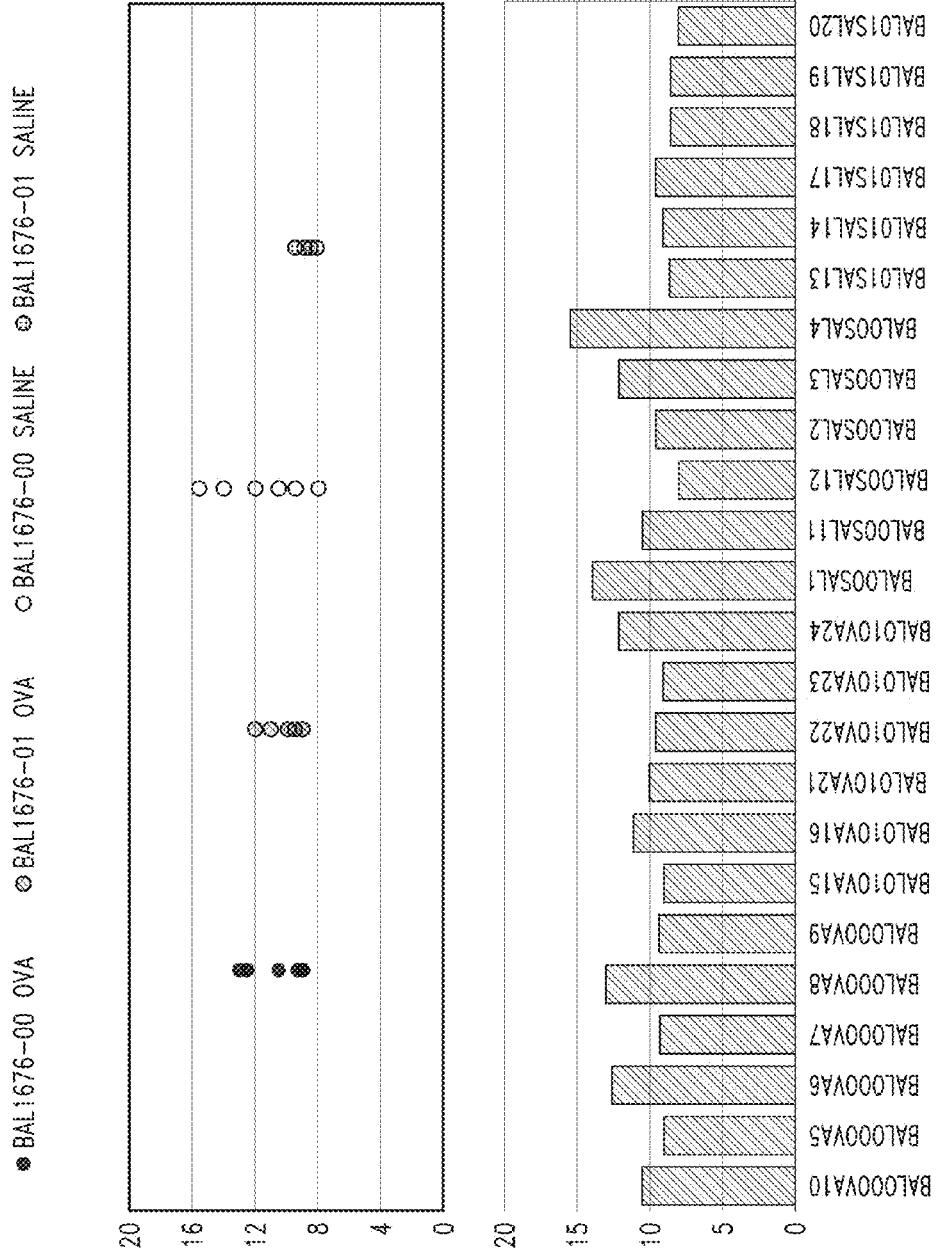
FIGS. 59-68 show the corresponding cytokine results of bronchoalveolar lavage fluid (BAL) sample evaluations.

FIG. 59 shows analysis of KC in BAL data according to particular exemplary aspects. In this instance the response level, coupled with sampling variability, was inconclusive with respect to a difference between the RDC1676-01 and RDC1676-00-treated groups; that is, KC showed relatively little difference between the 2 groups, but the units of luminosity were very small.

Figure 60:
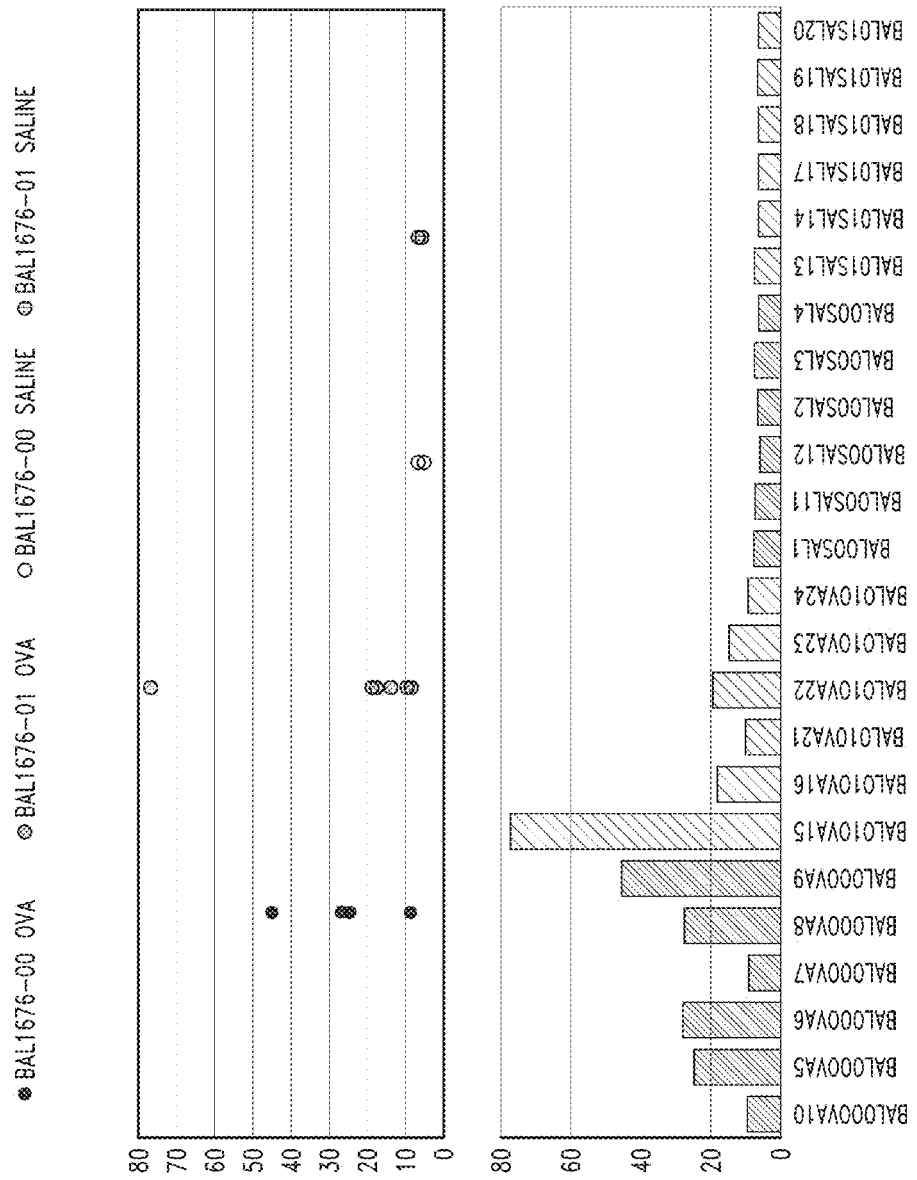

Likewise, FIG. 60 shows analysis of RANTES in BAL data according to particular exemplary aspects, and showing marked variability in the RDC1676-01 group with one reading being markedly higher than the others, skewing the results.

Figure 61:
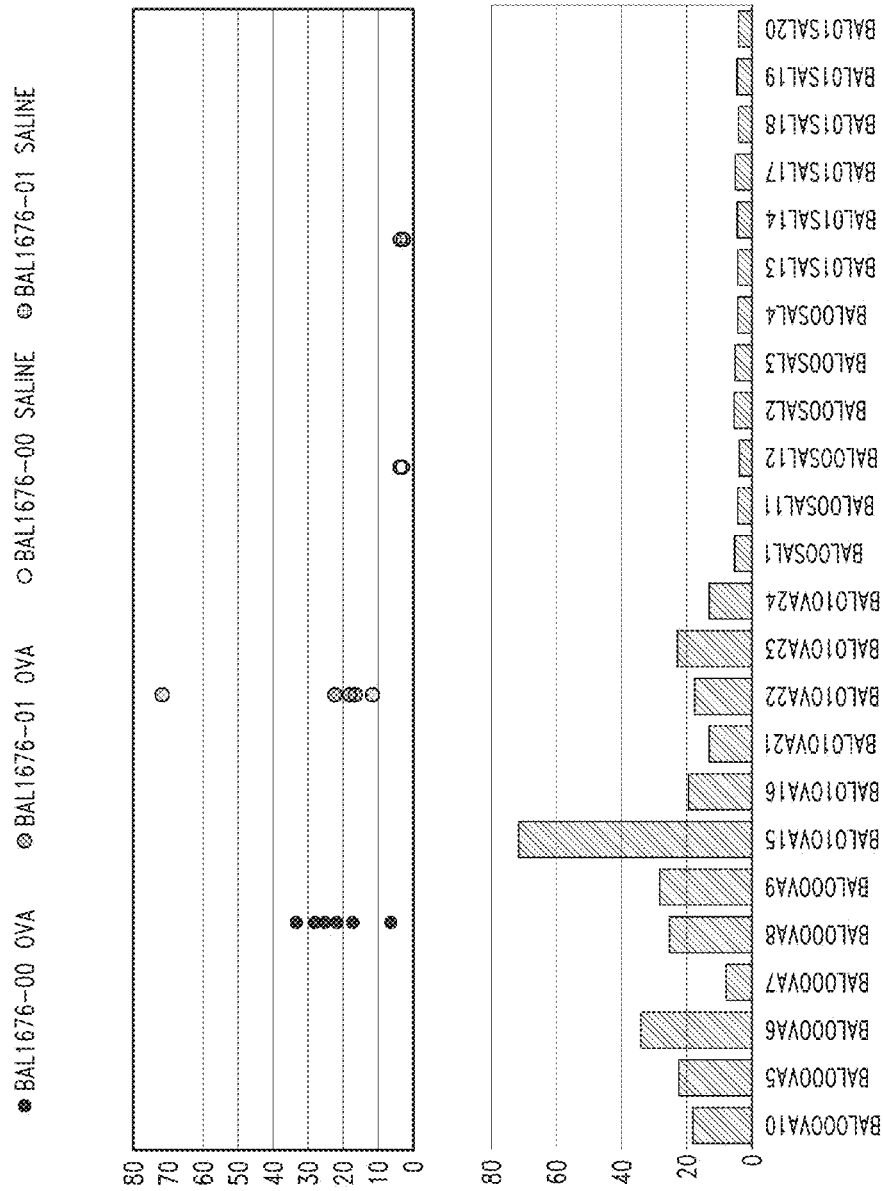

Likewise, FIG. 61 shows analysis of TNF alpha in BAL data according to particular exemplary aspects, and showing relatively little significance in the way of difference between the RDC1676-01 and RDC1676-00-treated groups.

Figure 62:
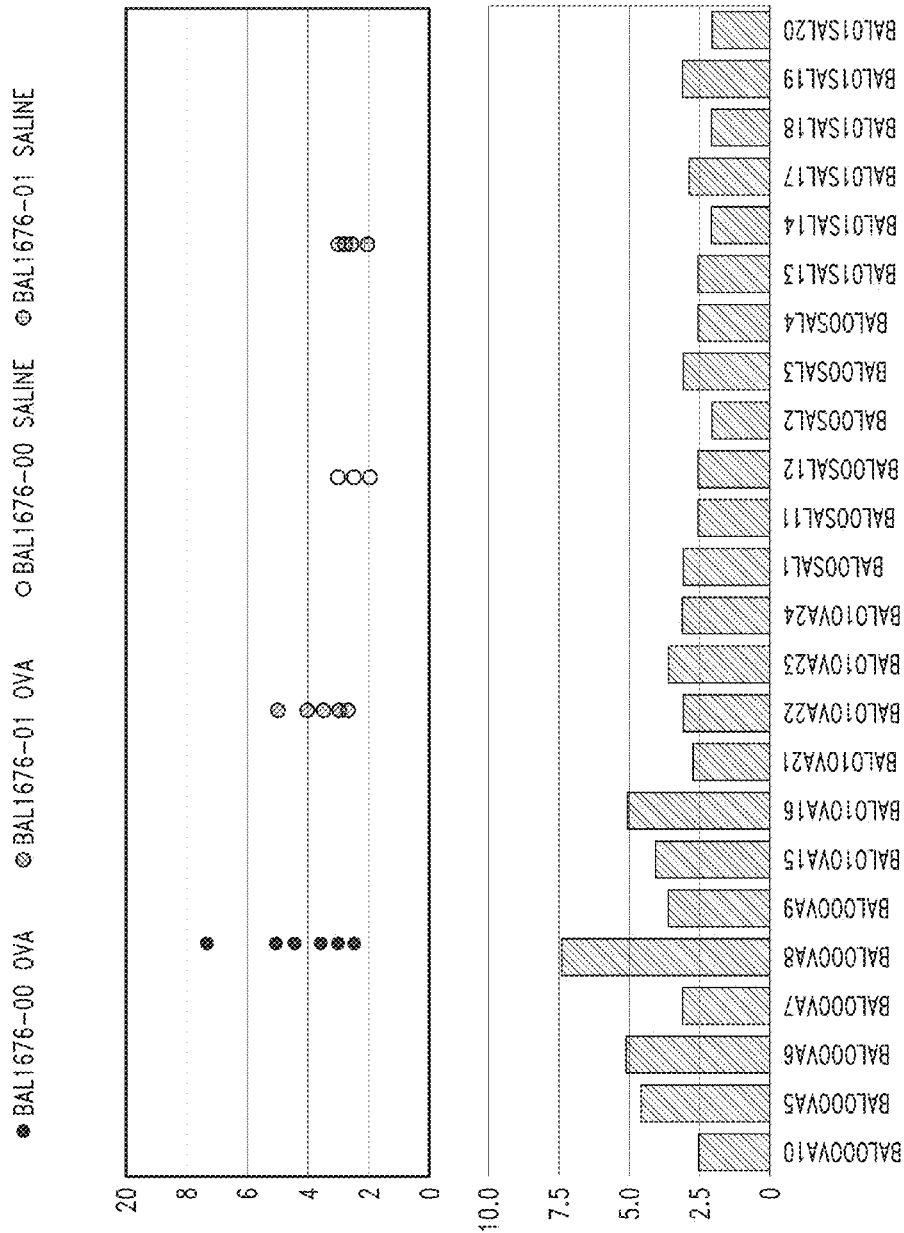
Figure 63:
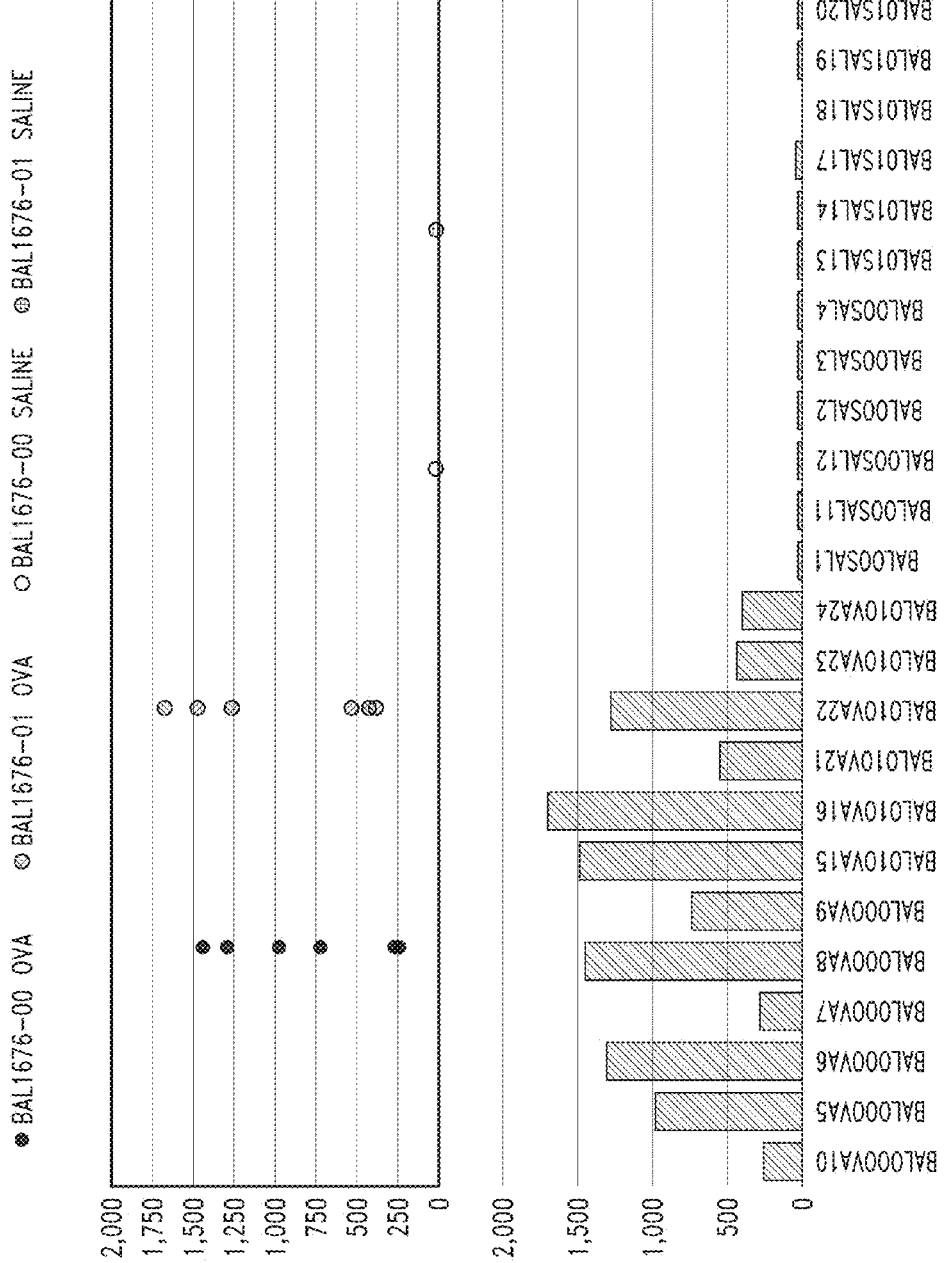
Figure 64:
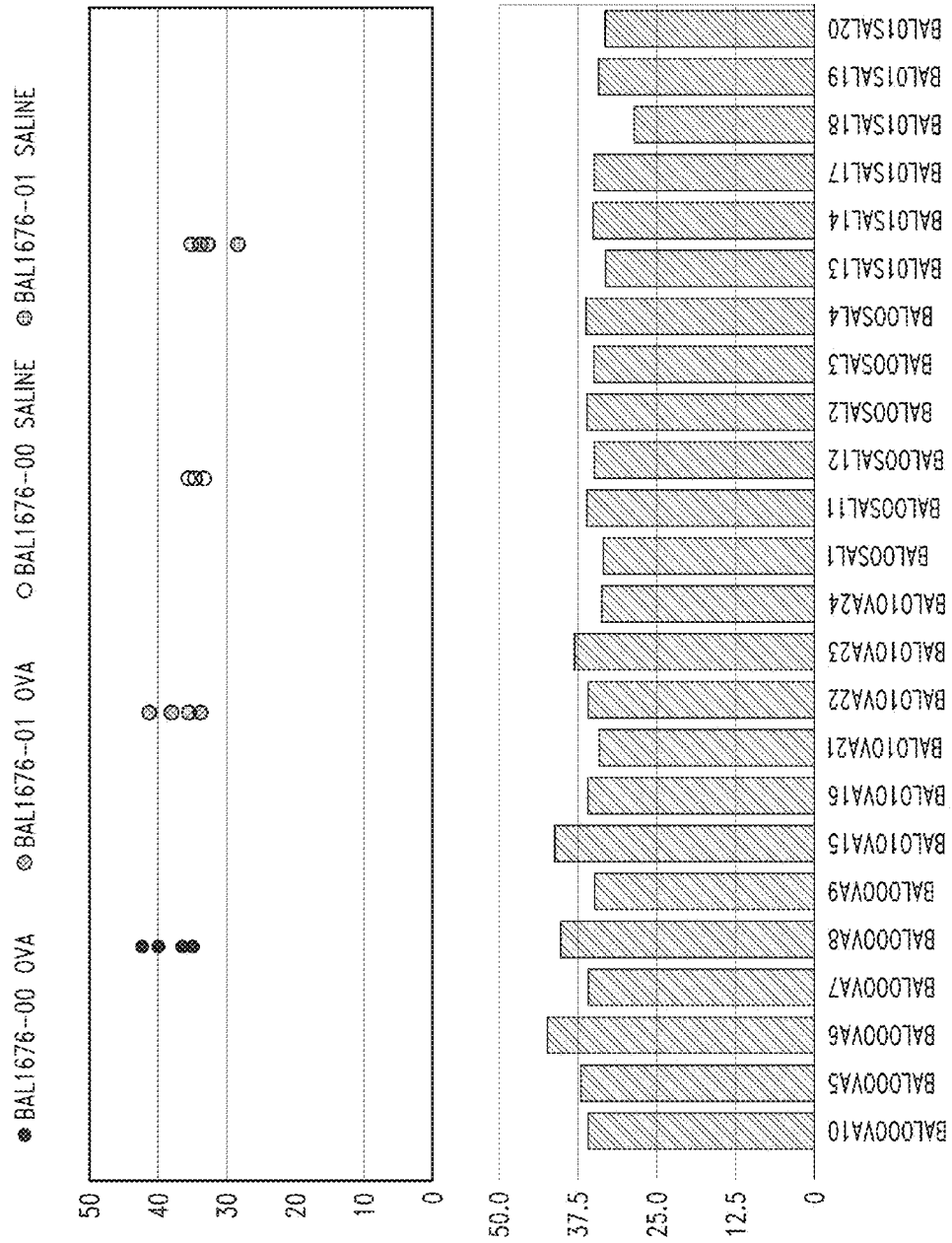
Figure 65:
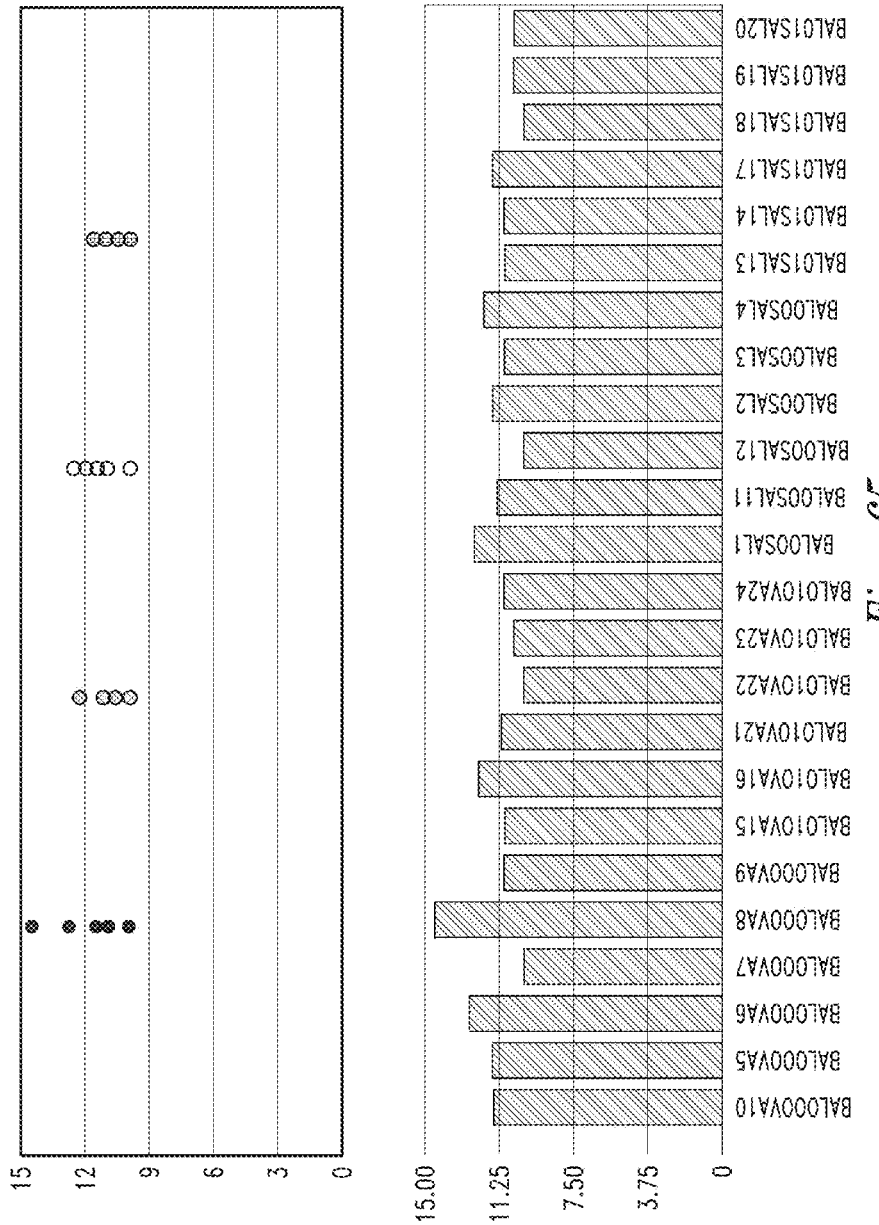
Figure 66:
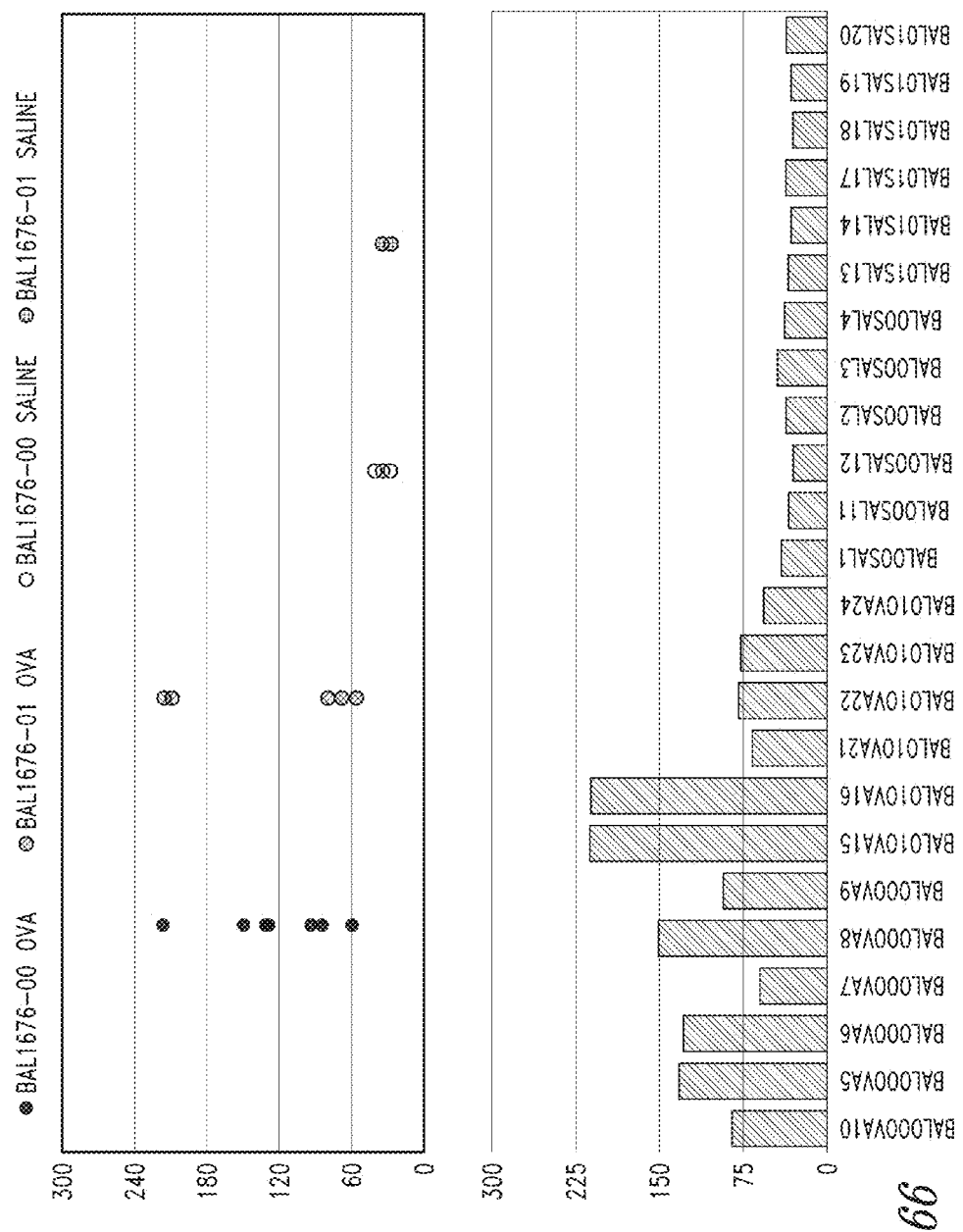
Figure 67:
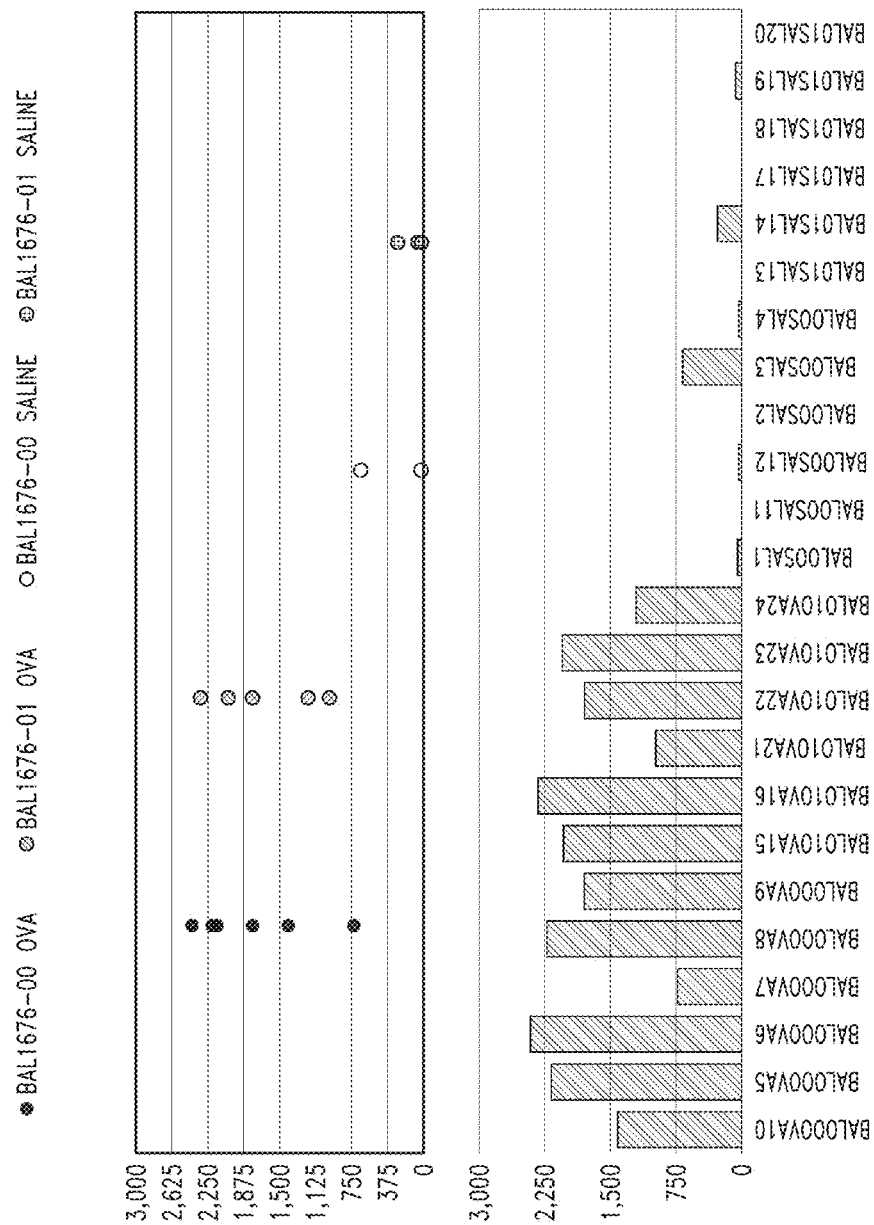
Figure 68:
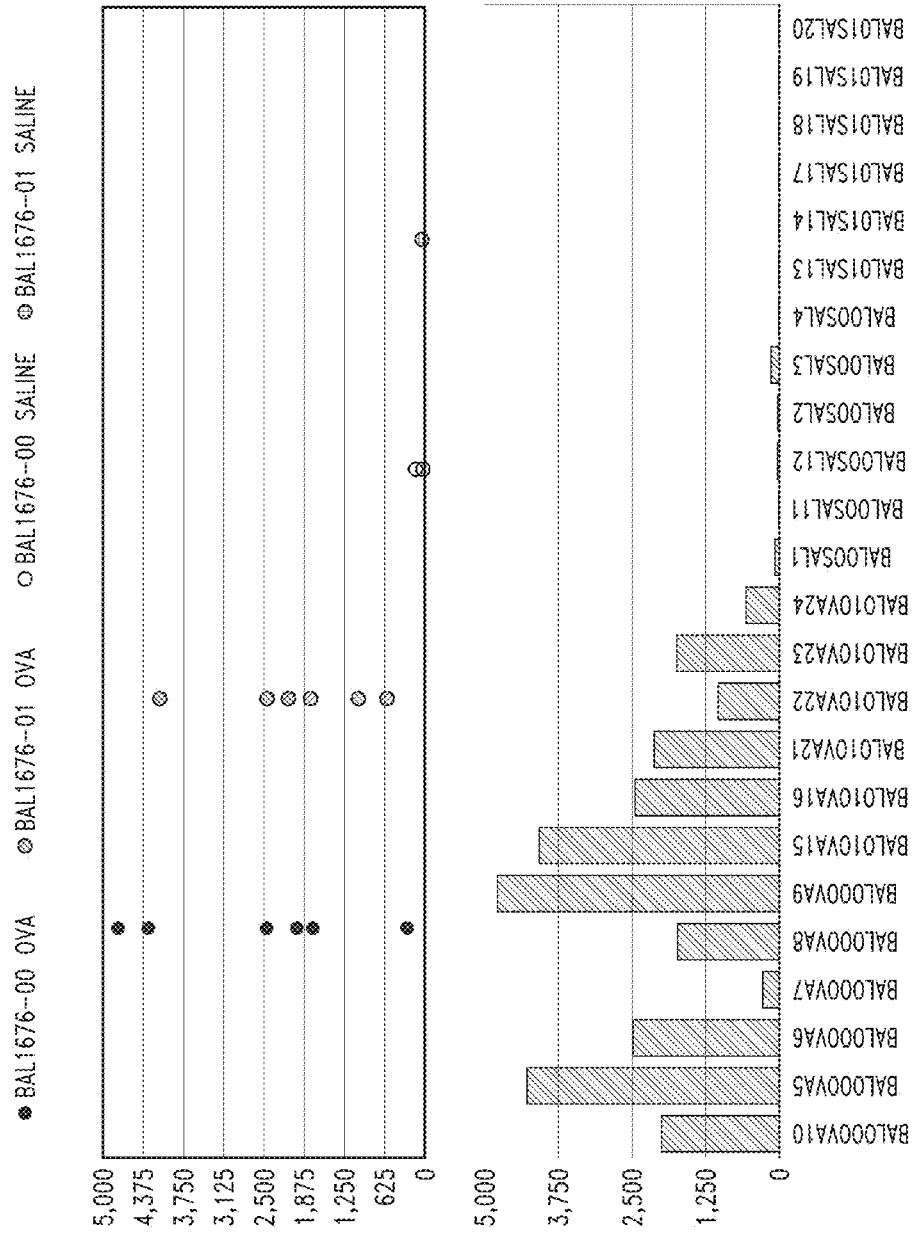

FIG. 62 shows analysis of MCP-1 in BAL data according to particular exemplary aspects, and showing relatively little significance in the way of difference between the RDC1676-01 and RDC1676-00-treated groups.

FIGS. 63 through 68 show analysis of MIP1-A, IL-1 alpha, Vcam, IL-1 beta, MCP-3, and Eotaxin, respectively, in BAL data according to particular exemplary aspects, and showing relatively little significance in the way of difference between the RDC1676-01 and RDC1676-00-treated groups.

In summary, this standard assay of inflammatory reaction to a known sensitization produced, at least in the blood samples, a marked clinical and serologic affect. Additionally, while significant numbers of control animals were physiologically stressed and nearly dying in the process, none of the RDC1676-01 treated group showed such clinical stress effects. This was reflected then in the circulating levels of cytokines, with approximately 30% differences between the RDC1676-01-treated and the RDC1676-01-treated groups in the OVA challenged groups. By contrast, there were small and fairly insignificant changes in cytokine, cellular and serologic profiles between the RDC1676-01-treated and the RDC1676-01-treated groups in the non-OVA challenged groups, which likely merely represent minimal baseline changes of the fluid itself.

Example 14

Bradykinin B2 Receptor Affinity Binding

A Bio-Layer Interferometry biosensor, Octet Rapid Extended Detection (RED) (forteBio™) was utilized in order to examine membrane receptor affinity binding of Bradykinin ligand with the Bradykinin B2 receptor. The biosensor system consists of a polished fiber optic embedded into a polypropylene hub with a sensor-specific chemistry at the tip. The biosensor set-up has a layer of molecules attached to the tip of an optic fiber that creates an interference pattern at the detector. Any change in the number of molecules bound causes a measured shift in the pattern of light.

Figure 69:
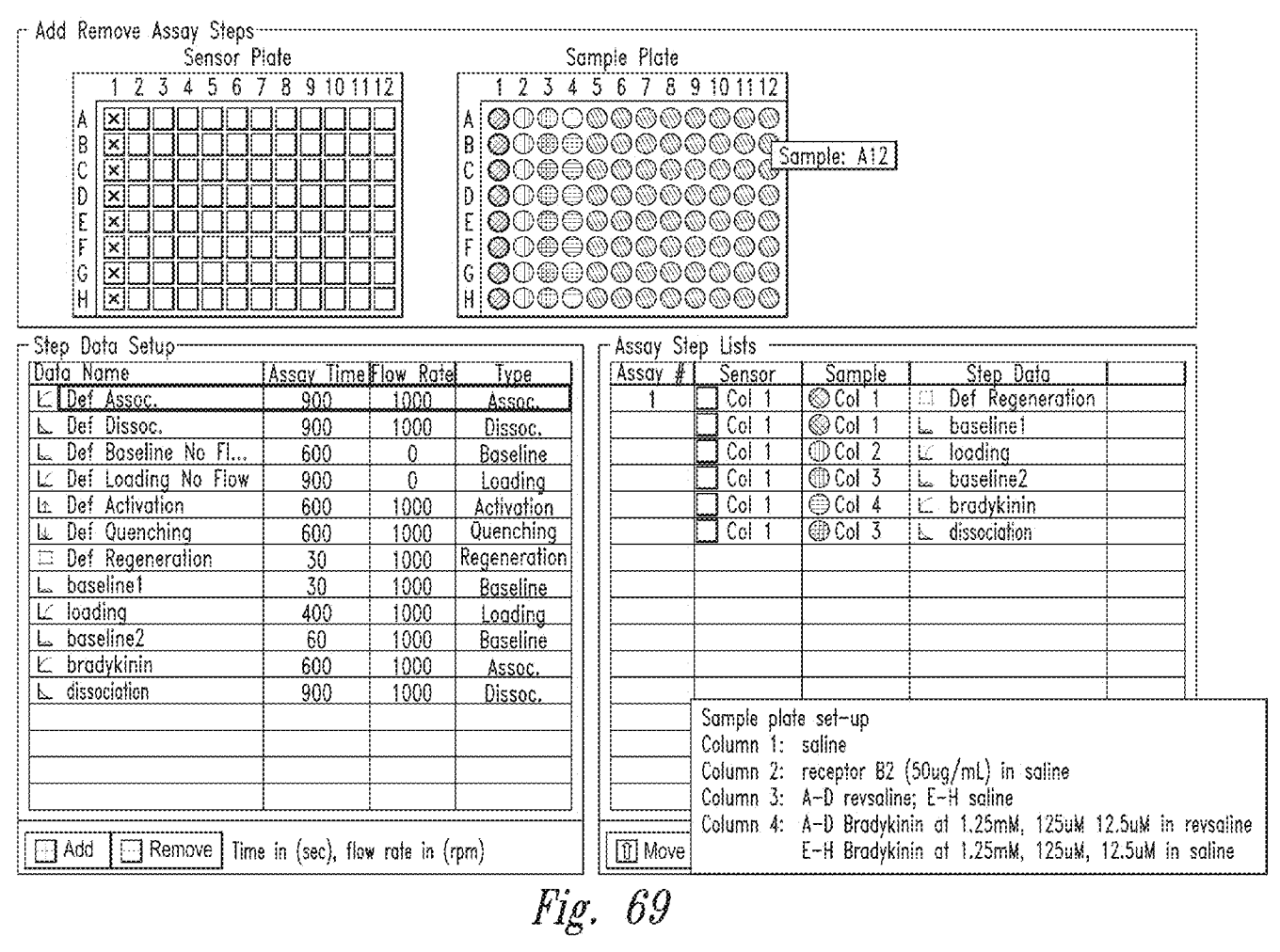
Figure 70:
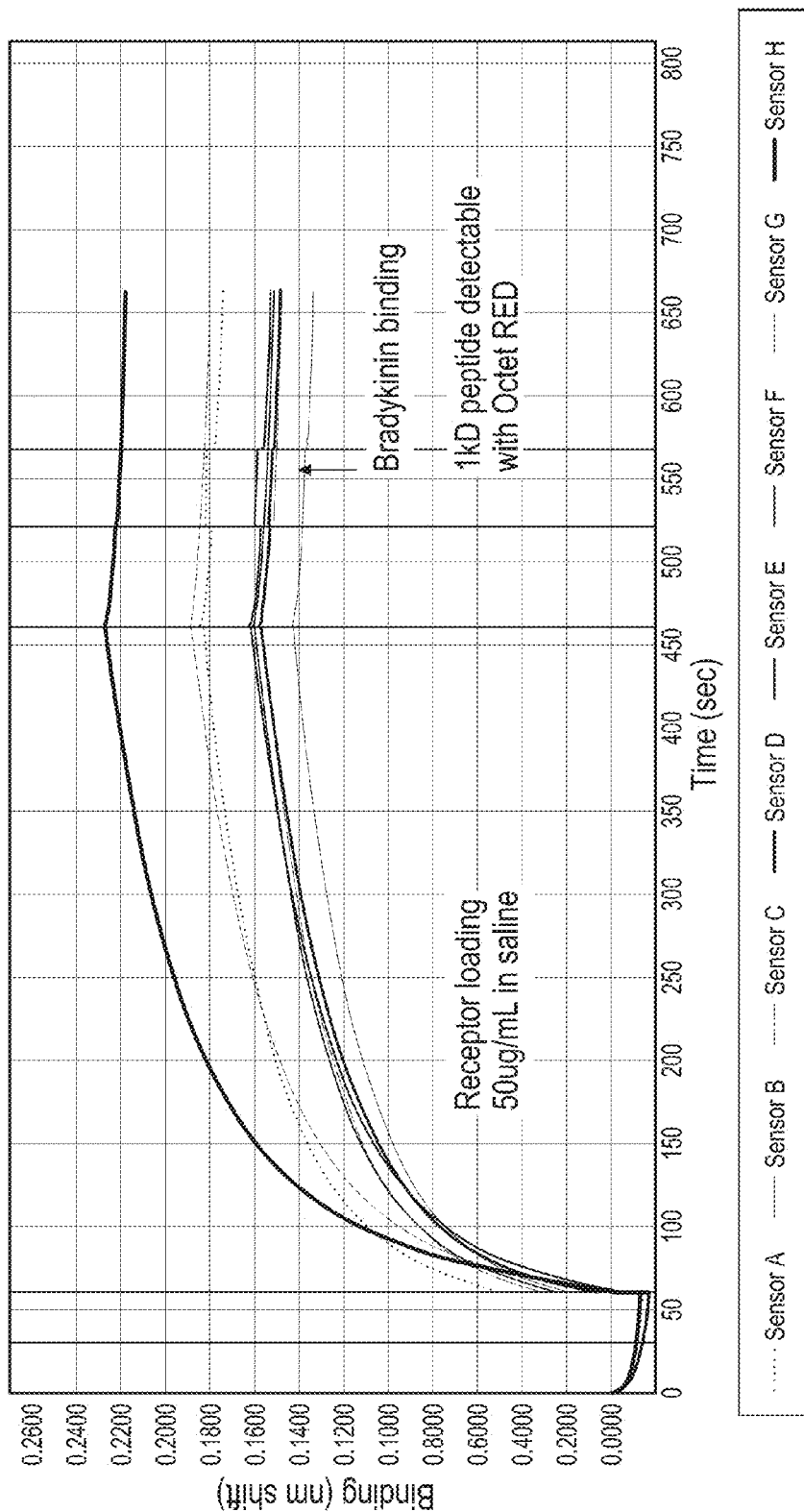
Figure 71:
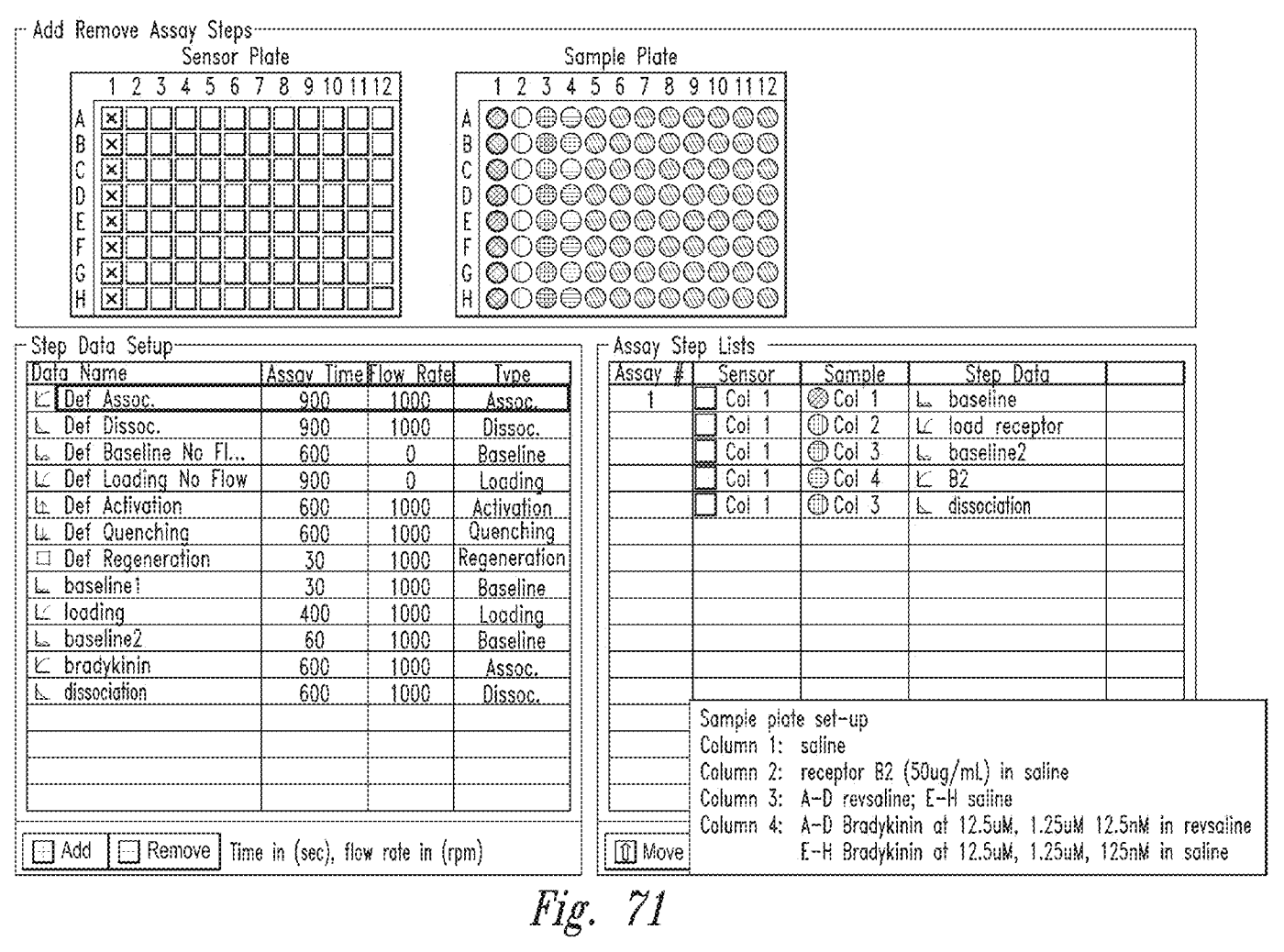
Figure 72:
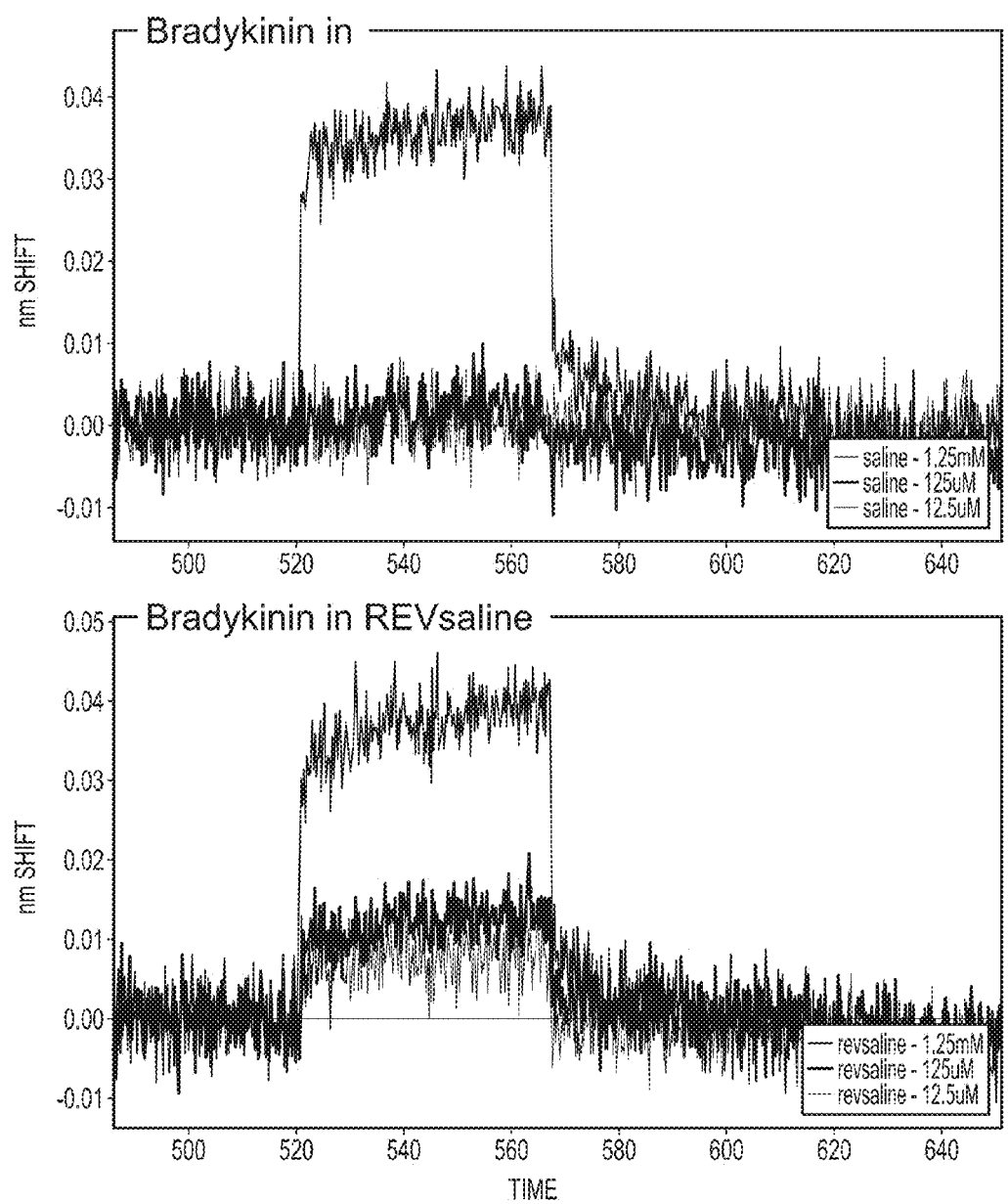
Figure 73:
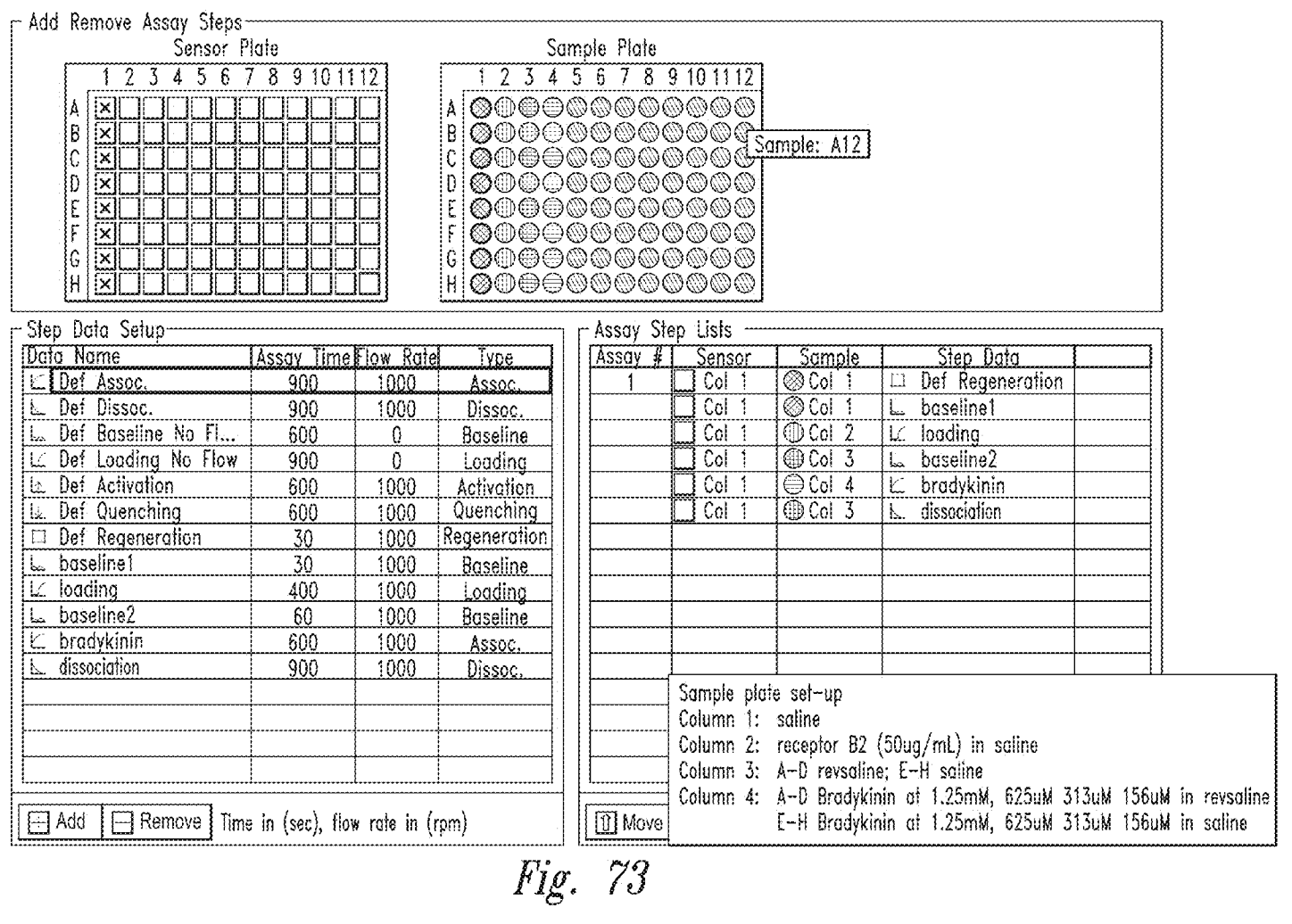

As shown in FIG. 69 the Bradykinin B2 membrane receptor was immobilized onto aminopropylsilane (APS) biosensor. The sample plate set up was designated in FIG. 69 and analyzed in FIG. 70. Next, the binding of Bradykinin to the immobilized receptor was assessed according to the sample set up as designated in FIG. 71. Results of Bradykinin binding are shown in FIG. 72. Bradykinin binding to the receptor was further titrated according to the set-up as designated in FIG. 73.

Figure 74:
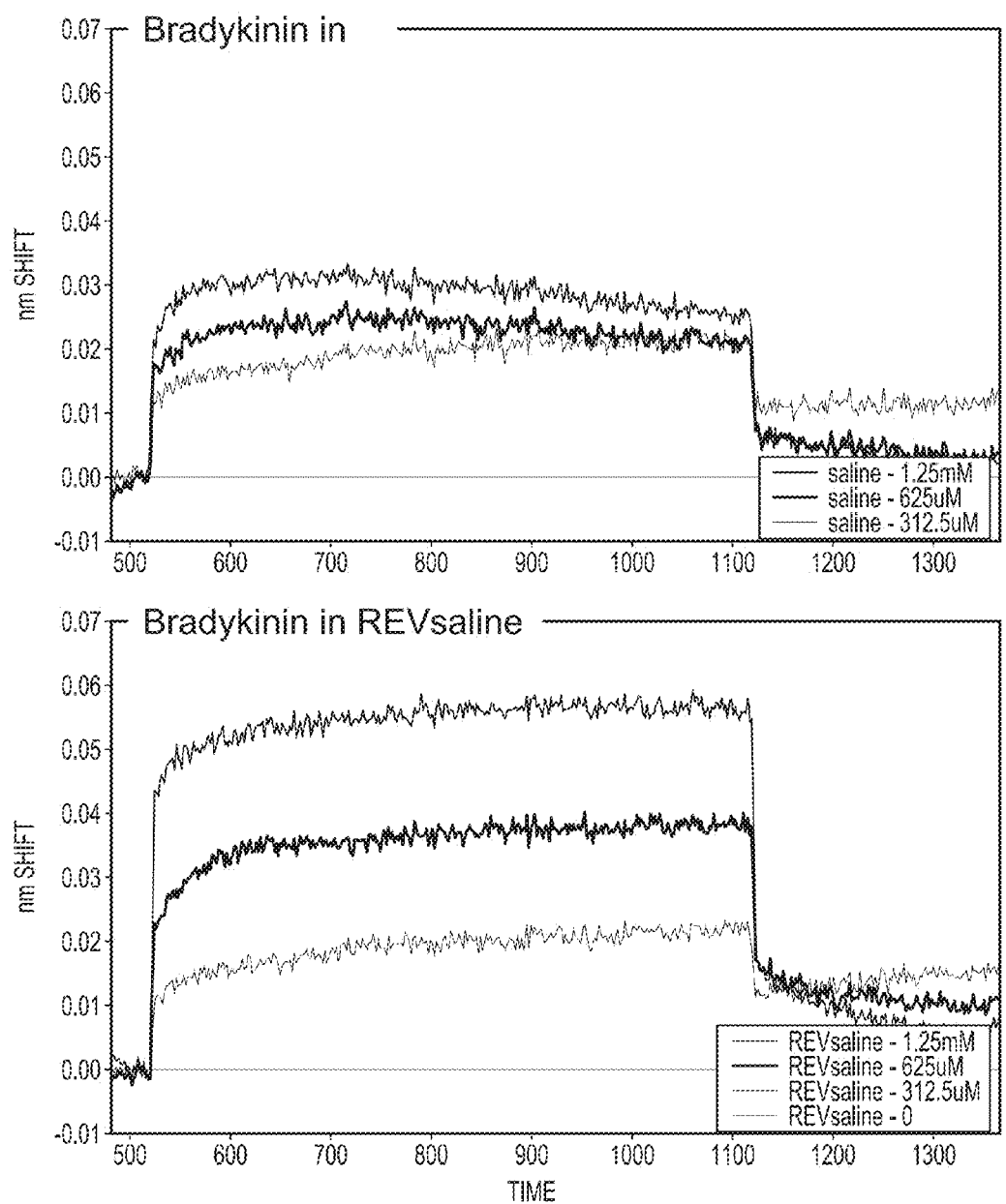
Figure 75:
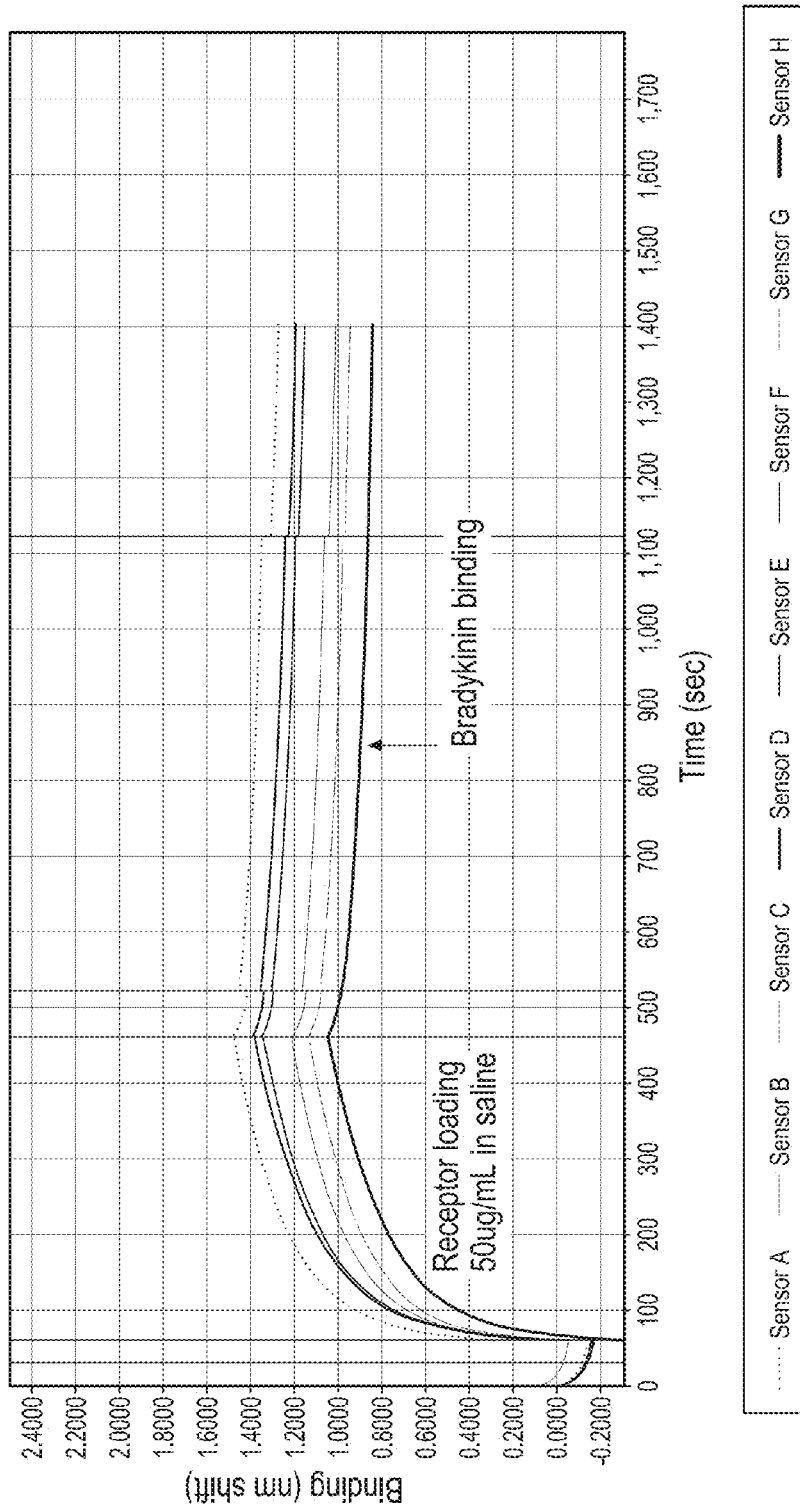

As indicated in FIG. 74, Bradykinin binding to the B2 receptor was concentration dependent, and binding affinity was increased in the proprietary gas-enriched saline fluid of the instant disclosure compared to normal saline. Stabilization of Bradykinin binding to the B2 receptor is shown in FIG. 75.

Example 15

A Regulatory T-Cell Assay was Used to Show Effects of the Inventive Electrokinetically Generated Fluids in Modulation of T-Cell Proliferation and Elaboration of Cytokines (11-10) and Other Proteins (e.g., GITR, Granzyme A, XCL1, pStat5, and Foxp3)) in Regulatory T-Cell Assays, and of, for Example, Tryptase in PBMC The ability of particular embodiments disclosed herein to regulate T cells was studied by irradiating antigen presenting cells, and introducing antigen and T cells. Typically, these stimulated T cells proliferate. However, upon the introduction of regulatory T cells, the usual T cell proliferation is suppressed.

Methods:

Briefly, FITC-conjugated anti-CD25 (ACT-1) antibody used in sorting was purchased from DakoCytomation (Chicago, Ill.). The other antibodies used were as follows: CD3 (HIT3a for soluble conditions), GITR (PE conjugated), CD4 (Cy-5 and FITC-conjugated), CD25 (APC-conjugated), CD28 (CD28.2 clone), CD127-APC, Granzyme A (PE-conjugated), FoxP3 (BioLegend), Mouse IgG1 (isotype control), and XCL1 antibodies. All antibodies were used according to manufacturer's instructions.

CD4+ T cells were isolated from peripheral whole blood with CD4+Rosette Kit (Stemcell Technologies). CD4+ T cells were incubated with anti-CD127-APC, anti-CD25-PE and anti-CD4-FITC antibodies. Cells were sorted by flow cytometry using a FACS Aria into CD4+CD25hiCD127lo/nTreg and CD4+CD25-responder T cells.

Suppression assays were performed in round-bottom 96 well microtiter plates. $3.75 \times 10^3$ CD4+CD25neg responder T cells, $3.75 \times 10^3$ autologous T reg, $3.75 \times 10^4$ allogeneic irradiated CD3-depleted PBMC were added as indicated. All wells were supplemented with anti-CD3 (clone HIT3a at 5.0 ug/ml). T cells were cultured for 7 days at 37° C. in RPMI 1640 medium supplemented with 10% fetal bovine serum. Sixteen hours before the end of the incubation, 1.0 mCi of $^3$H-thymidine was added to each well. Plates were harvested using a Tomtec cell harvester and $^3$H-thymidine incorporation determined using a Perkin Elmer scintillation counter. Antigen-presenting cells (APC) consisted of peripheral blood mononuclear cells (PBMC) depleted of T cells using StemSep human CD3+ T cell depletion (StemCell Technologies) followed by 40 Gy of irradiation.

Regulatory T cells were stimulated with anti-CD3 and anti-CD28 conditions and then stained with Live/Dead Red viability dye (Invitrogen), and surface markers CD4, CD25, and CD127. Cells were fixed in the Lyze/Fix PhosFlow™ buffer and permeabilized in denaturing Permbuffer III®. Cells were then stained with antibodies against each particular selected molecule.

Statistical analysis was performed using the GraphPad Prism software. Comparisons between two groups were made by using the two-tailed, unpaired Student's t-test. Comparisons between three groups were made by using 1-way ANOVA. P values less than 0.05 were considered significant (two-tailed). Correlation between two groups were determined to be statistically significant via the Spearman coefficient if the r value was greater than 0.7 or less than −0.7 (two-tailed).

Figure 76:
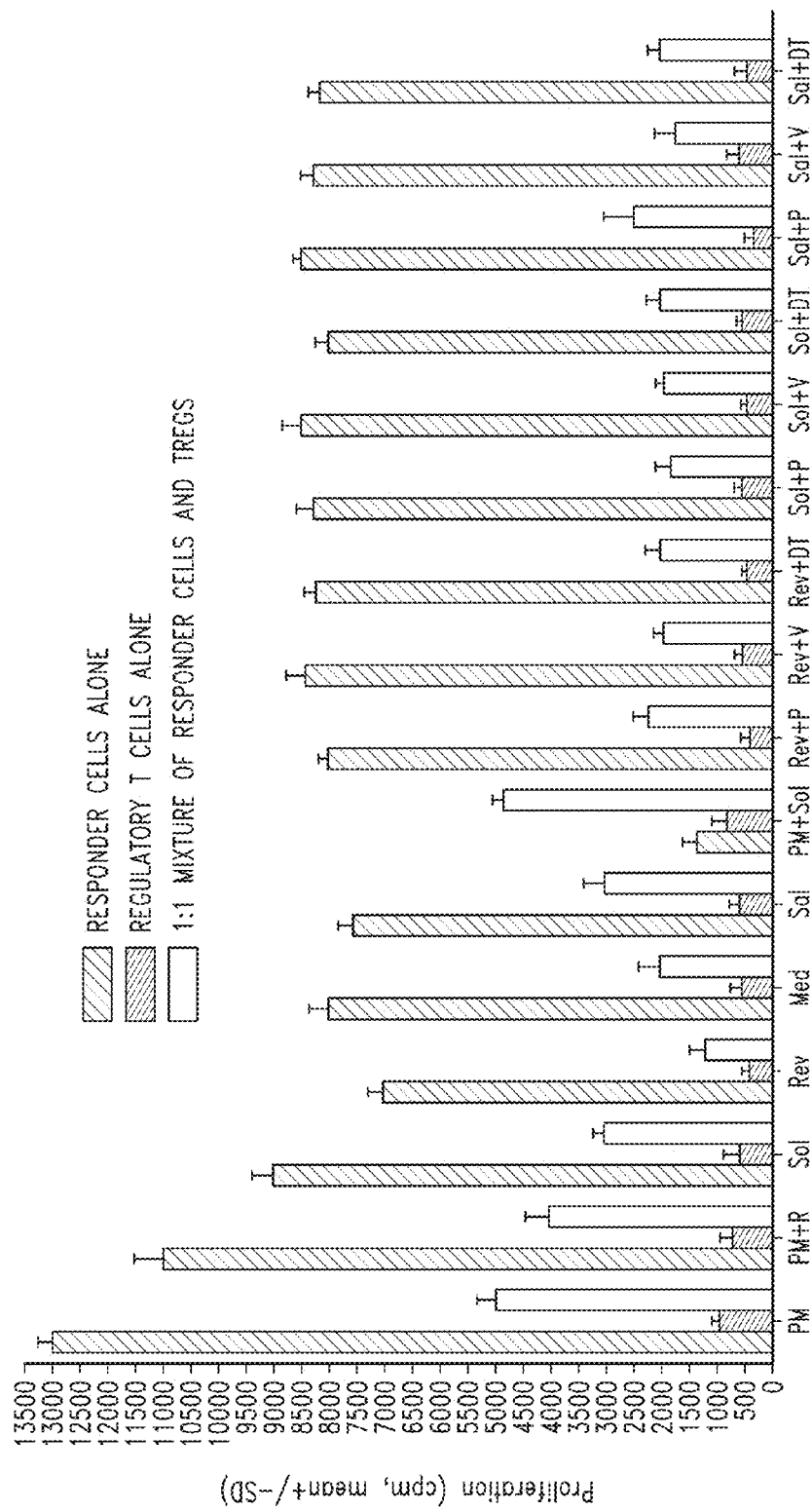
FIGS. 76-83 show data showing the ability of particular embodiments disclosed herein to affect regulatory T cells. The study involved irradiating antigen presenting cells, and introducing antigen and T cells.

Results:

As indicated in FIG. 76, regulatory T cell proliferation was studied by stimulating cells with diesel exhaust particulate matter (PM, from EPA). The x-axis of FIG. 76 shows activated autologous CD4+ effector T cells (responder cells) as a solid black bar, and regulatory T cells alone in the gray bar (shown for confirmation of anergy) which were mixed at a 1:1 ratio as shown in the white bar. The y axis shows proliferation as measured by uptake of $^3$H-thymidine. As shown from left to right along the x-axis, "PM" indicates diesel exhaust derived Particulate Matter, "PM+Rev" indicates PM plus a gas-enriched electrokinetically generated fluid (Rev) of the instant disclosure, "Solis" indicates an electrokinetically generated fluid of the instant disclosure and device that is not gas-enriched beyond ambient atmosphere, only (no PM added), "Rev" indicates Rev alone (no PM added) as defined above, "Media" indicates the cell growth media alone control (minus PM; no Rev, no Solis), and "Saline Con" indicates the saline control (minus PM; no Rev, no Solis), "V" indicates verapamil, and "P" indicates propanolol, and "DT" is DT390 at 1:50.

Figure 77:
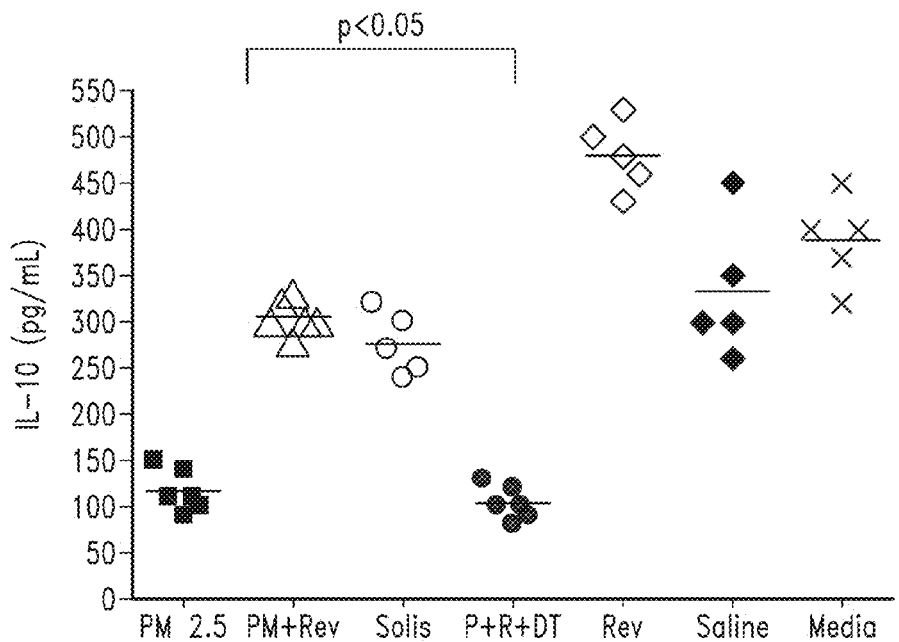
Figure 78:
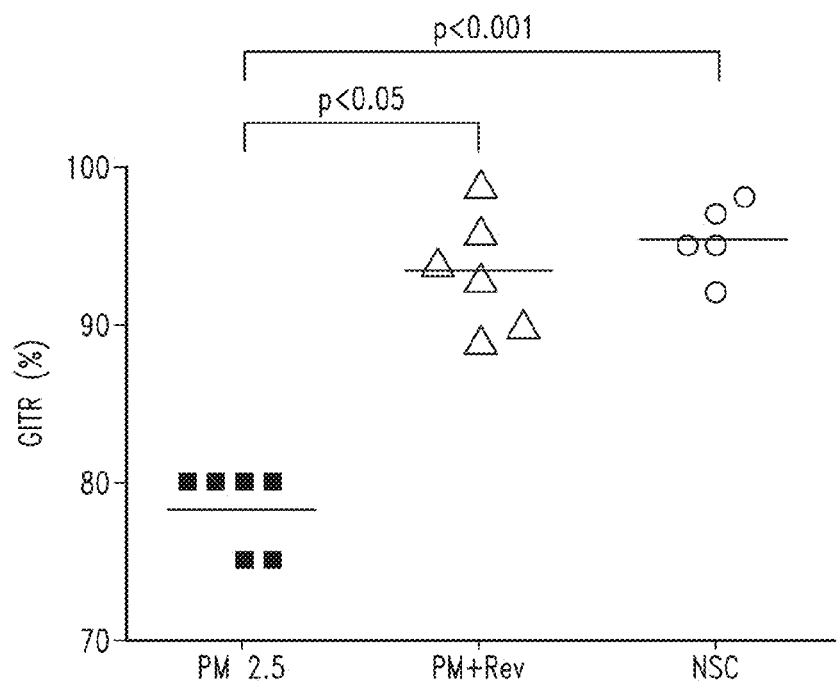
Figure 79:
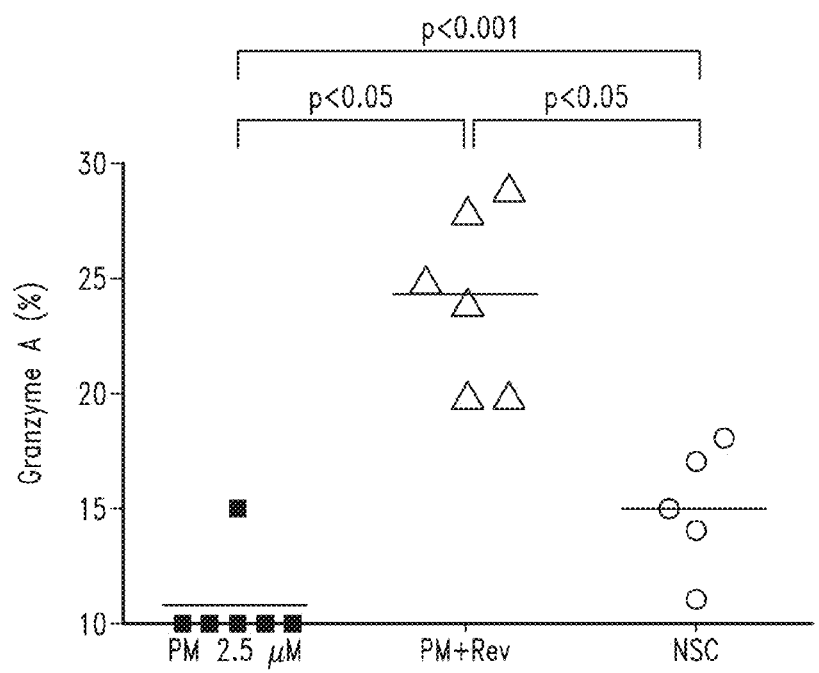
Figure 80:
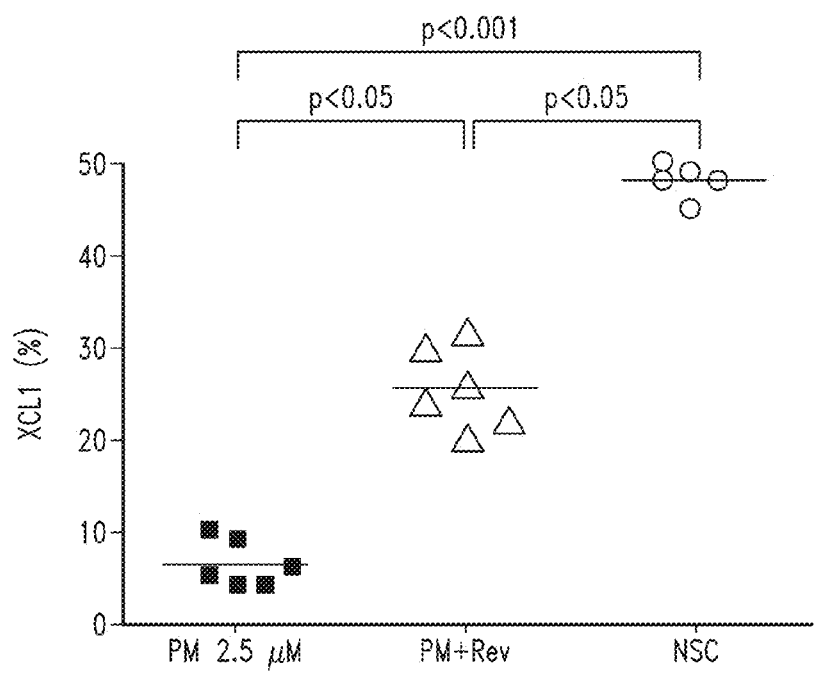
Figure 81:
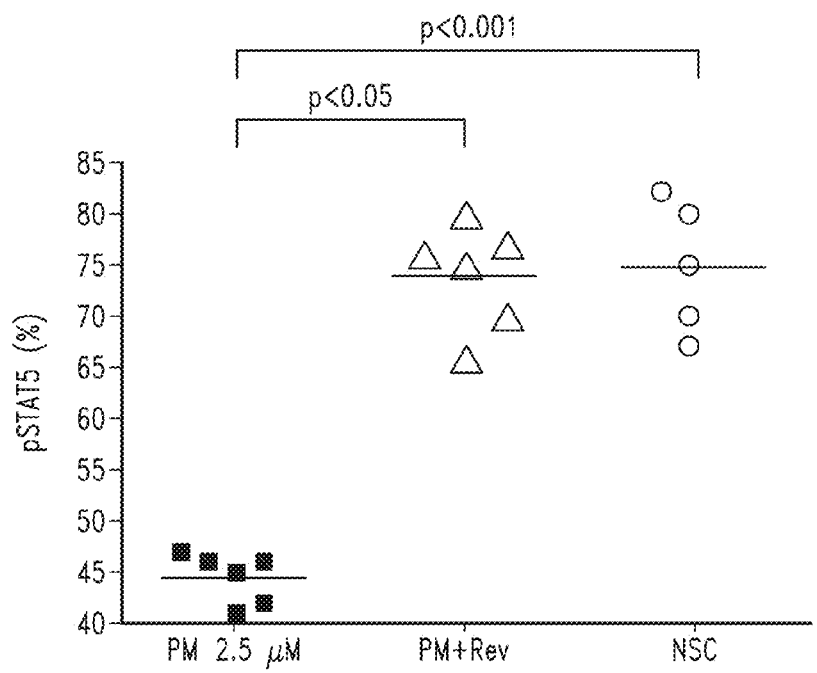
Figure 82:
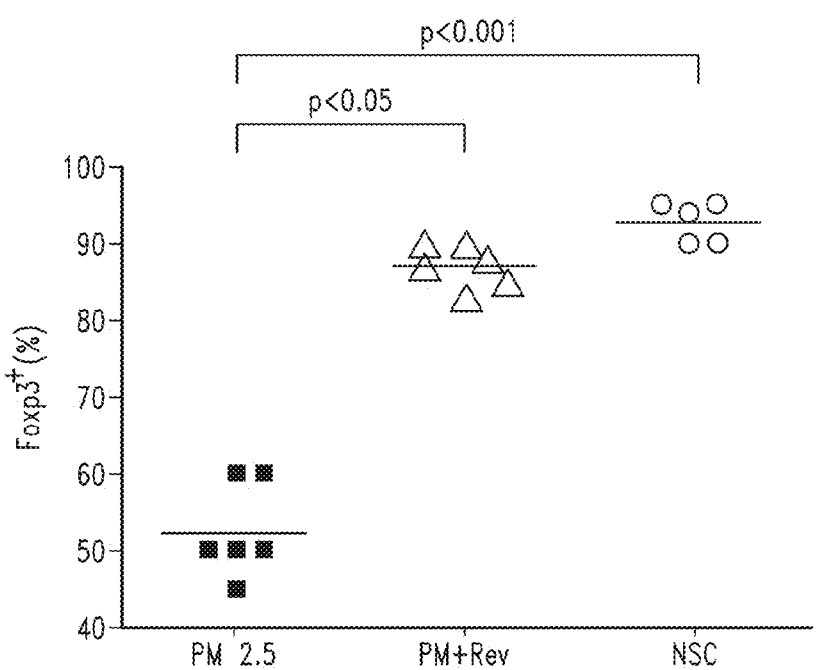

As shown in FIG. 77, cells stimulated with PM (no Rev, no Solis) resulted in a decrease in secreted IL-10, while cells exposed to PM in the presence of the fluids of the instant disclosure ("PM+Rev") resulted in a maintained or only slightly decreased production of IL-10 relative to the Saline and Media controls (no PM). Furthermore, *Diphtheria* toxin (DT390, a truncated *diphtheria* toxin molecule; 1:50 dilution of std. commercial concentration) was titrated into inventive fluid samples, and blocked the Rev-mediated effect of increase in IL-10 in FIG. 77. Note that treatment with Rev alone resulted in higher IL-10 levels relative to Saline and Media controls.

Likewise, similar results, shown in FIGS. 78-82, were obtained with GITR, Granzyme A, XCL1, pStat5, and Foxp3, respectively. In Figures, "NSC" is the same as "Solis" (no PM).

Figure 83:
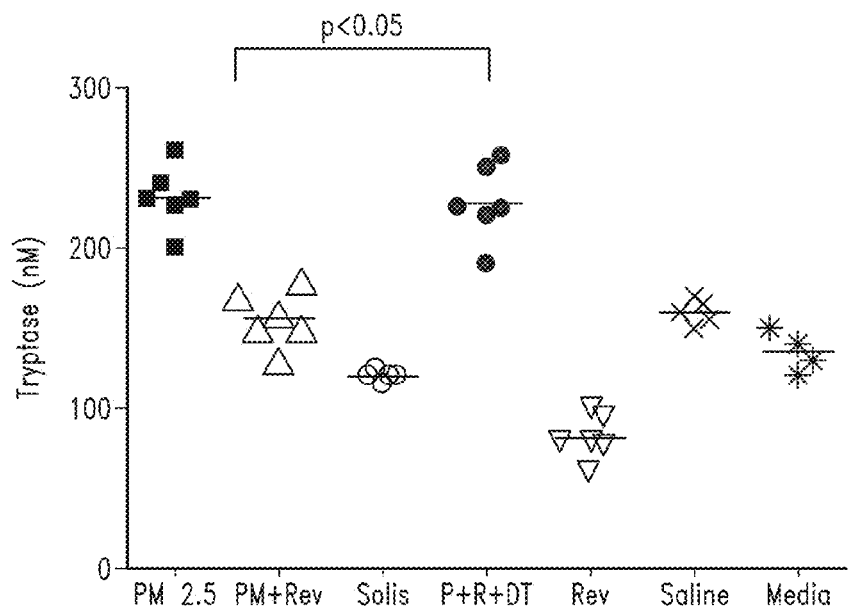
Figure 84:
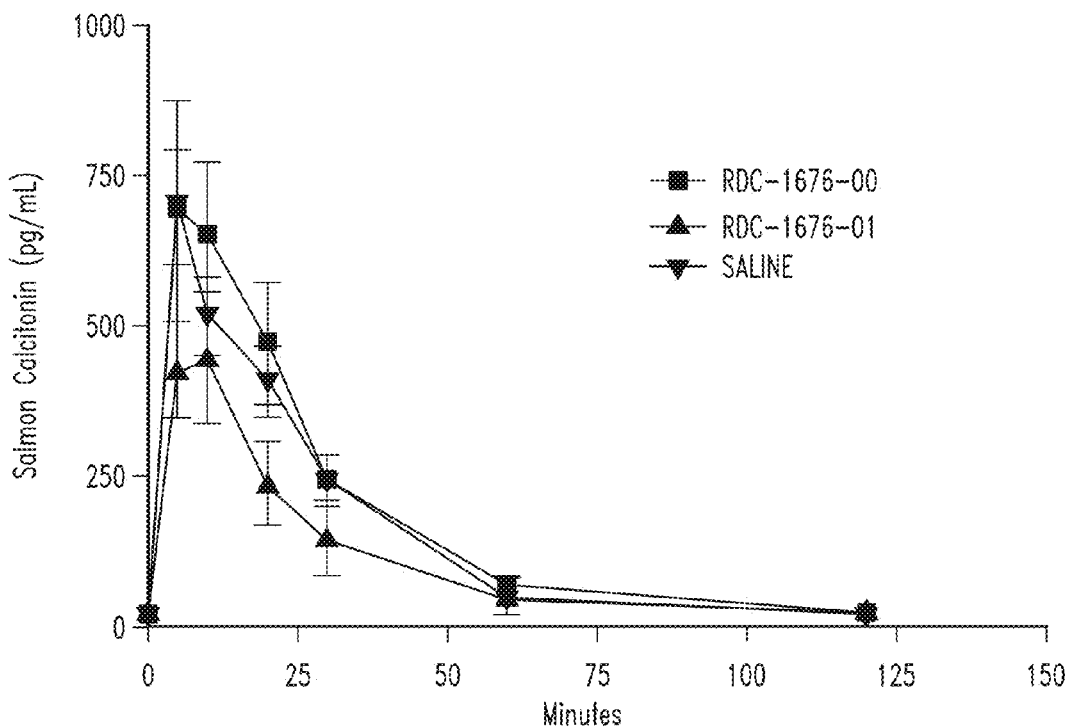
FIG. 84 shows that the inventive electrokinetically generated fluids decreased serum uptake of salmon calcitonin and an animal model. The results are consistent with enhancement of tight junctions.
Figure 85:
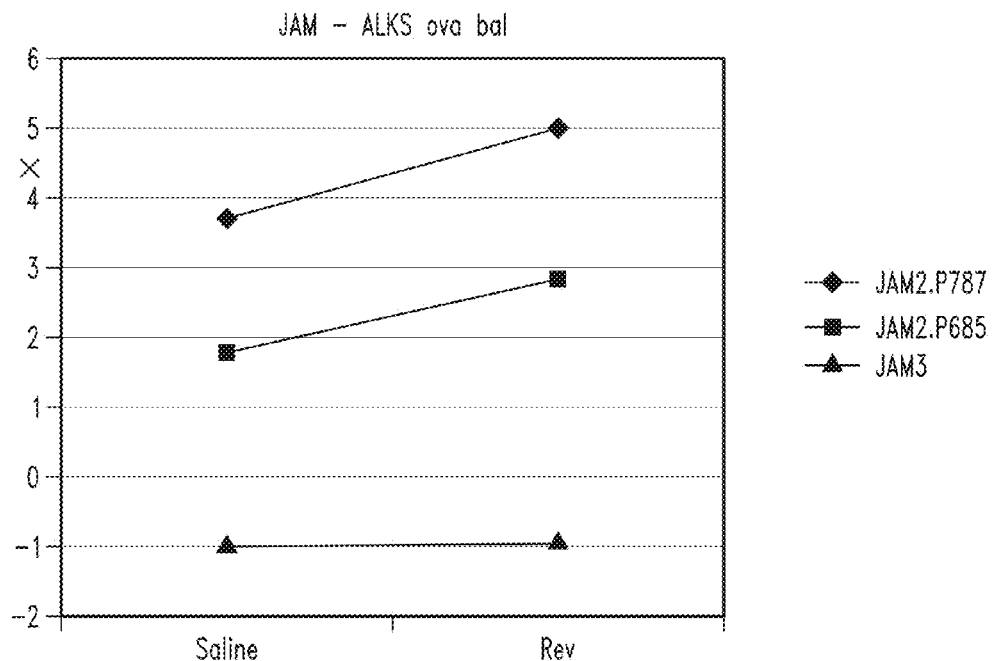
FIGS. 85-89 show the expression levels of tight junction-related proteins in lung tissue from the animal model used to generate the data of FIG. 84.
Figure 86:
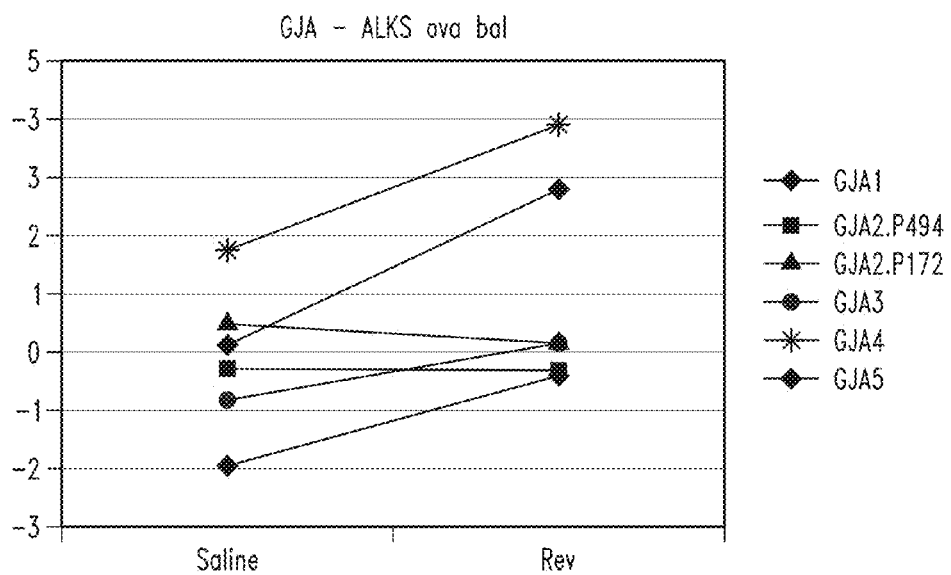
Figure 87:
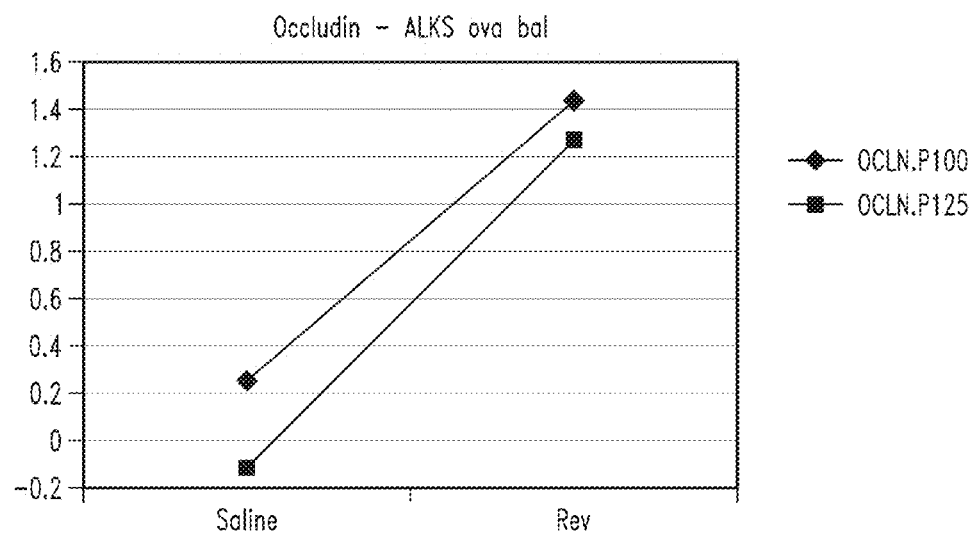
Figure 88:
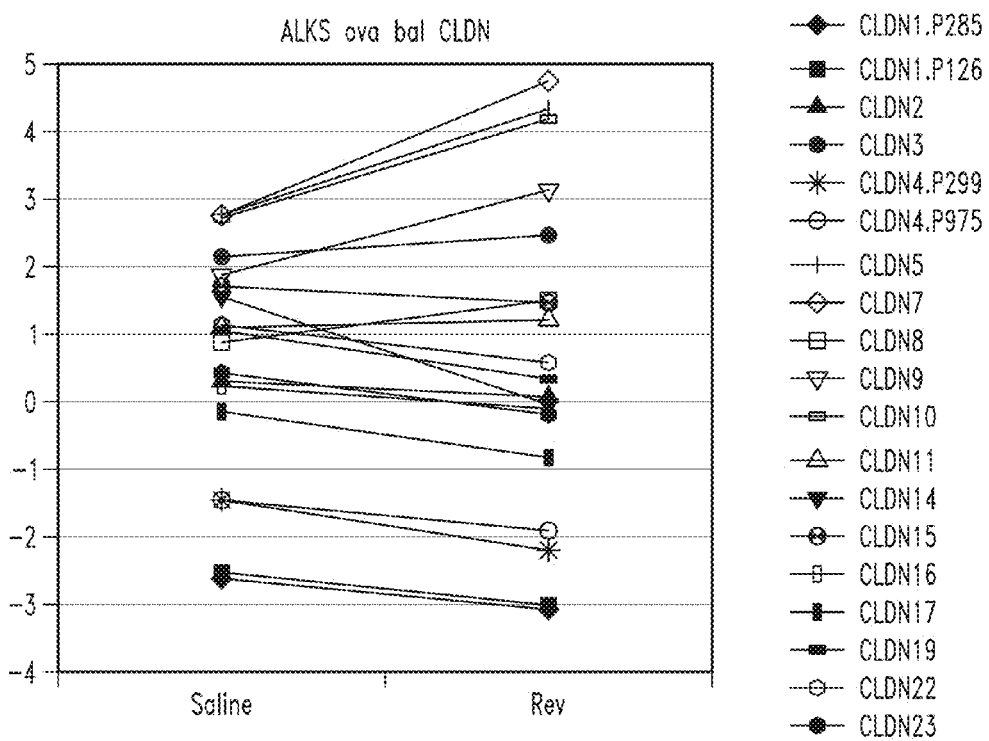
Figure 89:
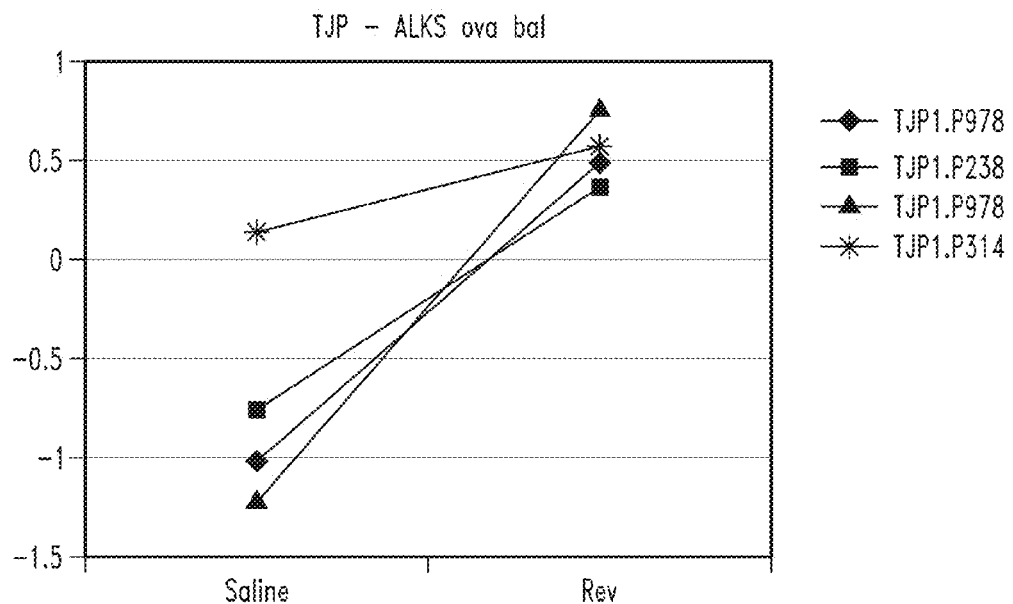
Figure 90:
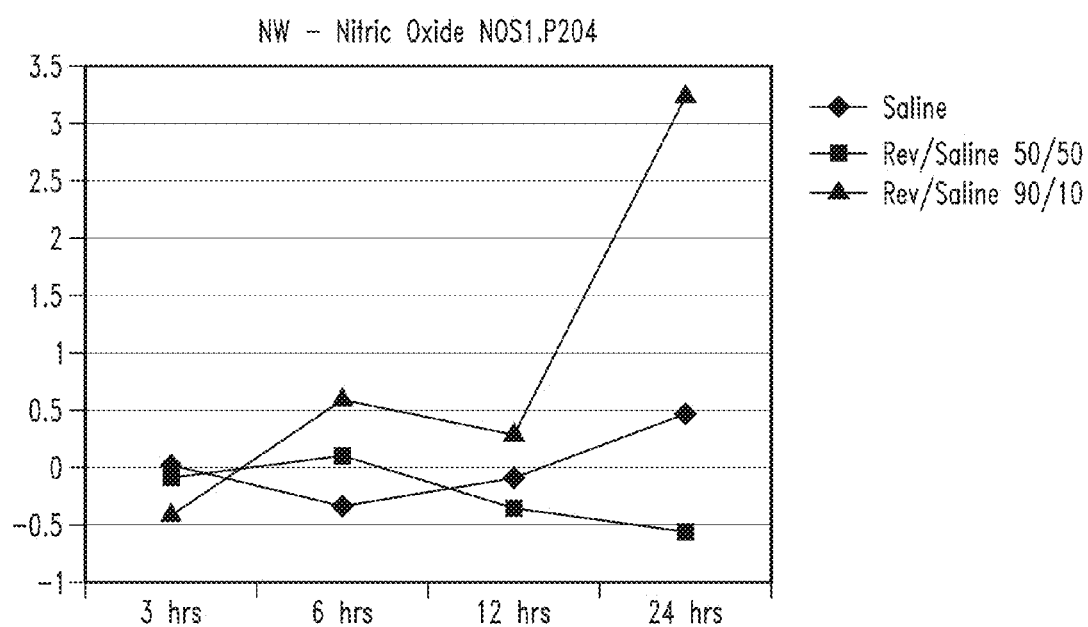
FIGS. 90-94 show data obtained from human foreskin keratinocytes exposed to RDC1676-01 (sterile saline processed through the instant proprietary device with additional oxygen added; gas-enriched electrokinetically generated fluid (Rev) of the instant disclosure) showing up-regulation of NOS1 and 3, and Nostrin, NOS3.
Figure 91:
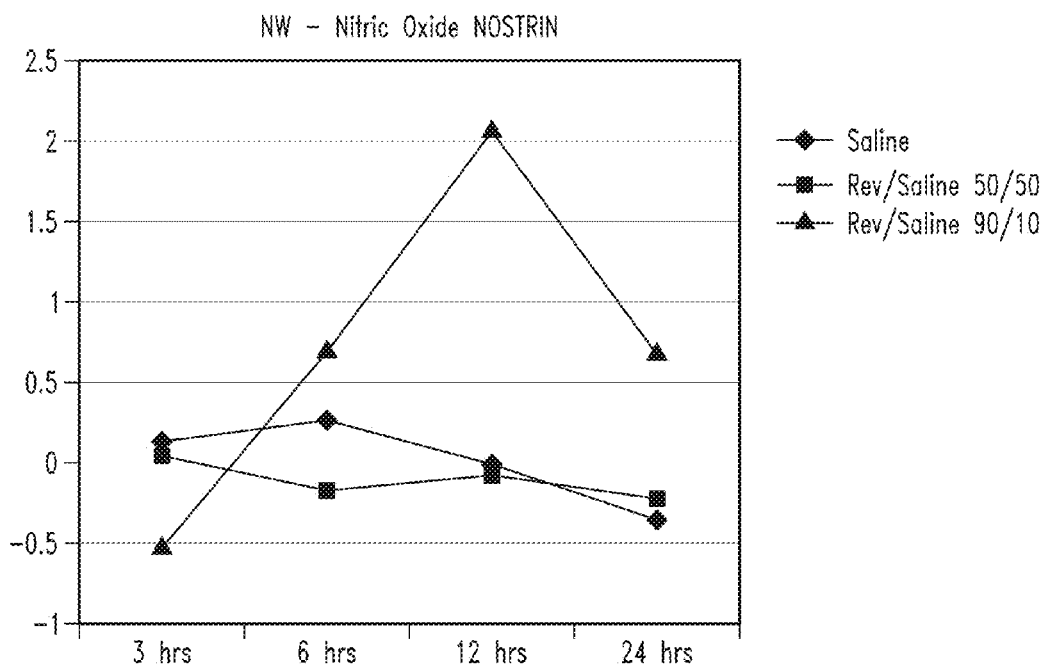
Figure 92:
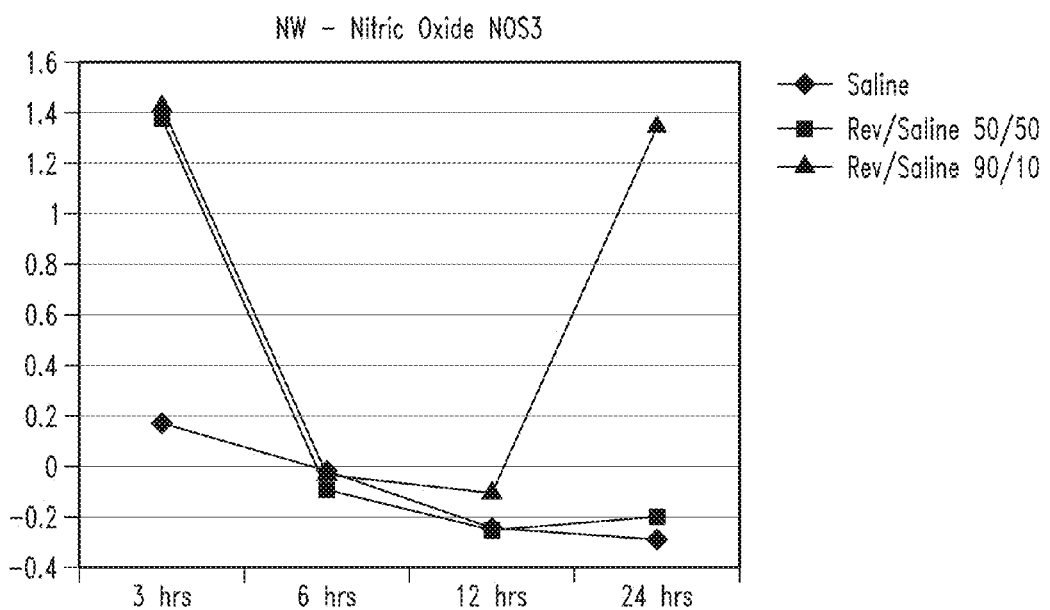

FIG. 83 shows AA PBMC data, obtained from an allergic asthma (AA) profile of peripheral blood mononuclear cells (PBMC) evaluating tryptase. The AA PBMC data was consistent with the above T-regulatory cell data, as cells stimulated with particulate matter (PM) showed high levels of tryptase, while cells treated with PM in the presence of the fluids of the instant disclosure ("PM+Rev") resulted in significantly lower tryptase levels similar to those of the Saline and Media controls. Consistent with the data from T-regulatory cells, exposure to DT390 blocked the Rev-mediated effect on tryptase levels, resulting in an elevated level of tryptase in the cells as was seen for PM alone (minus Rev, no Rev, no Solis). Note that treatment with Rev alone resulted in lower tryptase levels relative to Saline and Media controls.

In summary, the data of FIG. 76, showing a decreased proliferation in the presence of PM and Rev relative to PM in control fluid (no Rev, no Solis), indicates that the inventive electrokinetically generated fluid Rev improved regulatory T-cell function as shown by relatively decreased proliferation in the assay. Moreover, the evidence of this Example and FIGS. 76-83, indicate that beta blockade, GPCR blockade and Ca channel blockade affects the activity of Revera on Treg function.

Example 16

Treatment of Primary Bronchial Epithelial Cells (BEC) with the Inventive Electrokinetically Generated Fluids Resulted in Reduced Expression and/or Activity of Two Key Proteins of the Airway Inflammatory Pathways, MMP9 and TSLP Overview.

As shown in Example 14 above (e.g., FIG. 75, showing Stabilization of Bradykinin binding to the B2 receptor using Bio-Layer Interferometry biosensor, Octet Rapid Extended Detection (RED) (forteBio™)), Bradykinin binding to the B2 receptor was concentration dependent, and binding affinity was increased in the electrokinetically generated fluid (e.g., Rev; gas-enriched electrokinetically generated fluid) of the instant disclosure compared to normal saline. Additionally, as shown in Example 15 in the context of T-regulatory cells stimulated with diesel exhaust particulate matter (PM, standard commercial source), the data showed a decreased proliferation of T-regulatory cells in the presence of PM and Rev relative to PM in control fluid (no Rev, no Solis) (FIG. 76), indicating that the inventive electrokinetically generated fluid Rev improved regulatory T-cell function; e.g., as shown by relatively decreased proliferation in the assay. Moreover, exposure to the inventive fluids resulted in a maintained or only slightly decreased production of IL-10 relative to the Saline and Media controls (no PM). Likewise, in the context of the allergic asthma (AA) profiles of peripheral blood mononuclear cells (PBMC) stimulated with particulate matter (PM), the data showed that exposure to the fluids of the instant disclosure ("PM+Rev") resulted in significantly lower tryptase levels similar to those of the Saline and Media controls. Additionally, the *Diphtheria* toxin (DT390, a truncated *diphtheria* toxin molecule; 1:50 dilution of std. commercial concentration) effects shown in Example 15 and FIGS. 76-83, indicate that beta blockade, GPCR blockade and Ca channel blockade affects the activity of the electrokinetically generated fluids on Treg and PBMC function. Furthermore, the data of Example 18 shows that, according to additional aspects, upon exposure to the inventive fluids, tight junction related proteins were upregulated in lung tissue. FIGS. 85-89 show upregulation of the junction adhesion molecules JAM 2 and 3, GJA1, 3, 4 and 5 (junctional adherins), OCLN (occludin), claudins (e.g., CLDN 3, 5, 7, 8, 9, 10), TJP1 (tight junction protein 1), respectively. Furthermore, as shown in the patch clamp studies of Example 23, the inventive electrokinetically generated fluids (e.g., RNS-60) affect modulation of whole cell conductance (e.g., under hyperpolarizing conditions) in Bronchial Epithelial Cells (BEC; e.g., Calu-3), and according to additional aspects, modulation of whole cell conductance reflects modulation of ion channels.

In this Example, Applicants have extended these discoveries by conducting additional experiments to measure the effects of production of two key proteins of the airway inflammatory pathways. Specifically, MMP9 and TSLP were assayed in primary bronchial epithelial cells (BEC).

Materials and Methods:

Commercially available primary human bronchial epithelial cells (BEC) (HBEpC-c from Promocell, Germany) were used for these studies. Approximately 50,000 cells were plated in each well of a 12 well plate until they reached ~80% confluence. The cells were then treated for 6 hours with normal saline, control fluid Solas or the test fluid Revera 60 at a 1:10 dilution (100 ul in 1 ml of airway epithelial growth medium) along with the diesel exhaust particulate matter (DEP or PM) before being lifted for FACS analysis, as described in Example 8 herein. Both MMP9 and TSLP receptor antibodies were obtained from BD Biosciences and used as per manufacturer's specifications.

Figure 115:
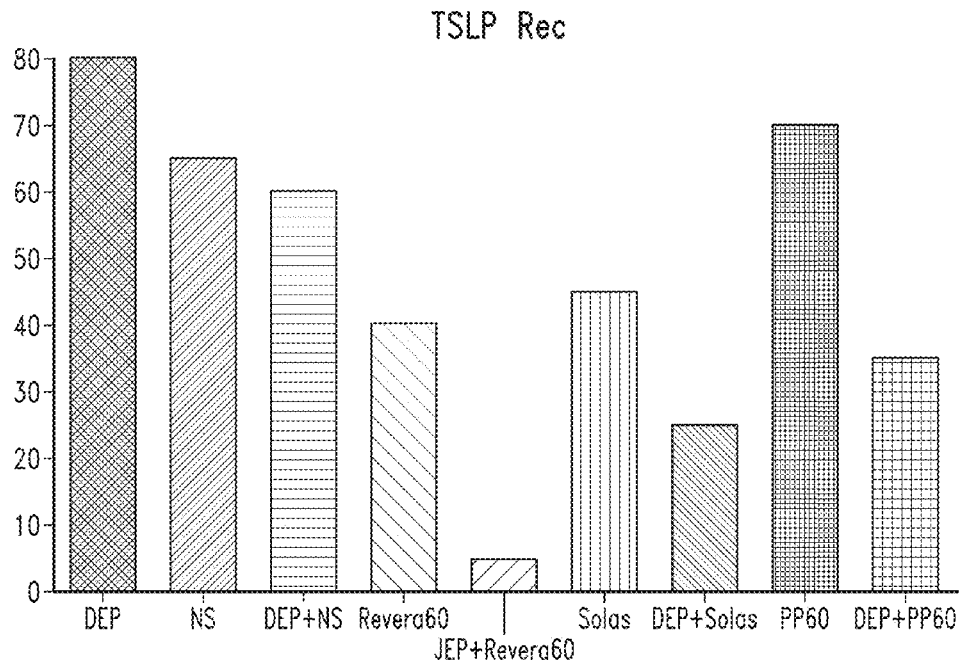
FIG. 115 shows that the inventive electrokinetically generated fluid (e.g., Revera 60 and Solas) reduced DEP-induced TSLP receptor expression in bronchial epithelial cells (BEC) by approximately 90% and 50%, respectively, whereas normal saline (NS) had only a marginal effect.
Figure 116:
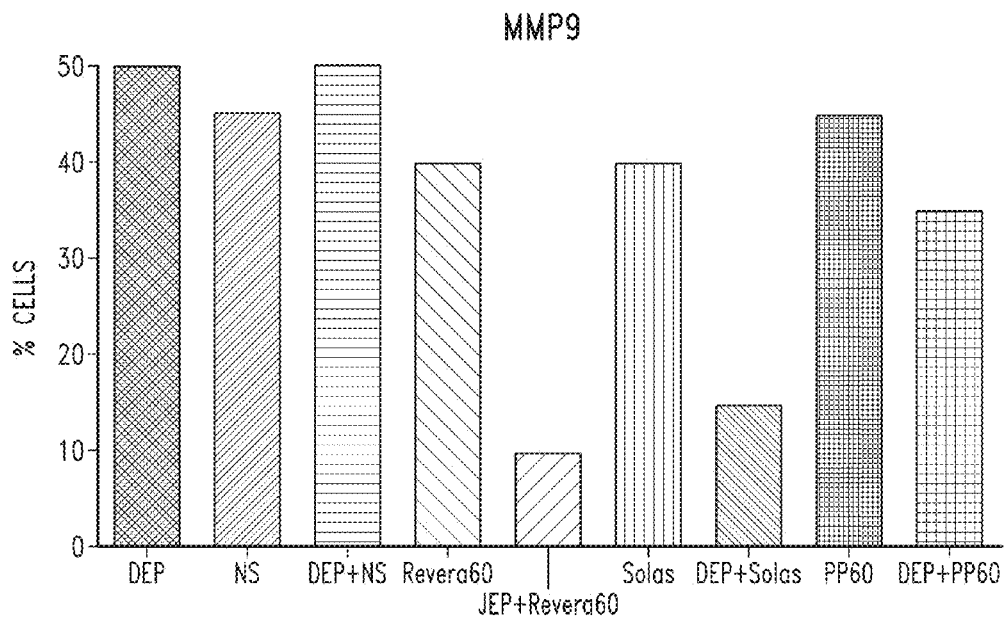
FIG. 116 shows the inventive electrokinetically generated fluid (e.g., Revera 60 and Solas) inhibited the DEP-induced cell surface bound MMP9 levels in bronchial epithelial cells by approximately 80%, and 70%, respectively, whereas normal saline (NS) had only a marginal effect.

Results:

In FIGS. 115 and 116, DEP represents cells exposed to diesel exhaust particulate matter (PM, standard commercial source) alone, "NS" represents cells exposed to normal saline alone, "DEP+NS" represent cells treated with particulate matter in the presence of normal saline, "Revera 60" refers to cells exposed only to the test material, "DEP+Revera 60" refer to cells treated with particulate matter in the presence of the test material Revera 60. In addition, "Solas" and "DEP+Solas" represents cells exposed to the control fluid Solas alone or in combination with the particulate matter, respectively.

FIG. 115 shows that the test material Revera 60 reduces DEP induced TSLP receptor expression in bronchial epithelial cells (BEC) by approximately 90%. Solas resulted in a 55% reduction in TSLP receptor expression, while Normal saline failed to produce similar level of reduction in TSLP receptor expression (approximately 20% reduction). The effect of the inventive solution in reducing TSLP receptor expression is a significant discovery in view of recent findings showing that TSLP plays a pivotal role in the pathobiology of allergic asthma and local antibody mediated blockade of TSLP receptor function alleviated allergic disease (Liu, Y J, Thymic stromal lymphopoietin: Master switch for allergic inflammation, *J Exp Med* 203:269-273, 2006; Al-Shami et al., A role for TSLP in the development of inflammation in an asthma model, *J Exp Med* 202:829-839, 2005; and Shi et al., Local blockade of TSLP receptor alleviated allergic disease by regulating airway dendritic cells, *Clin Immunol.* 2008, Aug. 29. (Epub ahead of print)).

Likewise, FIG. 116 shows the effect of Revera 60, Solas and normal saline on the DEP-mediated increase in MMP 9. Specifically, Revera 60 inhibited the DEP-induced cell surface bound MMP9 levels in bronchial epithelial cells by approximately 80%, and Solas had an inhibitory effect of approximately 70%, whereas normal saline (NS) had a marginal effect of about 20% reduction. MMP-9 is one of the major proteinases involved in airway inflammation and bronchial remodeling in asthma. Recently, it has been demonstrated that the levels of MMP-9 are significantly increased in patients with stable asthma and even higher in acute asthmatic patients compared with healthy control subjects. MMP-9 plays a crucial role in the infiltration of airway inflammatory cells and the induction of airway hyperresponsiveness indicating that MMP-9 may have an important role in inducing and maintaining asthma (Vignola et al., Sputum metalloproteinase-9/tissue inhibitor of metalloproteinase-1 ratio correlates with airflow obstruction in asthma and chronic bronchitis, *Am J Respir Crit Care Med* 158:1945-1950, 1998; Hoshino et al., Inhaled corticosteroids decrease subepithelial collagen deposition by modulation of the balance between matrix metalloproteinase-9 and tissue inhibitor of metalloproteinase-1 expression in asthma, *J Allergy Clin Immunol* 104:356-363, 1999; Simpson et al., Differential proteolytic enzyme activity in eosinophilic and neutrophilic asthma, *Am J Respir Crit Care Med* 172:559-565, 2005; Lee et al., A murine model of toluene diisocyanate-induced asthma can be treated with matrix metalloproteinase inhibitor, *J Allergy Clin Immunol* 108:1021-1026, 2001; and Lee et al., Matrix metalloproteinase inhibitor regulates inflammatory cell migration by reducing ICAM-1 and VCAM-1 expression in a murine model of toluene diisocyanate-induced asthma, *J Allergy Clin Immunol* 2003; 111:1278-1284).

According to additional aspects, therefore, the inventive electrokinetically generated fluids have substantial therapeutic utility for modulating (e.g., reducing) TSLP receptor expression and/or for inhibiting expression and/or activity of MMP-9, including, for example, for treatment of inflammation and asthma.

Example 17

The Inventive Electrokinetically Generated Fluids were Shown to have a Synergistic Anti-Inflammatory Effect with Budesonide in an Art-Recognized Animal Model for Allergic Asthma This working Example describes experiments performed to assess the airway anti-inflammatory properties of the inventive electrokinetically generated fluids (e.g., RDC-1676-03) in a Brown Norway rat ovalbumin sensitization model. The Brown Norway rat is an art-recognized model for determining the effects of a test material on airway function and this strain has been widely used, for example, as a model of allergic asthma. Airway pathology and biochemical changes induced by ovalbumin sensitization in this model resemble those observed in man (Elwood et al., *J Allergy Clin Immuno* 88:951-60, 1991; Sirois & Bissonnette, *Clin Exp Immunol* 126:9-15, 2001). The inhaled route was selected to maximize lung exposure to the test material or the control solution. The ovalbumin-sensitized animals were treated with budesonide alone or in combination with the test material RDC 1676-03 for 7 days prior to ovalbumin challenge. 6 and 24 hours following the challenge, total blood count and levels of several pro and anti-inflammatory cytokines as well as various respiratory parameters were measured to estimate any beneficial effect of administering the test material on various inflammatory parameters.

Materials and Methods:

Brown Norway rats of strain Bn/Crl were obtained from Charles River Kingston, weighing approximately 275±50 g at the onset of the experiment. All animal studies were conducted with the approval by PCS-MTL Institutional Animal Care and Use Committee. During the study, the use and care of animals were conducted according to guidelines of the USA National Research Council as well as Canadian Council of Animal Care.

Sensitization.

On day 1 of the experiment, animals (14 animals in each treatment group) were sensitized by administration of a 1 ml intraperitoneal injection of a freshly prepared solution of 2 mg ovalbumin/100 mg Aluminum Hydroxide per 1 ml of 0.9% Sodium Chloride, followed by repeat injection on day 3.

Treatment.

Fifteen days following the initial sensitization, animals were subjected to nebulized exposure to control (Normal saline) or test solutions (electrokinetically generated fluids RDC1676-00, RDC1676-02 and RDC-1676-03), either administered alone or in combination with Budesonide, once daily for 15 minutes for 7 consecutive days. Animals were dosed in a whole body chamber of approximately 20 L, and test atmosphere was generated into the chamber air inlet using aeroneb ultrasonic nebulizers supplied with air from a Buxco bias flow pump. The airflow rate was set at 10 liters/min.

Ovalbumin Challenge.

On day 21, 2 hours following treatment with the test solutions, all animals were challenged with 1% ovalbumin nebulized solution for 15 minutes (in a whole body chamber at airflow 2 L/min).

Sample Collection.

At time points of 6 and 24 hours after the ovalbumin challenge, blood samples were collected for total and differential blood cell counts as well as for measuring levels of various pro and anti-inflammatory cytokines. In addition, Immediately after and at 6 and 24 hours following ovalbumin challenge the enhanced pause Penh and tidal volume were measured for a period of 10 minutes using the Buxco Electronics BioSystem XA system.

Results:

Eosinophil Count: As expected, and shown in FIG. 109, treatment with Budesonide ("NS+Budesonide 750 µg/Kg"; densely crosshatched bar graph) reduced the total eosinophil count in the challenged animals relative to treatment with the normal saline "NS" alone control (open bar graph). Additionally, while treatment with the inventive fluid "RDC1676-03" alone (lightly crosshatched bar graph) did not significantly reduce the eosinophil count, it nonetheless displayed a substantial synergy with Budesonide in reducing the eosinophil count ("RDC1676-03+Budesonide 750 µg/Kg", solid dark bar graph). Similarly, in FIG. 110, the Eosinophil % also reflected a similar trend. While RDC1676-03 (lightly crosshatched graph bar) or Budesonide 750 ug/kg (densely crosshatched bar graph) alone did not have a significant effect on Eosinophil % count in the challenged animals, the two in combination reduced the Eosinophil significantly (solid dark bar graph).

Figure 109:
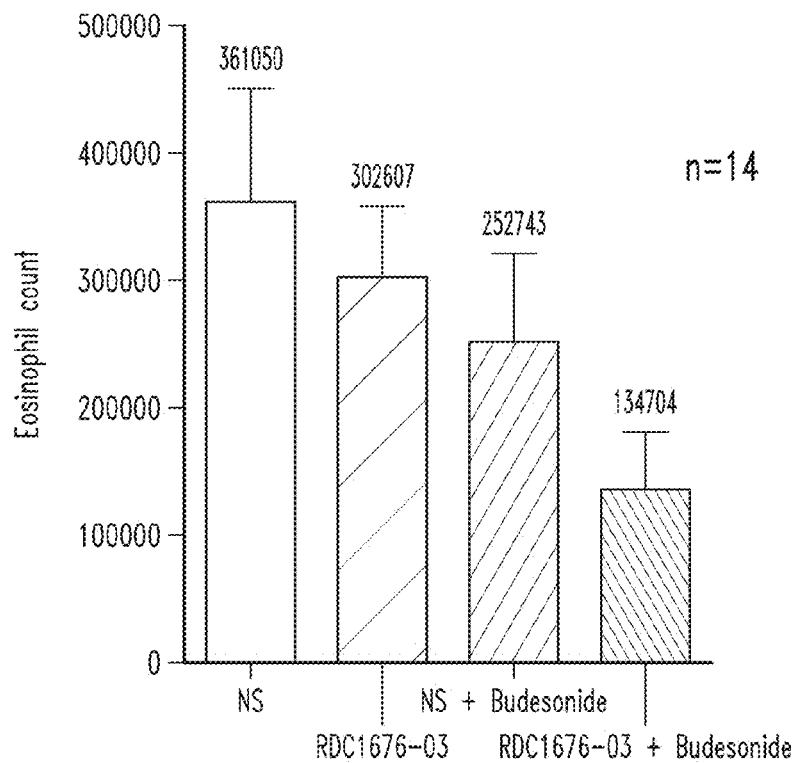
FIGS. 109-114 show results of budesonide experiments performed to assess the airway anti-inflammatory properties of the inventive electrokinetically generated fluids in a Brown Norway rat ovalbumin sensitization model. The inventive electrokinetically generated fluids decreased eosinophil count, showed strong synergy with Budesonide in decreasing eosinophil count, decreased Penh values, increased Tidal Volume, decreased blood levels of Eotaxin, significantly enhanced the Blood levels of two major key anti-inflammatory cytokines, IL10 and Interferron gamma at 6 hours after challenge as a result of treatment with the inventive electrokinetically generated fluid (e.g., Rev 60) alone or in combination with Budesonide, and decreased systemic levels of Rantes. The data show that there is a substantial synergistic effect of Budesonide 750 ug/kg and the inventive electrokinetically generated fluids (e.g., Rev 60).
Figure 110:
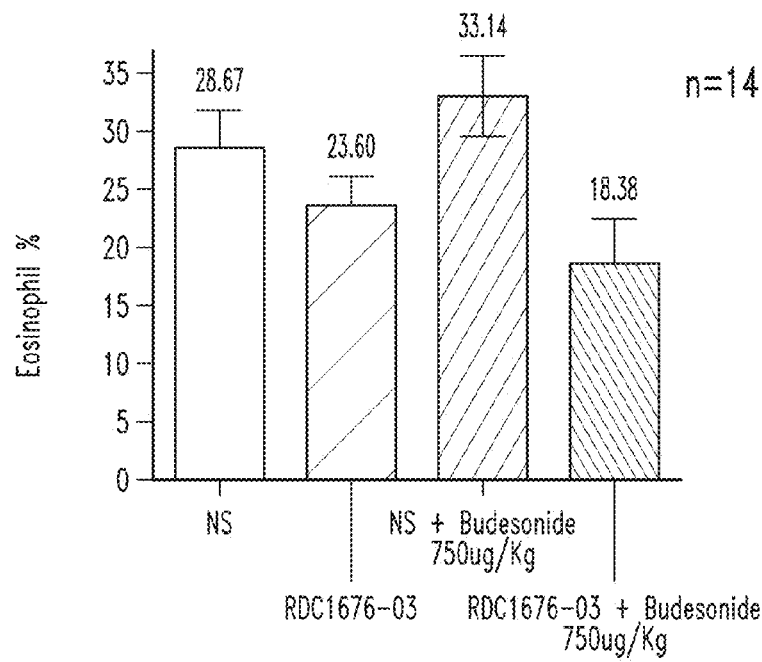

Therefore, FIGS. 109 and 110 show, according to particular aspects of the present invention that the inventive electrokinetically generated fluids (e.g., RDC1676-03) were demonstrated to have a substantial synergistic utility in combination with Budesonide to significantly reduce eosinophil count ("Eosinophil %" and total count) in an art-recognized rat model for human allergic asthma.

Figure 111A:
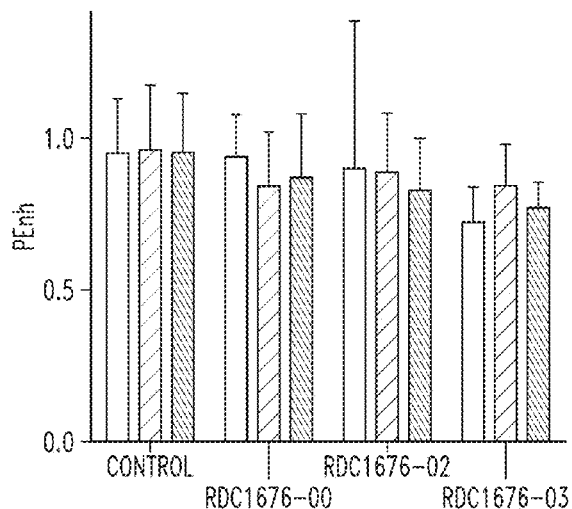
Figure 111B:
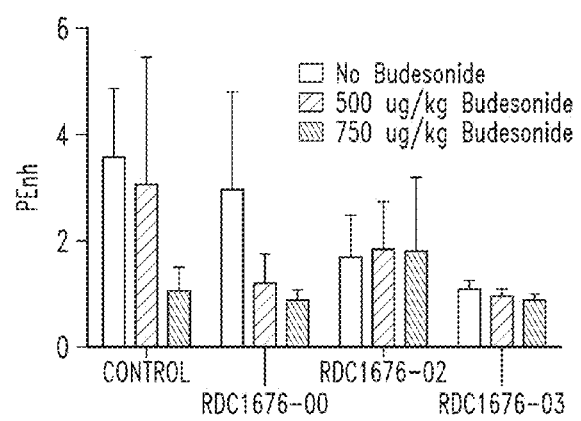
Figure 111C:
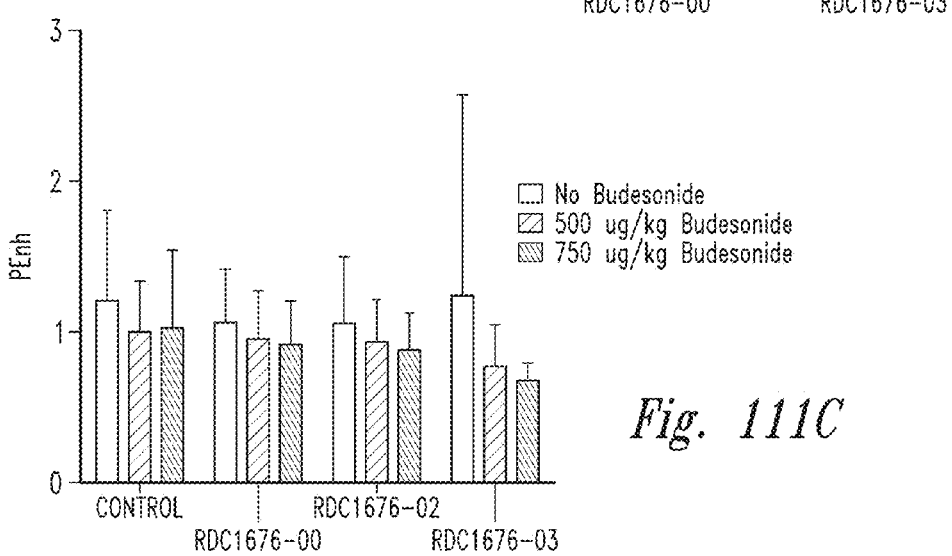

Respiratory Parameters:

FIGS. 111 A-C and 112 A-C demonstrate the observed effect of the test fluids on Penh and tidal volume as measured immediately, 6 and 24 hours after the ovalbumin challenge. Penh is a derived value obtained from peak inspiratory flow, peak expiratory flow and time of expiration and lowering of penh value reflects a favorable outcome for lung function.

$$\text{Penh} = (\text{Peak expiratory flow/Peak inspiratory flow})^* \\ (\text{Expiratory time/time to expire 65\% of expiratory volume}-1).$$

As evident from FIGS. 111 A-C, treatment with Budesonide (at both 500 and 750 ug/kg) alone or in combination with any of the test fluids failed to significantly affect the Penh values immediately after the challenge. However, 6 hours after the challenge, animals treated with RDC1676-03 alone or in combination with Budesonide 500 or 750 ug/kg demonstrated a significant drop in Penh values. Although the extent of this drop was diminished by 24 hours post challenge, the trend of a synergistic effect of Budesonide and RDC fluid was still observed at this time point.

Figure 112A:
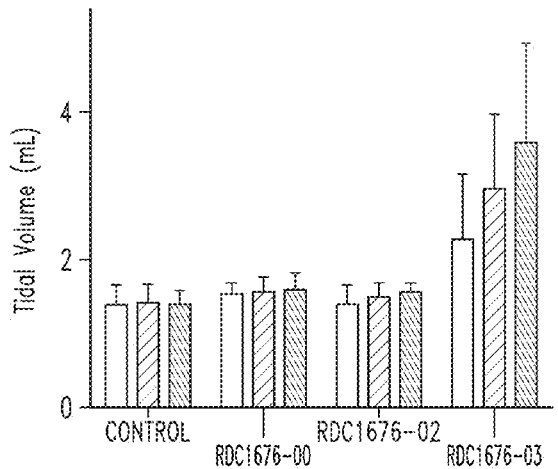
Figure 112B:
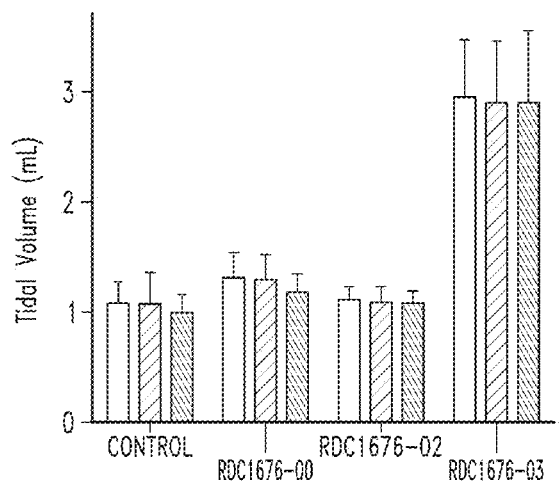
Figure 112C:
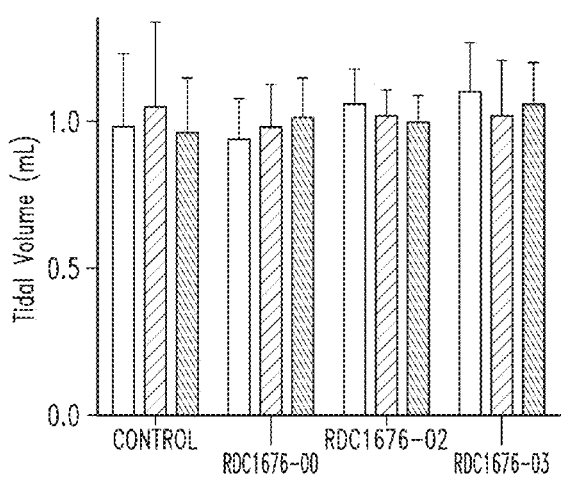

Tidal volume is the volume of air drawn into the lungs during inspiration from the end-expiratory position, which leaves the lungs passively during expiration in the course of quiet breathing. As shown in FIGS. 112 A-C, animals treated with Budesonide alone showed no change in tidal volumes immediately after the challenge. However, RDC1676-03 alone had a significant stimulatory effect on tidal volume even at this early time point. And again, RDC1676-03 in combination with Budesonide (both 500 and 750 ug/kg) had an even more pronounced effect on Tidal volume measurements at this time point. Six hours after the challenge, RDC1676-03 alone was sufficient to cause a significant increase in tidal volume and addition of Budesonide to the treatment regimen either alone or in combination had no added effect on tidal volume. Any effect observed at these earlier time points were, however, lost by the 24 hours time point.

Taken together, these data demonstrate that RDC1676-03 alone or in combination with Budesonide provided significant relief to airway inflammation as evidenced by increase in tidal volume and decrease in Penh values at 6 hours post challenge.

Cytokine Analysis:

To analyze the mechanism of the effects seen on the above discussed physiological parameters, a number of pro as well as anti-inflammatory cytokines were measured in blood samples collected at 6 and 24 hours after the challenge, immediately following the physiological measurements.

Figure 113A:
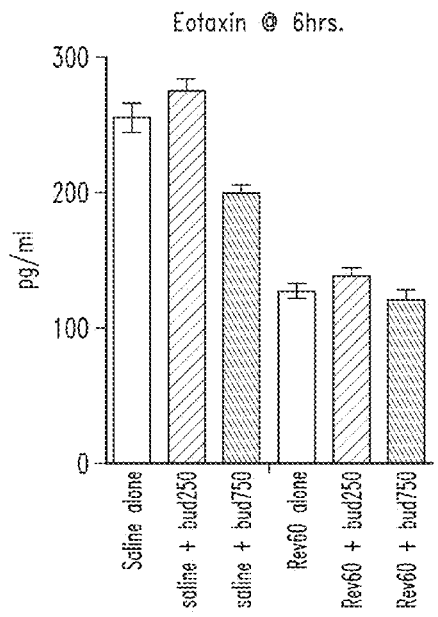
Figure 113B:
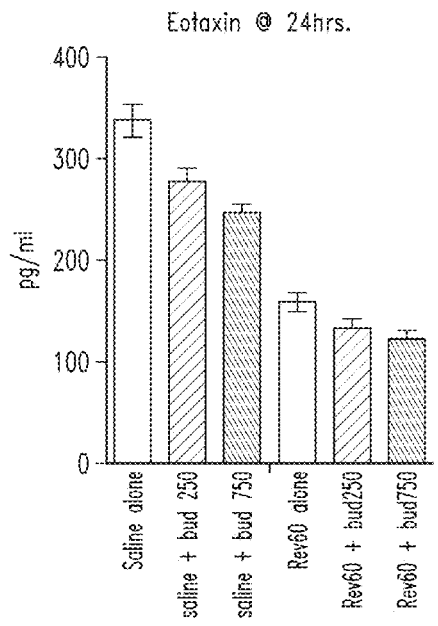

FIGS. 113A and 113B clearly demonstrate that Rev 60 (or RDC1676-03) alone lowered the blood level of eotaxin significantly at both 6 and 24 hours post challenge. Budesonide 750 ug/kg also reduced the blood eotaxin levels at both of these time points, while Budesonide 250 ug/kg only had a notable effect at the later time point. However, the test solution Rev 60 alone showed effects that are significantly more potent (in reducing blood eotaxin levels) than both concentrations of Budesonide, at both time points. Eotaxin is a small C—C chemokine known to accumulate in and attract eosinophils to asthmatic lungs and other tissues in allergic reactions (e.g., gut in Crohn's disease). Eotaxin binds to a G protein coupled receptor CCR3. CCR3 is expressed by a number of cell types such as Th2 lymphocytes, basophils and mast cells but expression of this receptor by Th2 lymphocyte is of particular interest as these cells regulate eosinophil recruitment.

Several studies have demonstrated increased production of eotaxin and CCR3 in asthmatic lung as well as establishing a link between these molecules and airway hyperresponsiveness (reviewed in Eotaxin and the attraction of eosinophils to the asthmatic lung, Dolores M Conroy and Timothy J Williams Respiratory Research 2001, 2:150-156). It is of particular interest to note that these studies completely agree with the results in FIGS. 109 and 110 on eosinophil counts.

Taken together these results strongly indicate that treatment with RDC1676-03 alone or in combination with Budesonide can significantly reduce eosinophil total count and % in blood 24 hours after the ovalbumin challenge. This correlates with a significant drop in eotaxin levels in blood observed as early as 6 hours post challenge.

Figure 113C:
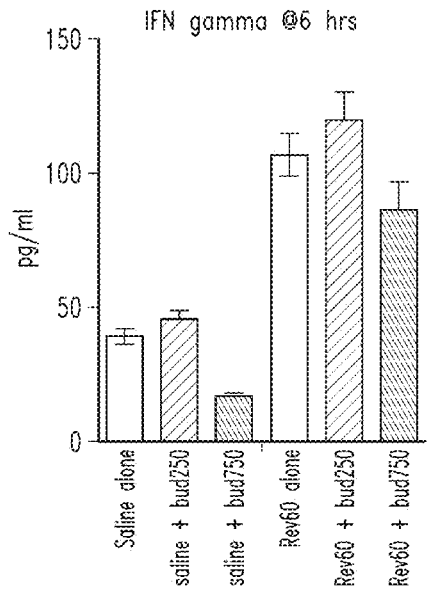
Figure 113D:
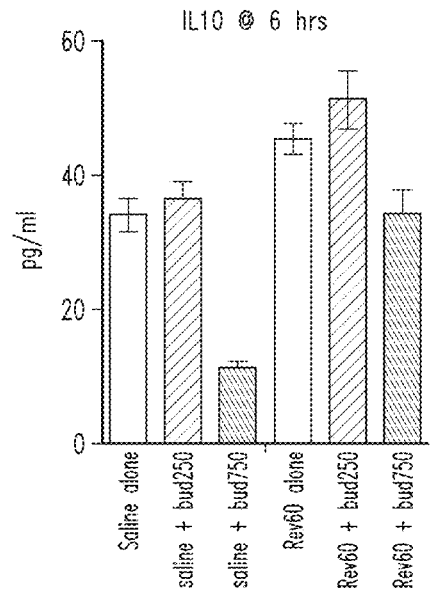

Blood levels of two major key anti-inflammatory cytokines, IL10 and Interferon gamma are also significantly enhanced at 6 hours after challenge as a result of treatment with Rev 60 alone or in combination with Budesonide. FIGS. 113C and 113D show such effects on Interferon gamma and IL 10, respectively. It is evident from these figures that Rev 60 alone or Rev 60 in combination with Budesonide 250 ug/kg significantly increased the blood level of IL10 in the challenged animals up to 6 hrs post challenge. Similarly, Rev 60 alone or in combination with Budesonide 250 or 750 ug/kg significantly increased the blood level of IFN gamma at 6 hours post challenge. Increase in these anti-inflammatory cytokines may well explain, at least in part, the beneficial effects seen on physiological respiratory parameters seen 6 hours post challenge. The effect on these cytokines was no longer observed at 24 hour post challenge (data not shown).

Rantes or CCL5 is a cytokine expressed by circulating T cells and is chemotactic for T cells, eosinophils and basophils and has an active role in recruiting leukocytes into inflammatory sites. Rantes also activates eosinophils to release, for example, eosinophilic cationic protein. It changes the density of eosinophils and makes them hypodense, which is thought to represent a state of generalized cell activation. It also is a potent activator of oxidative metabolism specific for eosinophils.

Figure 114:
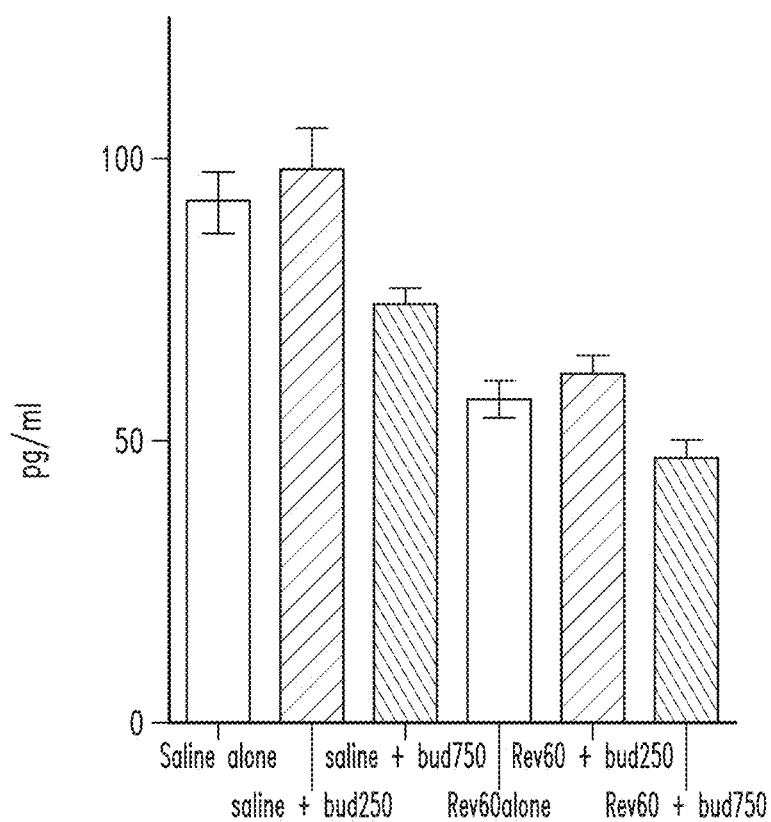

As shown in FIG. 114, systemic levels of Rantes was reduced significantly at 6 hours, but not at 24 hours post challenge in animals treated with Rev 60 alone or in combination of Budesonide 250 or 750 ug/kg. Once again, there is a clear synergistic effect of Budesonide 750 ug/kg and Rev 60 that is noted in this set of data. A similar downward trend was observed for a number of other pro-inflammatory cytokines, such as KC or IL8, MCP3, IL1b, GCSF, TGFb as well as NGF, observed either at 6 or at 24 hours post challenge, in animals treated with Rev60 alone or in combination with Budesonide.

Example 18

The Inventive Therapeutic Fluids have Substantial Utility for Modulating Intercellular Tight Junctions According to particular aspects, the inventive diffuser processed therapeutic fluids have substantial utility for modulating intercellular tight junctions, including those relating with pulmonary and systemic delivery and bioavailability of polypeptides, including the exemplary polypeptide salmon calcitonin (sCT).

Example Overview.

Salmon calcitonin (sCT) is a 32 amino acid peptide with a molecular weight of 3,432 Daltons. Pulmonary delivery of calcitonin has been extensively studied in model systems (e.g., rodent model systems, rat model systems, etc) to investigate methods to enhance pulmonary drug delivery (e.g., intratracheal drug delivery). According to particular exemplary aspects, the inventive diffuser processed therapeutic fluid has substantial utility for modulating (e.g., enhancing) intercellular tight junctions, for example those associated with pulmonary and systemic delivery and bioavailability of sCT in a rat model system.

Methods:

Intratracheal Drug Delivery.

According to particular embodiments, sCT is formulated in the inventive therapeutic fluid and administered to rats using an intratracheal drug delivery device. In certain aspects, a Penn Century Micro-Sprayer device designed for rodent intratracheal drug delivery is used, allowing for good lung delivery, but, as appreciated in the art, with relatively low alveolar deposition resulting in poor systemic bioavailability of peptides. According to particular aspects, this art-recognized model system was used to confirm that the inventive diffuser processed therapeutic fluid has substantial utility for modulating (e.g., enhancing) intercellular tight junctions, including those associated with pulmonary and systemic delivery and bioavailability of polypeptides.

Animal Groups and Dosing.

In certain aspects, rats are assigned to one of 3 groups (n=6 per group): a) sterile saline; b) base solution without 02 enrichment (base solution'); or c) inventive diffuser processed therapeutic fluid (Inventive enriched based solution'). The inventive enriched based solution is formed, for example by infusing oxygen in 0.9% saline. Preferably, the base solution comprises about 0.9% saline to minimize the potential for hypo-osmotic disruption of epithelial cells. In certain embodiments, sCT is separately reconstituted in the base solution and the inventive enriched based solution and the respective solutions are delivered to respective animal groups by intratracheal instillation within 60 minutes (10 μg sCT in 200 μL per animal).

Assays.

In particular aspects, blood samples (e.g., 200 μl) are collected and placed into EDTA coated tubes prior to dosing and at 5, 10, 20, 30, 60, 120 and 240 minutes following dosing. Plasma is harvested and stored at ≤−70° C. until assayed for sCT using an ELISA.

For Agilant gene array data generation, lung tissue was isolated and submerged in TRI Reagent (TR118, Molecular Research Center, Inc.). Briefly, approximately 1 mL of TRI Reagent was added to 50-100 mg of tissue in each tube. The samples were homogenized in TRI Reagent, using glass-Teflon™ or Polytron™ homogenizer. Samples were stored at −80° C.

Results:

Enhancement of Tight Junctions.

FIG. 84 shows that RDC1676-01 (sterile saline processed through the instant proprietary device with additional oxygen added; gas-enriched electrokinetically generated fluid (Rev) of the instant disclosure) decreased systemic delivery and bioavailability of sCT. According to particular aspects, the decreased systemic delivery results from decreased adsorption of sCT, most likely resulting from enhancement of pulmonary tight junctions. RDC1676-00 signifies sterile saline processed according to the presently disclosed methods, but without oxygenation.

Additionally, according to particular aspects, tight junction related proteins were upregulated in lung tissue. FIGS. 85-89 show upregulation of the junction adhesion molecules JAM 2 and 3, GJA1, 3, 4 and 5 (junctional adherins), OCLN (occludin), claudins (e.g., CLDN 3, 5, 7, 8, 9, 10), TJP1 (tight junction protein 1), respectively.

Example 19

Figure 93:
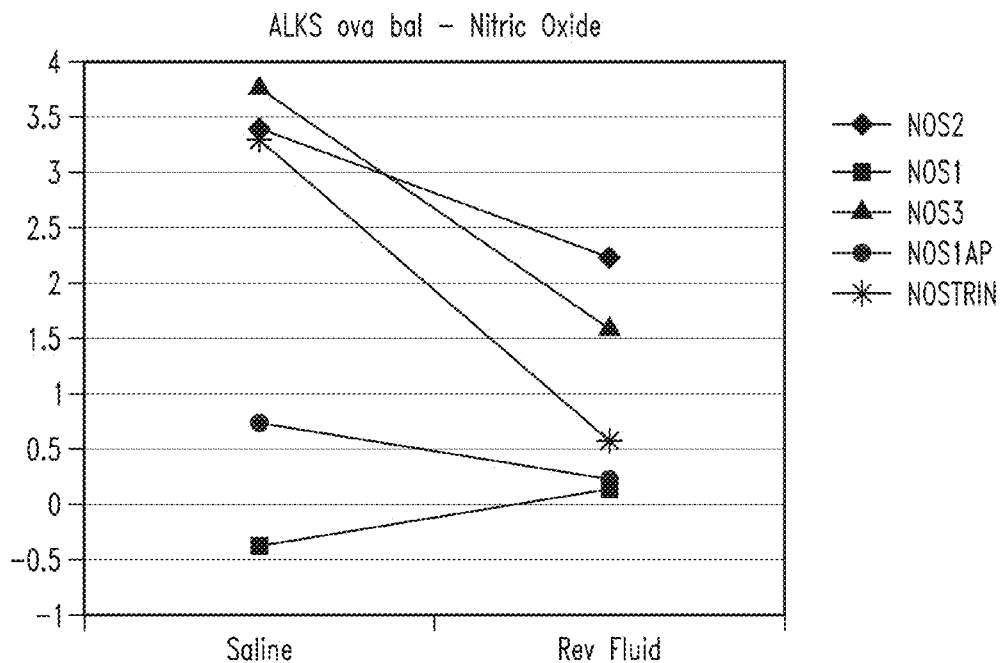
Figure 94:
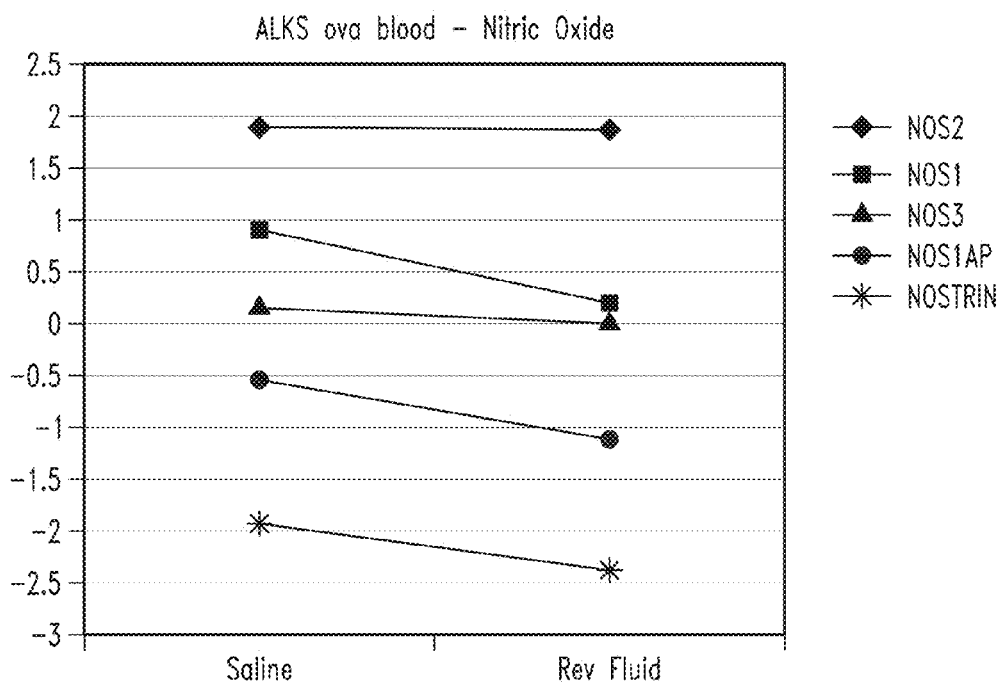

The Inventive Therapeutic Fluids have Substantial Utility for Modulating Nitric Oxide Levels According to particular aspects, the inventive diffuser processed therapeutic fluids have substantial utility for modulating nitric oxide levels, and/or related enzymes. FIGS. 90-94 show data obtained from human foreskin keratinocytes exposed to RDC1676-01 (sterile saline processed through the instant proprietary device with additional oxygen added; gas-enriched electrokinetically generated fluid (Rev) of the instant disclosure) showing up-regulation of NOS1 and 3, and Nostrin, NOS3. By contrast, data obtained from rat lung tissue (tissue of above Example entitled "Cytokine Expression") shows down regulation of NOS2 and 3, Nostrin and NOS1AP with Rev (FIGS. 93, 94).

Example 20

Localized Electrokinetic Effects (Voltage/Current) were Demonstrated Using a Specially Designed Mixing Device Comprising Insulated Rotor and Stator Features In this Example, feature-localized electrokinetic effects (voltage/current) were demonstrated using a specially designed mixing device comprising insulated rotor and stator features.

Overview.

As discussed in detail herein above under "Double Layer Effect" (see also FIGS. 26 and 28) the mixing device 100 may be configured to create the output material 102 by complex and non-linear fluid dynamic interaction of the first material 110 and the second material 120 with complex, dynamic turbulence providing complex mixing that further favors electrokinetic effects. According to particular aspects, the result of these electrokinetic effects may be present within the output material 102 as charge redistributions and redox reactions, including in the form of solublized electrons that are stabilized within the output material.

In addition to general surface-related double layer effects in the mixing chamber, Applicants additionally reasoned that localized electrokinetic effects may be imparted by virtue of the feature-induced microcavitation and fluid acceleration and deceleration in the vicinity of the features. The studies of this Example were thus performed to further investigate and confirm said additional electrokinetic aspects.

Figure 95:
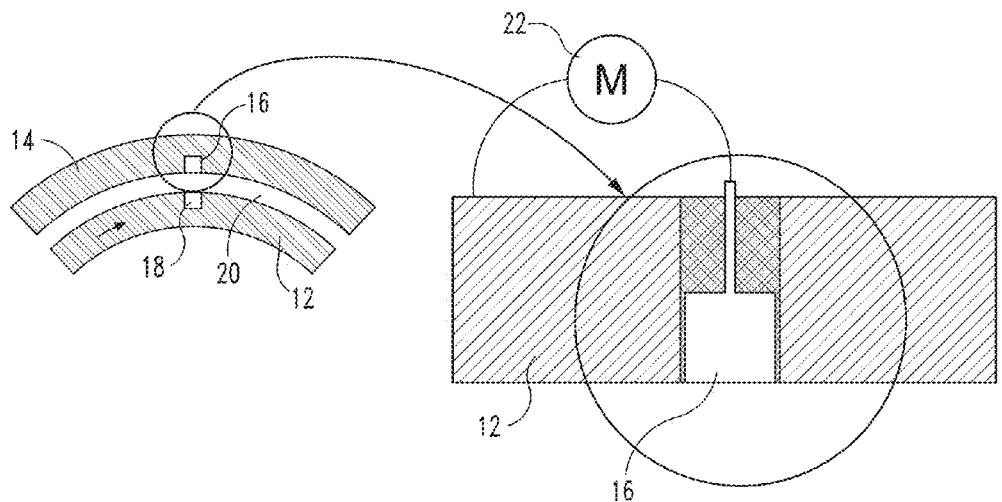
FIGS. 95 and 96 show data supporting localized electrokinetic effects (voltage/current) occurring in a mixing device comprising insulated rotor and stator features to allow for detection of voltage/current effects during electrokinetic fluid generation.

Materials:

A test device similar to the inventive mixing devices described herein was constructed, comprising a stainless steel rotor 12 having two features 18 (disposed at 180 degrees), and a stator 14 with a single feature 16 positioned to be rotationally opposable to the rotor features 18 and stator features 16. Significantly, the rotor and stator features, in each case, are insulated from the respective rotor and stator bodies (FIG. 95). The device was machined to provide for a consistent rotor:stator gap 20 of 0.020 inches to conform with the devices disclosed elsewhere herein. There is a rotating contact (not shown) at the end of the rotor shaft (not shown) that provides an electrical path for the rotor surface and for the insulated rotor features. Likewise the stator has a similar insulated feature 16 (FIG. 95), wherein the stator inner surface and the insulated stainless steel feature are connected to respective contacts on the stator exterior.

A operational amplifier (OpAmp) circuit (M) 22 is connected between the contacts. The operational amplifier (OpAmp) circuit was constructed to provide for collection of very low voltage measurements by taking advantage of the high input impedance of such amplifiers. The outputs of the OpAmp are fed to the inputs of an oscilloscope (e.g., a battery powered laptop running an oscilloscope application with a Pico Scope 3000™).

To eliminate the introduction of any ambient noise (e.g., RF radiation from wireless network signals and from the 60 Hz power line) during testing of the device, a fine copper mesh, RF-shielded compartment (approx. three by four by four feet) was constructed to provide a Faraday cage. This configuration provided for excellent signal to noise ratios during experimental testing, as interfering signals from 60 Hz AC noise (e.g., of approximately two volts) and high frequency RF was reduced well below the signals of interest. Using a battery powered laptop running an oscilloscope application with a Pico Scope 3000 enabled detection of the 30 mV signals (as in FIG. 96) created by the features of the test device. In addition, a variable speed DC motor was positioned outside the Faraday cage and coupled to the rotatable test device via a non-metallic shaft to effectively isolate the motor noise away from the test device.

Methods:

The OpAmp circuit was used to measure voltage potential between the contacts connecting the stator inner surface 12 and the insulated stator feature 16. With the particular circuit arrangement, only a potential was measured. The rotational speed of the device could be varied between about 700 to about 2800 rpm (with the data of FIG. 96 being measured with the device running at about 1800 rpm).

To avoid any extraneous voltage generation due to a pump or peristaltic pump, fluid flow through the device was accomplished using inert nitrogen or air or argon acting on fluid in tanks connected to the device. There was no perceptible voltage contribution from the flow mechanism, and typically air was used as the pumping force to provide for fluid flow through the device.

Fluid flow rate through the device was about 1 L/min.

An initial set of non-rotational experiments was conducted by directing fluid flow through the device chamber but without rotation of the rotor in order to assess the presence of any voltage between the stator body 12 and the isolated feature 16. Separate experiments were conducted for both flow directions.

An additional set of rotational experiments was then conducted with the same fluid flow rate, and with the device rotor rotating at various speeds from about 300 to about 1800 rpm. For any given experiment, the flow rate and rotational speed were held constant.

Results:

With respect to the non-rotational experiments, with fluid flowing through the device in either direction without any rotor rotation there was only a barely perceptible voltage (e.g., 1 to 2 mV)) between the body of the stator and the insulated feature.

Figure 96:
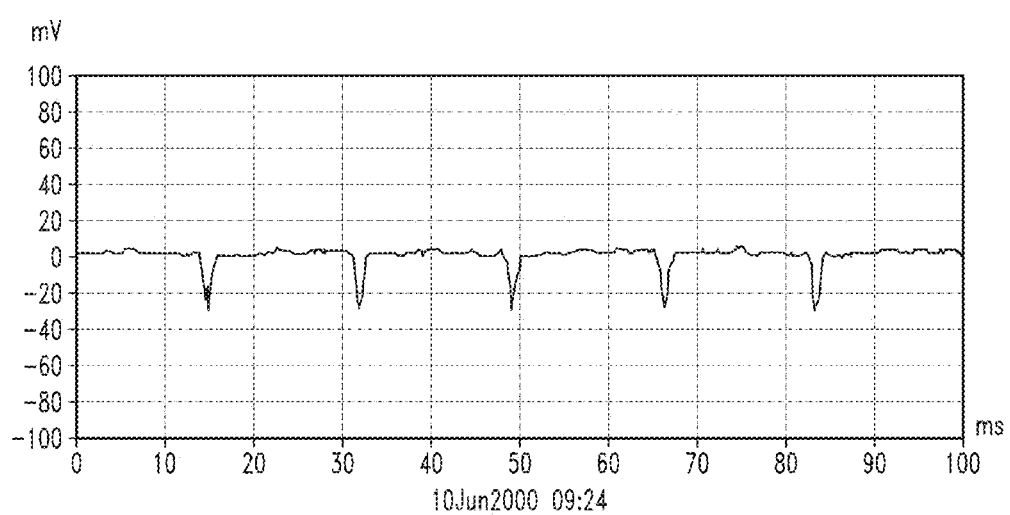

With respect to the rotational experiments, and with reference to FIG. 96, it can be seen that voltage pulses (potential pulses), temporally correlating (in this case at about 1800 rpm) with rotational alignment of opposing rotor stator features, were measurable with the OpAmp in the operating test device. Moreover, such periodic voltage pulses, correlating with feature alignments, could be observed over a range from about 250 or 300 rpm to about 1800. Additionally, with or without fluid flow, such voltage pulses were observed in the rotational experiments as long as the cavity/fluid chamber of the device was filled with fluid. According to particular aspects, and without being bound by mechanism, rapid, violent compression (e.g., cavitation), acceleration and deceleration of fluid flow in the vicinity of the repetitive rotationally aligned features created the respective local voltage pulses that correlate exactly with the rotational period, providing, at least in part, for electrokinetically generated fluid according to the present invention. Additional experiments revealed that the amplitude (peak shape and height) of the voltage pulses increased with increasing rotational velocity, being initially observable at about 250 to 300 rpm in this particular test device, and increasing up to at least about 2800 rpm. The magnitude of the violent acceleration and deceleration, etc., of fluid flow in the vicinity of the rotationally aligned features would be expected to generally increase with increasing rotational velocity; at least until a maximum was reached reflecting physical limits imposed by the geometry, configuration and/or flow rate of the device. According to additional aspects, because localized voltage spikes are present, localized current flow (e.g., current pulses) is generated in the vicinity of the features, providing, at least in part, for electrokinetically generated fluid according to the present invention (e.g., without being bound by mechanism, providing for electrochemical reactions as discussed elsewhere herein).

According to additional aspects, and without being bound by mechanism, such feature-localized effects (e.g., voltage pulses and current and/or currents pulses) contribute to generation of the electrokinetically generated fluids in combination with more general surface-related double layer and streaming current effects discussed elsewhere herein above under "Double Layer Effect" (see also FIGS. 26 and 28).

Example 21

Relative to Non-Electrokinetically Generated Control Fluids, the Inventive Electrokinetically Generated Fluids were Shown to Differentially Affect Line Widths in $^{13}$C NMR Analysis of the Dissolved Solute α,α-Trehalose)

Overview.

Applicants data disclosed elsewhere herein support utility and mechanism wherein the inventive electrokinetically generated fluids mediate regulation or modulation of intracellular signal transduction by modulation of at least one of cellular membranes, membrane potential/conductance, membrane proteins (e.g., membrane receptors such as G protein coupled receptors), calcium dependent cellular signaling systems, and intercellular junctions (e.g., tight junctions, gap junctions, zona adherins and desmasomes). Specifically, using a variety of art-recognized biological test systems and assays, Applicants data shows, relative to control fluids, differential effects of the inventive fluid on, for example: regulatory T cell proliferation; cytokine and protein levels (e.g, IL-10, GITR, Granzyme A, XCL1, pStat5, and Foxp3, tyrptase, tight junction related proteins, TSLP receptor, MMP9, etc.); binding of Bradykinin ligand with the Bradykinin B2 receptor; expression of TSLP receptor, whole cell conductance; etc. Moreover, the *Diphtheria* toxin (DT390) effects shown herein indicate that beta blockade (beta 2 adrenergic receptor), and/or GPCR blockade and/or Ca channel blockade affects the activity of the electrokinetically generated fluids on, for example, Treg and PBMC function.

Taken together these effects indicate that the inventive electrokinetically generated fluids are not only fundamentally distinguished from prior art fluids, but also that they provide for novel compositions and substantial utilities such as those presently disclosed and claimed herein.

In this Example.

Applicants have in this Example performed nuclear magnetic resonance (NMR) studies to further characterize the fundamental nature of the inventive electrokinetically generated fluids. Specifically, Applicants have analyzed the $^{13}$C NMR spectra of α,α-Trehalose dissolved in the electrokinetically generated fluid, compared to dissolution in non-electrokinetically generated fluid. Trehalose (shown below with carbons numbered for reference) is a cosmotrophic solute and is known, for example to protect against protein denaturation, membrane desiccation, organism viability upon freezing, etc. Applicants, given the data summarized above, reasoned that α,α-Trehalose might provide an effective tool to further probe the properties/structure of the inventive electrokinetically generated fluids. Applicants reasoned that NMR-related 'chemical shifts' and effects on 'line widths' could be used to assess properties of the inventive fluids. For these studies, a non-superoxygenated inventive electrokinetically generated fluid (referred to herein as "Solas") was employed to minimize the possibility that paramagnetic impurities, such as dissolved oxygen, might act to counter or otherwise mask the effects being analyzed.

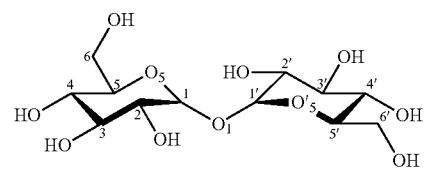

α,α-Trehalose

Materials and Methods:

Solution Preparation.

The Phosphate (sodium salt) and D-(+)-Trehalose dihydrate (T9531-10G, reduced metal content) and 99.9% D20 containing 1% DSS were purchased from Sigma. The "Normal Saline" is 0.9% Sodium Chloride, pH 5.6 (4.5-7.0), from Hospira. The 0.25 M α,α-Trehalose solutions were prepared by dissolving 0.949 g trehalose into 965 μL Normal Saline and 35 mL Phoshate Buffered Saline (100 mM Phosphate Buffer in 0.9% NaCl preparted in such a way that when 35 μL of this buffer are added to 1.0 mL trehalose solution the pH becomes 6.93).

Nuclear Magnetic Resonance Spectra Collection.

Spectra were collected at the University of Washington NMR facility using either an 500 MHz or 300 MHz Bruker Avance series instrument fitted with a Bruker BBO: X {1H} probe and running XWINNMR 3.5. $^{13}$C NMR spectra were collected at 125.7 MHz or 75.46 MHz using a 14000 Hz or 7900 Hz sweep width using 64K or 128K data points and 128 or 256 scans. The resulting FIDs were zero-filled twice and processed with a 1.0 Hz line broadening factor. Temperature was controlled using the Bruker Biospin Variable Temperature unit. External deuterium locking was employed by placing 99.9% D2O+1% DSS+a trace of acetone in a coaxial NMR insert tube, purchased from Wilmad. The NMR data was processed using the iNMR software v. 2.6.4 from Mestrelab Research.

Results:

Sample Spectra.

Figure 97A:
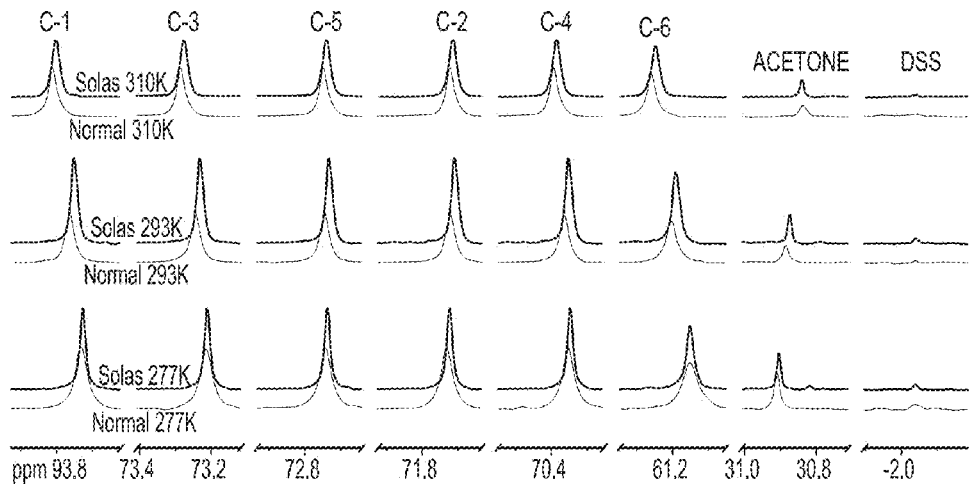
FIGS. 97A-C show results of nuclear magnetic resonance (NMR) studies conducted to further characterize the fundamental nature of the inventive electrokinetically generated fluids. The electrokinetically generated fluids increased the $^{13}$C-NMR line-widths of the reporter Trehalose solute.
Figure 97B:
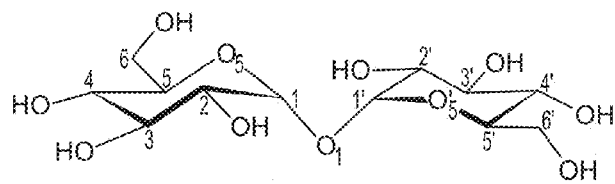
Figure 97C:
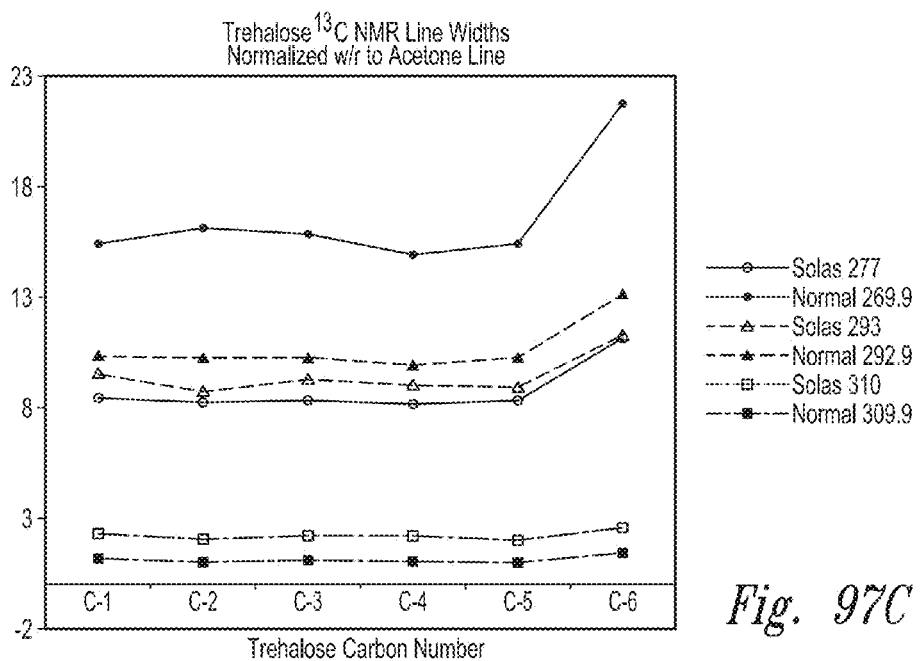

FIG. 97A-C shows expansions of six $^{13}$C-NMR spectra overlaid on top of each other such that the DSS signals line up at −2.04 ppm. The DSS signals are shown at the far right of the figure, and the acetone methyl signal is shown near 30.9 ppm. The remaining signals correspond to the 6 carbons of trehalose as shown in the α,α-Trehalose structure above. As can be seen, the carbon signals in the Solas solutions show small chemical shifts (generally upfield) compared to the control solutions.

Line Width Measurements.

TABLE 9 below shows the measured $^{13}$C-NMR line widths for the six carbons of trehalose and the methyl carbon of acetone at 3 different temperatures for Solas Saline (an inventive electrokinetically generated fluid). The corresponding Normal Saline samples represent non-electrokinetic control solutions at each temperature. In the Solas solutions, the line widths are significantly different from the line widths in the control solution for each carbon atom. The smaller linewidths in the Solas solutions at lower temperatures likely result from a faster tumbling rate of the trehalose molecule as a whole (including any solvated water molecules) compared to the control solutions.

TABLE 9

$^{13}$C NMR Line Widths for α,α-Trehalose in Solas & Normal Saline[a,b]

| Test Fluid (Temp. degrees K) | C-1 | C-2 | C-3 | C-4 | C-5 | C-6 | Acetone |
|---|---|---|---|---|---|---|---|
| Solas (277) | 8.4 | 8.22 | 8.3 | 8.15 | 8.3 | 11.1 | 5.1 |
| Normal (269.9) | 15.4 | 16.1 | 15.8 | 14.9 | 15.4 | 21.7 | 5.1 |
| Solas (293) | 9.52 | 8.7 | 9.28 | 9 | 8.9 | 11.25 | 5.63 |
| Normal (292.9) | 10.33 | 10.23 | 10.23 | 9.93 | 10.23 | 13.13 | 5.63 |
| Solas (310) | 2.28 | 2.03 | 2.18 | 2.19 | 2 | 2.55 | 0.67 |
| Normal (309.9) | 1.17 | 0.99 | 1.1 | 1.02 | 0.97 | 1.42 | 0.67 |

[a]1.0 Hz was subtracted from all line width values due to the 1.0 Hz line broadening used during processing. In addition, line width values were normalized relative to the acetone signal in the external reference tube in order to compensate for magnetic field inhomogeneities. This was done by subtracting from the Normal Saline line widths the amount by which the acetone peak was broadened in the corresponding Solas Saline spectra.
[b]Error in line width measurements estimated to be within +/−0.30 Hz The $^{13}$C NMR line widths for α,α-Trehalose in Solas and normal saline, in each case normalized with respect to the Acetone line, are shown graphically in FIG. 97A. In conclusion, the NMR data for $^{13}$C NMR line widths for α,α-Trehalose in Solas and normal saline indicate that there is a property of the inventive solution which alters solute tumbling.

Taken together with the biological activities summarize above and elsewhere herein, these $^{13}$C-NMR line width effects indicate that the inventive electrokinetically generated fluids are not only fundamentally distinguished from prior art fluids in terms of solute interactions, but also that they provide for novel compositions and substantial utilities such as those presently disclosed and claimed herein.

Example 22

Relative to Non-Electrokinetically Generated Control Fluids, the Inventive Electrokinetically Generated Fluids Produced Differential Square Wave Voltametry Profiles and Displayed Unique Electrochemical Properties Under Stripping Polarography Overview.

Applicants' data disclosed elsewhere herein support utility and mechanism wherein the inventive electrokinetically generated fluids mediate regulation or modulation of intracellular signal transduction by modulation of at least one of cellular membranes, membrane potential/conductance, membrane proteins (e.g., membrane receptors such as G protein coupled receptors), calcium dependent cellular signaling systems, and intercellular junctions (e.g., tight junctions, gap junctions, zona adherins and desmasomes). Specifically, using a variety of art-recognized biological test systems and assays. Applicants data shows, relative to control fluids, differential effects of the inventive fluid on, for example: regulatory T cell proliferation; cytokine and protein levels (e.g, IL-10, GITR, Granzyme A, XCL1, pStat5, and Foxp3, tyrptase, tight junction related proteins, TSLP receptor, MMP9, etc.); binding of Bradykinin ligand with the Bradykinin B2 receptor; expression of TSLP receptor, whole cell conductance; etc. Moreover, the *Diphtheria* toxin (DT390) effects shown herein indicate that beta blockade (beta 2 adrenergic receptor), and/or GPCR blockade and/or Ca channel blockade affects the activity of the electrokinetically generated fluids on, for example, Treg and PBMC function.

Taken together these effects indicate that the inventive electrokinetically generated fluids are not only fundamentally distinguished from prior art fluids, but also that they provide for novel compositions and substantial utilities such as those presently disclosed and claimed herein.

In this Example.

Applicants have, in this Example, performed voltametry studies to further characterize the fundamental nature of the inventive electrokinetically generated fluids. Voltametry is frequently used to determine the redox potential or measure kinetic rates and constants of fluids. The common characteristic of all voltametric methods is that they involve the application of a potential to an electrode and the resultant current flowing is monitored through an electrochemical cell. The applied potential produces a change in the concentration of an electroactive species at the electrode surface by electrochemically reducing or oxidizing the species.

Specifically, Applicants have utilized voltametric methods (i.e., square wave voltametry and stripping polarography) to further characterize fundamental differences between control saline fluid and the inventive electrokinetically generated test fluids (e.g., Solas and Revera). Applicants, given the biological and membrane effects data summarized above, reasoned that square wave voltametry and stripping polarography would provide an effective means to further characterize the unique properties of the inventive electrokinetically generated fluids.

Applicants further reasoned that differences in current at specific voltages, production of different concentrations of an electroactive redox compound, creation of new redox compounds, and possession of unique electrochemical properties could be used to assess and characterize properties of the inventive fluids. For these studies, both a superoxygenated electrokinetically generated fluid (Revera), and a non-superoxygenated inventive electrokinetically generated fluid (Solas) were used.

Materials and Methods:

Materials and Solution Preparation.

The experiments were conducted on an EG & G SMDE 303A polarographer (Princeton Applied Research). The electrolyte, NaOH, used in the square wave voltametry experiment, was purchased from Sigma. A 10 mL sample of the inventive fluid solution was prepared by adding 100 μL of NaOH to 9.9 mL of Revera Saline to make a 0.18 molar solution. With regards to the stripping polarography experiment, no extra electrolyte was utilized.

Square Wave Voltametry.

As stated above, voltametry is used to determine the redox potential or measure kinetic rates and constants in fluids. In the square wave voltametry experiment, a potential of 0.0 to approximately −1.75 V was applied to an electrode and the resultant current flowing through the electrochemical cell was monitored.

Stripping Polarography.

The stripping polarography method is similar to the square wave voltametry method. However, no electrolyte was utilized as stated above and also involved a pre-step. In the pre-step, the static mercury drop electrode was held for 30 seconds at −1.1 V to amalgamate any compounds whose reduced form was soluble in mercury. Then, the potentials between −1.1 V and 0.0 V were scanned and the resultant current flowing through the electrochemical cell was monitored. A linear scan into the negative potentials on this amalgam provided a sensitive measurement of these compounds.

Results:

Square Wave Voltametry.

Figure 98:
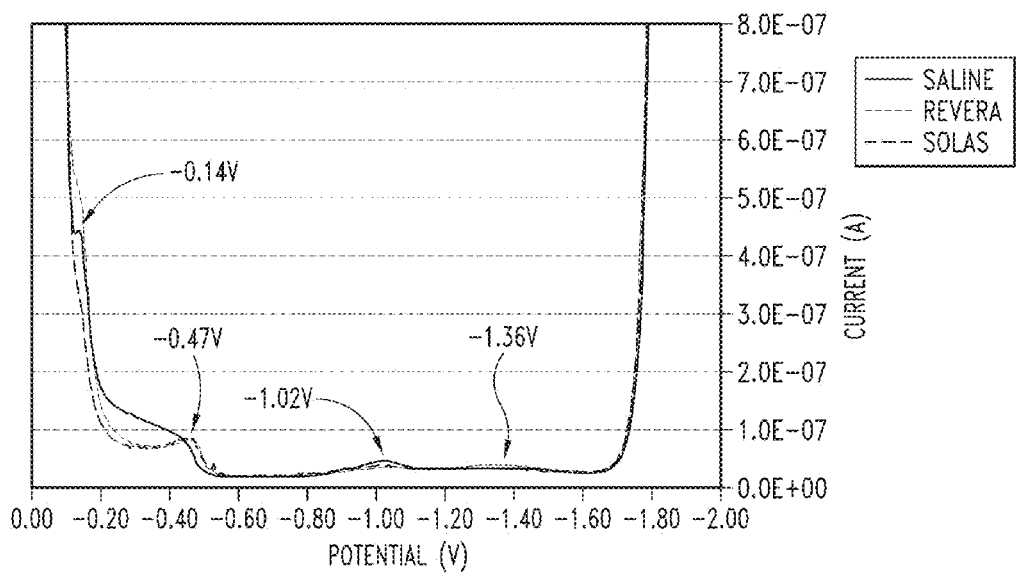
FIGS. 98 and 99 show results of voltametric studies (i.e., square wave voltametry (FIG. 98) and stripping polarography (FIG. 99)) conducted to further characterize the fundamental nature of the inventive electrokinetically generated fluids. Square wave voltametry peak differences (with respect to control) unique to the electrokinetically generated fluids were observed at −0.14V, −0.47V, −1.02V and −1.36V. Pronounced polaragraphic peaks were seen at −0.9 volts for the electrokinetically generated Revera and Solas fluids, and the spectra of the non-electrokinetically generated blank and saline control fluids show characteristic peaks at −0.19 and −0.3 volts that are absent in the spectra for the electrokinetically generated fluids.
Figure 99:
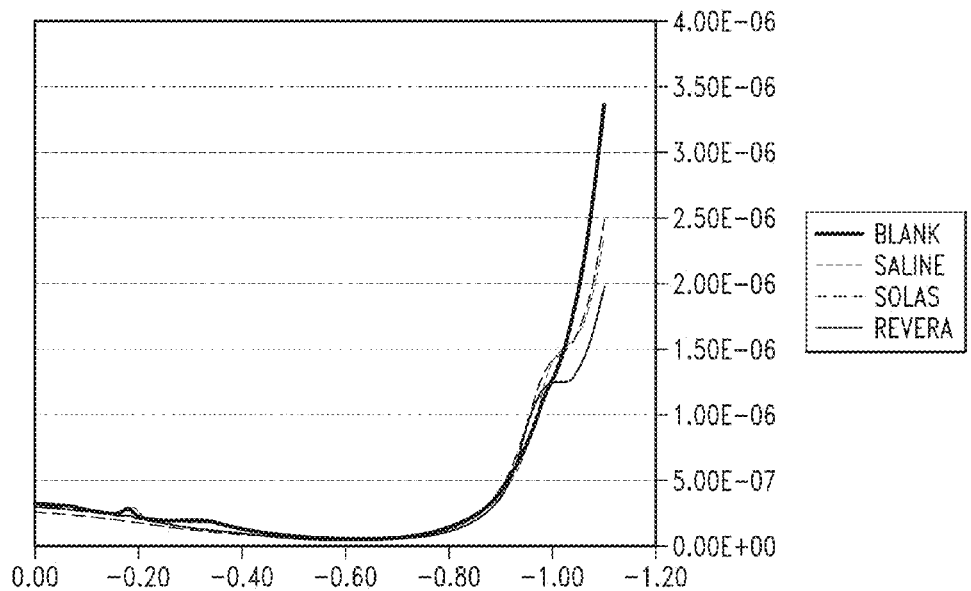

As evident from FIG. 98, the current profiles at −0.14V, −0.47V, −1.02V and −1.36V differ between the various tested agents. According to particular aspects, the differences in current generated at the various specific voltages indicate at least one of a different concentration of an electroactive redox compound and/or a new or unique electroactive redox compound, and/or a change in the diffusion-limiting electrical double layer surrounding the mercury drop.

Stripping Polarography.

FIG. 99 shows that the inventive electrokinetically generated fluids, Revera and Solas, show unique spectra with pronounced peaks at −0.9 volts that are not present in the non-electrokinetically generated blank and saline control fluids. Additionally, the spectra of the non-electrokinetically generated blank and saline control fluids show characteristic peaks at −0.19 and −0.3 volts that are absent in the spectra for the electrokinetically generated Solas and Revera fluids.

According to particular aspects, therefore, these results show unique electrochemical properties of the inventive electrokinetically generated Solas and Revera fluids compared to non-electrokinetically generated Saline control fluid. According to additional aspects, the results indicate the presence or generation of at least one of a different concentration of an electroactive redox compound and a new and/or unique electroactive redox compound in electrokinetically generated versus non-electrokinetically generated fluids.

On top of the various biological data presented elsewhere herein, this differential voltametry data, particularly when considered along with the differential effects on whole cell conductance, $^{13}C$ NMR line-width analysis, and the mixing device feature-localized effects (e.g., voltage pulses and current and/or currents pulses) indicate that the inventive electrokinetically generated fluids are not only fundamentally distinguished from prior art fluids, but also provide for novel compositions and substantial utilities such as those presently disclosed and claimed herein.

Example 23

Patch Clamp Analysis Conducted on Bronchial Epithilial Cells (BEC) Perfused with Inventive Electrokinetically Generated Fluid (RNS-60) Revealed that Exposure to RNS-60 Resulted in a Decrease in Whole Cell Conductance, and Stimulation with a cAMP Stimulating "Cocktail", which Dramatically Increased the Whole-Cell Conductance, and Also Increased the Drug-Sensitive Portion of the Whole-Cell Conductance, which was Ten-Times Higher than that Observed Under Basal Conditions In this Example, patch clamp studies were performed to further confirm the utility of the inventive electrokinetically generated fluids to modulate intracellular signal transduction by modulation of at least one of membrane structure, membrane potential or membrane conductivity, membrane proteins or receptors, ion channels, and calcium dependent cellular messaging systems.

Overview.

As shown in Example 14 above (e.g., FIG. 75, showing Stabilization of Bradykinin binding to the B2 receptor using Bio-Layer Interferometry biosensor, Octet Rapid Extended Detection (RED) (forteBio™)), Bradykinin binding to the B2 receptor was concentration dependent, and binding affinity was increased in the electrokinetically generated fluid (e.g., Rev; gas-enriched electrokinetically generated fluid) of the instant disclosure compared to normal saline. Additionally, as shown in Example 15 in the context of T-regulatory cells stimulated with particulate matter (PM), the data showed a decreased proliferation of T-regulatory cells in the presence of PM and Rev relative to PM in control fluid (no Rev, no Solis) (FIG. 76), indicating that the inventive electrokinetically generated fluid Rev improved regulatory T-cell function; e.g., as shown by relatively decreased proliferation in the assay. Moreover, exposure to the inventive fluids resulted in a maintained or only slightly decreased production of IL-10 relative to the Saline and Media controls (no PM). Likewise, in the context of the allergic asthma (AA) profiles of peripheral blood mononuclear cells (PBMC) stimulated with particulate matter (PM), the data showed that exposure to the fluids of the instant disclosure ("PM+Rev") resulted in significantly lower tryptase levels similar to those of the Saline and Media controls. Additionally, the *Diphtheria* toxin (DT390) effects shown in Example 15 and FIGS. 76-83, indicate that beta blockade, GPCR blockade and Ca channel blockade affects the activity of the electrokinetically generated fluids on Treg and PBMC function. Furthermore, the data of Example 18 shows that, according to additional aspects, upon expose to the inventive fluids, tight junction related proteins were upregulated in lung tissue. FIGS. 85-89 show upregulation of the junction adhesion molecules JAM 2 and 3, GJA1,3,4 and 5 (junctional adherins), OCLN (occludin), claudins (e.g., CLDN 3, 5, 7, 8, 9, 10), TJP1 (tight junction protein 1), respectively.

Patch clamp studies were performed to further investigate and confirm said utilities.

Materials and Methods:

The Bronchial Epithelial line Calu-3 was used in Patch clamp studies. Calu-3 Bronchial Epithelial cells (ATCC #HTB-55) were grown in a 1:1 mixture of Ham's F12 and DMEM medium that was supplemented with 10% FBS onto glass coverslips until the time of the experiments. In brief, a whole cell voltage clamp device was used to measure effects on Calu-3 cells exposed to the inventive electrokinetically generated fluids (e.g., RNS-60; electrokinetically treated normal saline comprising 60 ppm dissolved oxygen; sometimes referred to as "drug" in this Example).

Patch clamping techniques were utilized to assess the effects of the test material (RNS-60) on epithelial cell membrane polarity and ion channel activity. Specifically, whole cell voltage clamp was performed upon the Bronchial Epithelial line Calu-3 in a bathing solution consisting of: 135 mM NaCl, 5 mM KCl, 1.2 mM CaCl2, 0.8 mM MgCl2, and 10 mM HEPES (pH adjusted to 7.4 with N-methyl D-Glucamine). Basal currents were measured after which RNS-60 was perfused onto the cells.

More specifically, patch pipettes were pulled from borosilicate glass (Garner Glass Co, Claremont, Calif.) with a two-stage Narishige PB-7 vertical puller and then fire-polished to a resistance between 6-12 Mohms with a Narishige MF-9 microforge (Narishige International USA, East Meadow, N.Y.). The pipettes were filled with an intracellular solution containing (in mM): 135 KCl, 10 NaCl, 5 EGTA, 10 Hepes, pH was adjusted to 7.4 with NMDG (N-Methyl-D-Glucamine).

The cultured Calu-3 cells were placed in a chamber containing the following extracellular solution (in mM): 135 NaCl, 5 KCl, 1.2 CaCl2, 0.5 MgCl2 and 10 Hepes (free acid), pH was adjusted to 7.4 with NMDG.

Cells were viewed using the 40×DIC objective of an Olympus IX71 microscope (Olympus Inc., Tokyo, Japan). After a cell-attached gigaseal was established, a gentle suction was applied to break in, and to attain the whole-cell configuration. Immediately upon breaking in, the cell was voltage clamped at −120, −60, −40 and 0 mV, and was stimulated with voltage steps between ±100 mV (500 ms/step). After collecting the whole-cell currents at the control condition, the same cell was perfused through bath with the test fluid comprising same exatracelluar solutes and pH as for the above control fluid, and whole-cell currents at different holding potentials were recorded with the same protocols.

Electrophysiological data were acquired with an Axon Patch 200B amplifier, low-pass filtered at 10 kHz, and digitized with 1400A Digidata (Axon Instruments, Union City, Calif.). The pCLAMP 10.0 software (Axon Instruments) was used to acquire and to analyze the data. Current (I)-to-voltage (V) relationships (whole cell conductance) were obtained by plotting the actual current value at approximately 400 msec into the step, versus the holding potential (V). The slope of the IN relationship is the whole cell conductance.

Drugs and Chemicals.

Whenever indicated, cells were stimulated with a cAMP stimulatory cocktail containing 8-Br-cAMP (500 mM), IBMX (isobutyl-1-methylxanthie, 200 mM) and forskolin (10 mM). The cAMP analog 8-Br-cAMP (Sigma Chem. Co.) was used from a 25 mM stock in $H_2O$ solution. Forskolin (Sigma) and IBMX (Sigma) were used from a DMSO solution containing both 10 mM Forskolin and 200 mM IBMX stock solution.

Figure 100:
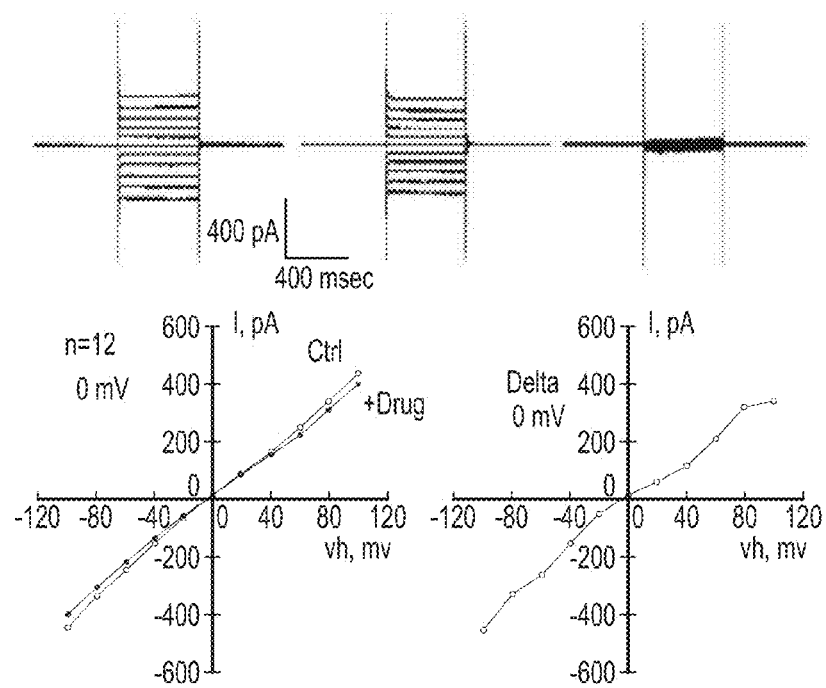
FIGS. 100-106 show results of patch clamping techniques that assessed the effects of the electrokinetically generated fluid test on epithelial cell membrane polarity and ion channel activity. The results indicate that the inventive electrokinetically generated fluids affect a voltage-dependent contribution of the whole-cell conductance.

Patch Clamp Results:

FIG. 100 shows whole-cell currents under basal (no cAMP) conditions, with a protocol stepping from zero mV holding potential to +/−100 mV. Representative tracings are the average of n=12 cells. The tracings on the left are the control, followed by the whole-cell tracings while perfusing the test solution (middle). The tracings on the right are the composite delta obtained by subtraction of the test average values, from those under control conditions. The whole-cell conductance, obtained from the current-to-voltage relationships is highly linear under both conditions, and reflects a modest, albeit significant change in conductance due to the test conditions. The contribution to the whole-cell conductance, i.e., the component inhibited by the drug (inventive electrokinetically generated fluid) is also linear, and the reversal potential is near zero mV. There is a decrease in the whole cell conductance under hyperpolarizing conditions.

Figure 101:
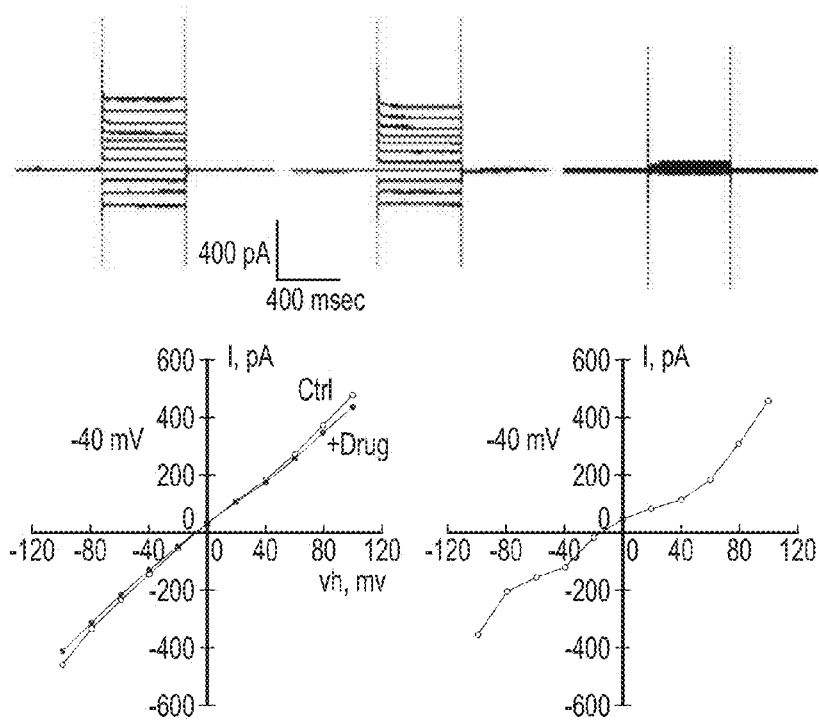

FIG. 101 shows whole-cell currents under basal conditions, with a protocol stepping from −40 mV holding potential to ±100 mV. Representative tracings are the average of n=12 cells. The tracings on the left are the control, followed by the whole-cell tracings while perfusing the test solution (middle). The tracings on the right are the composite delta obtained by subtraction of the test average values, from those under control conditions. The whole-cell conductance obtained from the current-to-voltage relationships is highly linear under both conditions, and reflects a modest, albeit significant change in conductance due to the test conditions. The contribution to the whole-cell conductance, i.e., the component inhibited by the drug (inventive electrokinetically generated fluid) is also linear, and the reversal potential is near zero mV. Values are comparatively similar to those obtained with the zero mV protocol.

Figure 102:
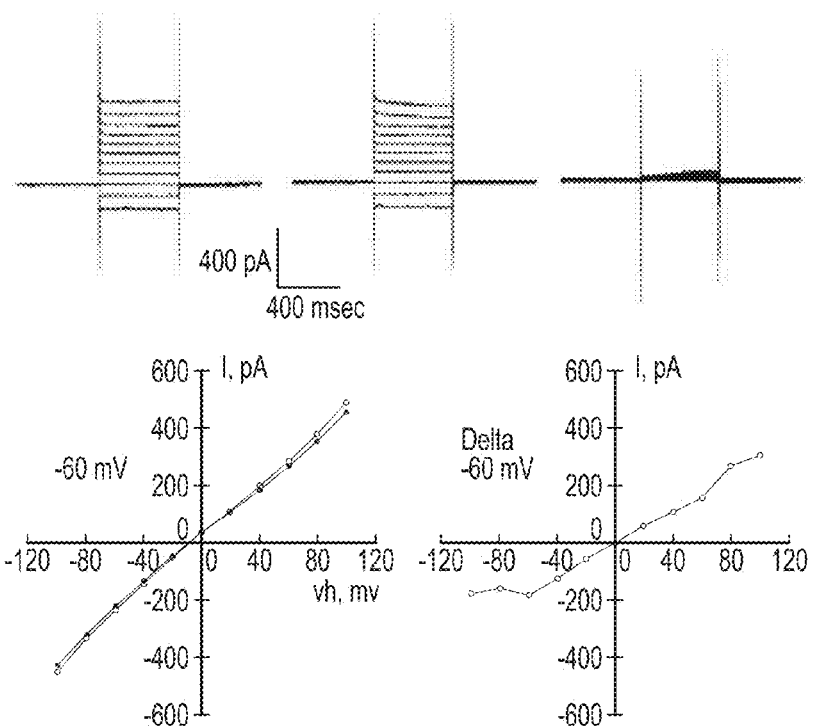

FIG. 102 shows whole-cell currents under basal conditions, with a protocol stepping from −60 mV holding potential to ±100 mV. Representative tracings are the average of n=12 cells. The tracings on the left are the control, followed by the whole-cell tracings while perfusing the test solution (middle). The tracings on the right are the composite delta obtained by subtraction of the test average values, from those under control conditions. The whole-cell conductance obtained from the current-to-voltage relationships is highly linear under both conditions, and reflects a minor, albeit significant change in conductance due to the test conditions. The contribution to the whole-cell conductance, i.e., the component inhibited by the drug is also linear, and the reversal potential is near zero mV. Values are comparatively similar to those obtained with the zero mV protocol.

Figure 103:
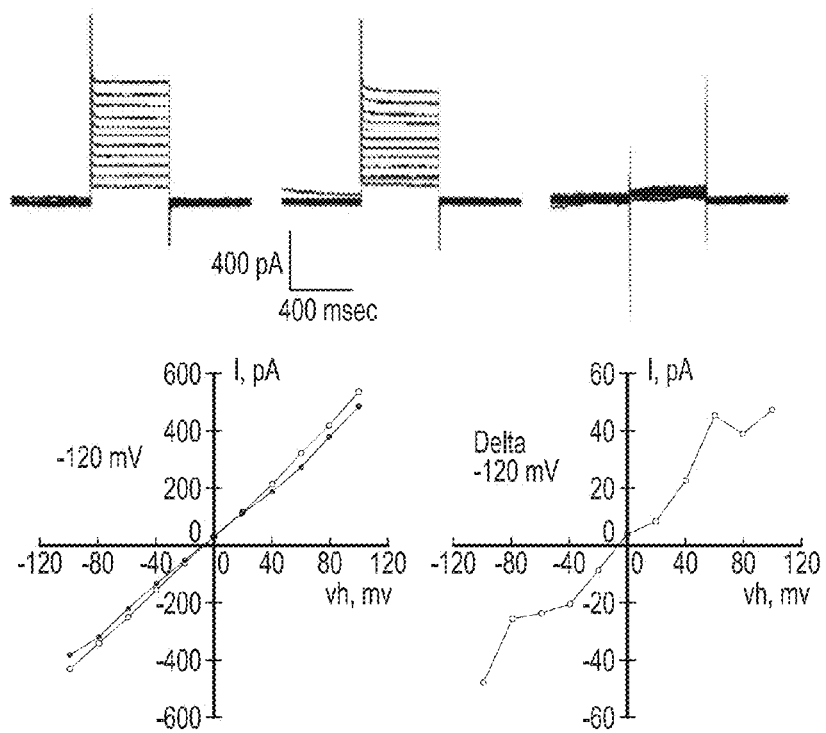

FIG. 103 shows whole-cell currents under basal conditions, with a protocol stepping from −120 mV holding potential to ±100 mV. Representative tracings are the average of n=12 cells. The tracings on the left are the control, followed by the whole-cell tracings while perfusing the test solution (middle). The tracings on the right are the composite delta obtained by subtraction of the test average values, from those under control conditions. The whole-cell conductance obtained from the current-to-voltage relationships is highly linear under both conditions, and reflects a minor, albeit significant change in conductance due to the test conditions. The contribution to the whole-cell conductance, i.e., the component inhibited by the drug is also linear, and the reversal potential is near zero mV. Values are comparatively similar to those obtained with the zero mV protocol.

Figure 104:
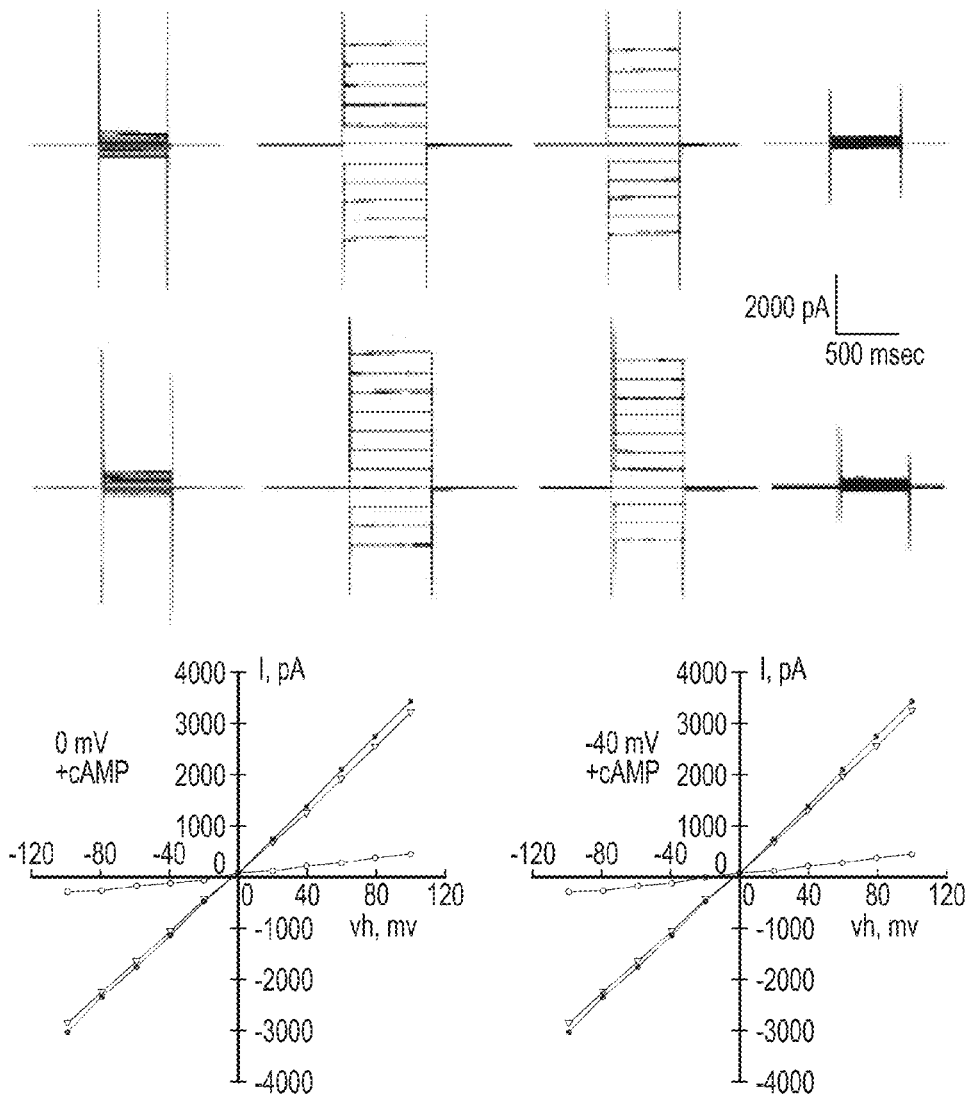

FIG. 104 shows whole-cell currents under cAMP-stimulated conditions, obtained with protocols stepping from various holding potentials to ±100 mV. Representative tracings are the average of n=5 cells. The tracings on the left are the control, followed by the whole-cell tracings after cAMP stimulation, followed by perfusion with the drug-containing solution. The tracings on the right are the composite delta obtained by subtraction of the test average values in drug+cAMP, from those under control conditions (cAMP alone). The tracings on the Top are those obtained from voltage protocol at zero mV, and the ones below, at −40 mV. The whole-cell conductance obtained from the current-to-voltage relationships is highly linear under all conditions, and reflects a change in conductance due to the test conditions.

Figure 105:
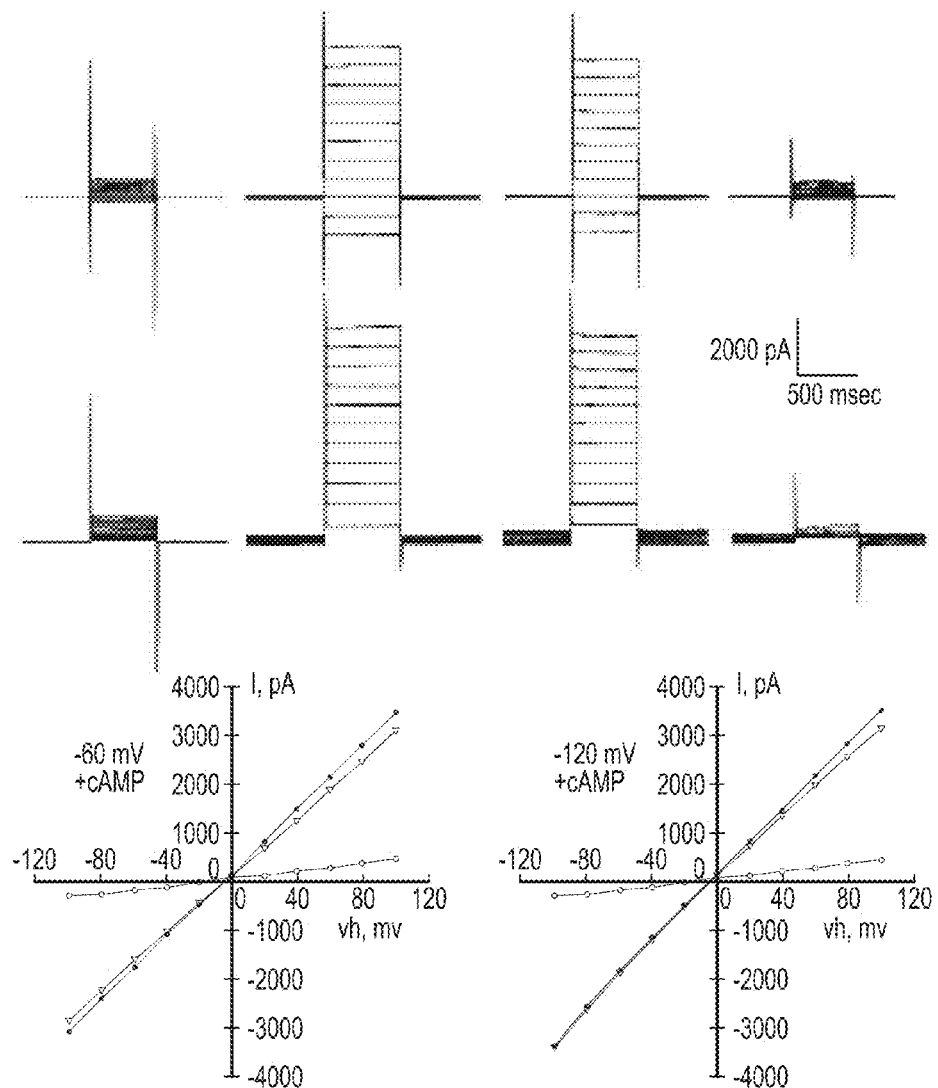

FIG. 105 shows whole-cell currents under cAMP-stimulated conditions, obtained with protocols stepping from various holding potentials to ±100 mV. Representative tracings are the average of n=5 cells. The tracings on the left are the control, followed by the whole-cell tracings after cAMP stimulation, followed by perfusion with the drug-containing solution. The tracings on the right are the composite delta obtained by subtraction of the test average values in drug+cAMP, from those under control conditions (cAMP alone). The tracings on the Top are those obtained from voltage protocol at −60 mV, and the ones below, at −120 mV. The whole-cell conductance, obtained from the current-to-voltage relationships, is highly linear under all conditions, and reflects a change in conductance due to the test conditions.

Figure 106:
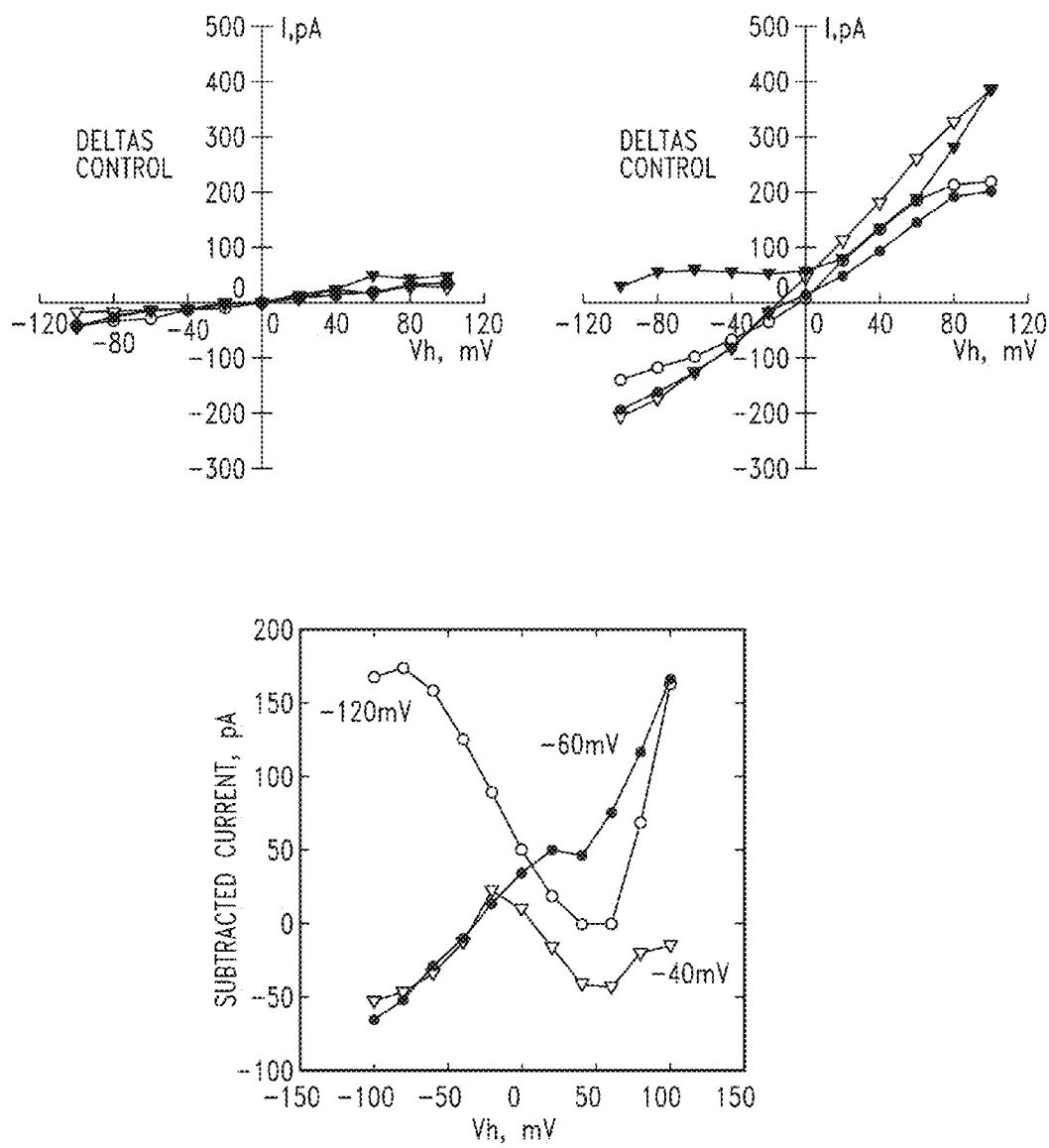
Figure 107A:
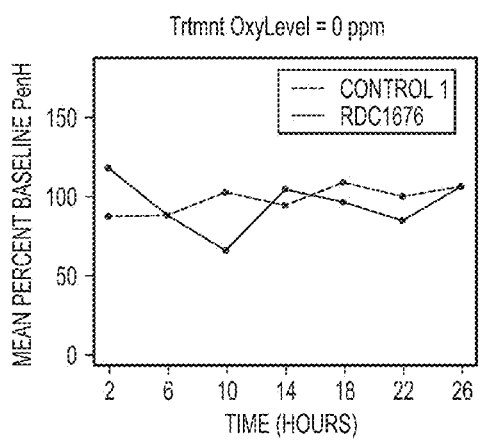
FIGS. 107A-D and 108A-D show data indicating that the inventive electrokinetically generated fluids (e.g., RDC1676-00, RDC1676-01, RDC1676-02 and RDC1676-03) protected against methacholine-induced bronchoconstriction when administered alone or as diluents for albuterol sulfate in male guinea pigs.
Figure 107B:
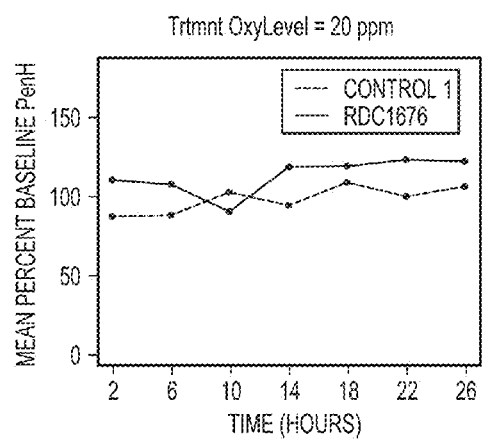
Figure 107C:
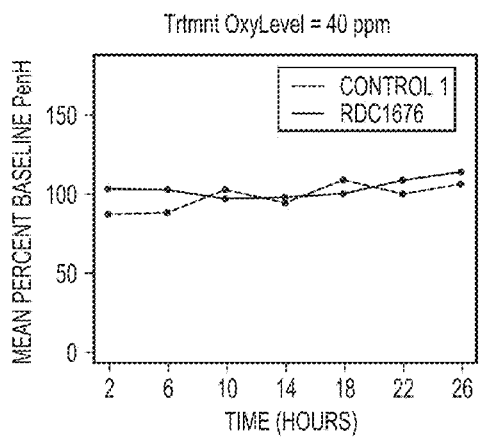
Figure 107D:
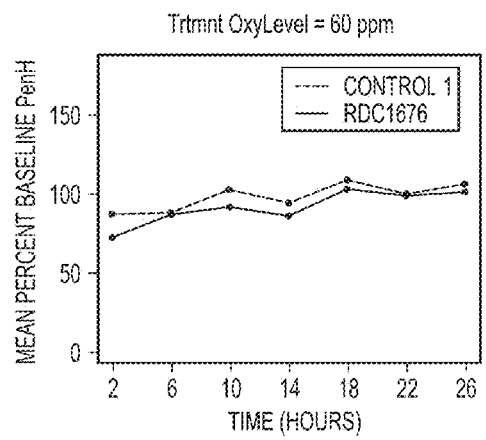
Figure 108A:
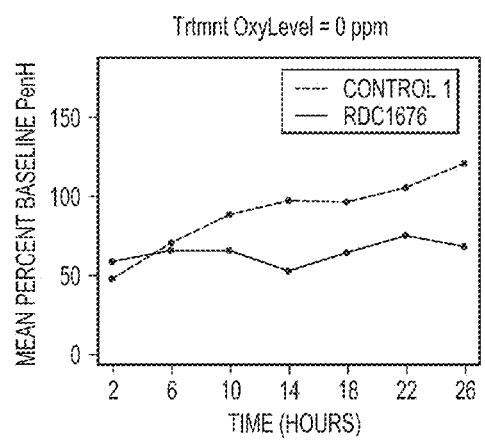
Figure 108B:
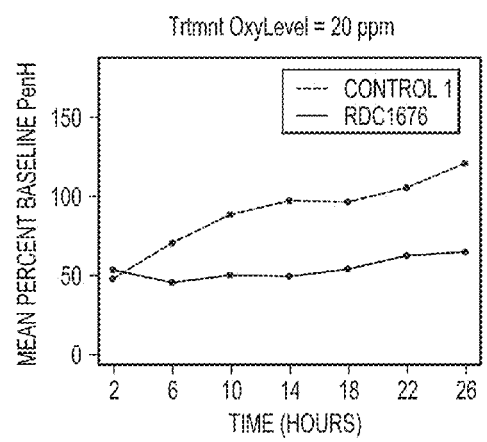
Figure 108C:
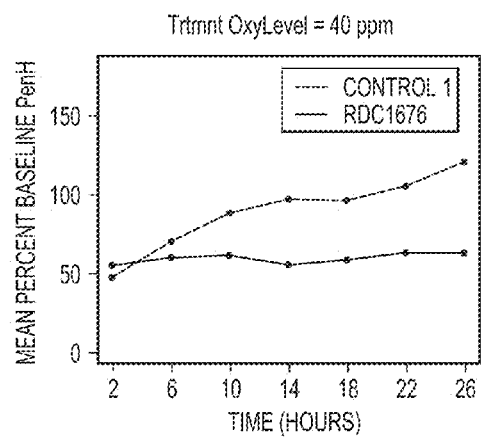
Figure 108D:
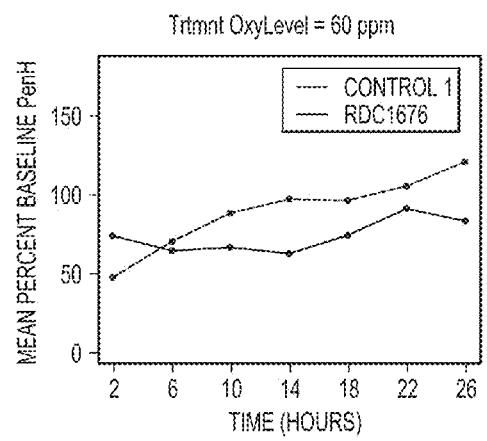

FIG. 106 shows the effect of holding potential on cAMP-activated currents. The effect of the drug (the inventive electrokinetically generated fluids; RNS-60; electrokinetically treated normal saline comprising 60 ppm dissolved oxygen) on the whole-cell conductance was observed under different voltage protocols (0, −40, −60, −120 mV holding potentials). Under basal conditions, the drug-sensitive whole-cell current was identical at all holding potentials (voltage-insensitive contribution, Top Left panel). In the cAMP-activated conditions, however, the drug-sensitive currents were much higher, and sensitive to the applied voltage protocol. The current-to-voltage relationships are highly nonlinear. This is further observed in the subtracted currents (Bottom panel), where the contribution of the whole cell conductance at zero mV was further subtracted for each protocol (n=5).

Summary of Example

According to particular aspects, therefore, the data indicate that there is a modest but consistent effect of the drug (the inventive electrokinetically generated fluids; RNS-60; electrokinetically treated normal saline comprising 60 ppm dissolved oxygen) under basal conditions. To enhance the effect of the drug on the whole-cell conductance, experiments were also conducted by perfusing the drug after stimulation with a cAMP stimulating "cocktail", which dramatically increased the whole-cell conductance. Interestingly, this protocol also increased the drug-sensitive portion of the whole-cell conductance, which was ten-times higher than that observed under basal conditions. Additionally, in the presence of cAMP stimulation, the drug showed different effects with respect to the various voltage protocols, indicating that the electrokinetically generated fluids affect a voltage-dependent contribution of the whole-cell conductance. There was also a decrease in a linear component of the conductance, further suggesting at least a contribution of the drug to the inhibition of another pathway (e.g., ion channel, voltage gated cation channels, etc.).

In particular aspects, and without being bound by mechanism, Applicants' data are consistent with the inventive electrokinetically generated fluids (e.g., RNS-60; electrokinetically treated normal saline comprising 60 ppm dissolved oxygen) producing a change either on a channel(s), being blocked or retrieved from the plasma membrane.

Taken together with Applicants' other data (e.g., the data of working Examples) particular aspects of the present invention provide compositions and methods for modulating intracellular signal transduction, including modulation of at least one of membrane structure, membrane potential or membrane conductivity, membrane proteins or receptors, ion channels, and calcium dependent cellular signalling systems, comprising use of the inventive electrokinetically generated solutions to impart electrochemical and/or conformational changes in membranous structures (e.g., membrane and/or membrane proteins, receptors or other components) including but not limited to GPCRs and/or g-proteins. According to additional aspects, these effects modulate gene expression, and may persist, dependent, for example, on the half lives of the individual messaging components, etc.

It will be appreciated that the compounds of the combination may be administered: (1) simultaneously by combination of the compounds in a co-formulation or (2) by alternation, i.e., delivering the compounds serially, sequentially, in parallel or simultaneously in separate pharmaceutical formulations. In alternation therapy, the delay in administering the second, and optionally a third active ingredient, should not be such as to lose the benefit of a synergistic therapeutic effect of the combination of the active ingredients. According to certain embodiments by either method of administration (1) or (2), ideally the combination should be administered to achieve the most efficacious results. In certain embodiments by either method of administration (1) or (2), ideally the combination should be administered to achieve peak plasma concentrations of each of the active ingredients. A one pill once-per-day regimen by administration of a combination co-formulation may be feasible for some patients suffering from inflammatory neurodegenerative diseases. According to certain embodiments effective peak plasma concentrations of the active ingredients of the combination will be in the range of approximately 0.001 to 100 µM. Optimal peak plasma concentrations may be achieved by a formulation and dosing regimen prescribed for a particular patient. It will also be understood that the inventive fluids and glatiramer acetate, interferon-beta, mitoxantrone, and/or natalizumab or the physiologically functional derivatives of any thereof, whether presented simultaneously or sequentially, may be administered individually, in multiples, or in any combination thereof. In general, during alternation therapy (2), an effective dosage of each compound is administered serially, where in co-formulation therapy (1), effective dosages of two or more compounds are administered together.

The combinations of the invention may conveniently be presented as a pharmaceutical formulation in a unitary dosage form. A convenient unitary dosage formulation contains the active ingredients in any amount from 1 mg to 1 g each, for example but not limited to, 10 mg to 300 mg. The synergistic effects of the inventive fluid in combination with glatiramer acetate, interferon-beta, mitoxantrone, and/or natalizumab may be realized over a wide ratio, for example 1:50 to 50:1 (inventive fluid: glatiramer acetate, interferon-beta, mitoxantrone, and/or natalizumab). In one embodiment the ratio may range from about 1:10 to 10:1. In another embodiment, the weight/weight ratio of inventive fluid to glatiramer acetate, interferon-beta, mitoxantrone, and/or natalizumab in a co-formulated combination dosage form, such as a pill, tablet, caplet or capsule will be about 1, i.e., an approximately equal amount of inventive fluid and glatiramer acetate, interferon-beta, mitoxantrone, and/or natalizumab. In other exemplary co-formulations, there may be more or less inventive fluid and glatiramer acetate, interferon-beta, mitoxantrone, and/or natalizumab. In one embodiment, each compound will be employed in the combination in an amount at which it exhibits anti-inflammatory activity when used alone. Other ratios and amounts of the compounds of said combinations are contemplated within the scope of the invention.

A unitary dosage form may further comprise inventive fluid and glatiramer acetate, interferon-beta, mitoxantrone, and/or natalizumab, or physiologically functional derivatives of either thereof, and a pharmaceutically acceptable carrier.

It will be appreciated by those skilled in the art that the amount of active ingredients in the combinations of the invention required for use in treatment will vary according to a variety of factors, including the nature of the condition being treated and the age and condition of the patient, and will ultimately be at the discretion of the attending physician or health care practitioner. The factors to be considered include the route of administration and nature of the formulation, the animal's body weight, age and general condition and the nature and severity of the disease to be treated.

It is also possible to combine any two of the active ingredients in a unitary dosage form for simultaneous or sequential administration with a third active ingredient. The three-part combination may be administered simultaneously or sequentially. When administered sequentially, the combination may be administered in two or three administrations. According to certain embodiments the three-part combination of inventive fluid and glatiramer acetate, interferon-beta, mitoxantrone, and/or natalizumab may be administered in any order.

Example 24

Patch Clamp Analysis Conducted on Calu-3 Cells Perfused with Inventive Electrokinetically Generated Fluids (RNS-60 and Solas) Revealed that (i) Exposure to RNS-60 and Solas Resulted in Increases in Whole Cell Conductance, (ii) that Exposure of Cells to the RNS-60 Produced an Increase in a Non-Linear Conductance, Evident at 15 Min Incubation Times, and (iii) that Exposure of Cells to the RNS-60 Produced an Effect of RNS-60 Saline on Calcium Permeable Channels Overview.

In this Example, patch clamp studies were performed to further confirm the utilities, as described herein, of the inventive electrokinetically generated slaine fluids (RNS-60 and Solas), including the utility to modulate whole-cell currents. Two sets of experiments were conducted.

The summary of the data of the first set of experiments indicates that the whole cell conductance (current-to-voltage relationship) obtained with Solas saline is highly linear for both incubation times (15 min, 2 hours), and for all voltage protocols. It is however evident, that longer incubation (2 hours) with Solas increased the whole cell conductance. Exposure of cells to the RNS-60 produced an increase in a non-linear conductance, as shown in the delta currents (Rev-Sol subtraction), which is only evident at 15 min incubation time. The effect of the RNS-60 on this non-linear current disappears, and is instead highly linear at the two-hour incubation time. The contribution of the non-linear whole cell conductance, as previously observed, was voltage sensitive, although present at all voltage protocols.

The summary of data of the second set of experiments indicates that there is an effect of the RNS-60 saline on a non-linear current, which was made evident in high calcium in the external solution. The contribution of the non-linear whole cell conductance, although voltage sensitive, was present in both voltage protocols, and indicates an effect of RNS-60 saline on calcium permeable channels.

First Set of Experiments (Increase of Conductance; and Activation of a Non-Linear Voltage Regulated Conductance)

Methods for First Set of Experiments:

See EXAMPLE 23 for general patch clamp methods. In the following first set of experiments, patch clamp studies were performed to further confirm the utility of the inventive electrokinetically generated saline fluids (RNS-60 and Solas) to modulate whole-cell currents, using Calu-3 cells under basal conditions, with protocols stepping from either zero mV holding potential, −120 mV, or −60 mV.

The whole-cell conductance in each case was obtained from the current-to-voltage relationships obtained from cells incubated for either 15 min or two hours, to further confirm the results of EXAMPLE 23. In this study, groups were obtained at a given time, for either Solas or RNS-60 saline solutions. The data obtained are expressed as the mean±SEM whole cell current for 5-9 cells.

Figure 117A:
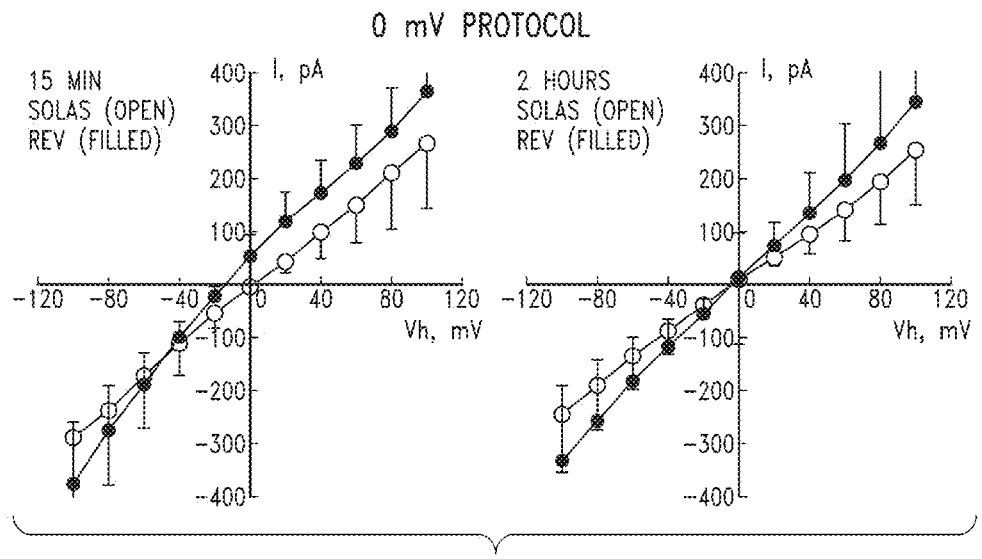
FIGS. 117 A-C demonstrate the results of a series of patch clamping experiments that assessed the effects of the electrokinetically generated fluid (e.g., RNS-60 and Solas) on epithelial cell membrane polarity and ion channel activity at two time-points (15 min (left panels) and 2 hours (right panels)) and at different voltage protocols.
Figure 117B:
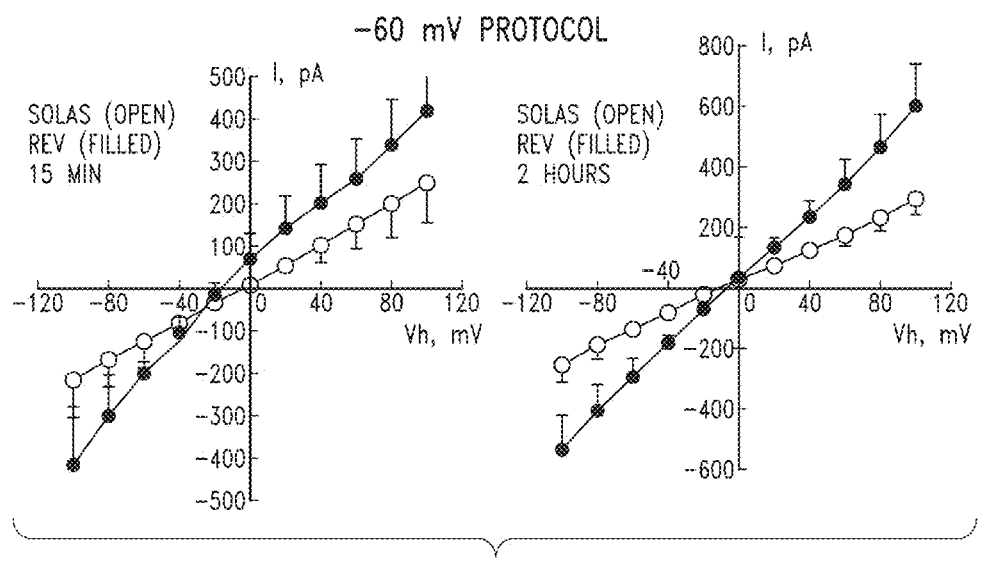
Figure 117C:
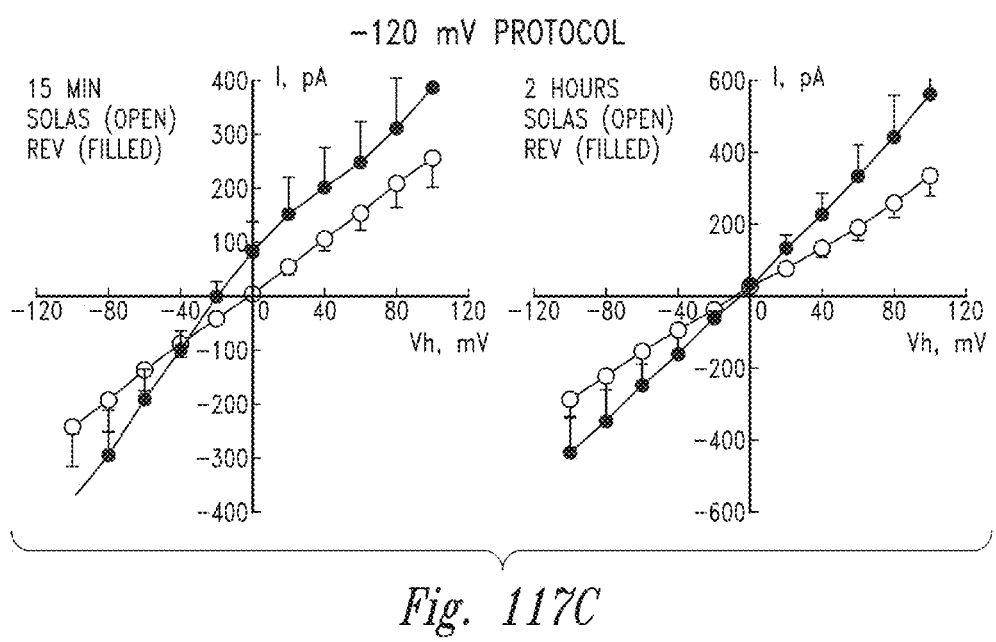

Results:

FIGS. 117 A-C show the results of a series of patch clamping experiments that assessed the effects of the electrokinetically generated fluid (e.g., RNS-60 and Solas) on epithelial cell membrane polarity and ion channel activity at two time-points (15 min (left panels) and 2 hours (right panels)) and at different voltage protocols (A, stepping from zero mV; B, stepping from −60 mV; and C, stepping from −120 mV). The results indicate that the RNS-60 (filled circles) has a larger effect on whole-cell conductance than Solas (open circles). In the experiment similar results were seen in the three voltage protocols and at both the 15 minute and two-hour incubation time points.

Figure 118A:
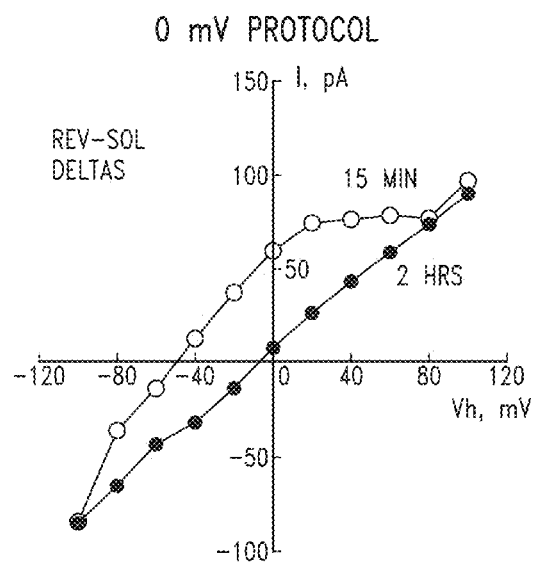
FIGS. 118A-C show, in relation to the experiments relating to FIGS. 117A-C, the graphs resulting from the subtraction of the Solas current data from the RNS-60 current data at three voltage protocols (A. stepping from zero mV; B. stepping from −60 mV; C. stepping from −120 mV) and the two time-points (15 mins (open circles) and 2 hours (closed circles)).
Figure 118B:
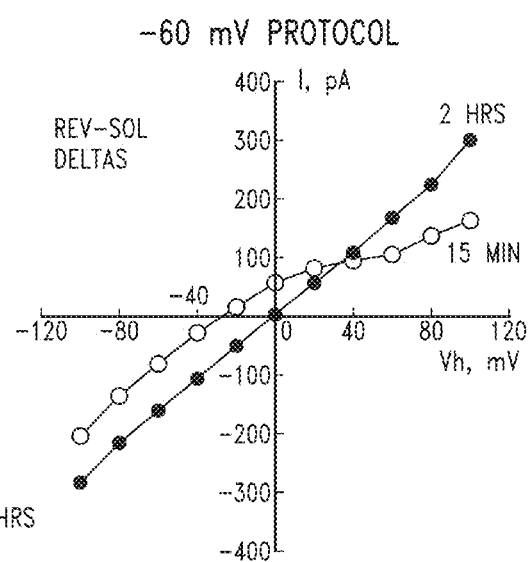
Figure 118C:
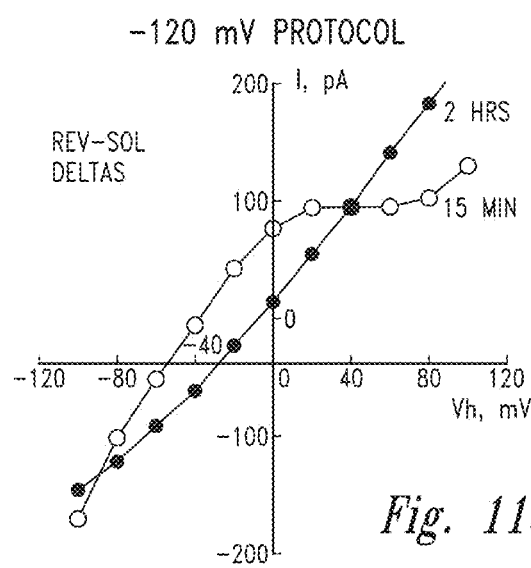
Figure 119A:
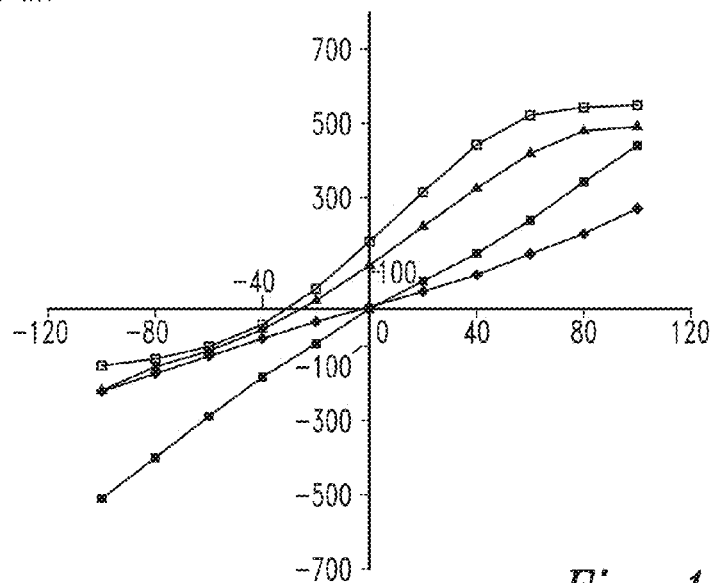
FIGS. 119 A-D demonstrate the results of a series of patch clamping experiments that assessed the effects of the electrokinetically generated fluid (e.g., Solas (panels A. and B.) and RNS-60 (panels C. and D.)) on epithelial cell membrane polarity and ion channel activity using different external salt solutions and at different voltage protocols (panels A. and C. show stepping from zero mV; panels B. and D. show stepping from −120 mV).
Figure 119B:
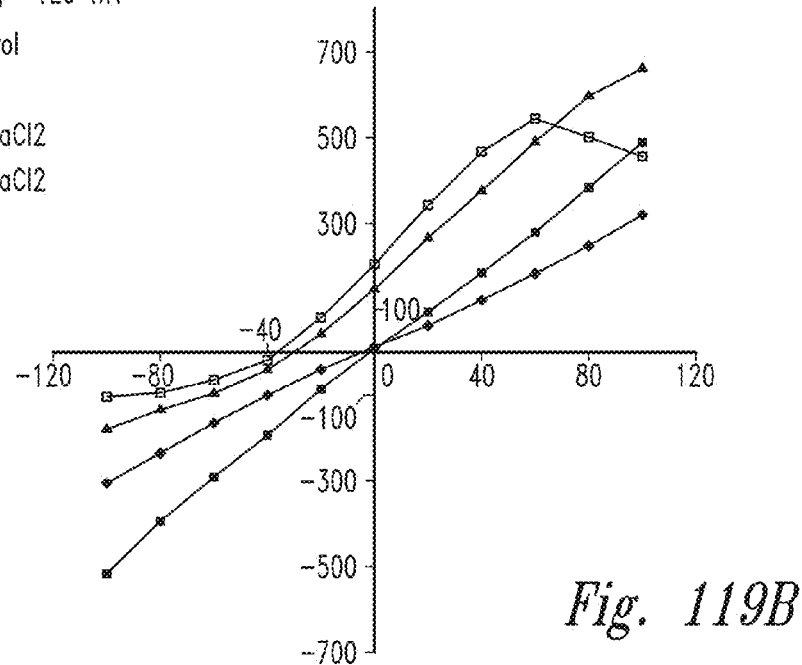
Figure 119C:
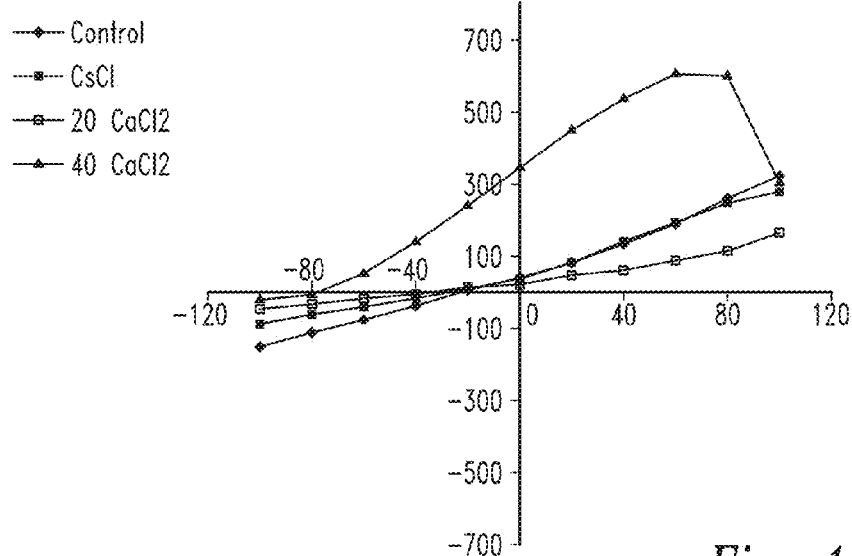
Figure 119D:
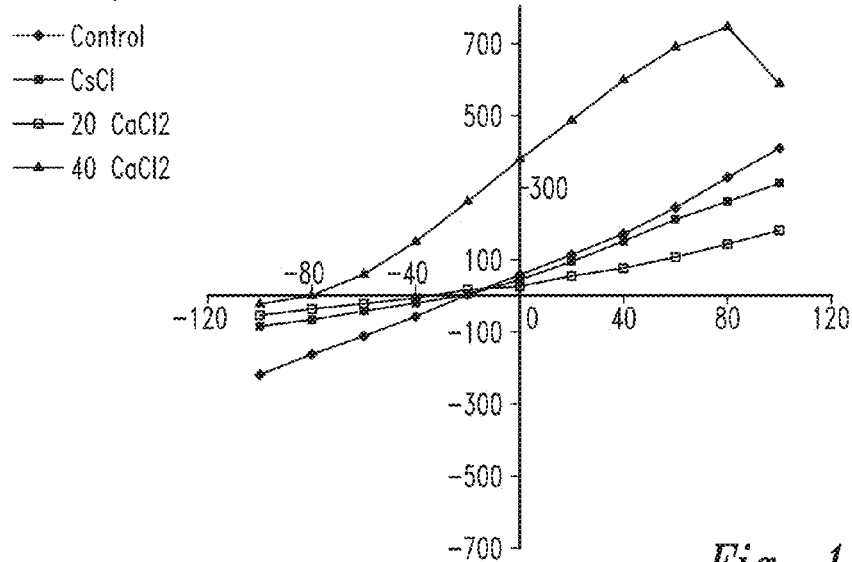
Figure 120A:
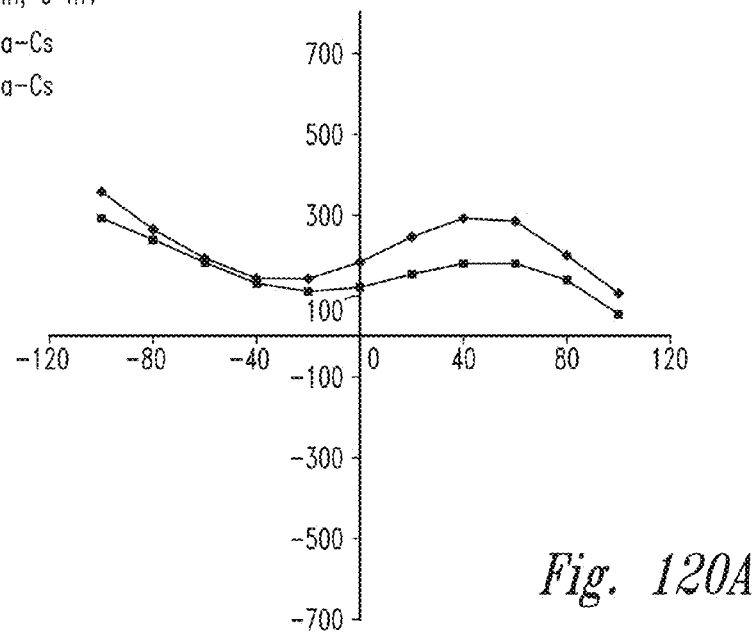
FIGS. 120 A-D show, in relation to the experiments relating to FIGS. 119 A-D, the graphs resulting from the subtraction of the CsCl current data (shown in FIG. 119) from the 20 mM $CaCl_2$ (diamonds) and 40 mM $CaCl_2$ (filled squares) current data at two voltage protocols (panels A. and C. stepping from zero mV; B. and D. stepping from −120 mV) for Solas (panels A. and B.) and Revera 60 (panels C. and D.).
Figure 120B:
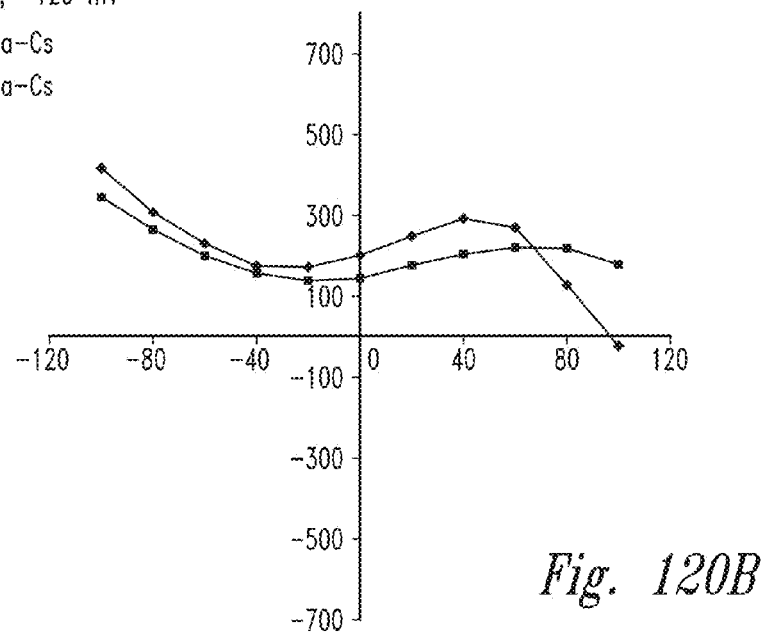
Figure 120C:
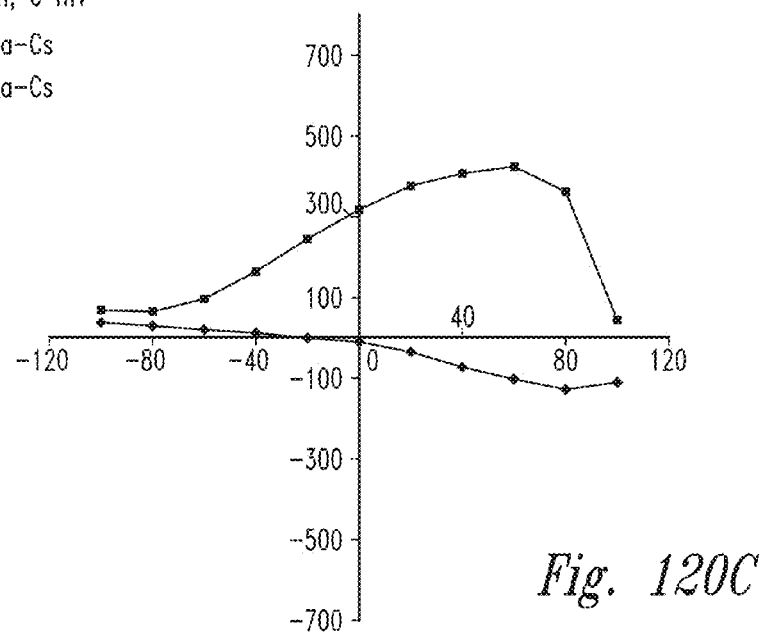
Figure 120D:
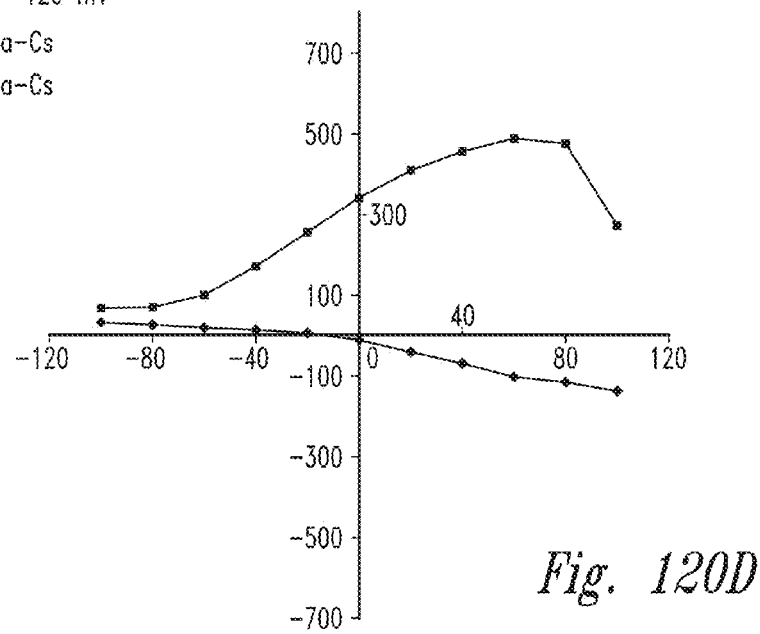

FIGS. 118 A-C show graphs resulting from the subtraction of the Solas current data from the RNS-60 current data at three voltage protocols ("Delta currents") (A, stepping from zero mV; B, stepping from −60 mV; and C, stepping from −120 mV) and the two time-points (15 mins (open circles) and 2 hours (filled circles)). These data indicated that at the 15 minute time-point with RNS-60, there is a non-linear voltage-dependent component that is absent at the 2 hour time point.

As in previous experiments, data with "Normal" saline gave a very consistent and time-independent conductance used as a reference. The present results were obtained by matching groups with either Solas or RNS-60 saline, and indicate that exposure of Calu-3 cells to the RNS-60 saline under basal conditions (without cAMP, or any other stimulation), produces time-dependent effect(s), consistent with the activation of a voltage-regulated conductance at shorter incubation times (15 min). This phenomenon was not as apparent at the two-hour incubation point. As described elsewhere herein, the linear component is more evident when the conductance is increased by stimulation with the cAMP "cocktail". Nonetheless, the two-hour incubation time showed higher linear conductance for both the RNS-60 and the Solas saline, and in this case, the RNS-60 saline doubled the whole cell conductance as compared to Solas alone. This evidence indicates that at least two contributions to the whole cell conductance are affected by the RNS-60 saline, namely the activation of a non-linear voltage regulated conductance, and a linear conductance, which is more evident at longer incubation times.

Second Set of Experiments (Effect on Calcium Permeable Channels)

Methods for Second Set of Experiments:

See EXAMPLE 23 for general patch clamp methods. In the following second set of experiments, yet additional patch clamp studies were performed to further confirm the utility of the inventive electrokinetically generated saline fluids (RNS-60 and Solas) to modulate whole-cell currents, using Calu-3 cells under basal conditions, with protocols stepping from either zero mV or −120 mV holding potentials.

The whole-cell conductance in each case was obtained from the current-to-voltage relationships obtained from cells incubated for 15 min with either saline. To determine whether there is a contribution of calcium permeable channels to the whole cell conductance, and whether this part of the whole cell conductance is affected by incubation with RNS-60 saline, cells were patched in normal saline after the incubation period (entails a high NaCl external solution, while the internal solution contains high KCl). The external saline was then replaced with a solution where NaCl was replaced by CsCl to determine whether there is a change in conductance by replacing the main external cation. Under these conditions, the same cell was then exposed to increasing concentrations of calcium, such that a calcium entry step is made more evident.

Results:

FIGS. 119 A-D show the results of a series of patch clamping experiments that assessed the effects of the electrokinetically generated fluid (e.g., Solas (panels A and B) and RNS-60 (panels C and D)) on epithelial cell membrane polarity and ion channel activity using different external salt solutions and at different voltage protocols (panels A and C show stepping from zero mV, whereas panels B and D show stepping from −120 mV). In these experiments one time-point of 15 minutes was used. For Solas (panels A and B) the results indicate that: 1) using CsCl (square symbols) instead of NaCl as the external solution, increased whole cell conductance with a linear behavior when compared to the control (diamond symbols); and 2) $CaCl_2$ at both 20 mM $CaCl_2$ (circle symbols) and 40 mM $CaCl_2$ (triangle symbols) increased whole cell conductance in a non-linear manner. For RNS-60 (panels C and D), the results indicate that: 1) using CsCl (square symbols) instead of NaCl as the external solution had little effect on whole cell conductance when compared to the control (diamond symbols); and 2) $CaCl_2$ at 40 mM (triangle symbols) increased whole cell conductance in a non-linear manner.

FIGS. 120 A-D show the graphs resulting from the subtraction of the CsCl current data (shown in FIG. 119) from the 20 mM $CaCl_2$ (diamond symbols) and 40 mM $CaCl_2$ (square symbols) current data at two voltage protocols (panels A and C, stepping from zero mV; and B and D, stepping from −120 mV) for Solas (panels A and B) and RNS-60 (panels C and D). The results indicate that both Solas and RNS-60 solutions activated a calcium-induced non-linear whole cell conductance. The effect was greater with RNS-60 (indicating a dosage responsiveness), and with RNS-60 was only increased at higher calcium concentrations. Moreover, The non-linear calcium dependent conductance at higher calcium concentration was also increased by the voltage protocol.

The data of this second set of experiments further indicates an effect of RNS-60 saline and Solas saline for whole cell conductance data obtained in Calu-3 cells. The data indicate that 15-min incubation with either saline produces a distinct effect on the whole cell conductance, which is most evident with RNS-60, and when external calcium is increased, and further indicates that the RNS-60 saline increases a calcium-dependent non-linear component of the whole cell conductance.

The accumulated evidence suggests activation by Revalesio saline of ion channels, which make different contributions to the basal cell conductance.

Taken together with Applicants' other data (e.g., the data of Applicants other working Examples) particular aspects of the present invention provide compositions and methods for modulating intracellular signal transduction, including modulation of at least one of membrane structure, membrane potential or membrane conductivity, membrane proteins or receptors, ion channels, lipid components, or intracellular components with are exchangeable by the cell (e.g., signaling pathways, such as calcium dependent cellular signaling systems, comprising use of the inventive electrokinetically generated solutions to impart electrochemical and/or conformational changes in membranous structures (e.g., membrane and/or membrane proteins, receptors or other membrane components) including but not limited to GPCRs and/or g-proteins. According to additional aspects, these effects modulate gene expression, and may persist, dependent, for example, on the half lives of the individual messaging components, etc.

Example 25

Atomic Force Microscopy (AFM) Measurements of the Inventive Electrokinetic Fluid (RNS-60) Indicated the Presence and/or Formation of Hydrophobic Surface Nanobubbles that were Substantially Smaller that Those Present in Control 'Pressure Pot' (PNS-60) Fluid Overview.

Applicants used Atomic Force Microscopy (AFM) measurements to characterize hydrophobic nanobubbles in the inventive electrokinetic fluid (RNS-60).

Materials and Methods:

AFM Studies.

AFM studies were preformed at an art-recognized Nanotech User Facility (NTUF). For AFM studies, a very small and sensitive needle is dipped into a droplet of water placed onto a hydrophobic surface. The needle then scans over the water/surface interface at rates such as 1 mm² in ~15 minutes. The needle records any imperfections in the surface geometry, and is sensitive enough to record the presence of small bubbles.

The Silicon substrate upon which the water droplets were placed was prepared using Trichloro(1H,1H,2H,2H-perfluorooctyl)silane), and the resulting hydrophobic surface causes water to bead up with contact angles of approximately 95 degrees. This coating is used in many AFM studies, in part, because it is particularly durable.

Solution Preparation.

Two test solutions were studied: RNS-60 and PNS-60. RNS-60 is an inventive electrokinetic fluid comprising 60 ppm oxygen, whereas PNS-60 is a non-electrokinetic control fluid comprising 60 ppm oxygen prepared by conventional exposure to a pressurized oxygen head (i.e., pressure pot oxygenated fluid). Each test solution was initially buffered by addition of a small amount of neutral phosphate buffer (pH 7) solution, and approximately 60-70 uL of each buffered test solution (approximately 22° C.) was placed onto a previously prepared silica plate.

Figure 121A:
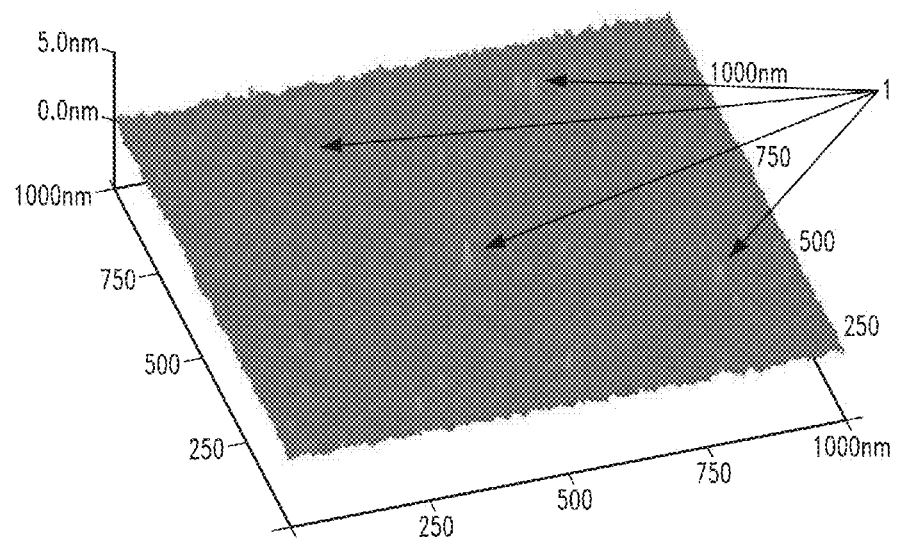
FIG. 121A shows 1 mm2 AFM scan for RNS60-1 (rns60-1 1 um 3D.jpg). The small peaks ("1") represent hydrophobic nanobubbles which are ~20 nm wide and ~1.5 nm tall or smaller.
Figure 121B:
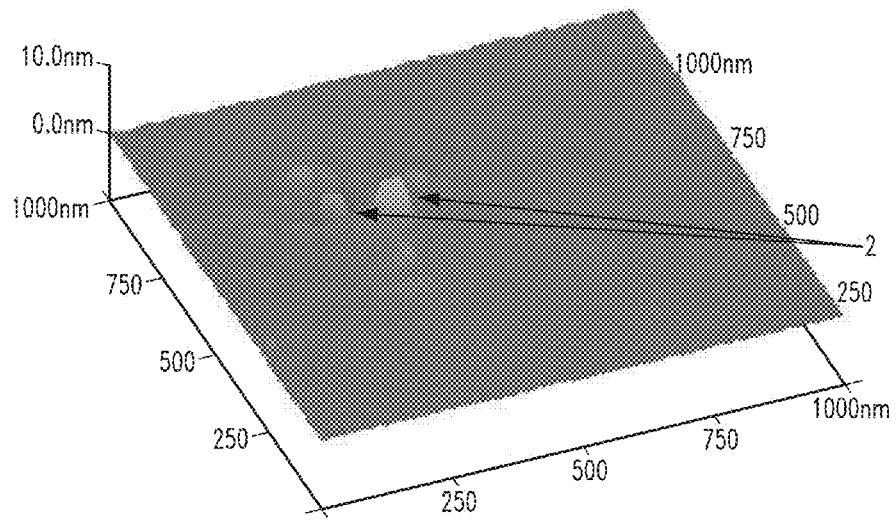
FIG. 121 B shows 1 mm2 scan for PNS60-1 (pp60-1 1 um 3d.jpg). This scan reveals peaks ("2") (hydrophobic nanobubbles) that are substantially larger (~60 nm wide and ~5 nm tall) than those visible with RNS60-1.

Results:

Under AFM, the RNS-60 droplet displayed a distribution of about 20 hydrophobid nanobubbles in a 1 mm² area, having dimensions of ~20 nm wide and ~1.5 nm tall or smaller (FIG. 121 A). By contrast, under AFM, the PNS-60 droplet displayed approx 5 hydrophobic nanobubbles in a 1 mm² area, having dimensions of ~60 nm wide and ~5 nm tall (FIG. 121 B). The PNS-60 droplet, therefore, had much fewer and much larger hydrophobic nanobubbles compared to the RNS60 droplet.

According to particular aspects, therefore, there is a substantial difference in the size and distribution of hydrophobic surface nanobubbles between the RNS-60 and PNS-60 test solutions, where the nanobubbles are either initially present in, and/or formed within the test fluids during AFM measurement.

As discussed elsewhere herein, according to particular aspects of the present invention, the inventive electrokinetically altered fluids comprise an ionic aqueous solution of charge-stabilized oxygen-containing nanostructures substantially having an average diameter of less than about 100 nanometers and stably configured in the ionic aqueous fluid in an amount sufficient to provide, upon contact of a living cell by the fluid, modulation of at least one of cellular membrane potential and cellular membrane conductivity.

Applicants point out, however, that the hydrophobic bubbles (forming on a hydrophobic surface), such as those observed in AFM experiments are likely fundamentally different from inventive biologically-active charge-stabilized nanostructure disclosed herein. According to particular aspects therefore, while the AFM experiments in this working Example support, based on the size and distribution hydrophobic bubble formation, that the inventive electrokinetic fluids (e.g., RNS-60) are fundamentally distinct from non-electrokinetic control fluids, the hydrophobic bubbles are likely distinct from and/or derived from the inventive charge-stablilized oxygen-containing nanostrutures described in detail elsewhere herein. In any event, relative to the inventive electrokinetic fluids, control pressure pot oxygenated fluids do not comprise charge-stabilized oxygen-containing nanostructures capable of modulation of at least one of cellular membrane potential and cellular membrane conductivity.

Example 26

*Pseudomonas* Inhibition, Plates

Applying gas-enriched saline solution of the present invention limits *Pseudomonas* growth. These tests were performed using an inventive oxygen-enriched saline solution.

Two test strains of *Pseudomonas* (ATCC accession no. 10145 and ATCC accession no. 27853) were prepared from fresh 24-hour cultures to a McFarland 1 concentration (approximately $3 \times 10^8$ microorganisms/mL). Each of the bacterial aliquots (1 mL) was serially diluted in 10 fold dilutions in 9 mL of broth-saline made from 1 part TSB broth and 9 parts sterile saline. The bacterial concentrations tested were $10^7$, $10^6$, $10^5$, $10^4$, $10^3$, and $10^2$. A negative control tube (no bacteria and no gas-enriched fluid of the present invention) was prepared. The positive control tubes (containing no gas-enriched fluid, normal saline and each of the 6 bacterial concentrations) were included in each set of tubes for testing of each bacterial strain.

Using the 10 fold dilutions of each bacterial strain, a set of 36 tubes was inoculated as follows:

Six tubes received 1 mL of each of the dilutions; then 4 mL of each of the test gas-enriched fluids were added to each tube (bringing the total volume to 5 mL). The gas-enriched fluids were labeled as 50 ppm, 40 ppm, 30 ppm, 20 ppm, 10 ppm, and normal saline. The positive control was normal saline, against which all of the other tubes were measured for growth.

All tubes of each 36-tube experiment set for each *Pseudomonas* species were measured serially at 2 hour intervals within a 24 hour period after initial incubation at 35° C. Between readings of each set, the tubes were returned to 35° C. for continued incubation. Readings were performed using a calibrated spectrophotometer set at $OD_{540}$.

The results of these tests indicate that the gas-enriched fluid of the present invention positively inhibits *Pseudomonas* strains at several bacterial dilutions within 4 to 12 hours after the start of incubation at 35° C., as well as later (16-24 hours) for both strains tested.

Specifically, the highest positive inhibition was found during 16 to 24 hours for both strains, at 30 or 50 concentration. The positive inhibition varies slightly depending on the concentration of test solutions, and concentration of bacterial samples tested.

TABLE 10

Time at positive inhibition of *Pseudomonas*

| | Time (hours) | | | | | | | | | | |
|---|---|---|---|---|---|---|---|---|---|---|---|
| | 2 | 4 | 6 | 8 | 10 | 12 | 16 | 18 | 20 | 22 | 24 |
| ATCC 27853 | 0 | 1 | 3 | 1 | 2 | 2 | 5 | 0 | 5 | 7 | 6 |
| % + | — | 3 | 10 | 3 | 6 | 6 | 16 | — | 16 | 23 | 20 |
| ATCC 10145 | 0 | 4 | 3 | 4 | 3 | 3 | 2 | 1 | 5 | 6 | 8 |
| % + | — | 13 | 10 | 13 | 10 | 10 | 6 | 3 | 16 | 20 | 26 |

% + = number +/30 (6 bacterial concentrations × 5 solution concentrations)

Example 27

MIC Studies on *Pseudomonas* Inhibition, Tubes

Minimum inhibitory concentration (MIC) test solutions in two-fold dilutions were prepared in a base of broth-saline mixture made from 1 part TSB broth and 4 parts CFU-NS. The negative control tube (containing no bacteria and no gas-enriched fluid) and the positive control tube (containing no gas-enriched fluid and bacteria) were included in each set of tubes tested. The fluid dilutions were: 50, 25, 12.5, 6.25, 3.12, 1.55, and 0.7 ppm, respectively. Following preparation of the tubes for each bacterial strain, pH was measured on samples from the two solutions. CFU-gas-enriched fluid pH was about 6.8-7.2, while CFU-NS was pH about 6.2.

Following preparation of the 2 sets of covered tubes at 35° C. for 18 hours, visual inspection of all tubes revealed that the first tube labeled 50 in each set showed no growth and all other tubes (except the negative control tube) showed moderate growth.

The tubes labeled 50 and showed no growth upon visual inspection from the MIC studies were further tested for minimum bactericidal concentrations (MBC). Samples were taken from each of these two tubes using sterile calibrated disposable loops of 0.1 mL capacity and were immediately streaked on BA plates to detect growth or inhibition of growth on the challenge bacteria. Following 18 hours incubation at 35° C., samples collected from each of the tubes showing no visual growth (tube 50 from ATCC 10145 and tube 50 from ATCC 27853) both showed growth at very high levels when streaked and plated on BA plates. The numbers of colonies were too numerous to count. Thus, a slight delay in growth was experienced with the tube 50 gas-enriched fluids.

Example 28

*Pseudomonas* Inhibition, Dressings

Aquacel dressings were tested dry and hydrated with either test fluids 52 (pH 7.2-7.8), 50 (pH 6.0-6.2), 42 (pH 7.2), 34 (pH 7.2), 25 (pH 6.8), and 10 (pH 6.2), or normal saline (pH 6.2), against *Pseudomonas* strains ATCC accession no. 10145 and ATCC accession no. 27853 A first application of the gas-enriched test fluids or normal saline fluid to the dressings (0.4 mL) was followed by a second application 12 hours later (0.25 mL).

Results revealed a 3-4 mm clear area of inhibition around one of the three dressing pieces (1 cm square) treated with sterile 25 fluid applied to the three *Pseudomonas* ATCC accession no. 10145 seeded plates, and a 3-4 mm clear area of inhibition around one of the three dressing pieces (1 cm square) treated with sterile 25 fluid applied to one of the three *Pseudomonas* ATCC accession no. 27853 seeded plates. A clear area of less than 1-2 mm of inhibition was around 2 sides of the dry dressing on both strains. No zones of inhibition were detected around the other test or control dressings.

Example 29

Microbial Inhibition, Dressings

Blood Agar plates were used and wound dressings used were Promogram Prisma matrix dressing (A) and hydrofiber dressing (B). The sterile dressings were tested with microorganisms from a 24 hour culture at a cell density with McFarland equivalence turbidity standards of $3.0 \times 10^8$/mL.

Test microorganisms were *Staphlycoccus aureaus, Staphylococcus epidermidis, Pseudomonas aeruginosa, E. coli*, and *Candida albicans*.

Dressings of each type were hydrated with approximately 0.8 mL of either gas-enriched fluid or normal saline, and left for approximately 30 minutes. Dry dressings were used as controls. Plates were then grown for 24 hours and results recorded.

As viewed in the cell plates, the hydrofiber dressing (B) had no effect on growth of test microorganisms whether dry or hydrated with either fluid. The Prisma dressing (A) hydrated with gas-enriched fluid showed a zone of partial inhibition with colonies for *Staph. aureaus*, a 1 mm zone of inhibition for *Staph. epidermidis*, a 2-3 mm zone of inhibition with an added halo effect extending out an additional 2-3 mm for *Pseudomonas*, a 2 mm zone of inhibition for *Candida*, and no effect for *E. coli*.

The dry control hydrofiber dressing (A) had a zone of 2-3 mm of inhibition for *Staph. auereaus, Staph. epidermidis, Pseudomonas*, and a partial inhibition of about 1-2 mm for *E. coli* and *Candida*, with break-through colonies observed.

The normal saline control hydrofiber dressing (A) showed a 2 mm zone of partial inhibition for *Staph. auereaus, Staph. epidermidis*, and *Pseudomonas*. Colonies were observed grown into *E. coli* and *Candida* test strains.

Example 30

MIC/MBC Testing with Tobramycin

The gas-enriched fluids of the present invention were tested randomly against three *Pseudomonas* strains, PA 01, PA 14, and PA K. Each bacterial culture was prepared from fresh 24-hour cultures to McFarland 1 concentration (approximately $3 \times 10^8$ microorganisms/mL). Each of the bacterial samples (1 mL) were then serially diluted in 10 fold dilutions to 9 mL of a broth-saline mixture made from 1 part MH broth and 9 parts sterile saline. The bacterial concentrations tested were $10^5$, $10^4$, $10^3$, and $10^2$. Negative control tubes (containing no bacteria and no gas-enriched saline solution, and no Tobramycin), as well as positive control tubes (containing test bacteria concentrations and normal saline but no Tobramycin, and no gas-enriched fluid), were run side-by-side with the test solutions. Cells were incubated at 35° C.

Results are shown in Table 11 below. Sheared normal saline was passed through the gas-enriching diffuser device of the present invention without the addition of a gas to the fluid.

TABLE 11

Better kill rate with Tobramycin and Gas-enriched fluid than Tobramycin Alone

| Fluid | Description | Dissolved Gas (Oxygen, ppm) | PA01 | PA 14 | PAK |
|---|---|---|---|---|---|
| A | Gas-enriched Saline | 33.4 | Yes | Yes | No |
| B | Gas-enriched saline | 23.8 | No | Yes | No |
| C | Gas-enriched saline | 49.6 | Yes | Yes | Yes |
| D | Normal saline | 9.6 | No | No | No |
| E | Gas-enriched saline | 42.8 | Yes | Yes | Yes |
| F | Sheared normal saline (no gas enrichment) | 14.1 | Yes | Yes | Yes |

Figure 39:
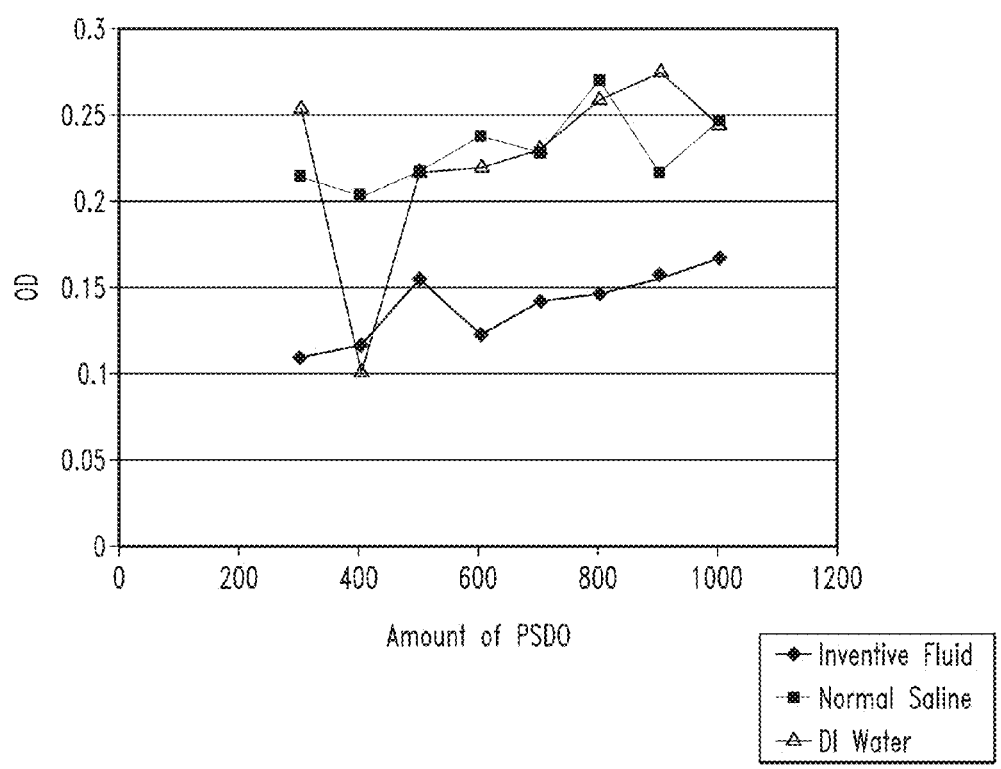
FIG. 39 illustrates the difference in the growth rates of Pseudomonas bacteria at various dissolved oxygen saturation ratios.

Test results shown in FIG. 39 illustrate the results of testing *Pseudomonas* growth inhibition with deionized water, an oxygen-enriched fluid of the present invention, as well as normal saline.

Example 31

Corneal Fibroblast Proliferation

Figure 46:
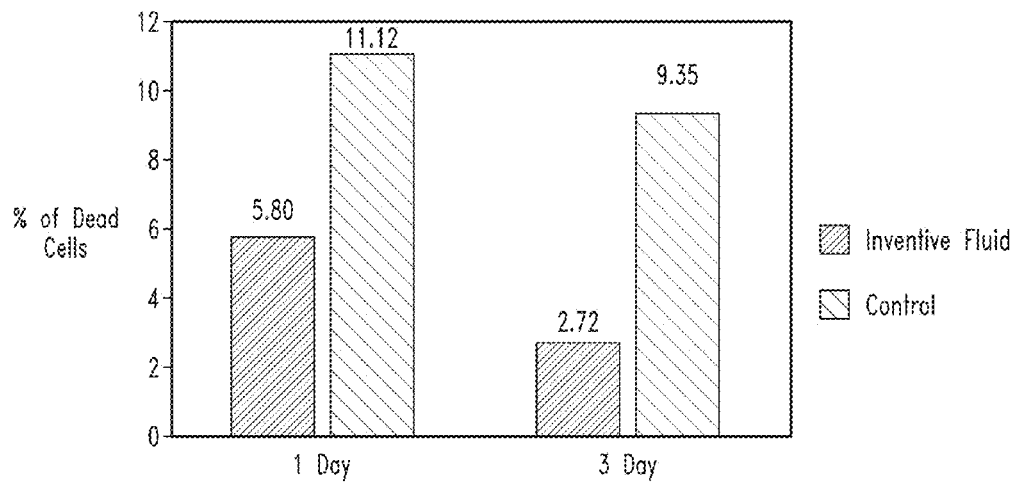
FIG. 46 illustrates the percentage of dead cells at separate time points in a corneal fibroblast assay using inventive gas-enriched culture media and control culture media.
Figure 47:
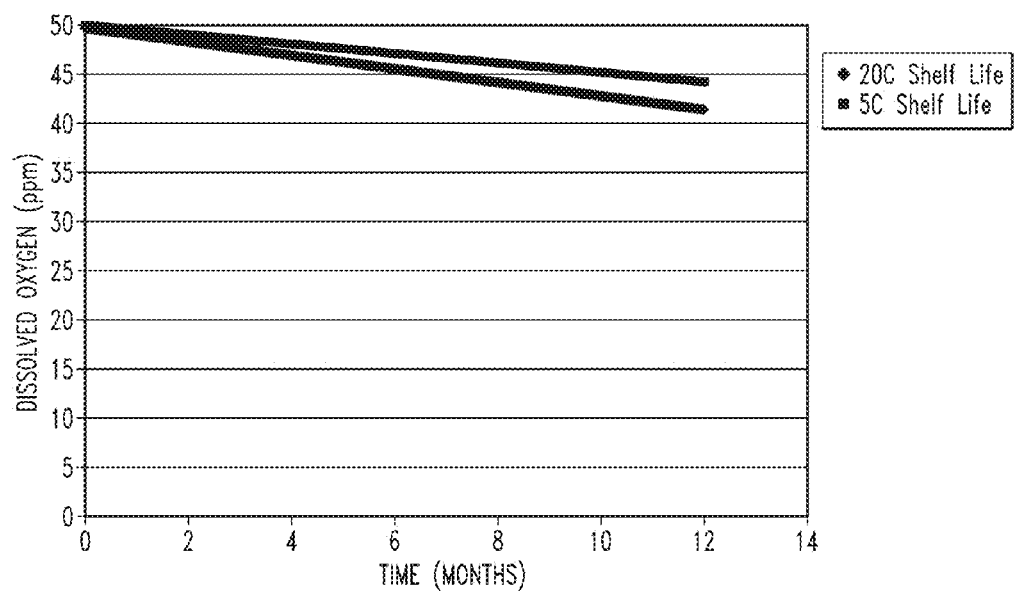
FIG. 47 illustrates the shelf life of the inventive gas-enriched fluid in a polymer pouch.

Sterile gas-enriched water (with oxygen content of approximately 50 ppm), or standard sterile deionized water was utilized in preparing cell culture media. A human corneal stromal fibroblast cell line was plated in 24 well tissue culture plates at a density of $1 \times 10^5$ cells/cm$^2$ and cells were tested for viability using a standard Live/Dead assay from Molecular Probes, Inc. Viability tests were conducted at 1 or 3 days of continuous culture with media changes twice per day. Viable and non-viable cells were counted in 10 random 20×fields (0.2 mm$^2$ area/field) in each well. The percentage of dead cells was then calculated. Cells in the inventive gas-enriched media had fewer dead cells than in standard culture media. Results are shown in FIG. 46.

Example 32

MRSA Bacteriocidal Effects

According to particular aspects, the inventive diffuser processed therapeutic fluids have substantial utility for treating MRSA. Methicillin-Resistant *Staphylococcus Aureus* (MRSA) was tested with fluids described herein. For MRSA, ATCC#29213 was used (Methicillin Sensitive Strain (MSSA)). In particular aspects, ATCC#33591 was used (technically MRSA; resistant to methicillin but oxacillin sensitive). In particular aspects, ORSA (ATCC#43300) was used (resistant to both oxacillin and methicillin).

MRSA was exposed to oxacillin in combination with fluid that was processed through the inventive device disclosed herein, or fluid that was processed through the inventive device with gas enrichment. Results are shown in the Table 12 below. As indicated, fluid processed through the described device (Solas) showed an increased killing of MRSA bacteria, as did fluid passed through the device that was gas-enriched (OS 20, fluid enriched with oxygen at 20 ppm concentration; OS40, fluid enriched with oxygen at 40 ppm; OS60, fluid enriched with oxygen at 60 ppm concentration) than did the control.

TABLE 12

Treatment of the MRSA strain with the inventive electrokenetically generated solutions. Percentage data values are the percentage of plates with No growth of MRSA.

| Composition | Percentage of plates with no growth at indicated time (mins) | | | | | | |
|---|---|---|---|---|---|---|---|
| | 0 min | 30 min | 120 min | 240 min | 480 min | 1080 min | 1440 min |
| Solas | 50.00% | 0.00% | 16.67% | 33.33% | 50.00% | 100.00% | 33.33% |
| OS 20 | 50.00% | 0.00% | 16.67% | 0.00% | 0.00% | 0.00% | 0.00% |
| OS 40 | 16.67% | 0.00% | 0.00% | 0.00% | 0.00% | 0.00% | 0.00% |
| OS 60 | 16.67% | 0.00% | 16.67% | 16.67% | 33.33% | 0.00% | 0.00% |
| Drug | 16.67% | 0.00% | 0.00% | 0.00% | 0.00% | 0.00% | 0.00% |
| Bacteria | 16.67% | 0.00% | 0.00% | 0.00% | 0.00% | 0.00% | 0.00% |

Example 33

Adjunctive Therapies

According to particular aspects, the inventive diffuser processed therapeutic fluids have substantial utility for use in adjunctive therapy settings, including, but not limited to use with at least one of the following exemplary compositions and/or methods:

| Absorptive Dressing | |
|---|---|
| Product | Manufacturer |
| Medipore | 3M |
| Silon Dual-Dress 04P ® Multi-Function Wound Dressing & | Bio Med Sciences |
| Silon Dual-Dress 20F ® Multi-Function Wound Dressing | |
| Aquacel Hydrofiber | ConvaTec |
| CombiDERM | |
| Absorptive Border | DermaRite |
| MULTIPAD | DeRoyal |
| SOFSORB | |
| IODOFLEX | HEALTHPOINT |
| TIELLE | Johnson & Johnson |
| CURITY ABD | Kendall |
| TELFAMAX | |
| TENDERSORB ABD | |
| Mepore | Molnlycke Health Care |
| EXU-DRY | Smith & Nephew |
| Primapore | |

| Alginates | |
|---|---|
| Product | Manufacturer |
| AlgiCell | Dumex Medical |
| AlgiDERM | Bard |
| AlgiSite M | Smith & Nephew, Inc. Wound Managment Division |
| Askina Sorg | Swiss-American |
| CarraSorb H | Carrington |
| CarraGinate with Acemannan gel | |
| CURASORB | Kendall/Tyco |
| CURASORB Zinc | |
| Dermacea | Sherwood - Davis & Geck |
| DermaGinate | DermaRite |
| DermaGinate AG | |
| FyBron | B. Braun |
| Gentell | Gentell |
| Hyperion Advanced Alginate Dressing | Hyperion Medical, Inc. |
| KALTOSTAT (various presentations) | ConvaTec |
| KALGINATE | DeRoyal |
| Algidex (various presentations) | |

-continued

| Alginates | |
|---|---|
| Product | Manufacturer |
| Maxorb | Medline |
| Melgisorb | Molnlycke Health Care |
| PolyMem | Ferris Mfg. |
| Restore CalciCare | Hollister |
| SILVERCELL | Johnson & Johnson |
| Sorbalgon | Harmann-Conco Inc. |
| SORBSAN | Mylan Bertek |
| SeaSorb | Coloplast Corp. |
| Tegagen HG | 3M Health Care |
| Tegagen HI | |

| Antimicrobials | |
|---|---|
| Product | Manufacturer |
| 3M Tegaderm Ag Mesh | 3M |
| Amerigel (various presentations) | Amerx Health Care Corp. |
| Anasept | Anacapa |
| Silverlon | Argentum Medical LLC |
| Di-Dak-Sol | Century Pharmaceuticals |
| Contreet (various presentations) | Coloplast Corp. |
| Aquacel Ag | ConvaTec |
| SilverDerm7 | DermaRite |
| Algidex | DeRoyal |
| ColActive Ag | Hartmann-Conco Inc. |
| Hydrofera Blue | Hydrofera Inc. |
| Actisorb | Johnson & Johnson |
| Kerlix AMD | Kendall/Tyco |
| Curity AMD | |
| Excilon AMD | |
| TELFA AMD | |
| Arglase (various presentations) | Medline |
| Maxorb Extra Ag | |
| Optifoam AG | |
| SilvaSorb (various presentations) | |
| XCell AM | |
| SelectSilver | Milliken Company |
| Acticoat 3 | Smith & Nephew |
| Acticoat 7 | |
| Acticoat Moisture Control | |
| IODOFLEX | |
| IODOSORB | |
| Silver Seal | X-Static/Noble Biomaterials |

| Cleansers | |
|---|---|
| Product | Manufacturer |
| 3M Cavilon | 3M |
| Wound Wash Saline | Blairex Labs |

Cleansers

| Product | Manufacturer |
|---|---|
| Clinical Care | Care-Tech |
| Techni-Care | |
| Puri-Clens | Coloplast |
| Sea-Clens | |
| Optipore Sponge | ConvaTec |
| SAF-Clens | |
| Shur-Clens | |
| Clean 'N Moist | Darja Laboratories Inc. |
| Repair Wound Cleanser | |
| DermaKlenz | DermaRite |
| Dermagran | Derma Sciences |
| ALLCLENZ | HEALTHPOINT |
| Restore | Hollister |
| Hyperion Wound Cleanser | Hyperion Medical, Inc. |
| DEBRISAN | Johnson & Johnson |
| Constant-Clens | Kendall |
| Skin Tegrity | Medline |
| MPM | MPM |
| MPM Antimicrobial | |
| Elta Dermal | Swiss-American Products |

Closure Devices

| Product | Manufacturer |
|---|---|
| WoundTek's S.T.A.R. Device | WoundTek, Inc. |
| DP Woundcare Dressing | DP Wound Care |
| Dermabond | JnJ/Ethicon www.dermabond.com |
| DermaClose RC | Woundcare Technologies |

Collagen

| Product | Manufacturer |
|---|---|
| Medifil | BioCore |
| Skin Temp | |
| BGC Matrix | Brennen |
| WOUN'DRESS | Coloplast Sween |
| Collagen/AG | DermaRite |
| ColActive Ag | Hartmann-Conco, Inc. |
| FIBRACOL plus Collagen | Johnson & Johnson |
| Prisma | |
| Promogran Prisma | |
| Mepore Pro | Molnlycke |
| Stimulen | Southwest |
| Primatrix | TEI Biosciences |
| hyCURE | The Hymed Group |
| hyCURE Smart Gel | |
| CellerateRx | Wound Care Innovations |

Compression Dressing & Wraps (Leg)

| Product | Manufacturer |
|---|---|
| 3M Coban 2 layer | 3M |
| ArtAssist | ACI Medical |
| Gelocast Unna Boot | BSN |
| Artiflex | |
| Comprilan | |
| Tricofix | |
| CIRCULON | ConvaTec |
| DuoDERM SCB | |
| Setopress | |
| SurePress | |
| UNNA-FLEX | |
| Primer | Glenwood, Inc. |
| Unna-Pak | |
| 4-Layer Compression | Hartmann-Conco |
| DYNA-FLEX | Johnson & Johnson |
| TENDERWRAP | Kendall |
| Profore | Smith & Nephew |
| Profore LF | |
| Profore Lite | |

Composite Dressing

| Product | Manufacturer |
|---|---|
| Tegaderm Trasparent Dressing with Absorbent Pad | 3M |
| Silon Dual-Dress 04P ® Multi-Function Wound Dressing & Silon Dual-Dress 20F ® Multi-Function Wound Dressing | Bio Med Sciences |
| Coverlet | BSN |
| COVADERM | DeRoyal |
| TELFA | Kendall |
| VENTEX | |
| StrataSorb | Medline |
| Alldress | Molnlycke Health Care |
| MPM | MPM |
| Viasorb | Sherwood-Davis & Geck |
| AIRSTRIP | Smith & Nephew |
| Coverlet | |
| CovRSite Plus | |
| Cutifilm | |
| OpSite Plus | |
| OpSite Post-Op | |
| Centurion SorbaView | Tri-State Hospital Supply |

Contact Layer

| Product | Manufacturer |
|---|---|
| Tegapore | 3M |
| Silon-TSR ® Temporary Skin Replacement | Bio Med Sciences |
| DERMANET | DeRoyal |
| TELFA CLEAR | Kendall |
| Mepitel | Molnlycke Health Care |
| Profore Wound Contact Layer | Smith & Nephew |
| N-TERFACE | Winfield Laboratories |

Enzymatic Debriders

| Product | Manufacturer |
|---|---|
| Accuzyme | HEALTHPOINT |
| Panafil | |
| Collagenase | |
| Ethezyme ™ 830 Papain Urea Debriding Ointment | Ethex |
| Ethezyme ™ Papain-Urea Debriding Ointment | Ethex |
| Kovia Ointment | Stratus |
| Ziox Ointment | Pharmaceutical |
| Gladase | Smith & Nephew |

Fillers (wound)

| Product | Manufacturer |
| --- | --- |
| AcryDerm Strands | AcryMed |
| DermAssist | AssisTec |
| Cutinova Cavity | Beiersdorf-Jobst |
| Humatrix Microclysmic Gel | Care-Tech |
| Mesalt | Molnlycke Health Care |
| MULTIDEX | DeRoyal |
| PolyWic | Ferris Mfg. |
| BIAFINE | Medix |

Foam Dressings

| Product | Manufacturer |
| --- | --- |
| 3M Foam Dressing (nonadhesive) | 3M |
| 3M Foam Adhesive Dressing | |
| Vigi-FOAM | Bard |
| FLEXZAN | Bertek (Dow Hickam) |
| Silon Dual-Dress 20F ® Multi-Function Wound Dressing | Bio Med Sciences |
| Lyofoam | ConvaTec |
| Lyofoam A | |
| Lyofoam C | |
| Lyofoam Extra | |
| Lyofoam T | |
| POLYDERM | DeRoyal |
| PolyMem | Ferris Mfg. |
| Hydrofera Blue | Hydrofera LLC |
| BIOPATCH | Johnson & Johnson |
| CURAFOAM | Kendall |
| Mepilex | Molnlycke Health Care |
| Mepilex Border | |
| Mitraflex | |
| Mitraflex Plus | |
| Allevyn Adhesive | Smith & Nephew |
| Allevyn Cavity | |
| Allevyn Dressing | |
| Allevyn Island | |
| Allevyn Tracheostomy | |
| Allevyn Sacral | |

Hydrocolloid

| Product | Manufacturer |
| --- | --- |
| Tegasorb | 3M |
| Tegasorb THIN | |
| Hydrocol | Bertek (Dow Hickam) |
| BGC Matrix | Brennen |
| Comfeel (multiple presentations) | Coloplast |
| DuoDERM CGF | ConvaTec |
| DuoDERM (multiple presentations) | |
| SignaDRESS Sterile | |
| DermaFilm HD | DermaRite |
| DermaFilm Thin | |
| Restore (multiple presentations) | Hollister |
| NU-DERM | Johnson & Johnson |
| Ultec | Kendall |
| ExuDERM (multiple presentations) | Medline |
| RepliCare (multiple presentations) | Smith & Nephew |
| Cutinova Hydro | |
| Cutinova Thin | |

Hydrofiber

| Product | Manufacturer |
| --- | --- |
| AQUACEL | ConvaTec |

Hydrogel

| Product | Manufacturer |
| --- | --- |
| Tegagel | 3M |
| Amerigel Topical Ointment | Amerx Health Care |
| Bard Absorption Dressing | Bard Medical |
| Biolex | |
| Iamin | |
| CarraSorb | Carrington Laboratories |
| Carrasyn | |
| DIAB GEL | |
| Woun'Dres | Coloplast |
| Purilon | |
| DuoDERM | ConvaTec |
| SAF-Gel | |
| Repair Hydrogel | Darja Laboratories Inc. |
| DermaSyn | DermaRite |
| Dermagran | Derma Sciences, Inc. |
| CURASOL | HEALTHPOINT |
| Restore | Hollister Inc. |
| NU-GEL | Johnson & Johnson |
| CURAFIL | Kendall |
| SkinTegrity | Medline |
| Hypergel | Molnlycke Health Care |
| Normlgel | |
| MPM | MPM Medical, Inc. |
| Iamin | ProCyte |
| PanoPlex | Sage Laboratories |
| IntraSite | Smith & Nephew |
| SoloSite | |
| Elta Dermal | Swiss-American Products, Inc. |

Hydrogel Impregnated Gauze

| Product | Manufacturer |
| --- | --- |
| DermAssist | AssisTec Medical, Inc. |
| Biolex | Bard |
| CarraGauze | Carrington |
| ClearSite | Conmed Corp. |
| DermGauze | DermaRite |
| Dermagran | Derma Sciences |
| Gentell | Gentell |
| CURASOL | HEALTHPOINT |
| Restore | Hollister |
| Hyperion Hydrophilic Wound Dressings | Hyperion Medical, Inc. |
| INTEGRA-GEL | Integrity Medical Devices, Inc. |
| CURAFIL | Kendall |
| SkinTegrity | Medline Industries |
| Normlgel Impregnated Gauze | Molnlycke Health Care |
| MPM Conductive Gel Pad | MPM |
| MPM GelPad | |
| PanoGauze | Sage |
| SoloSite Gel Conformable | Smith & Nephew |
| Elta Dermal | Swiss-American Products, Inc. |

Hydrogel Sheet

| Product | Manufacturer |
| --- | --- |
| Tegagel | 3M |
| Vigilon | Bard |
| ClearSite | Conmed Corporation |
| AQUASORB | DeRoyal |

Hydrogel Sheet

| Product | Manufacturer |
|---|---|
| FLEXDERM | Bertek (Dow Hickam) |
| NU-GEL | Johnson & Johnson |
| CURAGEL | Kendall |
| Derma-Gel | Medline Industries |
| FlexiGel | Smith & Nephew |

Measuring Devices

| Product | Manufacturer |
|---|---|
| Tru-Area Determination | Molnlycke Health Care NTL |

Miscellaneous Devices

| Product | Manufacturer |
|---|---|
| EPIFLO-Transdermal sustained delivery of oxygen | Ogenix www.ogenix.net |
| Circulator Boot | Circulator Boot Corporation www.circulatorboot.com |

Negative Pressure Wound Therapy

| Product | Manufacturer |
|---|---|
| Engenex | Boehringer Wound Systems, LLC www.boehringerwound.com |
| Prospera PRO-I | Medica-Rents, Inc. www.medicarents.com |
| V.A.C. (various models) | KCI www.kcil.com |
| Versatile 1, V1STA | Smith & Nephew |
| Invia | Medela |

Odor Absorbing

| Product | Manufacturer |
|---|---|
| CarboFlex | ConvaTec |
| LyoFoam C | |
| Odor Absorbing Dressing | Dumex |

Scar Therapy and Makeup

| Product | Manufacturer |
|---|---|
| Oleeva (various) | Bio Med Sciences |
| Silon | |
| Mepiform | Molnlycke |
| Cica-Care | Smith & Nephew |
| Various | Local Pharmacy |

Skin Care

For patients with wounds or patients at risk of skin breakdown, some of the categories you should be aware of include:
Antifungals
Anti-inflammatory
Barriers
Moisturizers
Sealants
Companies like Smith & Nephew, HEALTHPOINT, ConvaTec and 3M offer a full range of products.

Skin Substitutes

| Product | Manufacturer |
|---|---|
| Dermagraft | Advanced Biohealing |
| Transcyte | |
| Hyalofil-F | ConvaTec |
| Hyalofil-R | |
| Integra (various presentations) | Integra LifeSciences |
| Alloderm | Lifecell |
| Biobrane | Mylan Bertek |
| Apligraf | Organogenesis |
| Primatrix | TEI Biosciences |

Tissue Engineering/Growth Factors

| Product | Distributor/Manufacturer | Details |
|---|---|---|
| Apligraf | Organogenesis | http://www.apligraf.com |
| Dermagraft | Advanced Biohealing | http://www.advancedbiohealing.com |
| Transcyte | | |
| GRAFTJACKET ® Regenerative Tissue Matrix Ulcer Repair | Wright Medical Technologies, Inc. | http://www.wmt.com/graftjacket/ |
| GRAFTJACKET ® XPRESS Flowable Soft-Tissue Scaffold | Wright Medical Technologies, Inc. | http://www.wmt.com |
| Oasis | Healthpoint | http://www.healthpoint.com |
| Orcel | Ortec International, Inc. | http://ortecinternational.com |
| Regranex | Johnson & Johnson | www.regranex.com |

| Transparent Films | |
| --- | --- |
| Product | Manufacturer |
| Tegaderm HP | 3M |
| Tegaderm | |
| Silon-TSR ® Temporary Skin Replacement | Bio Med Sciences |
| CarraFilm | Carrington |
| DermaView | DermaRite |
| TRANSEAL | DeRoyal |
| BIOCLUSIVE MVP | Johnson & Johnson |
| BIOCLUSIVE | |
| Blisterfilm | Kendall |
| POLYSKIN II | |
| POLYSKIN M.R. | |
| SureSite | Medline |
| Mefilm | Molnlycke Health Care |
| ProCyte | ProCyte |
| OpSite FLEXIGRID | Smith & Nephew |
| OpSite | |
| UniFlex | |

INCORPORATION BY REFERENCE

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

It should be understood that the drawings and detailed description herein are to be regarded in an illustrative rather than a restrictive manner, and are not intended to limit the invention to the particular forms and examples disclosed. On the contrary, the invention includes any further modifications, changes, rearrangements, substitutions, alternatives, design choices, and embodiments apparent to those of ordinary skill in the art, without departing from the spirit and scope of this invention, as defined by the following claims. Thus, it is intended that the following claims be interpreted to embrace all such further modifications, changes, rearrangements, substitutions, alternatives, design choices, and embodiments.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method for treating a wound to a surface tissue or a symptom thereof, comprising administering to a subject in need thereof a therapeutically effective amount of an oxygenated ionic aqueous solution of charge-stabilized oxygen nanobubbles having an average diameter of less than 100 nanometers sufficient to promote treating a wound to a surface tissue or a symptom thereof.

2. The method of claim 1, wherein the charge-stabilized oxygen nanobubbles are stably configured in the ionic aqueous solution in an amount sufficient to provide, upon contact of a living cell by the solution, modulation of at least one of cellular membrane potential and cellular membrane conductivity.

3. The method of claim 1, wherein treating the wound comprises treating to decrease scarring in the wound to the surface tissue, wherein scarring is reduced.

4. The method of claim 3, wherein the oxygenated ionic aqueous solution further increases the level of chemokines at the wound.

5. The method of claim 1, wherein treating the wound comprises treating to increase or decrease nitric oxide production or degradation in the wound to the surface tissue, wherein an increased or decreased level of nitric oxide is afforded.

6. The method of claim 1, wherein the oxygenated ionic aqueous solution is contacted to the wound by means of a wound dressing.

7. The method of claim 1, wherein the oxygenated ionic aqueous solution accelerates epidermal or dermal layering.

8. The method of claim 1, wherein the oxygenated ionic aqueous solution increases cellular migration of at least one type of cell to the wound.

9. The method of claim 8, wherein the type of cellular migration or proliferation comprises at least one cell selected from the group consisting of: keratinocytes, fibroblasts, epidermal cells, dermal cells, epithelial cells, mast cells, neutrophils, lymphocytes, and macrophages.

10. The method of claim 1, wherein the oxygenated ionic aqueous solution accelerates neoangiogenesis of blood vessels or lymphatic vessels.

11. The method of claim 1, wherein the oxygenated ionic aqueous solution increases collagen deposition at the wound.

12. The method of claim 1, wherein the oxygenated ionic aqueous solution reduces growth of at least one microbe in the wound.

13. The method of claim 12, wherein the microbe comprises *Pseudomonas*.

14. The method of claim 1, wherein the charge-stabilized oxygen nanobubbles are the major charge-stabilized gas-containing nanobubble species in the fluid.

15. The method of claim 1, wherein the percentage of dissolved oxygen molecules present in the oxygenated ionic aqueous solution as the charge-stabilized oxygen nanobubbles is a percentage selected from the group consisting of greater than: 0.01%, 0.1%, 1%, 5%; 10%; 15%; 20%; 25%; 30%; 35%; 40%; 45%; 50%; 55%; 60%; 65%; 70%; 75%; 80%; 85%; 90%; and 95%.

16. The method of claim 1, wherein the total dissolved oxygen is substantially present in the charge-stabilized oxygen nanobubbles.

17. The method of claim 1, wherein the charge-stabilized oxygen nanobubbles have an average diameter of less than a size selected from the group consisting of: 90 nm; 80 nm; 70 nm; 60 nm; 50 nm; 40 nm; 30 nm; 20 nm; 10 nm; and less than 5 nm.

18. The method of claim 1, wherein the oxygenated ionic aqueous solution comprises a saline solution.

19. The method of claim 1, wherein the oxygenated ionic aqueous solution is superoxygenated.

20. The method of claim 1, wherein the oxygenated ionic aqueous solution comprises a form of solvated electrons.

21. The method of claim 1, wherein the wound to a surface tissue or the symptom thereof comprises at least one wound type selected from the group consisting of lacerations, abrasions, rupture, puncture wounds, chemical, thermal, or radiation-induced burns, cuts, scrapes, incisions, blisters, diabetic ulcers, bedsores or pressure ulcers, skin grafts, and surgical wounds.

22. The method of claim 21, wherein the wound to a surface tissue or the symptom thereof comprises at least one of diabetic ulcers, bedsores or pressure ulcers, skin grafts, and surgical wounds.

23. The method of claim 22, wherein the wound to a surface tissue or the symptom thereof comprises diabetic ulcers, and bedsores or pressure ulcers.

24. The method of claim 1, wherein the symptom is related to at least one condition selected from the group consisting of epidmeral or dermal layering, cellular migration, collagen deposition at the wound, neoangiogenesis at the wound, elastin deposition at the wound, inflammation at the wound, expression of proteoglycans or glycosaminoglycans, cellular proliferation, and hyaluronic acid concentration at the wound.

25. The method of claim 1, wherein the oxygenated ionic aqueous solution modulates localized or cellular levels of nitric oxide.

26. The method of claim 1, wherein the oxygenated ionic aqueous solution promotes a localized decrease at the site of administration of at least one cytokine selected from the group consisting of: IL-1beta, IL-8, TNF-alpha, and TNF-beta.

27. The method of claim 1, further comprising a synergistic or non-synergistic inhibition or reduction in inflammation by simultaneously or adjunctively treating the subject with another anti-inflammatory agent.

28. The method of claim 27, wherein said other anti-inflammatory agent comprises a steroid or glucocorticoid steroid.

29. The method of claim 28, wherein said steroid comprises a glucocorticoid steroid.

30. The method of claim 1, further comprising combination therapy, wherein at least one additional therapeutic agent is administered to the patient.

31. The method of claim 30, wherein the one additional therapeutic agent is selected from the group consisting of anti-microbial agents, antifungal agents, and antibiotic agents.

32. The method of claim 30, wherein, the at least one additional therapeutic agent is selected from the group consisting of: ciclosporin, hyaluronic acid, carmellose, macrogol(s), dextran and hyprolose, sodium and calcium, sodium and povidone, hypromellose, carbomer, amikacin, gentamicin, kanamycin, neomycin, netilmicin, streptomycin, tobramycin, paromomycin, geldanamycin, herimycin, loracarbef, ertapenem, imipenem/cilastatin, meropenem, cefadroxil, cefazolin, cefalotin/cefalothin, cephalexin, cefaclor, cefamandole, cefoxitin, cefuroxime, cefixime, cefdinir, cefditoren, cefoperazone, cefotaxime, cefpodoxime, ceftazidime, ceftibuten, ceftizoxime, ceftriaxone, cefeprime, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, nafcillin, penicillin, peperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, protosil, sulfacetamide, sulfamethizole, sulfanilamide, sulfasalazine, sulfisoxazole, trimethoprim, trimethoprim-sulfamethoxazole, demeclocycline, doxycycline, minocycline, oxytetracycline, tetracycline, arsphenamine, chloramphenicol, clindamycin, lincoamycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin, tinidazole, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, terbinafine, amorolfine, naftifine, butenafine, anidulafungin, caspofungin, micafungin, ciclopirox, flucytosine, griseofulvin, Gentian violet, haloprogin, tolnaftate, undecylenic acid, and combinations thereof.

33. The method of claim 30, wherein the at least one additional therapeutic agent is a thymic stromal lymphopoietin (TSLP) and/or thymic stromal lymphopoietin receptor (TSLPR) antagonist.

34. The method of claim 33, wherein the TSLP and/or TSLPR antagonist is selected from the group consisting of neutralizing antibodies specific for TSLP and the TSLP receptor, soluble TSLP receptor molecules, and TSLP receptor fusion proteins, including TSLPR-immunoglobulin Fc molecules or polypeptides that encode components of more than one receptor chain.

35. The method of claim 2, wherein modulation of at least one of cellular membrane potential and cellular membrane conductivity comprises altering of a conformation, ligand binding activity, or a catalytic activity of a membrane associated protein.

36. The method of claim 35, wherein the membrane associated protein comprises at least one selected from the group consisting of receptors, transmembrane receptors, ion channel proteins, intracellular attachment proteins, cellular adhesion proteins, and integrins.

37. The method of claim 36, wherein the transmembrane receptor comprises a G-Protein Coupled Receptor (GPCR).

38. The method of claim 37, wherein the G-Protein Coupled Receptor (GPCR) interacts with a G protein a subunit.

39. The method of claim 38, wherein the G protein a subunit comprises at least one selected from the group consisting of $G\alpha_s$, $G\alpha_i$, $G\alpha_q$, and $G\alpha_{12}$.

40. The method of claim 39, wherein the at least one G protein a subunit is $G\alpha_q$.

41. The method of claim 2, wherein modulating cellular membrane conductivity, comprises modulating whole-cell conductance.

42. The method of claim 41, wherein modulating whole-cell conductance, comprises modulating at least one of linear and non-linear voltage-dependent contribution of the whole-cell conductance.

43. The method of claim 2, wherein modulation of at least one of cellular membrane potential and cellular membrane conductivity comprises modulation of a calcium dependent cellular messaging pathway or system.

44. The method of claim 2, wherein modulation of at least one of cellular membrane potential and cellular membrane conductivity comprises modulation of phospholipase C activity.

45. The method of claim 2, wherein modulation of at least one of cellular membrane potential and cellular membrane conductivity comprises modulation of adenylate cyclase (AC) activity.

46. The method of claim 2, wherein modulation of at least one of cellular membrane potential and cellular membrane conductivity comprises modulation of intracellular signal transduction associated with at least one condition or symptom selected from the group consisting of epidmeral or dermal layering, cellular migration, collagen deposition at the wound, neoangiogenesis at the wound, elastin deposition at the wound, inflammation at the wound, expression of proteoglycans or glycosaminoglycans, cellular proliferation, and hyaluronic acid concentration at the wound.

47. The method of claim 1, comprising administration to a cell network or layer, and further comprising modulation of an intercellular junction therein.

48. The method of claim 47, wherein the intercellular junction comprises at least one selected from the group consisting of tight junctions, gap junctions, zona adherins and desmasomes.

49. The method of claim 47, wherein the cell network or layers comprises at least one selected from the group consisting of epithelial cell layer or network.

50. The method of claim 1, wherein the oxygen in the oxygenated ionic aqueous solution is present in an amount selected from the group consisting of at least 8 ppm, at least 15, ppm, at least 25 ppm, at least 30 ppm, at least 40 ppm, at least 50 ppm, and at least 60 ppm oxygen at atmospheric pressure.

51. The method of claim 1, wherein the oxygenated ionic aqueous solution comprises at least one of a form of solvated electrons and electrokinetically modified or charged oxygen species.

52. The method of claim 51, wherein the form of solvated electrons or electrokinetically modified or charged oxygen species are present in an amount selected from the group consisting of at least 0.01 ppm, at least 0.1 ppm, at least 0.5 ppm, at least 1 ppm, at least 3 ppm, at least 5 ppm, at least 7 ppm, at least 10 ppm, at least 15 ppm, and at least 20 ppm.

53. The method of claim 51, wherein the oxygenated ionic aqueous solution comprises a form of solvated electrons stabilized, at least in part, by molecular oxygen.

54. The method of claim 2, wherein the ability to modulate at least one of cellular membrane potential and cellular membrane conductivity persists for a time period selected from the group consisting of at least two, at least three, at least four, at least five, at least 6, and at least 12 months, in a closed gas-tight container.

* * * * *